(12) United States Patent
Christensen et al.

(10) Patent No.: US 7,456,276 B2
(45) Date of Patent: Nov. 25, 2008

(54) PEPTIDE PURIFICATION BY MEANS OF METAL ION AFFINITY CHROMATOGRAPHY

(75) Inventors: Thorkild Christensen, Allerod (DK);
William Milton Thomas Hearn, Victoria (AU); Leone Spiccia, Victoria (AU); Wei Jiang, Victoria (AU); Therese Jane Mooney, Victoria (AU); Bimbil Graham, Victoria (AU)

(73) Assignees: Novo Nordisk A/S, Bagsvaerd (DK); Monash University, Clayton, Victoria (AU)

( * ) Notice: Subject to any disclaimer, the term of this patent is extended or adjusted under 35 U.S.C. 154(b) by 192 days.

(21) Appl. No.: 10/495,302

(22) PCT Filed: Nov. 12, 2002

(86) PCT No.: PCT/DK02/00758

§ 371 (c)(1),
(2), (4) Date: Dec. 9, 2004

(87) PCT Pub. No.: WO03/042249

PCT Pub. Date: May 22, 2003

(65) Prior Publication Data

US 2006/0287432 A1    Dec. 21, 2006

Related U.S. Application Data

(60) Provisional application No. 60/333,650, filed on Nov. 27, 2001.

(30) Foreign Application Priority Data

Nov. 12, 2001    (DK) ................................ 2001 01681

(51) Int. Cl.
*C07H 1/00* (2006.01)
*C07D 251/00* (2006.01)

(52) U.S. Cl. .................. 536/123.1; 536/55.1; 544/180; 544/181; 544/186

(58) Field of Classification Search .................. 536/31, 536/51, 55.1, 56, 99, 101, 106, 112, 121, 536/123.1; 544/180, 181, 186
See application file for complete search history.

(56) References Cited

U.S. PATENT DOCUMENTS 5,169,936 A    12/1992 Staples et al. ............... 530/350

FOREIGN PATENT DOCUMENTS

EP         972566         1/2000
WO    WO 00/41721       7/2000

OTHER PUBLICATIONS

Jiang et al., Anal Biochem, vol. 255, pp. 47-58 (1998).
Matyska et al., Anal Chem, vol. 73, pp. 5116-5125 (Nov. 1, 2001).
Rajan et al., Prot Expres Purif, vol. 13, pp. 67-72 (1998).
Sulkowski, E., Trends Biotechnol, vol. 3, pp. 1-6 (Jan. 1985).
Porath et al., Nature, vol. 258, pp. 598-599 (Dec. 18, 1975).
Kågedal, L., Res Dev, pp. 227-251 (1989).
Zachariou et al., BioChem, vol. 35, pp. 202-211 (1996).
Zachariou et al., J. Phys Chem, vol. 100, pp. 12680-12690 (1996).
Zawistowska et al., Cereal Chemistry, vol. 65 (5), pp. 5413-5416 (1988).
Weerasinghe et al., Biochem Biophys Acta, vol. 839, pp. 57-65 (1985).
Otsuka, S (Editor), Kondansha Ltd., pp. 18-45 (1988).
Hoculi et al., BioTechnology, vol. 6, pp. 1321-1325 (Nov. 1988).
Porath, J., Trends in Analytical Chem., vol. 7 (7), pp. 254-256 (1988).
Mantovaara et al., Biotechnol Appl Biochem., vol. 11, pp. 564-570 (1989).
Zachariou et al., J Chromatogr, vol. 646, pp. 107-120 (1993).
Chaouk et al., J Biochem Biophys Methods, vol. 39 (3), pp. 161-177 (May 13, 1999).
Chaouk et al. IJBC, vol. 2 (3), pp. 153-190 (1997).
Hidaka et al., FEBS Letters, vol. 400, pp. 238-242 (1997).
Porath, J., Prot Expres Purif, vol. 3, pp. 263-281 (1992).
Oswald et al., Biotechnol Appl. Biochem., vol. 25, pp. 109-115 (1997).
Zachariou et al., Anal. Chem., vol. 69, pp. 813-822 (Mar. 1, 1997).
Wong et al., Separation and Purification Methods, vol. 4, pp. 49-57 (1991).

*Primary Examiner*—Elli Peselev
(74) *Attorney, Agent, or Firm*—Richard W. Bork

(57) ABSTRACT

A polymer substrate functionalized with a functionality comprising at least one cyclic, metal ion coordinating ligand group, the cyclic ligand group comprising at least 3 metal ion coordinating donor atoms independently selected from the group consisting of N, O and S.

22 Claims, 61 Drawing Sheets

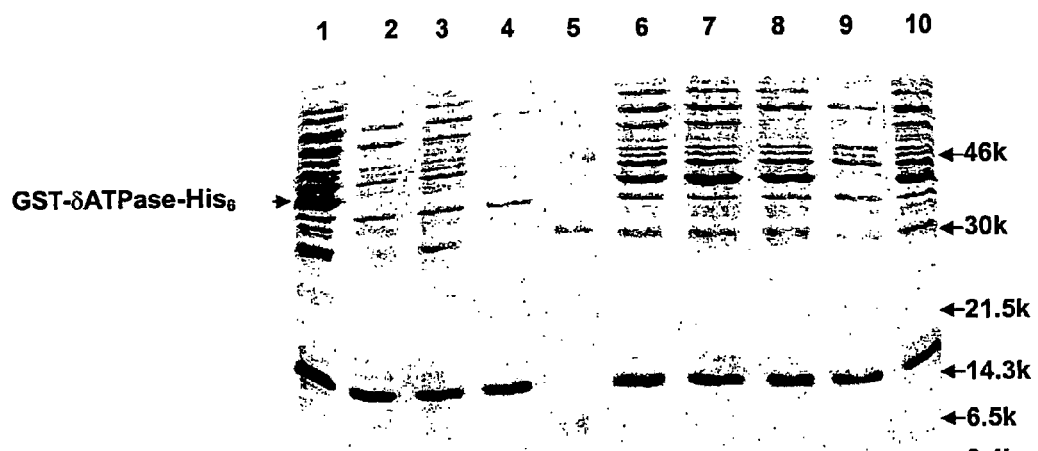
A
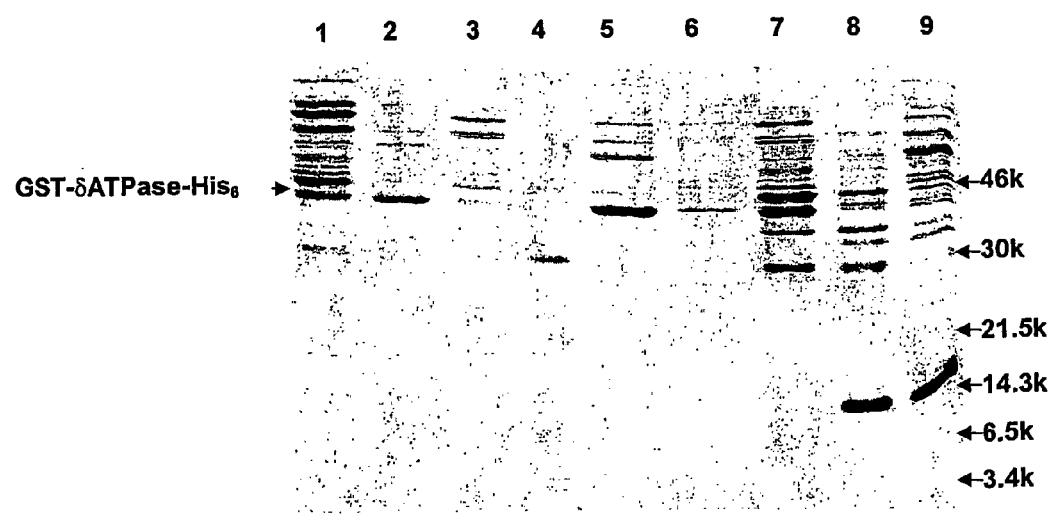
B
Fig. 16

Gel 1

Gel 3

Gel 5

Gel 8

Fig. 44 Gel 9

Gel 10

Gel 14

Gel 15

Gel 16

Fig. 60
A
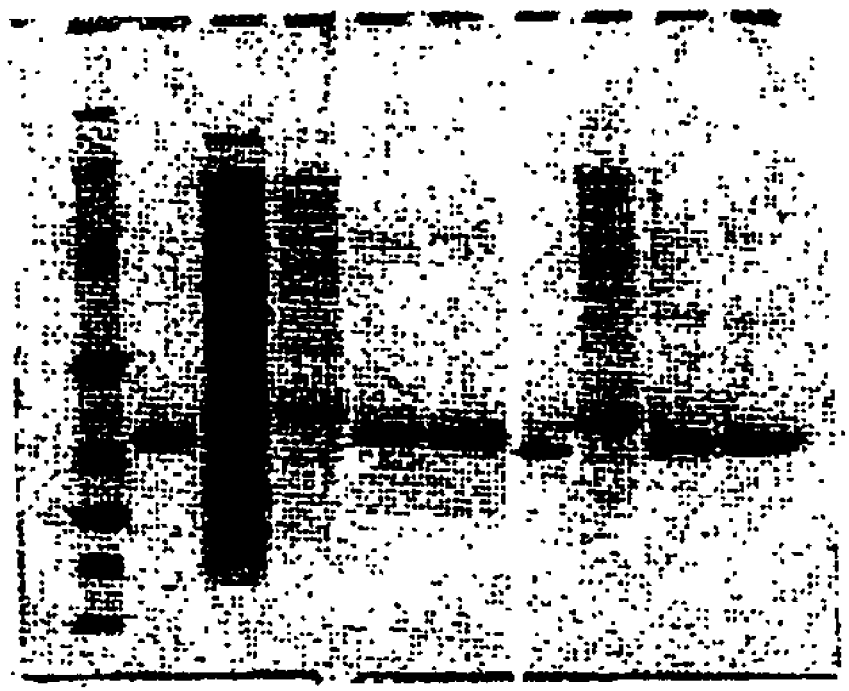
B
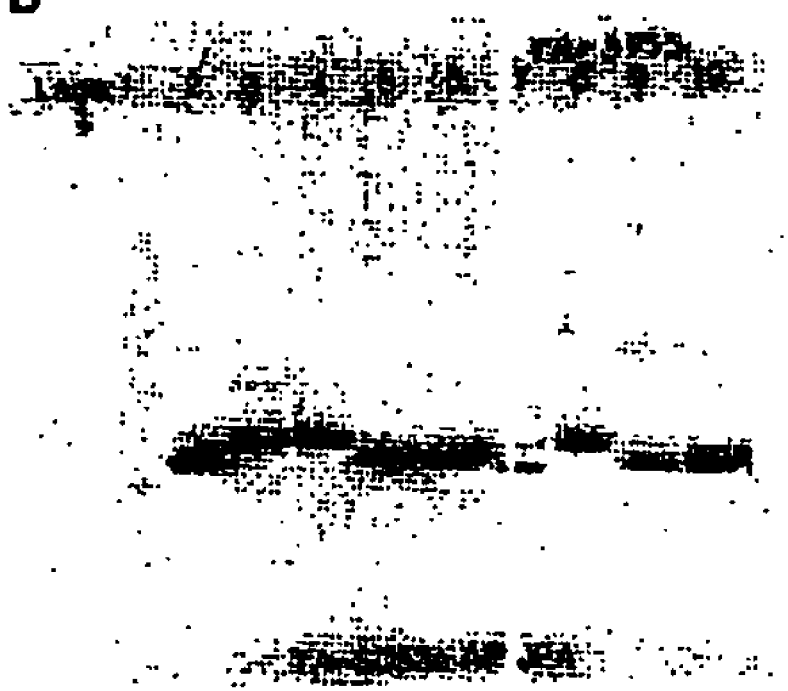

ic sorbent. In the pre-sent application, the terms "sorbent" and "adsorbent" are used primarily to denote a functionalized polymer substrate (polymer substrate with ligand immobilized thereto) with coordinatively bound metal ion(s), although these terms are also occasionally employed to denote a functionalised polymer substrate without metal ion(s) bound thereto.

PEPTIDE PURIFICATION BY MEANS OF METAL ION AFFINITY CHROMATOGRAPHY

CROSS-REFERENCE TO RELATED APPLICATIONS

This application is a 35 U.S.C. § 371 national stage application of International Patent Application PCT/DK02/00758 (published as WO 03/042249), filed Nov. 12, 2002, which claimed priority of Danish Patent Application PA 2001 01681 filed on Nov. 12, 2001; this application further claims priority under 35 U.S.C. § 119 of U.S. Provisional Application 60/333,650 filed Nov. 27, 2001.

FIELD OF THE INVENTION

The present invention relates, inter alia, to the field of isolation and purification of peptides, notably polypeptides, such as recombinant proteins, by means of immobilized metal ion affinity chromatography.

BACKGROUND OF THE INVENTION

An important aspect of the production of recombinant (genetically engineered) peptides, including oligo- and polypeptides, notably proteins, intended for therapeutic use in humans or animals is purification of the peptides in question to a sufficiently high level of purity, in particular such that the desired protein is essentially completely free of contamination with, in particular, (a) any extraneous proteins which may arise in the production process (typically a fermentation process or the like employing a selected or genetically modified strain of an appropriate microorganism) and (b) undesirable metal ions (notably heavy-metal ions) that may have been introduced in the course of the production process.

Immobilized metal ion affinity chromatography (IMAC) is a versatile separation procedure that exploits differences in the affinities exhibited by many biopolymers for metal ions. The technique involves the chelation of a suitable metal ion onto a solid support matrix whose surface has previously been chemically modified with a polydentate ligand. The resulting immobilized metal ion chelating complex then has the potential to coordinate with one or more electron donor groups resident on the surface of the interacting protein (Sulkowski, E., *Trends in Biotechnology*, 3 (1985) 1-6; Porath, J., Carlsson, I., Olsson, I. and Belfrage, G., *Nature*, 258 (1975) 598-599; Kagedal, L., in "*Protein Purification*" (Ed., J. C. Janson, and L. Ryden), VCH Publishers (1989) pp. 227-251; Zachariou, M. and Hearn, M. T. W., *Biochemistry*, 35 (1996) 202-211. Separation selectivity is then achieved on the basis of differences in the thermodynamic stabilities of the adsorbed protein/immobilized metal ion complexes. Proteins whose adsorption complexes are the least stable will be eluted first, whilst proteins that form more stable complexes will be eluted later. The greater the difference in the equilibrium association constants, i.e. the larger the differences in the dissociation constants ($K_D$) of the respective protein/immobilized metal ion coordination complexes, the higher the resolution obtained. Consequently, the amino acid composition, surface distribution of particular amino acid residues, as well as the conformation of the protein all play important roles in determining the affinity of a protein for a particular IMAC system. As a result, proteins with very similar properties with respect to charge, molecular size and amino acid composition, but with differences in their tertiary structures, may be resolved.

Most of the research interest into the use of IMAC over the past 20 years has revolved around the application of 1st row transition metal ions of borderline hardness (vide infra), such as $Cu^{2+}$, $Zn^{2+}$ and $Ni^{2+}$. These metal ions demonstrate intermediate metal ion stability constants, e.g. logo values between 5 and 10, for both aromatic and aliphatic amines, as well as for carboxylate functional groups (Wong, J. W., Albright, R. L. and Wang, N. H. L., *Separation and Purification Methods*, 20 (1991) 49-57; Zachariou, M., Traverso, I., Spiccia, L. and Hearn, M. T. W., *Journal of Physical Chemistry*, 100 (1996) 12680-12690). A number of unconstrained tridentate chelates that exhibit these binding properties with $M^{2+}$ ions can be chemically immobilized onto support materials. Despite their limitations with regard to the magnitude of the corresponding log β values and their resulting relatively low selectivity capabilities, unconstrained types of chelating compounds such as iminodiacetic acid (IDA) constitute the principle types of chelating ligand employed hitherto in such IMAC investigations [see, e.g., Kagedal, L., in "*Protein Purification*" (Eds. J. C. Janson and L. Ryden), VCH Publishers (1989) pp 227-251]. Applications illustrative of the use of immobilized $M^{2+}$-IDA-based IMAC systems include the purification of α-amylases from germinated wheat using immobilized $Cu^{2+}$-IDA [Zawistowska, U., Sangster, K., Zawistowski, J., Langstaff, J. and Friessen, A. D., *Cereal Chemistry*, 65 (1988) 5413-5418]; and purification of human clotting factor VII [Weeransinghe, K. M., Scully, M. F. and Kadder, V. V., *Biochimica Biophysica Acta*, 839 (1985) 57-65] and of $α_1$-thiol proteinases [Otsuka, S, and Yamanaka, T. (Eds), "Metalloproteins-Chemical Properties and Biological Effects" in "*Bioactive Molecules*", Kodansha Ltd, Tokyo (1988), pp 18-45] from human plasma using immobilized $Zn^{2+}$-IDA. An extension of the use of IDA-based IMAC procedures, viz. the purification of recombinant proteins using immobilized $Ni^{2+}$-nitrilotriacetic acid ($Ni^{2+}$-NTA) [Hochuli, E., Bannwarth, W., Döbeli, H. and Stuber, D., *Bio/Technology*, 6 (1988) 1321-1324] (NTA being a structural homologue of IDA), relies on the incorporation at the gene level of a polynucleotide sequence corresponding to a poly-histidine peptide, typically hexa-His, which confers on the protein a higher affinity for binding to immobilized $Ni^{2+}$-NTA chelating complex, thus enabling the protein to be selectively retained on this IMAC sorbent. In the pre-sent application, the terms "sorbent" and "adsorbent" are used primarily to denote a functionalized polymer substrate (polymer substrate with ligand immobilized thereto) with coordinatively bound metal ion(s), although these terms are also occasionally employed to denote a functionalised polymer substrate without metal ion(s) bound thereto.

As will be noted from the above description of applications of IDA- and NTA-based IMAC systems, an alternative means of altering protein binding selectivity with IMAC systems is through variation in the structure of the chelating ligate. In recent years however, only a handful of new IMAC chelating ligates have been introduced. These include systems based on the bidentate chelators aminohydroxamic acid (AHM) and 8-hydroxyquinoline (8-HQ) [Zachariou, M., Traverso, I., Spiccia, L. and Hearn, M. T. W., *Journal of Physical Chemistry*, 100 (1996) 12680-12690]; carboxymethylaspartic acid (CM-ASP) which has a higher affinity for $Ca^{2+}$ than IDA [Porath, J., *Trends in Analytical Chemistry*, 7 (1988), 254-256; Mantovaara, T., Pertofz, H. and Porath, J., *Biotechnology Applied Biochemistry*, 11 (1989), 564-569]; ortho-phosphoserine (OPS), which is able to chelate "hard" metal ions such as $Fe^{3+}$, $Al^{3+}$, $Ca^{2+}$ and $Yb^{3+}$ due to the participation of the phosphate group [Zachariou, M., Traverso, I. and Hearn, M. T. W., *Journal of Chromatography*, 646 (1993), 107-115];

and other tridentate ligates, such as (2-pyridylmethyl)aminoacetate (CPMA), dipicolylamine (DPA) and cis- or trans-carboxymethyl-proline [Chaouk, H., Middleton S., Jackson W. R. and Hearn, M. T. W., *International Journal of BioChromatography,* 2 (1997) 153-190; Chaouk, H. and Hearn, M. T. W., *Journal of Biochemical and Biophysical Research Methods,* 39 (1999) 161-177], tetradentate ligands, such as nitrilotriacetic acid (NTA) [Hochuli, E., Bannwarth, W., Dobeli, H., Gentz, R. and Stuber, D. *Bio/Technology,* 6 (1988) 1321-1325], which have higher affinities for $M^{2+}$ ions than IDA due to their quadridentate nature, exhibit lower protein binding association constants due to the loss of one coordination site compared to the IDA-type tridentate ligates; and pentadentate ligands, such as tetraethylenepentamine (TEPA) [Hidaka Y., Park, H. and Inouye, M., *FEBS Letters,* 400 (1997) 238-242] or N,N,N'-tris(carboxymethyl)ethylene-diamine (TED) [Porath, J., *Protein Expression & Purification,* 3 (1992) 263-281], which coordinate metal ions via five donor atoms (i.e. two nitrogen atoms of primary amine groups and three nitrogen atoms of secondary amine groups in the case of TEPA, and two nitrogen atoms of secondary amine groups and three oxygen atoms from the three carboxylic groups in the case of TED).

Significant leakage of metal ions has been observed with immobilized metal ion iminodiacetic acid chelate (im-$M^{n+}$-IDA) systems when using relatively mild elution conditions in the chromatographic process [Oswald, T., Hornbostel, G., Rinas, U. and Anspach, F. B., *Biotechnology Applied Biochemistry,* 25 (1997) 109-115; Kagedal, L. in *Protein Purification* (eds. J. C. Janson and L Ryden) VCH Publishers, New York (1989), pp 227-251]. Thus, in addition to the issue of selectivity modulation, an additional motivation for the development of new classes of chelating ligates has been a need for achieving significant increases in the metal ion stability constants compared to the IDA-based or NTA-based systems which have hitherto been employed [Zachariou, M., Traverso, I., Spiccia, L. and Hearn, M. T. W., *Analytical Chemistry,* 69 (1996) 813-822].

BRIEF DESCRIPTION OF THE INVENTION

It has surprisingly been found that the strength and/or selectivity of metal ion coordination binding of a desired protein in the form of a "fusion protein" which, in addition to the polypeptide chain of the protein of interest, comprises (as an extension of the amino acid sequence of the desired protein per se) a covalently bound oligopeptide chain (sometimes termed a "tag") incorporating one or more appropriately positioned amino acid residues capable of forming a coordination bond to a metal ion may be significantly increased by employing, as a matrix for the metal ion or metal ions to which binding of the fusion protein is to take place, a polymer substrate functionalized with a functionality comprising at least one cyclic, metal ion coordinating ligand group. The generally significantly greater strength and/or selectivity of binding of the fusion protein to such a matrix compared with that of the binding of extraneous proteins then facilitates separation and isolation of the fusion protein from a mixture which contains the fusion protein together with one or more extraneous proteins.

A first aspect of the invention thus provides a polymer substrate functionalized with a functionality comprising at least one cyclic, metal ion coordinating ligand group which comprises at least 3 metal ion coordinating donor atoms independently selected from N, O and S. A second aspect of the invention relates to a functionalized polymer substrate of the latter type, which further comprises a metal ion coordinated to at least one of the cyclic ligand groups in the functionality. Other aspects of the invention include methods for preparing such functionalized polymer substrates.

Further important aspects of the present invention relate to:

oligopeptides that are well suited for incorporation as "tags" in fusion proteins in the context of the pre-sent invention;

fusion proteins of the type in question, comprising a protein of interest fused at its amino terminus or carboxy terminus or both, or alternatively at a location within the internal amino acid sequence of the protein of interest, to at least one such oligopeptide;

polynucleotide constructs, e.g. vectors, encoding such fusion proteins;

host cells that comprise such a polynucleotide construct;

a method for producing a fusion protein of the type in question, wherein a host cell of the latter type is cultivated in a growth medium under conditions whereby the fusion protein is expressed, and whereby the fusion protein is recovered from the medium; and a method for purifying a protein of interest, wherein a protein sample containing such a fusion protein (comprising the protein of interest) as well as other proteins (extraneous proteins) is contacted with a metal ion-containing functionalized polymer substrate according to the invention.

DETAILED DESCRIPTION OF THE INVENTION

As already indicated above, a first aspect of the invention relates to a polymer substrate functionalized with a functionality comprising at least one cyclic, metal ion coordinating ligand group, the cyclic ligand group comprising at least 3 metal ion coordinating donor atoms independently selected from the group consisting of N, O and S. In general, at least one, preferably two, and more preferably all three of these metal ion coordinating donor atoms in the cyclic ligand group is a ring atom, i.e. forms part of the ring of the cyclic, metal ion coordinating ligand group.

Useful polymer substrates in the context of the invention include both water-soluble polymers and substantially water-insoluble polymers, and may be selected from a very wide range of polymeric materials. Examples hereof are the following:

Polysaccharides and derivatives thereof, including agaroses, dextrans, celluloses, hemicelluloses, starches, xylans and the like, and derivatives of these polysaccharides. Suitable polysaccharide derivatives will, in general, include derivatives in which some proportion of the hydroxy groups of the polysaccharide in question is derivatized to form ethers (e.g. lower alkyl ethers, such as methyl ethers) or esters (e.g. lower carboxylic acid esters, such as acetate, propionate and the like), as well as materials in which the starting polysaccharide or a derivative thereof has been cross-linked by treatment with an appropriate cross-linking reagent.

Generally speaking, functionalized polymer substrates of the invention based on substantially water-insoluble polymers are, for example, well suited for packing into chromatography columns, for direct introduction into a medium (batchwise use) and the like, and polysaccharides that are particularly well suited for this type of application in the context of the invention include agaroses, dextrans and derivatives thereof, a variety of suitable types of which are readily commercially available. Thus, for example, a variety of agarose products are produced by Amersham Pharmacia Biotech, Uppsala, Sweden, and marketed under the name Sepharose™; available grades include Sepharose™ 2B, 4B and 6B. Cross-linked derivatives of these various grades of agarose (prepared by cross linking of Sepharose™ with 2,3-dibromopropanol) are also available from the same company, and are marketed as Sepharose™ CL-2B, CL-4B and CL-6B, Sepharose™ 4 and 6 Fast Flow, Sepharose™ 6 MB, and Superose™ 6 and 12, respectively.

A number of dextran-based or dextran-agarose composite materials suitable for use in the context of the present invention are also available from Amersham Pharmacia Biotech under the names Sephadex™, Superdex™ (e.g. Superdex™ 30, 75 and 200) and Sephacryl™. Products in the Sephadex™ range are prepared by cross-linking dextran with epichlorohydrin and are available in the following grades: Sephadex™ G-10, G-15, G-25, G-50, G-75, G-100, G-150 and G-200, the degree of cross-linking decreasing with increasing G number. Products in the Sephacryl™ range are prepared by cross-linking allyl-dextran with N,N'-methylene-bisacrylamide, and include Sephacryl™ S-100, S-200, S-300, S-400, S-500 and S-1000; the latter six products differ with respect to their range of pore size and particle size distribution. Products in the Superdex™ range are prepared by cross-linking allyl-dextran with agarose derivatives of various compositions.

Polyalkylene glycols and derivatives thereof, including, in particular, polyethylene glycols (PEG), i.e. condensation polymers of ethylene glycol having the general formula $HOCH_2(CH_2OCH_2)_nCH_2OH$ or $H(OCH_2CH_2)_nOH$ and typically having average molecular weights in the range from 200 to 6000. A number of PEG's (including PEG's of average molecular weight 400, 600, 1500, 4000 and 6000, respectively) are available under various names (e.g. Macrogol™, PEG™, Carbowax™, Nycoline™, Pluracol E™, Poly-G™, Polyglycol E™, Solbase™) from a variety of commercial sources. PEG's are generally soluble in or miscible with water, as well as in ethanol and a number of other organic solvents, including aromatic hydrocarbons. The analogous polypropylene glycols [having the general formula $H(OC_3H_6)_nOH$], the lower molecular weight members of which are soluble in water, are also of relevance in the context of the invention. Relevant derivatives of such polyalkylene glycols include partially etherified derivatives, e.g. derivatives in which one of the terminal hydroxy groups has been converted to a lower alkyl ether group, such as a methyl ether group.

Such polymers can readily be immobilized to support materials, thereby producing substrates that can subsequently be activated and then functionalized or derivatized with macrocyclic metal ion binding chelating ligands by procedures according to the present invention.

Polyvinyl polymers, including polyvinyl alcohols—i.e. hydroxylic polymers normally produced by hydrolysis ("alcoholysis") of various molecular weight fractions of polyvinyl acetate, typically by base or acid hydrolysis—and derivatives thereof. The degree of "alcoholysis" may be varied by either allowing the hydrolysis of acetate ester groups in polyvinyl acetate to proceed to substantial completion, or by stopping it at a desired degree of alcoholysis. Polyvinyl alcohols are normally commercially available in four molecular weight ranges, viz. ca. 250,000-300,000 (termed super-high viscosity), ca. 170,000-ca. 220,000 (termed high-viscosity), ca. 120,000-150,000 (termed medium-viscosity) and ca. 25,000-ca. 35,000 (termed low-viscosity). In general, the lower the molecular weight of polyvinyl alcohols, the higher is their water sensitivity or ease of water solubility; however, the degree of alcoholysis also plays a role with regard to the water-solubility and other properties of polyvinyl alcohols. Polyvinyl alcohols within all of the above-outlined categories are or relevance in the context of the present invention, as are, for example, ether derivatives thereof, such as methyl ether derivatives.

Other polyvinyl polymer materials of interest include materials such as the Toyopearl™ HW range of porous, semi-rigid spherical gel particles designed for medium- and low-pressure liquid chromatography. Such materials, after activation and functionalization/derivatization, provide another option for the preparation of IMAC sorbents of relevance in the context of the invention. Toyopearl™ HW gels (obtainable from Tosoh Corp, Yamaguchi, Japan, and other suppliers) are synthesized from hydrophilic vinyl polymer containing exclusively C, H and O atoms. Available grades (differing with respect to particle and pore sizes) include Toyopearl™ HW-40, HW-40C, HW-40F, HW-40S, HW-50, HW-50F, HW-50S, HW-55, HW-55F, HW-55S, HW-65F, HW-65S and HW-75F.

Polyacrylamides and derivatives thereof, including composite materials based on polyacrylamide and agarose, such as Ultrogel™ AcA gels (composite polyacrylamide-agarose gel in bead form, available from, e.g., Amersham Pharmacia Biotech). The Ultrogel™ AcA gel range includes AcA 22, AcA 34, AcA 44 and AcA 54, where the number refers to the percentage of acrylamide and agarose, i.e., AcA 22 contains 2% acrylamide and 2% agarose. Activation of hydroxylic groups of these support materials provides an avenue to the preparation of IMAC sorbents.

Surface-modified silicas, including glycidylpropoxy-modified porous silica, such as LiChroSpher™ Diol (E. Merck, Darmstadt, Germany), Toyosoda™ TSKSW3000 (Tosoh Corp., Yamaguchi, Japan); aminopropyl-modified silica, prepared by reaction (in the presence of a suitable catalyst) of aminopropyldiethoxysilane with silicas of appropriate pore size and appropriate average diameter; and mercaptopropylsilicas, prepared by reaction (in the presence of a suitable catalyst) of mercaptopropyldiethoxysilane with silicas of appropriate pore sizes and appropriate average diameters. Alternatively, dextran modified or butadiene-vinyl copolymer modified silicas of appropriate pore sizes and appropriate average diameters can be employed as the chromatographic support materials. "Naked" porous silicas suitable for such derivatization and subsequent modification to generate the respective novel IMAC sorbents can readily be obtained from a variety of suppliers, including E. Merck, (Darmstadt, Germany), Tosoh Corporation, Yamaguchi, Japan), Eka-Nobel AB (Göteborg, Sweden) and Grace Davison GmbH (Worms, Germany).

Surface-modified metal oxides, including glycidylpropoxy-modified porous zirconias, titanias or aluminas, as well as modifications/variants thereof based on the respective metal oxide "doped" with a second metal oxide; amino-propyl-modified zirconia, titania or alumina, prepared by reaction (in the presence of a suitable catalyst) of aminopropyldiethoxysilane with the zirconia, titania or alumina of appropriate pore size and appropriate average diameter; and mercaptopropyl-modified zirconia, titania or alumina, prepared by reaction (in the presence of a suitable catalyst) of mercaptopropyldiethoxysilane with the zirconia, titania or alumina of appropriate pore size and appropriate average diameter. Alternatively, dextran modified or butadiene-vinyl copolymer modified zirconia, titania or alumina of appropriate pore sizes and average diameters can be employed as the chromatographic support materials. "Naked" porous zirconia, titania or alumina suitable for such derivatization and subsequent modification to generate the respective novel IMAC sorbents can readily be obtained from a variety of suppliers, including YMC Co. Ltd. (Kyoto, Japan), Grace GmbH (Worms, Germany) and BioSepra Corp. (Paris, France).

Well suited polymer substrates in the context of the invention include agaroses, dextrans and derivatives thereof, e.g. materials selected among those outlined above.

In one aspect of the invention, the cyclic, metal ion coordinating ligand group in a functionalized polymer substrate according to the invention is a heterocyclic group in which the at least 3 metal ion coordinating donor atoms are present in a ring having at least 6 ring atoms. Among such functionalized polymer substrates, particularly suitable types of heterocyclic groups appear to be groups derived from triazacycloalkanes having at least 6 ring atoms, and a preferred type of functionality (as defined above) in functionalized polymer substrates within this class is a functionality having the general formula (I):

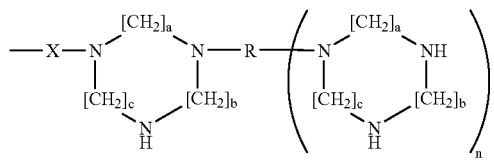

Formula (I)

wherein n is 0 or an integer from 1 to 3;

each of a, b and c in each triazacycloalkane ring, independently of each other and independently of any other triazacycloalkane ring, is an integer from 1 to 3;

one or both hydrogen atoms of each —CH$_2$— group in each triazacycloalkane ring, independently of each other and independently of any other triazacycloalkane ring, may optionally and independently be substituted with a substituent;

the hydrogen atom of each —NH— group in each triazacycloalkane ring, independently of each other and independently of any other triazacycloalkane ring, may optionally be substituted with a substituent;

when n is 0, R is H or a substituent;

when n is 1, i.e. such that the functionality comprises two triazacycloalkane rings, R is a bifunctional group which links (i.e. is covalently bonded to each of) the two triazacycloalkane rings, the bifunctional group optionally comprising one or more metal ion coordinating donor atoms;

when n is 2 or 3, i.e. such that the functionality comprises three or four triazacycloalkane rings, respectively, R is an (n+1)-functional group which links (i.e. is covalently bonded to each of) the three or four triazacycloalkane rings, respectively, the (n+1)-functional group optionally comprising one or more metal ion coordinating donor atoms; and X is a linker/spacer group.

In relation to this latter aspect of the invention, the above-mentioned optional substituent substituting a hydrogen atom in a ring —CH$_2$— group and/or a ring —NH— group in a functionality of Formula (I) as defined above is suitably selected among optionally substituted lower alkyl groups and optionally substituted aryl groups; further examples of optional substituents appropriate for substituting a hydrogen atom in, in particular, a ring —CH$_2$— group in a functionality of Formula (I) as defined above include optionally substituted lower alkoxy groups. The optional substituent(s) on the lower alkyl group, lower alkoxy group or aryl group in question may optionally comprise one or more metal ion coordinating donor atoms, in particular one or more N, O or S donor atoms.

In the case of lower alkyl groups (methyl, ethyl, propyl, etc.) as optional substituents replacing the hydrogen atom of one or more ring —NH— groups, O-containing substituents thereon of possible relevance with respect to the metal ion coordinating properties of the functionality with respect to certain metal ions [notably "hard" metal ions or metal ions of "borderline hardness" (vide infra), such as $Ca^{2+}$, $Mg^{2+}$, $Fe^{3+}$ or $Zn^{2+}$] include carboxy/carboxylate (—COOH/—COO$^-$, depending on pH), and examples of such substituents on a ring N atom are thus carboxy-substituted lower alkyl groups, in particular carboxymethyl (—CH$_2$COOH) (more particularly the corresponding deprotonated form, i.e. —CH$_2$COO$^-$). Similarly, relevant N-containing groups which may be present as substituents on lower alkyl groups attached to one or more ring N atoms include amino-substituted lower alkyl groups, in particular 2-aminoethyl (—CH$_2$CH$_2$NH$_2$) or 3-aminopropyl (—CH$_2$CH$_2$CH$_2$NH$_2$).

Other relevant types of optional substituents which may be present as substituents replacing the hydrogen atom on one or ring N atoms, and which themselves may be of relevance to the metal ion coordinating properties of the functionality with respect to certain metal ions [notably "hard" metal ions or metal ions of "borderline hardness" (vide infra), such as $Ca^{2+}$, $Mg^{2+}$, $Fe^{3+}$ or $Zn^{2+}$], include —PO$_3$H$_2$, (or a deprotonated form thereof, e.g. —PO$_3$H$^-$).

The term "lower alkyl group" as employed in the context of the present invention in intended to designate any linear (straight-chain), branched or cyclic alkyl group having from 1 to 6 carbon atoms. Examples of linear alkyl groups are methyl, ethyl, propyl, butyl, pentyl and hexyl; examples of branched alkyl groups are isopropyl, sec-butyl, tert-butyl, isopentyl and isohexyl; examples of cyclic alkyl groups are cyclopropyl, cyclobutyl, cyclopentyl and cyclohexyl. In general, lower alkyl groups having from 1 to 3 carbon atoms will be well suited in the context of the invention.

The term "lower alkoxy group" as employed in the context of the present invention in intended to designate any linear, branched or cyclic alkoxy group having from 1 to 6 carbon atoms. Examples of linear alkoxy groups are methoxy, ethoxy, propoxy, butoxy, pentoxy and hexoxy; examples of branched alkoxy groups are isopropoxy, sec-butoxy, tert-butoxy, isopentoxy and isohexoxy; examples of cyclic alkoxy groups are cyclopropyloxy, cyclobutyloxy, cyclopentyloxy and cyclohexyloxy. In general, lower alkoxy groups having from 1 to 3 carbon atoms will be well suited in the context of the invention.

In the present context, the term "aryl" is intended to designate any aromatic group and includes both carbocyclic and heterocyclic aromatic groups. Examples thereof are phenyl, naphthyl, pyridyl, tetrazolyl, thiazolyl, imidazolyl, indolyl, quinolinyl, pyrimidinyl, thiadiazolyl, pyrazolyl, oxazolyl, isoxazolyl, thienyl, furanyl or oxadiazolyl. Suitable optional substituents on aryl groups in the context of the invention include halogen, amino, hydroxy, lower alkyl and lower alkoxy.

The term "halogen" designates F, Cl, Br or I.

Substituents which are of relevance as optional substituents on a ring —CH$_2$— group and/or on a ring —NH— group in a functionality of Formula (I) as defined above thus include heterocyclic aromatic groups, comprising one or more N, O or S atoms in the heterocyclic ring. In addition hereto, further substituents which are relevant as optional substituents on a ring —CH$_2$— group and/or on a ring —NH— group in a functionality of Formula (I) as defined above include saturated heterocyclic groups comprising one or more N, O or S atoms in the heterocyclic ring; N-heterocyclic groups will often be well suited. Examples of saturated heterocyclic groups that are relevant in this context include 2-aziridyl, 2- and 3-azetidyl, 2- and 3-pyrrolidyl, 2-, 3- and 4-piperidyl and the like. One or more substituents, e.g. lower alkyl, lower alkoxy or halogen as defined above, may optionally be present in such saturated heterocyclic groups.

The term "metal ion coordinating donor atom" as employed in the present context denotes an atom, notably an N, O or S atom, which is capable—as present in the group/substituent in which it occurs of forming a coordinative bond (complex bond, donor bond) to a metal ion which is of relevance in the context of the present invention. Metal ions of particular interest in the present context are "hard", "soft" and "borderline" metal ions (a number of transition metal ions and certain non-transition metal ions) as defined herein (vide infra).

The linker or spacer group X in a functionality of Formula (I) as defined above may be any suitable type of linker or spacer, but will typically be one which may be derived from a bifunctional organic compound (e.g. an organic compound having at least two reactive functional groups selected from groups such as carboxyl, thiol, aminopropyl, halogen and epoxy) by reaction with, on the one hand, an appropriate reactive functionality on the polymer substrate and, on the other hand, an appropriate reactive functionality—typically an amino or substituted amino group—on a cyclic, metal ion coordinating ligand group. A type of linker or spacer group X which is generally very useful in the context of the present invention is one which can be derived from epichlorohydrin by reaction of the halogen end thereof with, e.g., an hydroxy group on the surface of the polymer substrate in question and then reaction of the epoxy group thereof with an amino or substituted amino group in a cyclic ligand group. This is illustrated schematically in Scheme 8 in Example 122 herein (vide infra).

In very versatile aspects of the invention, the polymer substrate in a functionalized polymer substrate of the invention is an agarose or agarose derivative (e.g. a Sepharose™ gel), and the metal ion coordinating functionality is of the type illustrated by Formula (I), above, comprising from 1 to 4 triazacycloalkane rings (i.e. n is 0, 1, 2 or 3), such as a functionality comprising 1, 2 or 3 triazacycloalkane rings. Each such triazacycloalkane ring may very suitably be a 1,4,7-triazacyclonon-1-yl group [i.e. deriving from 1,4,7-triazacyclononane (tacn)], i.e. one in which the parameters a, b and c [see Formula (I)] each have a value of 2.

When the functionality contains only one such ring (i.e. n=0) the group R is appropriately hydrogen, and when it contains two such rings (i.e. n=1), R is very suitably chosen among the following:

—[CH$_2$]$_m$—, wherein m is 2, 3 or 4,

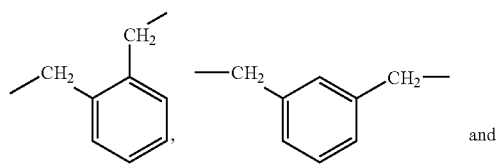

and

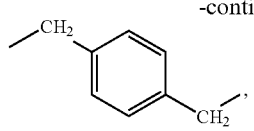

and substituted derivatives thereof; relevant optional substituents include those already mentioned above.

When the functionality in question contains three such rings (i.e. n=2), R is suitably a group of the type:

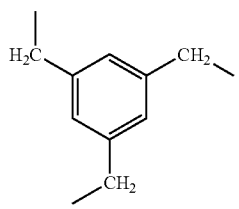

or a substituted derivative thereof; again, relevant optional substituents include those already mentioned above.

When the functionality in question contains four such rings (i.e. n=3), R is suitably a group of the type:

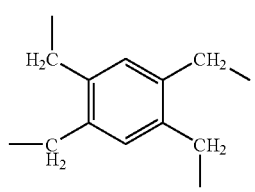

or a substituted derivative thereof; once again, relevant optional substituents include those already mentioned above.

The linker or spacer group X is very suitably a group derivable from epichlorohydrin by reaction thereof with the polymer substrate in the form of an agarose or agarose derivative, and subsequent reaction of the resulting product with a ring —NH— group of that triazacycloalkane ring which becomes bound to X.

As is apparent from the disclosure herein, an important feature of the materials (functionalized polymer substrates) employed according to the invention to isolate and purify a desired protein (protein of interest) is the presence, in the material, of a metal ion which itself is bound coordinatively to a cyclic ligand group (e.g. a triazacycloalkyl group such as a 1,4,7-triazacyclonon-1-yl group) in the functionality, and which in turn is capable of binding coordinatively, and suitably selectively, to donor atoms in the amino acid residues of the oligopeptide "tag" part of a fusion protein in which the oligopeptide "tag" is attached to the amino acid sequence of the protein of interest. A further aspect of the invention thus relates to a functionalized polymer substrate as described above, in which at least one of the cyclic ligand groups in the functionality has a metal ion coordinated thereto. In general, divalent (2+-charged) and trivalent (3+-charged) metal ions (including both non-transition metal ions and transition metal ions), such as metal ions chosen among $Ca^{2+}$, $Mg^{2+}$, $Cu^{2+}$, $Zn^{2+}$, $Ni^{2+}$, $Mn^{2+}$, $Co^{2+}$, $Fe^{3+}$, $Al^{3+}$ and $Cr^{3+}$, are well suited in this context. As documented by working examples provided herein (vide infra), $Cu^{2+}$ has been found to be a particularly versatile metal ion in this connection.

As already indicated briefly, a further aspect of the invention relates to a process for preparing a functionalized polymer substrate according to the invention, the process comprising the steps of:

selecting a polymer substrate having a reactive functional group capable of undergoing a first reaction with a first functional group of a bifunctional reagent having a first and a second functional group; the first reaction in question resulting in covalent bond formation between the polymer substrate and the bifunctional reagent; the second functional group of the resulting covalently bound reagent being subsequently capable of undergoing a second reaction with a reactive functional group present in a species comprising a cyclic, metal ion coordinating ligand group which comprises at least 3 metal ion coordinating donor atoms independently chosen among N, O and S; and the second reaction resulting in covalent bond formation between the species in question and the covalently bound reagent;

reacting the polymer substrate with the bifunctional reagent; and reacting the resulting covalently bound reagent with the species in question.

In relation to the latter process according to the invention, the polymer substrate employed, and the cyclic, metal ion coordinating ligand group in the reactive species employed in the process, may be chosen among those already discussed above in connection with functionalized polymer substrates according to the invention. The bifunctional reagent employed will typically be a bifunctional organic compound, e.g. an organic compound having at least two reactive functional groups chosen among groups such as carboxyl, thiol, aminopropyl, halogen and epoxy. Epichlorohydrin is particularly useful as a bifunctional reagent for a number of types of polymer substrate, including polysaccharides and derivatives thereof having surface hydroxyl groups.

As will be apparent from the discussion above in relation to functionalized polymer substrates according to the invention, the reactive species containing the cyclic, metal ion coordinating ligand group will suitably be one which gives rise to a functionality (in the resulting functionalized polymer substrate product) of the type shown in Formula (I), above. Appropriate reactive species for use in the process of the invention will then include species of the general Formula (II), below:

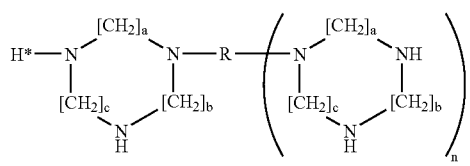

Formula (II)

The magnitude of the parameters n, a, b and c, and the nature of the group R, may then correspondingly be as already discussed above in relation to functionalized polymer substrates according to the invention. Moreover, one or both hydrogen atoms of each —$CH_2$— group in each triazacycloalkane ring, independently of each other and independently of any other triazacycloalkane ring, may optionally and independently be substituted with a substituent, the optional substituent optionally comprising one or more metal ion coordinating donor atoms (typically N, O or S). In addition, the hydrogen atom of each —NH— group in each triazacycloalkane ring, with the exception of H*, independently of each other and independently of any other triazacycloalkane ring, may optionally be substituted with a substituent, said optional substituent optionally comprising one or more metal ion coordinating donor atoms. Optional substituents in the present context may likewise suitably be chosen among those already mentioned above in relation to functionalities of Formula (I).

As will also be apparent from the foregoing discussion, agaroses and agarose derivatives (such as Sepharose™ products as described above) are well suited as polymer substrates in the context of the above-described process according to the invention, particularly in combination with a species of Formula (II). A well-suited bifunctional reagent will then be epichlorohydrin, and it may be advantageous in this connection to further incorporate a reducing agent, such as sodium borohydride, in the reaction mixture when reacting the polymer substrate with epichlorhydrin.

The scope of the present invention further encompasses functionalized polymer substrates obtained or obtainable by a process as described above for preparing a functionalized polymer substrate.

In addition, the scope of the present invention also encompasses a process for preparing a functionalized polymer substrate which is in accordance with the invention, and which further comprises a metal ion coordinated to at least one of the cyclic, metal ion coordinating groups therein, the process comprising contacting a functionalized polymer substrate according to the invention with an aqueous solution of an inorganic salt [e.g. a nitrate, halide (fluoride, chloride, bromide or iodide), sulfate, perchlorate, tetrafluoroborate, hexafluorophosphate or phosphate salt] or organic salt [e.g. a carboxylate (such as formate, acetate, propanoate or benzoate), tetraphenylborate or sulphonate salt] of the metal ion in question (e.g. one of the metal ions already mentioned above). A metal ion-containing functionalized polymer substrate obtained or obtainable by such a process is also within the scope of the pre-sent invention.

Criteria for Selection of Macrocyclic, Metal Ion Coordinating Ligands in Functionalized Polymer Substrates According to the Invention, and Criteria Concerning the Location, Structure and Characteristics of Preferred Peptide Tags A: Criteria for selection of macrocyclic, metal ion coordinating ligands: As already indicated, above, a very important and valuable application of functionalized polymer substrates as defined in the context of the present invention is the use of a metal ion containing embodiment thereof in the purification of a protein, the protein in question being in the form of a fusion protein wherein the protein of interest is fused at its amino or carboxy terminus to an oligopeptide "tag", notably a histidine-containing oligopeptide according to the invention. In addition, the simultaneous fusion of two molecules of a protein or polypeptide of interest, or alternatively two different proteins or polypeptides of interest attached at their amino- or carboxy-terminus, respectively, to an oligopeptide "tag", notably a histidine-containing oligopeptide according to the invention, generates a new fusion protein structure whereby the oligopeptide "tag" is located at an endo-position (i.e. an internal position) linking the two molecules of the protein(s) or polypeptide(s) of interest. On the basis of the results obtained in the investigations performed by the inventors in relation to the present invention, the inventors believe—without being bound or limited by any particular theory—that the phenomena underlying this aspect of the invention may suitably be regarded as a "molecular cassette" permitting molecular interactions between the metal ion/ligand complex and the complementary oligopeptide sequence present within the fusion protein as a N-terminal, C-terminal or endo-positioned oligopeptide "tag", and dictated by the molecular dimensions and facial orientation of the metal ion/ligand complex and its cognate binding counterpart within the peptide sequence of the "tag". Thus, it appears that the key attributes and advantages of the chelating, metal ion binding ligand systems in functionalized polymer substrates of the invention relative to all previously described chelating systems for the capture of recombinant proteins via an introduced peptide "tag" can be related at least to the following non-exclusive list of features:

(a) The chelating ligand systems of the present invention have very much higher stability constants (i.e. metal ion binding constants) than are achievable with systems based on iminodiacetic acid (IDA), nitrilotriacetic acid (NTA) and like ligands; as a result, adverse/undesirable effects due to buffer-induced or protein-stripping metal ion leakage are greatly reduced.

(b) The coordination geometry of the metal ion containing complex in metal ion containing functionalized polymer substrates of the invention is different from that observed with, e.g., IDA or NTA chelating ligands. Thus, for metal ions (M) of charge n+, coordination geometries of $M^{n+}$-IDA or $M^{n+}$-NTA for n=2 are often octahedral (see Scheme 1, below).

Scheme 1. Illustrative octahedral arrangement of the coordination structure of an $M^{n+}$ complex with a conventional IDA- or NTA-type chelating ligand, in which the ligand occupies a face on the coordination octahedron. A further arrangement of the ligand in which the two oxygen donor atoms from the carboxylate groups are located opposite to each other (i.e. in the trans arrangement) is also possible.

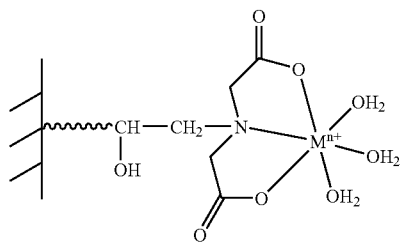

Coordination geometries corresponding to distorted trigonal bipyramidal or square pyramidal can, however, also arise. This means that the IDA- or NTA-type chelating ligand systems can behave as unconstrained chelating systems, with the consequence that the selectivity that can be achieved is limited and unpredictable. In may also be mentioned that with such chelating ligand systems, $Cu^{2+}$ favours a 5- or 6-coordination geometry, whilst $Ni^{2+}$ adopts predominately 6-coordinated structures. In contrast, the coordination geometry adopted with, for example, the $M^{n+}$-tacn, $M^{n+}$-dtne/-dtnp ligand systems and, for example, the bis-, tris- and tetrakis (tacn) ligand systems [whose preparation and use is described in the Experimental Section (vide infra) and which are very useful ligand systems in the context of the invention] with, e.g., $Cu^{2+}$ is primarily square pyramidal with all of the metal ion coordinating donor atoms on the ligand in the same plane and occupying a triangular face of the coordination polyhedron. With other macrocyclic ligands, e.g. ligands with 2 nitrogen donor atoms and 1 oxygen donor atom (N2O), ligands with 2 nitrogen donor atoms and 1 sulfur donor atom (N12), and ligands with 1 nitrogen donor atom and 2 sulfur donor atoms (NS2), similar "triangular" geometries are obtained. In addition, similar geometries are adopted by the bis(tacn) (N6), tris(tacn) (N9) and tetrakis(tacn) (N12) ligand systems. As a consequence, the cyclic or macrocyclic ligand systems employed in the present invention result in constrained and predictable coordination structures which are very well suited for use in novel, Immobilized Metal Ion Affinity Chromatography (IMAC) systems, and depending on the nature of the metal ion, solvation/buffer components which can interact with the metal ion, or even on the nature and orientation of the amino acid residue within the sequence of a peptide, a rationale can be given for selection of preferred peptide (oligopeptide) "tag" structures.

One of the guiding principles in the design and selection of oligopeptide "tag" sequences for use in the context of the invention was thus that practically all of these tacn-, bis (tacn)-, tris(tacn)- and tetrakis(tacn)-derived metal ion/macrocyclic ligand complexes and their structurally related analogues and derivatives have a triangular geometry for the coordination site, i.e. when coordinated to metal ions, practically all of these macrocyclic ligands occupy a triangular face on the coordination polyhedra of the metal ion. This notable characteristic has been factored into the invention and exploited to achieve higher specificities/selectivities for binding to the oligopeptide "tags" (or for that matter to amino acid residues in the peptide sequence of the protein of interest) than has hitherto been feasible. Once having been recognized by the inventors, this structural rationale was thus an important principle in the development of the invention disclosed herein. This fundamental difference between the cyclic or macrocyclic ligand systems of the present invention and previously employed ligand systems with respect to the arrangement of the coordination bonds means that in the case of the cyclic/macrocyclic ligand complexes the metal ion is positioned on a "puckered" face of the macrocyclic ligand, leading to an uni-directional approach and orientation for an incoming oligopeptide "tag" of a "tagged" protein (fusion protein). Examples of such important differences in structural organisation can be illustrated by comparing the arrangement shown as Scheme 2 below (which illustrates the orientational arrangement of an incoming imidazoyl group of a histidine residue relative to an immobilized, $M^{n+}$-containing N-carboxymethylated tacn ligand) with the previously used IDA or NTA system.

Scheme 2. "Puckered" orientational arrangement of an octahedrally cooridinated $M^{n+}$ ion with an N-carboxymethylated tacn chelating ligand, indicating the approach orientation for a imidazoyl group of an incoming His residue (acting in this case as an N-donor).

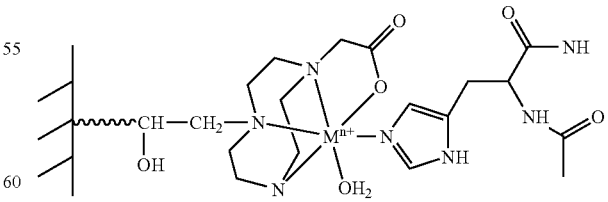

This N-carboxymethylated tacn example highlights further possibilities for controlling the number of sites available to the incoming oligopeptide "tag" and also for tuning the overall charge on the immobilized metal complex, thereby providing additional opportunities for controlling binding interactions. Analogous structures can be generated for the other monocyclic tridentate macrocycles that form part of the present invention, which further highlights the fact that appropriate combination of ligand design and metal ion enables control over binding interactions with the incoming oligopeptide "tag". Moreover, analogous tacn-, bis(tacn)-, tris(tacn)- and tetrakis(tacn)-derived metal ion/macrocyclic ligand complexes and their structurally related analogues and derivatives bearing pendant binding moieties, such as carboxymethyl, aminoethyl, aminopropyl, etc., can also be employed in the case of mononucleated macrocyclic ligands where two metal coordination sites are utilised to form aquo-hydrated or hydrolytic complexes. For example, Scheme 3 shows the orientational array for an (immobilized) di-copper (II) complex of an o-xylenyl-bridged bis(tacn)-type ligand illustrating the additional possibility of binding interaction between the π-electron systems of the phenyl ring (in the o-xylenyl bridge) and the imidazolyl ring (as present in a histidine residue) of an oligopeptide "tag" or fusion protein. Further introduction of a pendant structure (chemically attached to one or more of the secondary amino groups), such as an N-carboxymethyl, N-aminoethyl, N-aminopropyl etc. moiety, will provide additional structural analogues that can undergo metal ion chelation, depending on the charge state of the pendant arm.

Scheme 3. Orientational array for a $Cu^{2+}$-containing α,α'-bis (1,4,7-triazacyclononanyl)-ortho-xylene chelating ligand showing the notable feature in this case of π → π interaction between the imidazoyl group and the orthodisubstituted phenyl ring in the chelating ligand. NOTE: these bis-systems provide the possibility for two donor groups from differentially displayed surface accessible amino acid residues within the target protein of interest to simultaneously interact with the ligand. Alternatively, these residues can be present as part of the structure of the amino acid sequence of the tag. This was one of the considerations underlying the design and selection of preferred amino acid sequences for specific oligopeptide tags which consitute an aspect of the present invention.

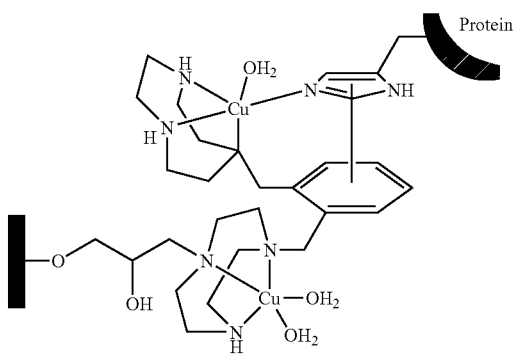

In the case of the bis-systems the issue of whether the complex exists in the "open" form (as illustrated in Scheme 3) or in the "sandwich" form (see Scheme 6) as found for some $Ni^{2+}$ systems needs also to be taken into account. These very special features of macrocyclic ligands of the types in question—particularly the bis-, tris- and tetrakis-type ligands—lead to considerable flexibility in terms of (a) the geometry of approach for an incoming oligopeptide "tag" (or for that matter a surface-accessible amino acid residues of the protein of interest per se); (b) the influence of pH, (c) the selectivity with respect to binding to oligopeptide "tags" having different, preferred amino acid sequences in terms of the interplay of O- and/or N-donor effects, (d) the consequences of highly specific buffer ion interactions and the number of macrocyclic ring units involved. All of the latter characteristics contribute to the inventiveness and significance of the present novel invention, and have to our knowledge not been demonstrated for previous IMAC systems for use with oligopeptide "tag" fusion proteins.

(c) With all of the 2+- and 3+-charged metal ions investigated to date, viz. $Cu^{2+}$, $Ni^{2+}$, $Zn^{2+}$, $Ca^{2+}$, $Mn^{2+}$, $Cr^{3+}$ and $Fe^{3+}$, our studies regarding selection of elution conditions (see the Experimental Section) have shown conclusively that when available, coordination bonding (electron donation) between metal ion binding donor groups on the incoming protein (i.e. on the oligopeptide "tag" and/or on the protein per se) and fillable coordination sites on the metal ion (e.g. coordination sites initially occupied by a readily displaceable water molecule, halide ion or the like) in the immobilized metal ion/macrocyclic ligand complex is the dominant binding mechanism, despite the fact that the metal ion/macrocyclic ligand complex formally carries a fractional positive charge (although the complex is overall electroneutral). This is apparent from the fact that desorption of bound protein requires highly selective elution buffer conditions. By comparison with, for example, the previously employed IDA- or NTA-based IMAC systems, much more selective elution conditions can be employed, which is indicative of different (higher) binding affinities, with interactions mediated via co-operative binding effects involving more than one amino acid residue within the structure of the oligopeptide "tag". Thus, it was very surprising to observe much more favourable elution behaviour in terms of ionic strength dependency and pH dependency compared to previously employed, unconstrained IDA- or NTA-type chelating ligands. As noted in the caption to Scheme 3, with the bis-systems (and also the tris- and tetrakis-systems) there is the possibility of simultaneous interaction of two (or more) donor groups from two (or more) differentially displayed surface-accessible amino acid residues within a protein with the present class of IMAC ligands. However, to achieve optimal interaction, the provision of suitable amino acid residues spaced appropriately within the sequence of the oligopeptide "tag" is the preferred option, since in this case amino acid sequences resulting in a desired range of affinities can be fine-tuned for the respective interaction between the chelated metal ion and the specific oligopeptide "tag" in question. Exploitation of this concept of orientationally spaced donor groups within the side-chains of the amino acid residues of the oligopeptide "tag" has been one of the considerations underlying the design and selection of preferred amino acid sequence patterns for the specific oliogpeptide "tags" which constitute an aspect of the present invention (see also sections B and D, below)

For convenience and simplicity of presentation this approach can be considered to form a molecular cassette system, whereby both the immobilized metal ion/ligand system and the tailored amino acid sequence properties of the oligopeptide "tag" form a "molecular tweezers" system with the binding sites within the immobilized metal ion/ligand system spaced at the correct atomic distances to enable correct recognition of the cognate sequence within the oligopeptide "tag".

(d) As a result of the adoption of a facially orientated "puckered" triangular coordination structure, which has proved to be a characteristic feature for $M^{n+}$ ions when bound to the present type of chelating macrocyclic ligand, different hydrolytic behaviour to that seen with IDA- or NTA-type chelating ligands with metal ions of borderline "hardness", e.g. $Cu^{2+}$, or with "hard" metal ions, e.g. $Fe^{3+}$, is exhibited by macrocyclic complexes of the present type. It should be noted here that the meaning of the terms "hard", "hardness" and "soft" as employed in the present specification in relation to metal ions is that according to R. G. Pearson (see, e.g., S. F. A. Kettle, *Coordination Chemistry*, Thomas Nelson and Sons Ltd., 1969, pp. 48-49). At one end of the scale, "hard" metal ions are those which parallel the proton with respect to their attachment to ligands, are small, are often of high charge, and which lack valence shell electrons which are easily distorted or removed; hard metal ions include, e.g., $Ca^{2+}$, $Mg^{2+}$, $Mn^{2+}$, $Cr^{3+}$ and $Fe^{3+}$. At the other end of the scale, "soft" metal ions are large, of low charge or have valence shell electrons which are easily distorted or removed; soft metal ions include, e.g., $Cu^+$, $Ag^+$ and $Cd^{2+}$. Metal ions whose properties place them on the borderline between hard and soft—i.e. are of borderline hardness—include, e.g., $Zn^{2+}$, $Fe^{2+}$, $Co^{2+}$, $Ni^{2+}$ and $Cu^{2+}$.

This means that the pH- and salt-dependencies of the present IMAC systems are different from those of the systems employed previously, and that the influence of the presence of any organic solvent(s), e.g. ethanol or acetonitrile, in the loading or elution buffers is also different. Moreover, the types of coordination geometries that the present IMAC systems can adopt are different from those found for the less constrained IDA- or NTA-type IMAC systems. These features are illustrated for examples of open-structure binuclear bis(tacn) ligand complexes of $Cu^{2+}$ and $Ni^{2+}$ in Scheme 4, for mononuclear non-sandwich structures for $Cu^{2+}$ and $Ni^{2+}$ in Scheme 5, and for mononuclear $Cu^{2+}$ and $Ni^{2+}$ sandwich complexes of tacn and bis(tacn) ligands in Scheme 6.

Scheme 4. Binuclear copper(II) and nickel(II) bis(tacn) complexes in the non-sandwich form

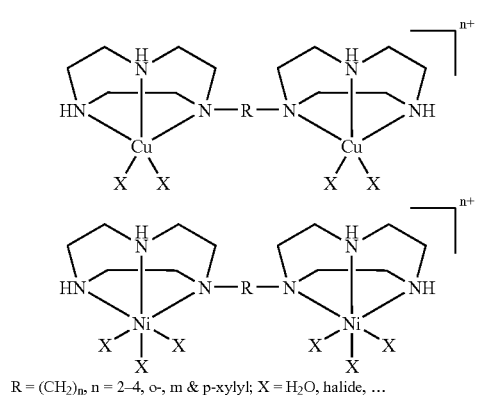

$R = (CH_2)_n$, $n = 2-4$, o-, m & p-xylyl; $X = H_2O$, halide, ...

Scheme 5. Mononuclear copper(II) and nickel(II) non-sandwich complexes of tacn and bis(tacn) ligands

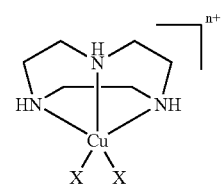

-continued

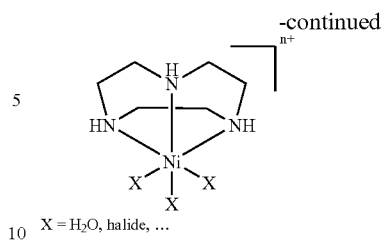

$X = H_2O$, halide, ...

Scheme 6. Mononuclear copper(II) and nickel(II) tacn and bis(tacn) sandwich complexes

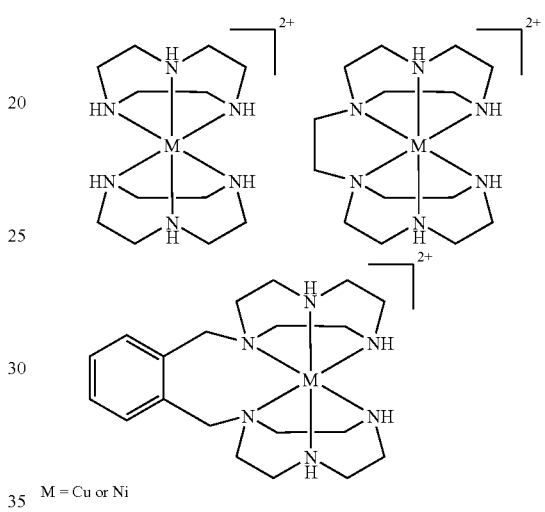

M = Cu or Ni

Several features of relevance to the present invention may be noted. Firstly, the coordination geometries of the present immobilized chelating macrocyclic ligands result in different patterns of steri-electronic effects, and this leads to different affinity regimes in terms of metal ion binding constants. Secondly, as is apparent from Schemes 4-6, the immobilization of metal ion chelating complexes for the mononuclear and binuclear open structure, the non-sandwich and the sandwich structures result in adsorbents of fundamentally different properties, with the molecular recognition balance shifting from a purely coordination-type interaction to a purely anion-exchange-type interaction, depending—in particular—on the nature of the metal ion, the chemical structure of the chelating ligand, the steric and conformational properties of the bridging group R in the bis-(as well as the tris- and tetrakis-) structures, and the solvent composition. It should be noted that control over the formation of the sandwich and non-sandwich structures can be achieved by functionalization of the macrocycles at a secondary amine group with non-coordinating groups. All of these features will impact on the ability of these IMAC systems to recognise with high affinity the sequence attributes of the oligopeptide "tags". In fact, the characteristics of the bridging group R dictate several key aspects of these new IMAC systems, including the molecular distance between the metal ion binding centres, the facial access of the coordination sites for interaction between the metal ion binding centres, the facial accessibility of the coordination sites for interaction with specific amino acid residues in the oligopeptide "tag" sequence, the polarisability and solvational potential of these centers, and the respective binding energies, and thus affinities, for these interactions (e) Many of the immobilized metal ion/macrocycle complexes are coloured, the features of their ultraviolet-visible absorption spectra being characteristic for the particular coordinated metal ion; hence, protein-binding phenomena as well as the general state/condition of packed columns containing the immobilized adsorbent can better be visualised.

(f) An attractive feature of family sets of the present macrocyclic ligands is their "combinatorial" relatedness in terms of routes to their synthesis, as well in terms of their binding (functional) properties. These characteristics result in the availability of a range of different selectivities that can be generated on the basis of essentially the same types of systems and chemistries. This type of synthetic opportunity is not available with known IDA- and NTA-type systems and the like.

(g) As a result of the different pH dependencies manifested by the various immobilized metal ion/chelating macrocyclic ligand complexes, the use of different metal ions with a given macrocyclic ligand can generate novel selectivities that relate to the electronegativity, the vacant d-orbital geometries and the packing effects of the metal ion; thus, the behaviour of $Cu^{2+}$ differs from that of $Ni^{2+}$, which again differs from that of $Zn^{2+}$, etc., in a surprising manner [as demonstrated by numerous working examples herein (vide infra)].

(h) As mentioned above, the topological features of the present bis(macrocycle) ligands (as well as those of the tris- and tetrakis-systems) can be "fine-tuned" in terms of, for example, their hydrophobicity, steri-electronic features, distance between metal ion binding centres, intrinsic charge, propensity for supra-molecular assembly, metal ion binding constants, or preferences for different buffer ions or different solvational species in a manner that cannot be achieved with known IDA- or NTA-type systems or with systems based on N,N,N'-tris(carboxymethyl)ethylenediamine (TED) or with related types of unconstrained chelating systems. In this connection, and as illustrated by working examples herein (vide infra), it appears that these properties may be exploited to achieve very satisfactory purification of "untagged" (native) proteins/polypeptides in many cases by judicious choice of metal ion, macrocyclic ligand system (e.g. bis- tris- or tetrakis-system as disclosed herein) and conditions (elution medium, pH etc.). Moreover, the selectivity and binding properties in question of metal ion/ligand sorbent systems according to the invention may render cleavage of a "tag" from a fusion protein in situ on the sorbent system to which it is bound (rather than in solution after elution/purification) both feasible and advantageous.

(i) Routes to synthesis of the present mono-, bis-, tris- and tetrakis-type ligands are different from those employed for the conventional, unconstrained IDA, NTA, etc. systems, and variants of the pre-sent types of ligands with pendant arms comprising further donor atoms, e.g. N-carboxymethyl-substituted variants, may readily be prepared by combinatorial synthesis; thus, different types of spacers (i.e. side-chain groups linking the macrocyclic chelating ligand to the support material, or alternatively—in the case of the bis(tacn), tris(tacn) and tetrakis(tacn) systems—interposing structural moieties that control the distance between the metal ions in the chelating complexes), different ligand geometries as well as different ligand densities can, in principle, be achieved. Thus, in addition to the ability to introduce different types of spacers between the macrocyclic compartments of the ligands, control of ligand coordination properties can be achieved by functionalization of secondary amine groups on the macrocycles with either coordinating groups or non-coordinating groups (j) The same "core" structures can be made with 3 nitrogen donor atoms, i.e. as N3 ligands (N6 for the bis-, N9 for the tris- and N12 for the tetrakis-ligands), or as analogous N2O, N2S, O2N or S2N ligands (with appropriate multiples thereof for the corresponding bis-, tris- and tetrakis-ligands). It should be mentioned here that higher homologues (pentakis-, hexakis-, heptakis- . . . etc) of ligands of the type employed in the context of the present invention are also feasible and of relevance in relation to the present invention.

(k) As already indicated in section (i), above, the immobilized macrocyclic "core" ligand may readily be derivatised chemically to introduce one or more pendant substituents containing a donor atom; thus, further classes of IMAC adsorbents can be generated, again with differing properties with regard to selectivity. Systems of this type—containing, e.g., a pendant carboxymethyl group—are within the scope of the invention and are contemplated to be of value, for example, as $Ca^{2+}$-specific IMAC systems. Corresponding types of ligand systems with such pendant substituents cannot be generated in an analogous manner from IDA, NTA and other unconstrained classes of chelating systems.

B: Preferred sequence and structural arrangement of peptide tags in relation to the macrocyclic. metal ion chelating ligands employed in the context of the invention: As outlined in section A above, several objective criteria were employed to select suitable amino acid sequences from a computer-generated database for the purpose of construction of appropriate oligopeptide "tags". Several common or generic characteristics of these oligopeptide "tags" distinguish them from other classes of known oligopeptide "tags" in terms of composition or structure. These common or generic characteristics can be summarized as follows:

(a) An amino acid sequence arrangement wherein an acidic amino acid residue (such as an aspartic acid residue or a glutamic acid residue) is located in an i→i+1, i→i+2, i→i+3 or i→i+4 position relative to a histidine residue (or other appropriate N-donor residue) whose sequence number in the amino acid sequence of the oligopeptide "tag" is i, with the atomic distance between the side-chain moiety of the acidic amino acid residue in question and the histidine residue (i.e. the average distance between the acidic amino acid residue and the histidine residue) matching or being similar to the atomic distances separating the available binding sites within a metal ion/macrocyclic ligand complex of the present type.

(b) An amino acid sequence arrangement wherein a histidine residue is located in an i→i+1, i→i+2, i→i+3 or i→i+4 sequence position relative to another histidine residue (or other appropriate N-donor residue), with the atomic distances between the side-chain moieties of the two histidine residues matching or being similar to the atomic distances separating the available binding sites within a metal ion/macrocyclic ligand complex of the present type.

(c) An amino acid sequence arrangement wherein a non-polar or neutral amino acid residue (such as an alanine, leucine, serine, threonine, asparagine or glutamine residue) is located in a i→i+1, i→i+2, i→i+3 or i→i+4 sequence position relative to a histidine residue, with the atomic distances between the side-chain moiety of the non-polar or neutral amino acid residue in question and the histidine residue matching or being similar to the atomic distances separating the available binding sites within a metal ion/macrocyclic ligand complex of the present type.

(d) An amino acid sequence arrangement wherein the first, third, fifth, seventh, ninth, . . . (etc) amino acid residue is preferably a histidine residue or a polar amino acid residue (such as a serine, threonine or tyrosine residue), provided the disposition of the amino acid residues results in atomic distances between the side-chain moieties of the first and third, and/or third and fifth, and/or fifth and seventh, and/or seventh and ninth, . . . (etc) amino acid residues which match or are similar to the atomic distances separating the available binding sites within a metal ion/macrocyclic ligand complex of the present type.

(e) An amino acid sequence arrangement wherein the second, fourth, sixth, eighth, . . . (etc) amino acid residue is preferably an ionisable or polar amino acid residue (such as an arginine, lysine, histidine or tyrosine residue) or a non-polar amino acid residue (such as a leucine, alanine, valine, phenylalanine, asparagine or glutamine residue), provided the disposition of the amino acid residues results in atomic distances between the side-chain moieties of the second and fourth, and/or fourth and sixth, and/or sixth and eighth, and/or eighth and tenth, . . . (etc) amino acid residues which match or are similar to the atomic distances separating the available binding sites within a metal ion/macrocyclic ligand complex of the present type.

(f) An amino acid sequence arrangement wherein the C-terminal amino acid residue is preferably a histidine or arginine residue or a non-polar amino acid residue (such as a leucine, asparagine or glutamine residue), provided the disposition of the amino acid residues results in atomic distances between the side-chain moieties of at least two of the amino acid residues, preferably the first and third, and/or third and fifth, and/or fifth and seventh, and/or seventh and ninth, . . . (etc) amino acid residues, which match or are similar to the atomic distances separating the available binding sites within a metal ion/macrocyclic ligand complex of the present type.

(g) An amino acid sequence for the oligopeptide "tag" wherein the N-terminal position of the oligopeptide is not biosynthetically acetylated or acylated.

(h) An amino acid sequence for the oligopeptide "tag" whereby the hydrophobic moment ($\Im$) calculated and defined according to Nozaki and Tanford (*J. Biol. Chem.* 238 (1963) 4074-4081; ibid 245 (1970) 1648-1652) and Eisenberg, D., Weiss, R. M. and Terwilliger, T. (*Proc. Natl. Acad. Sci. USA* 81 (1984) 140-144)] of the oligopeptide "tag" is such that $1 \leq \Im \leq 25$, and the global change in hydrophobicity [calculated according to Richards, F. M. (*Annual Reviews of Biophysics and Bioengineering* 6 (1977) 151-176) and Wilce, M. C. J., Aguilar, M. I. and Hearn, M. T. W. (*Anal. Chem.* 67 (1995) 1210-1219)] of the recombinant fusion protein (host protein with oligopeptide "tag") is not more than 0.3.

(i) An amino acid sequence for the oligopeptide "tag" whereby the overall contribution of the oligopeptide "tag" sequence to the isoelectric point (pI) value for the recombinant fusion protein is not more than 0.5 when compared to the value for the corresponding wild-type (untagged) host protein (protein of interest).

(j) An amino acid sequence for the oligopeptide "tag" that carries a net charge (q) at pH 7.0 in the range $1.5 \leq q \leq 1.0$.

(k) An amino acid sequence for the oligopeptide "tag" whereby the isoelectric point (pI) of the oligopeptide is within the range $5.8 \leq pI \leq 8.5$.

(l) An amino acid sequence for the oligopeptide "tag" whereby—in free solution or under capillary zonal electrophoretic conditions—the oligopeptide exhibits an affinity for soft, borderline or hard metal ions with an affinity constant ($K_{assco}$) in the range $100\,nM \leq K \leq 100\,mM$ at a pH near 7.0 and an ionic strength (l) of $\leq 50$ mM.

(m) An amino acid sequence for the oligopeptide "tag" whereby, at a molar concentration of $\leq 300$ μM in phosphate buffered saline at pH 7.0, the oligopeptide does not form a coiled coil structure.

On a more specific level, if—as in a very useful aspect of the invention—it is necessary or important to be able to cleave the oligopeptide "tag" in question from the fusion protein by the use of an aminopeptidase (rather than employ an endopeptidase or protease, such as enterokinase or Factor IXa, or alternatively a chemical procedure based on the use of, e.g., cyanogen bromide, hydroxylamine, N-bromosuccinimide, iodosobenzoic acid, 3-bromo-3-methyl-2-(2-nitrophenylsulphenyl)-indolenine-skatole or another suitable chemical reagent), then suitable aminopeptidases will include a dipeptidyl aminopeptidase, such as DAP-1 (also known as cathepsin C or DPP I; E.C. 3.4.14.1; obtainable from, e.g., Aldrich-Sigma, St Louis, Mo., U.S.A or Unizyme Laboratories, Horsholm, Denmark), whereby the desirable properties for such a "tag" for expression of the recombinant protein in *E. coli* and other appropriate prokaryotic expression systems/host cells appear to satisfy the following criteria:

(n) An amino acid sequence arrangement wherein the first, third, fifth, seventh, ninth, . . . (etc) amino acid residue is not a proline, arginine or lysine residue, provided the disposition of the amino acid residues results in atomic distances between the side-chain moieties of the first and third, and/or third and fifth, and/or fifth and seventh, and/or seventh and ninth, . . . (etc) amino acid residues which match or are similar to the atomic distances separating the available binding sites within a metal ion/macrocyclic ligand complex of the present type.

(o) An amino acid sequence arrangement wherein the second, fourth, sixth, eighth, . . . (etc) amino acid residue is not a proline residue, provided the disposition of the amino acid residues results in atomic distances between the side-chain moieties of the second and fourth, and/or fourth and sixth, and/or sixth and eighth, and/or eighth and tenth, . . . (etc) amino acid residues which match or are similar to the atomic distances separating the available binding sites within a metal ion/macrocyclic ligand complex of the present type.

Additionally, if—as in another aspect of the invention—it is to be possible to cleave the oligopeptide "tag" in question from the fusion protein by the use of an endopeptidase, appropriate criteria for such a "tag" include the following:

(p) Linkage of the amino acid sequence of the oligopeptide "tag" to the amino acid sequence of the protein of interest via a short amino acid sequence that contains a cleavage motif for an endopeptidase, e.g. an endopeptidase such as Factor IIa, Factor Xa, enterokinase, streptokinase, thrombin, furin or Kex (such as Kex1 or Kex2).

Moreover, if—as in a further aspect of the invention—it is to be possible to cleave the oligopeptide "tag" in question from the fusion protein by means of a chemical reaction, appropriate criteria for such a "tag" include the following:

(q) Linkage of the amino acid sequence of the oligopeptide "tag" to the amino acid sequence of the protein of interest via a short amino acid sequence that contains a cleavage motif for a chemical reagent, e.g. a reagent such as hydroxylamine, cyanogen bromide, N-bromosuccinimide, iodosobenzoic acid, 3-bromo-3-methyl-2-(2-nitrophenyl-sulphenyl)-indolenine-skatole or another suitable chemical reagent.

Furthermore, if—as in a still further aspect of the invention—it is to be possible to cleave the oligopeptide "tag" in question from the fusion protein by means of self-cleavage/self-splicing pseudoenzymatic reactions, such as the use of acylthiol self-ligation rearrangement, appropriate criteria for such a "tag" will include the following:

(r) Linkage of the amino acid sequence of the oligopeptide "tag" to the amino acid sequence of the protein of interest via an amino acid sequence that contains a self-cleavage intein domain for affinity separations (see, e.g., Wood, D. W., Derbyshire, V., Wu, W, Chartrain, M, Belfort, M. and Belfort, G. *Biotechnology Progress,* 16 (2000) 1055-1063; Wood, D. W., Wu, W, Belfort, G., Derbyshire, V. and Belfort, M. *Nature Biotechnology,* 17 (1999) 889-892).

In the case of eukaryotic expression systems, e.g. mammalian cells, such as Chinese hamster ovary (CHO) cells, baculovirus transfected insect Sf 9 cells from *Spodoptera furgiperda*, or various commercially important yeast cells (including *Saccharomyces cerevisiae* and *Pichia pastoris*), used for the manufacture of recombinant proteins, it is feasible to employ with these systems an oligopeptide "tag" sequence with:

(s) an amino acid sequence arrangement wherein the first amino acid residue is a proline residue, provided the disposition of other amino acid residues in the oligopeptide "tag" results in atomic distances between the side-chain moieties of the first and third, and/or third and fifth, and/or fifth and seventh, and/or seventh and ninth, . . . (etc) amino acid residues, or the second and fourth, and/or fourth and sixth, and/or sixth and eighth, . . . (etc) amino acid residues, that match or are similar to the atomic distances separating the available binding sites within a metal ion/macrocyclic ligand complex of the present type;

(t) an amino acid sequence arrangement wherein the second and all subsequent amino acid residues are not a proline residue (in those cases in which enzymatic cleavage involving an aminopeptidase such as DAP-1 represents the preferred methodology for removal of the oligopeptide "tag").

Oligopeptide "tags" displaying one or more of the above characteristics [(a) to (t)] are within the scope of the present invention.

C: The positioning of the peptide tag: Employing well known molecular biological approaches and techniques, preferably based on polymerase chain reaction (PCR) procedures, the introduction of an oligopeptide "tag" according to the invention into a protein of interest is achievable at the amino terminal, at the carboxyl terminal or at internal (endo-) positions. As a consequence, implementation of a C-terminally located oligopeptide "tag" still enables the described IMAC procedures to be employed with the present macrocyclic chelating ligand systems. Moreover, the oligopeptide "tag", notably a histidine-containing oligopeptide according to the invention, can be simultaneously fused to two molecules of the protein or polypeptide of interest, or alternatively to two different proteins or polypeptides of interest, at their amino- or carboxy-terminus, respectively, thereby forming a new fusion protein structure whereby the oligopeptide "tag" is located at an endo-position (i.e. at an internal position) linking the two molecules of the protein(s) or polypeptide(s) of interest. As described in working examples presented herein (see the Experimental Section), it has been found that C-terminally oligopeptide "tagged" recombinant proteins can be very efficiently captured by the new IMAC systems and selectively purified. For subsequent removal of an oligopeptide "tag" located at the C-terminal position of a recombinant protein, a specific carboxypeptidase may be employed, or a unique chemical cleavage site must be introduced at the junction of the C-terminal residue of the host protein and the N-terminal residue of the "tag" peptide. Criteria for selection of the chemical characteristics of these cleavage sites can be anticipated from the scientific literature, whilst optimisation of the kinetics of carboxypeptidase cleavage can be based on literature precedents. Depending on the sequence of the oligopeptide "tag" and the nature of the C-terminal amino acid sequence of the host protein, suitable carboxypeptidases may be, for example, carboxypeptidase Y (CpY) or zinc-dependent carboxypeptidase. Suitable carboxypeptidases are available from a number of suppliers, including Worthington Biochemicals Corporation, Lakewood, N.J., U.S.A.

D: Substitution requirements of preferred oligopeptide tags: As apparent from section B above, especially subsections (a)-(c) thereof, acceptable amino acid substitutions can be utilised to generate a number of variants, generated most easily via a combinatorial synthetic strategy. Regarding the choice of preferred amino acids, guidance may be sought in the criteria set out in section B, above, with particular reference to the susceptibility of the amino acid sequence of the combinatorially derived variants to cleavage by an exopeptidase with the oligopeptide "tag" located at the N- or C-terminus of the target protein as discussed in Section C or by a diaminopeptidase, e.g. a dipeptidyl aminopeptidase such as DAP-1 (vide supra). As a consequence, considerable molecular constraints can be introduced in terms of limitations on the total number of synthetic possibilities that can be utilised based on the generic definition of a "preferred oligopeptide "tag""; for example, in the case of prokaryotic expression systems such as *E. coli* proline-containing variants are generally excluded. In the case of sequence variants in which the first, third, fifth, seventh, . . . (etc) amino acid residue is a residue which is "forbidden" as a result of it acting as a sequence stop for cleavage by a diaminopeptidase (such as DAP-1), i.e. is kinetically unsuited for cleavage at this site after the n–1 cleavage reaction (Pro, Arg and Lys are illustrative of such "forbidden" amino acid residues), or sequence variants in which the second, fourth, sixth, eighth, . . . (etc) amino acid residue is non-preferred because it is kinetically unsuited for cleavage at this site (Met is illustrative of such an amino acid residue), then such variants from within the oligopeptide "tag" library are computationally excluded. Taking these considerations into account, the full combinatorial library variations for, say, the oligopeptide "tag" sequences HHHNSWDHDINR (hereafter referred to as NT1) or HTNIHQDQHNHFHR (hereafter denoted NT2), generated at the DNA level via multiple parallel PCR reactions of the corresponding cDNA, would not be considered as indicative or necessary for the expected utility requirement. Rather a sub-library would represent a suitable group of structural variations for the generation of oligopeptide "tag" sequences that are capable of affinity maturation, i.e. have the desired features of affinity for the specific macrocylic ligand and ability to be removed by the selected peptidase, such as DAP-1, with a specific protein member (or family of related proteins) as part of their binding interactions with the new immobilized metal ion/macrocyclic ligand complexes. The term "affinity maturation" in this context denotes the selective use of oligopeptide "tag" sequences that are related in primary structure to (i.e. are variants of) the parent oligopeptide "tag" (such as NT1 or NT2; vide supra) (i.e. are variants), such that these oligopeptide "tag" variants represent amino acid substitutions that give higher or lower binding affinities with the chosen immobilized metal ion affinity complex as a molecular recognition cassette, the affinity properties of the selected oligopeptide "tag" sequence variants and immobilized metal ion affinity complex disclosed above as an aspect of this invention being selected in accordance with the specific properties of the target protein of interest.

E: Truncation requirements of preferred peptide tags: Provided the criteria described in sections B, C and D above are satisfied, then truncation of the amino acid sequence of a preferred oligopeptide "tag" according to the invention, e.g. NT1 or NT2, from the N- and/or C-termini constitutes allowed occurrences with respect to removal of the oligopeptide "tag" utilizing a dipeptidyl aminopeptidase (e.g. DAP-1; vide supra) or another aminopeptidase, diaminopeptidase or triaminopeptidase. In this case, truncation leads to the following case (illustrated for a des uno-oligopeptide "tag" structure:

5' 1-2-3-4-5-6-7- . . . -[target protein]→-5' 2-3-4-5-6-7- . . . -[target protein]).

An important aspect here is to ensure that truncation does not lead to the an "out-of-phase" shift of the amino acid sequence. This may have no effect on the interaction between the oligopeptide "tag" and the immobilized metal ion/ligand complex during the purification procedure, but could result in an unfavourable arrangement of amino acid residues that renders the proteolytic cleavage of the oligopeptide "tag" from the fusion protein inefficient. As such, "in-phase" truncation variants represent a special subset (the T-subset) of the parent oligopeptide "tag" sequence "library", and are related to the respective parent oligopeptide "tag" via their similarities in compositional or sequential features and by their IMAC binding potential or cleavage characteristics with enzymes.

F: Deletion requirements of preferred peptide tags: Removal of internal amino acid residues will perturb the defined order of amino acid residues and will thus have two consequences. The first consequence relates to the effect on the preferred binding motif for molecular recognition of the vestigial oligopeptide "tag" by the immobilized metal ion/macrocyclic chelating ligand. This effect will be manifested as a phase shift in the amino acid sequence, with amino acid residue "m" becoming the "m-x" residue in the deletion variant, where "x" is the deletion amino acid or sequence. Such changes can have a second effect, namely that the propensity for DAP-1 cleavage may be greatly compromised. In this case, deletion leads to the following case (illustrated for a des dipeptide "tag" structure:

5' 1-2-3-4-5-6-7- . . . -[target protein]→5' 1-2-3-6-7- . . . -[target protein]).

Provided that the criteria outlined in sections B, C and D above are still met, however, then the possibility of employing deletion variants can also be incorporated as part of the selection requirements for the amino acid sequence(s) of preferred oligopeptide "tags". As such, "in-phase" deletion variants represent a special subset (the D-subset) of the parent oligopeptide "tag" sequence "library", being also related via their compositional or sequential similarities to the IMAC binding potential or enzymatic cleavage properties of the parent oligopeptide "tag" sequence.

G: Modularity requirements of the preferred oligopeptide tags: Pursuant to the considerations outlined in sections C, D, E and F above, the criterion of modularity of the oligopeptide "tag" sequence can be invoked. In this case modular re-arrangement leads to the following case (illustrated for a rearranged tetra-peptide "tag" structure below:

5' 1-2-3-4-5-6-7- . . . -14-15-16-17-[target protein] 5' 1,2-3-14-15-16-17-4-5-6-7- . . . -[target protein]).

This consideration raises the possibility of also including fragmental partial sequences of one or more preferred "full"-length "tags" as a basis for the design of a new peptide "tag". In this way the sequence will only be partially altered, so the outcome represents an additional subset of the parent sequence (the M-subset). In this case, the block size for replacement from the parent peptide "tags" to generate the modularity of the new peptide "tag" has to observe the criteria described for IMAC interaction and for enzymatic cleavage.

H: Sequence directionality of preferred oligopeptide tags: With biosynthetically prepared oligopeptide "tag" fusion proteins, the question arises as to whether the order of amino acid residues in a preferred sequence can be reversed. In the case, for example, of the oligopeptide "tag" sequence NT2 (vide supra), this would generate the sequence-R-H-F-H-N-H-Q-D-Q-H-I-N-T-H-. In relation hereto it should be noted that such sequence order reversal will in many cases lead to an unfavoured residue at position 1 (and possibly elsewhere).

I: Cassette sequence possibility of preferred peptide tags The issue of complementary interaction behaviour is discussed above with respect to a preferred oligopeptide "tag" sequence and the nature of the specific IMAC ligands employed. A dominant (although not exclusive) criterion for the selection of the amino acid sequence relates to the distance between, and angular orientation of, the amino acid residue side-chains with regard to the complementary angular and binding energy capabilities of the corresponding immobilized metal ion/ligand complex systems at a molecular, rather than bulk, level. For this reason the choice of the preferred oligopeptide "tag" is dependent also on the choice of the IMAC ligand, for which reason the concept of cassette interactions involving the two cognate partners was evoked earlier, above. This generic concept has helped in the characterization of many of the special binding properties of the novel oligopeptide "tag" systems described herein. In relation to the discussion above, but on a more specific level, oligopeptide "tags" which appear to be very well suited for use in protein purification strategies in which cleavage of the oligopeptide "tag" from the fusion protein (which is itself a polypeptide) is to take place via the agency of an aminopeptidase, e.g. a dipeptidyl-aminopeptidase such as DAP-1, include oligopeptides comprising an amino acid sequence chosen among the following:

```
HHHNSWDHDINR    (abbreviated herein  (SEQ. ID No. 1)
                 as NT1)

HTNIHQDQHNHFHR  (abbreviated herein  (SEQ. ID No. 2)
                 as NT2)

HAMLDRAHDHGTR                        (SEQ. ID No. 3)

SLHEHHSGDNLR                         (SEQ. ID No. 4)

THYNAVHSHNTLQ                        (SEQ. ID No. 5)

DIHHWTDHLQSSTH                       (SEQ. ID No. 6)

LYNHYSHTAHVNHL                       (SEQ. ID No. 7)
```

It will be understood that such a peptide (oligopeptide) "tag" may comprise, in addition to one of the amino acid sequences shown, one or more additional amino acid residues, such as from 2 to 6 or more additional amino acid residues, attached at the C- or N-terminal end of the oligopeptide "tag". Such a sequence extension may, for example, suitably be a dipeptide unit such as Met-Lys located at positions −2 and −1 (where position −1, Lys, is the first amino residue numbered from the N-terminus of the oligopeptide "tag") when the extension is at the N-terminus of the oligopeptide "tag" and the "tag" system is intended to be utilised with a prokaryotic expression system, such as E. coli, for the production of a recombinant protein; in the case of prokaryotic expression systems without periplasmic secretion, preferred first amino acid residues of an N-terminal extension of the oligopeptide "tag" comprise the sequence Met-Xaa, where Xaa is any amino acid residue other than proline. The inclusion of these amino acid sequence extensions could potentially lead to additional advantages of increased expression of the target protein in prokaryotic host cells.

In the case of eukaryotic expression systems, an N-terminal extension of the oligopeptide "tag" will very suitably contain at most ten, often less than ten, amino acid residues, normally with the proviso that the second amino acid residue of the extension is not a proline residue.

In an analogous manner, a sequence extension may, for example, suitably be a dipeptide unit such as Val-Asp located at positions +1 and +2 (where position +1, Val, is the first amino residue numbered from the C-terminus of the oligopeptide "tag") when the extension is at the C-terminus of the oligopeptide "tag" and the "tag" system is intended to be utilised with a prokaryotic expression system, such as E. coli, for the production of a recombinant protein.

Still further aspects of the invention include the following:

a polypeptide which is a fusion protein comprising a protein of interest fused at its amino terminus or carboxy terminus to at least one oligopeptide which is in accordance with one or more of the criteria discussed above, such as an oligopeptide among those referred to above in connection with SEQ. IDs Nos. 1-7; as already discussed (vide supra), fusion proteins of the type in question include fusion proteins wherein two molecules of a protein or polypeptide of interest, or alternatively two different proteins or polypeptides of interest, are attached simultaneously at their amino- or carboxy- terminus, respectively, to one and the same oligopeptide (i.e. oligopeptide "tag"), suitably a histidine-containing oligopeptide according to the invention, so as to form a fusion protein structure in which the oligopeptide (i.e. the "tag") is located at an endo-position (i.e. an internal position) linking the two molecules of the protein(s) or polypeptide(s) of interest; in fusion protein structures of this type, the amino acid sequence of the oligopeptide "tag" is suitably flanked by one or more enzymatic or chemical cleavage sites;

a polynucleotide construct, such as a vector, encoding such a polypeptide;

a polypeptide obtainable by cultivating a host cell (e.g. a prokaryote such as *Escherichia coli*) comprising such a polynucleotide construct in an appropriate growth medium under conditions allowing expression of the polypeptide, and recovering the polypeptide from the culture medium;

a host cell, more specifically a prokaryote cell (e.g. a strain of *Escherichia coli*) or a eukaryote cell (e.g. a strain of *Saccharomyces cerevisiae, Pichia pastoris* cells, Chinese hamster ovary (CHO) cells, or other mammalian cell lines such as BHK, HEK or COS), comprising such a polynucleotide construct; and a method for producing a polypeptide of the type in question, the method comprising cultivating a host cell of the type in question in an appropriate growth medium under conditions allowing expression of the polypeptide, and recovering the polypeptide from the culture medium;

Yet another aspect of the invention relates to a method for purifying a protein of interest, the method comprising the steps of:

contacting a protein sample which contains: a polypeptide which is a fusion protein comprising the protein of interest fused at its amino terminus or carboxy terminus to at least one oligopeptide (i.e. oligopeptide "tag") according to the invention (i.e. a fusion protein of one of the types already mentioned above, including a fusion protein in which the oligopeptide (i.e. the "tag") is situated in an endo position as already discussed); and other (extraneous) proteins; with a metal ion-containing functionalized polymer substrate according to the invention under conditions whereby the polypeptide (fusion protein) binds to the metal ion-containing functionalized polymer substrate so as to form a complex therewith;

washing the complex with a buffer solution to remove the other (extraneous) proteins; and eluting the bound polypeptide from the washed complex.

The latter method may further comprise a step wherein the oligopeptide (the "tag") is cleaved from the polypeptide or protein of interest, e.g. by chemical means or by means of an enzyme (such as a dipeptidyl-aminopeptidase in the case, for example, of a "tag" comprising an amino acid sequence among those listed as SEQ. IDs Nos. 1-7).

The invention also encompasses a purified protein obtained or obtainable by the latter method.

Polypeptides or proteins (polypeptides or proteins of interest) which are of relevance in relation to the purification methodology taught in the context of the present invention include the following: mammalian proteins, such as, e.g., growth hormone, including human growth hormone and bovine growth hormone; growth hormone releasing factor; parathyroid hormone; thyroid stimulating hormone; lipoproteins; $\alpha$-1-antitrypsin; insulin A-chain; insulin B-chain; proinsulin; follicle stimulating hormone; calcitonin; luteinizing hormone; glucagon; clotting factors, such as Factor VII (including Factor VIIa), Factor VIII, Factor IX, tissue factor, and von Willebrands factor; anti-clotting factors such as Protein C; atrial natriuretic factor; lung surfactant; a plasminogen activator, such as urokinase or tissue-type plasminogen activator (t-PA); bombazine; thrombin; tumor necrosis factor-$\alpha$ and -$\beta$; enkephalinase; RANTES (regulated on activation normally T-cell expressed and secreted); human macrophage inflammatory protein (MIP-1-$\alpha$); serum albumin, such as human serum albumin; mullerian-inhibiting substance; relaxin A-chain; relaxin B-chain; prorelaxin; mouse gonadotropin-associated peptide; DNase; an activin (e.g. activin A, activin B, activin C, activin D or activin E); an inhibin (e.g. inhibin A or inhibin B); vascular endothelial growth factor (VEGF); receptors for hormones or growth factors; an integrin; protein A or D; rheumatoid factors; a neurotrophic factor such as bone-derived neurotrophic factor (BDNF), neurotrophin-3, -4, -5, or -6 (NT-3, NT-4, NT-5 or NT-6), or a nerve growth factor such as NGF-$\beta$; platelet-derived growth factor (PDGF); fibroblast growth factor, such as aFGF and bFGF; epidermal growth factor (EGF); transforming growth factor (TGF), such as TGF-$\alpha$ and TGF-$\alpha$, including TGF-$\beta$, TGF-$\beta$1, TGF-$\beta$2, TGF-$\beta$3, TGF-$\beta$4 and or TGF-$\beta$5; insulin-like growth factor-I and -II (IGF-I and IGF-II); des(1-3)-IGF-I (brain IGF-1); insulin-like growth factor binding proteins; CD proteins, such as CD3, CD4, CD8, CD19 or CD20; erythropoietin (EPO); thrombopoietin (TPO); osteoinductive factors; immunotoxins; a bone morphogenetic protein 1-7 (BMP 1-7); an interferon, such as interferon-$\alpha$, -$\beta$ or -$\gamma$; colony stimulating factors (CSFs), e.g., M-CSF, GM-CSF or G-CSF; interleukins (ILs), e.g., IL-1 to IL-12; superoxide dismutase;

T-cell receptors; surface membrane proteins; decay accelerating factor (DAF); a viral antigen, such as, for example, a portion of the AIDS envelope; transport proteins; homing receptors; addressins; regulatory proteins; immunoadhesins; antibodies; and biologically active fragments or variants of any of the above-listed polypeptides or proteins.

The term "polynucleotide" as employed herein denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. The length of a polynucleotide molecule is given in terms of nucleotides (abbreviated "nt") or base pairs (abbreviated "bp"). The term "nucleotide" is used for both single- and double-stranded molecules, where the context permits. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

The term "host cell" as employed herein denotes any cell, including a hybrid cell, in which heterologous DNA can be expressed. Typical host cells includes, but are not limited to bacterial cells, insect cells, yeast cells and mammalian cells, including human cells, such as BHK, CHO, HEK, and COS cells.

The term "vector" as employed herein denotes any nucleic acid entity capable of amplification in a host cell. Thus, the vector may be an autonomously replicating vector, i.e. a vector that exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated. The choice of vector will often depend on the host cell into which it is to be introduced. Vectors include, but are not limited to plasmid vectors, phage vectors, viruses or cosmid vectors. Vectors usually contain a replication origin and at least one selectable gene, i.e. a gene that encodes a product which is readily detectable, or the presence of which is essential for cell growth.

In the present specification, amino acid residues are represented using abbreviations approved by the IUPAC-IUB Commission on Biochemical Nomenclature (CBN). With respect to amino acids, those represented by the following abbreviations are in the naturally occurring L-form. Further, the left and right ends of an amino acid sequence of a peptide are, respectively, the N- and C-termini unless otherwise specified.

| Abbreviations for amino acid residues | | |
| --- | --- | --- |
| Amino acid | Three-letter code | One-letter code |
| Glycine | Gly | G |
| Proline | Pro | P |
| Alanine | Ala | A |
| Valine | Val | V |
| Leucine | Leu | L |
| Isoleucine | Ile | I |
| Methionine | Met | M |

-continued

| Abbreviations for amino acid residues | | |
| --- | --- | --- |
| Amino acid | Three-letter code | One-letter code |
| Cysteine | Cys | C |
| Phenylalanine | Phe | F |
| Tyrosine | Tyr | Y |
| Tryptophan | Trp | W |
| Histidine | His | H |
| Lysine | Lys | K |
| Arginine | Arg | R |
| Glutamine | Gln | Q |
| Asparagine | Asn | N |
| Glutamic Acid | Glu | E |
| Aspartic Acid | Asp | D |
| Serine | Ser | S |
| Threonine | Thr | T |

The enzyme classification employed in the present specification with claims is in accordance with *Recommendations* (1992) *of the Nomenclature Committee of the International Union of Biochemistry and Molecular Biology*, an updated version of which (including supplements) is available on the world wide web at http://www.chem.qmw.ac.uk/iubmb/enzyme/.

BRIEF DESCRIPTION OF THE FIGURES

The present invention is further illustrated with reference to the accompanying figures, which are as follows:

FIG. 16. SDS-PAGE profile of the crude, column breakthrough and eluted fractions from the chromatographic separation of the crude *E. coli* extract containing the recombinant GST-δATPase-$His_6$ protein. The molecular weight standards were as follows: ovalbumin, 46 kDa, carbonic anhydrase, 30 kDa, trypsin inhibitor, 21.5 kDa, lysozyme, 14.3 kDa, aprotinin 6.5 kDa, and insulin B-chain, 3.4 kDa. The tracks in panel (a) correspond to: Lane 1, crude *E. coli* extract; Lane 2 to 4, breakthrough fractions obtained from the im-$Cu^{2+}$-tacn, -dtne and -dtnp Sepharose™ CL-6B columns, respectively; Lane 5, protein standards; Lane 6 to 9, breakthrough fractions obtained from the im-$Zn^{2+}$-tacn, im-$Zn^{2+}$-dtne, im-$Zn^{2+}$-dtnp, im-$Ni^{2+}$-tacn and im-$Ni^{2+}$-dtne Sepharose™ CL-6B columns, respectively. Similarly, the tracks in panel (b) correspond to: Lane 1 to 3, eluted fractions from the im-$Cu^{2+}$-tacn, -dtne and -dtnp Sepharose™ CL-6B columns, respectively; Lane 4, protein standards; Lane 5 to 7, eluted fractions from the im-$Ni^{2+}$-tacn, im-$Ni^{2+}$-dtnp, and im-$Ni^{2+}$-NTA Sepharose™ CL-6B columns, respectively; Lane 8 and 9, breakthrough fractions from the im-$Ni^{2+}$-NTA and im-$Ni^{2+}$-dtnp columns, respectively. The migration position of the recombinant GST-δATPase-$His_6$ protein is indicated by the arrow.

Group 1=fractions eluted from the im-Ni$^{2+}$-tacn column using the buffer containing 125 mM imidazole;

Group 2=fractions eluted from the im-Cu$^{2+}$-tacn column using the buffer containing 125 mM imidazole;

Group 3=fractions eluted from the im-Ni$^{2+}$-tacn column using the buffer containing 250 mM imidazole;

Group 4=fractions eluted from the im-Cu$^{2+}$-tacn column using the buffer containing 250 mM imidazole;

Group 5=fractions eluted from the im-Ni$^{2+}$-tacn column using the buffer containing 500 mM imidazole;

Group 6=fractions eluted from the im-Cu$^{2+}$-tacn column using the buffer containing 500 mM imidazole;

Group 7=fraction of non-bound protein from the im-Ni$^{2+}$-tacn column;

Group 8=fraction of non-bound protein from the im-Cu$^{2+}$-tacn column;

Group 9=loaded sample, recombinant protein GAD67/65 isolated by the im-Ni$^{2+}$-NTA column;

Group 10=washing fractions from the im-Ni$^{2+}$-tacn column obtained using wash buffer having an imidazole concentration of 40 mM; and Group 11=washing fractions from the im-Cu$^{2+}$-tacn column obtained using wash buffer having an imidazole concentration of 40 mM.

Figure 24:
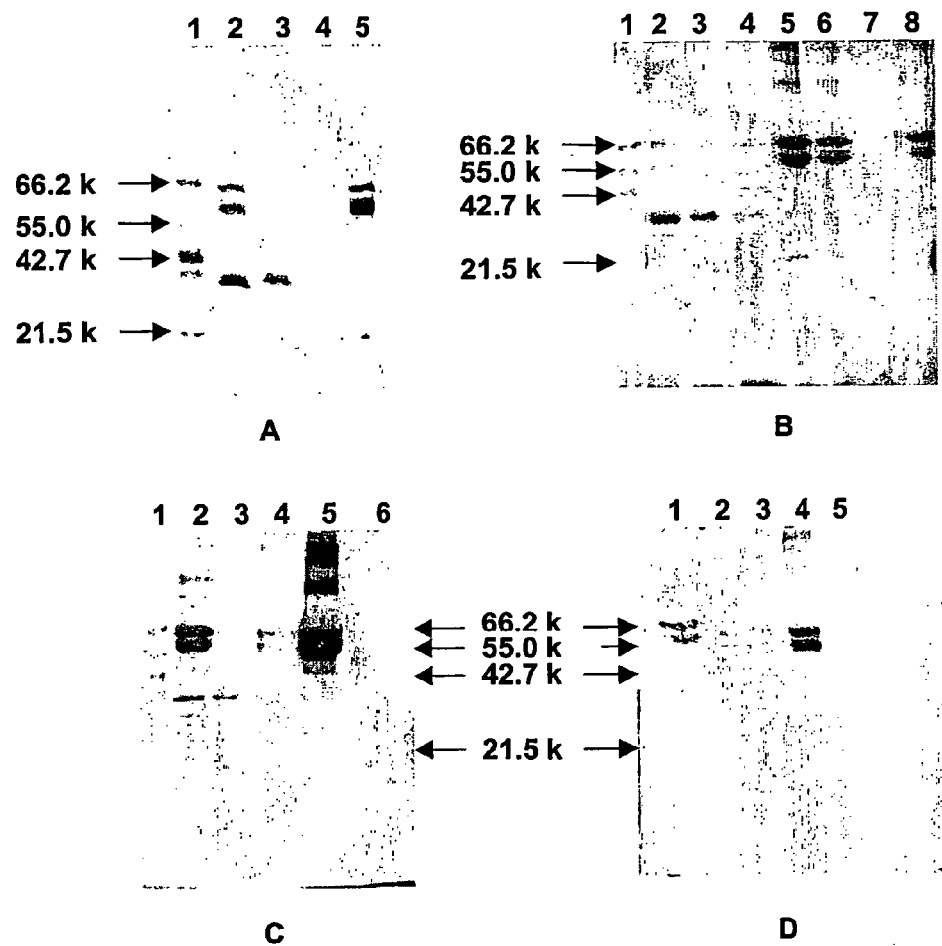

FIG. 24. SDS-PAGE and Western blot profiles of the fractions containing the recovered hexahistidine tagged recombinant protein glutamic acid decarboxylase (GAD67/65) isolated from the *Saccharomyces cerevisiae* BJ3505 strain using the im-Cu$^{2+}$-tacn Sepharose™ CL-6B columns. The loaded sample was isolated from *Pichia pastoris* using im-Ni$^{2+}$-NTA Sepharose™ CL-6B column. (A): SDS-PAGE of experiment 1: Lane 1: Molecular weight standards; Lane 2: loaded sample that was purified by im-Ni$^{2+}$-NTA Sepharose™ CL-6B; Lane 3: breakthrough fraction from im-Cu$^{2+}$-tacn Sepharose™ CL-6B; Lane 4: wash fraction from im-Cu$^{2+}$-tacn Sepharose™ CL-6B using equilibration buffer; Lane 5: elution fraction from im-Cu$^{2+}$-tacn Sepharose™ CL-6B using the buffer containing 250 mM imidazole; (B): SDS-PAGE of experiment 2: Lane 1: Molecular weight standards; Lane 2: loaded sample that was purified by im-Ni$^{2+}$-NTA Sepharose™ CL-6B; Lane 3: breakthrough fraction of im-Cu$^{2+}$-tacn Sepharose™ CL-6B; Lane 4: wash fraction of im-Cu$^{2+}$-tacn Sepharose™ CL-6B using equilibration buffer; Lane 5 and 6: elution fraction of im-Cu$^{2+}$-tacn Sepharose™ CL-6B using the buffer containing 250 mM imidazole; Lane 7: elution fraction of im-Cu$^{2+}$-tacn Sepharose™ CL-6B using the buffer containing 0.1 M histidine; Lane 8: elution fraction of im-Cu$^{2+}$-tacn Sepharose™ CL-6B using buffer containing 1% SDS. (C): SDS-PAGE of experiment 3: Lane 1: Molecular weight standards; Lane 2: loaded sample that was purified by im-Ni$^{2+}$-NTA Sepharose™ CL-6B; Lane 3: breakthrough fraction of im-Cu$^{2+}$-tacn Sepharose™ CL-6B; Lane 4: wash fraction of im-Cu$^{2+}$-tacn Sepharose™ CL-6B using equilibration buffer; Lane 5: elution fraction of im-Cu$^{2+}$-tacn Sepharose™ CL-6B using the buffer containing 250 mM imidazole; Lane 6: elution fraction of im-Cu$^{2+}$-tacn Sepharose™ CL-6B using buffer containing 0.2 M EDTA; (D) Western blot of experiment 3: Lane 1: loaded sample that was purified by im-Ni$^{2+}$-NTA Sepharose™ CL-6B; Lane 2: breakthrough fraction of im-Cu$^{2+}$-tacn Sepharose™ CL-6B; Lane 3: wash fraction of im-Cu$^{2+}$-tacn Sepharose™ CL-6B using equilibration buffer; Lane 4: elution fraction of im-Cu$^{2+}$-tacn Sepharose™ CL-6B using buffer containing 250 mM imidazole; Lane 5: elution fraction of im-Cu$^{2+}$-tacn Sepharose™ CL-6B using buffer containing 0.2 M EDTA.

Figure 25:
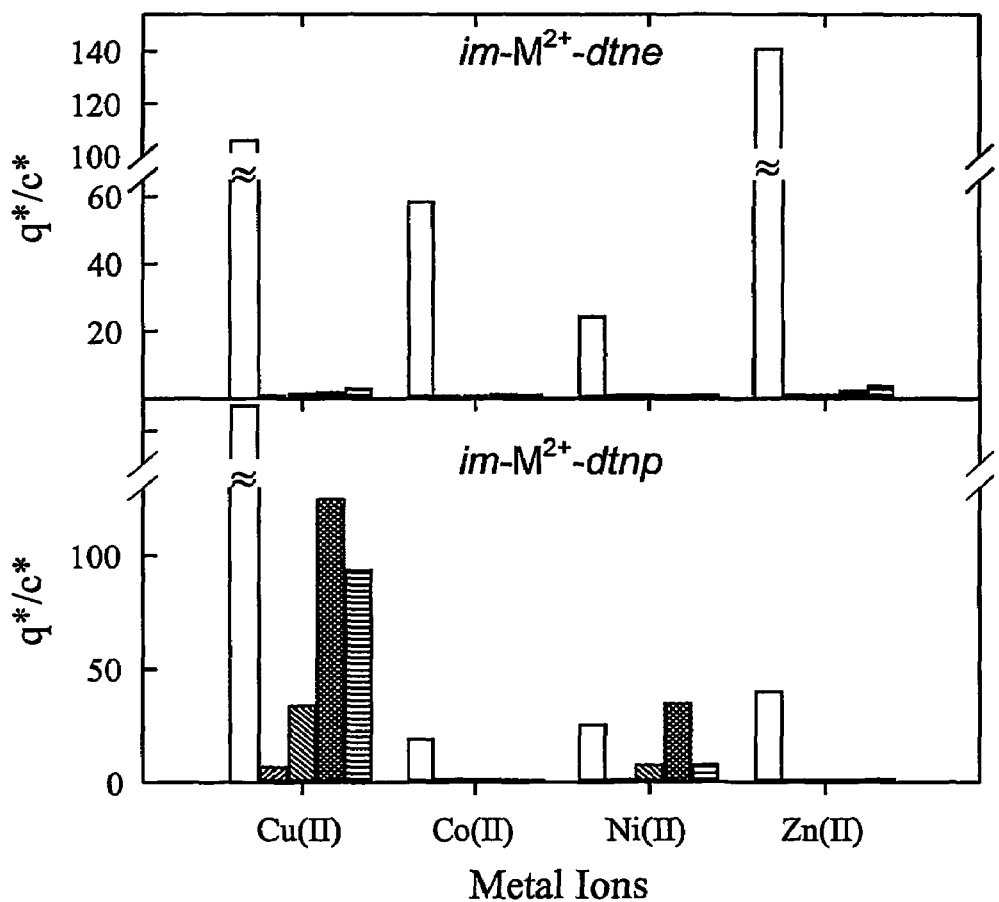

FIG. 25. The binding of horse muscle myoglobin (HMYO) to im-M$^{2+}$-dtne and im-M$^{2+}$-dtnp Sepharose CL-6B adsorbents under different pH conditions. In this study, the buffer conditions used were: ☐---buffer A, 20 mM sodium acetate/500 mM NaCl, pH 4.0; ▨---buffer B, 20 mM potassium phosphate/500 mM NaCl, pH 6.0; ▧---buffer C, 20 mM potassium phosphate/500 mM NaCl, pH 7.0; ▦---buffer D, 20 mM potassium phosphate/500 mM NaCl, pH 8.0; ▤---buffer E, 20 mM sodium bicarbonate/500 mM NaCl, pH 9.5. The Y-axis (q*/c*), as the capacity factor, indicates the apparent affinity of IMAC adsorbents for proteins based on the ration of the amount of protein bound on the adsorbent and amount of protein in solution at equilibrium.

Figure 26:
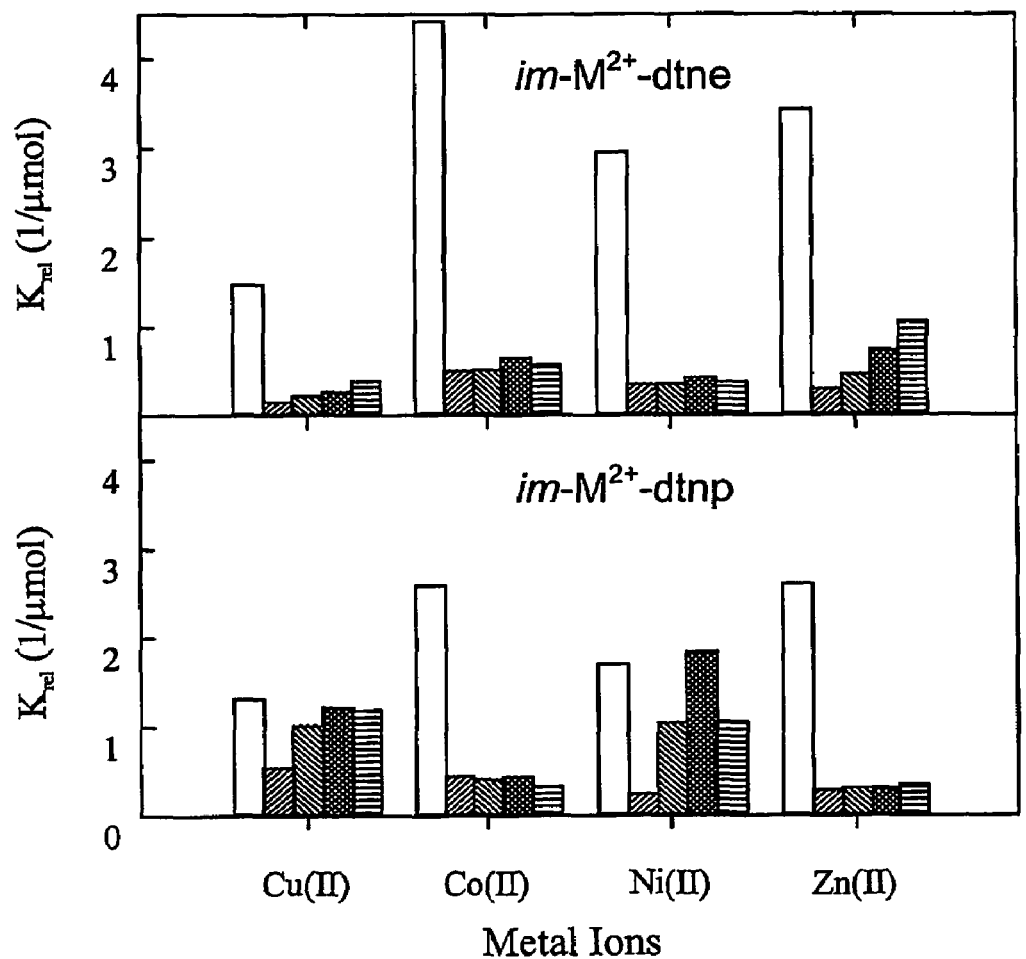

FIG. 26. The binding of horse muscle myoglobin (HMYO) to im-M$^{2+}$-dtne and im-M$^{2+}$-dtnp Sepharose CL-6B adsorbents under different pH conditions. In this study, the buffer conditions used were: ☐---buffer A, 20 mM sodium acetate/500 mM NaCl, pH 4.0; ▨---buffer B, 20 mM potassium phosphate/500 mM NaCl, pH 6.0; ▧---buffer C, 20 mM potassium phosphate/500 mM NaCl, pH 7.0; ▦---buffer D, 20 mM potassium phosphate/500 mM NaCl, pH 8.0; ▤---buffer E, 20 mM sodium bicarbonate/500 mM NaCl, pH 9.5. The Y-axis, the relative binding constant, K$_{rel}$ (1/μmol), indicates the relative binding capacity based on per mole of metal ion immobilised in adsorbents at equilibrium.

Figure 27:
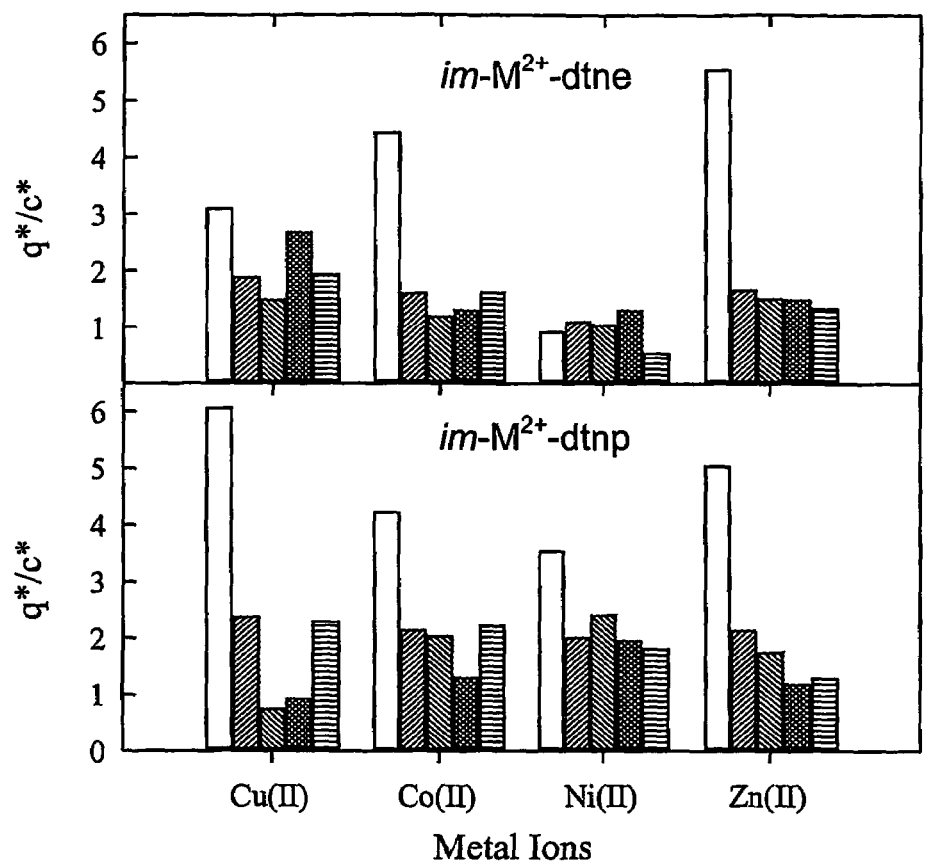

FIG. 27. The binding of horse heart cyclochrome c (HCC) to im-M$^{2+}$-dtne and im-M$^{2+}$-dtnp Sepharose CL-6B adsorbents under different pH conditions. In this study, the buffer conditions used were: ☐---buffer A, 20 mM sodium acetate/500 mM NaCl, pH 4.0; ▨---buffer B, 20 mM potassium phosphate/500 mM NaCl, pH 6.0; ▧---buffer C, 20 mM potassium phosphate/500 mM NaCl, pH 7.0; ▦---buffer D, 20 mM potassium phosphate/500 mM NaCl, pH 8.0; ▤---buffer E, 20 mM sodium bicarbonate/500 mM NaCl, pH 9.5. The Y-axis q*/c*, as the capacity factor, indicates the apparent affinity of IMAC adsorbents for proteins based on the ratio of the amount of protein bound on the adsorbent and amount of protein in solution at equilibrium.

Figure 28:
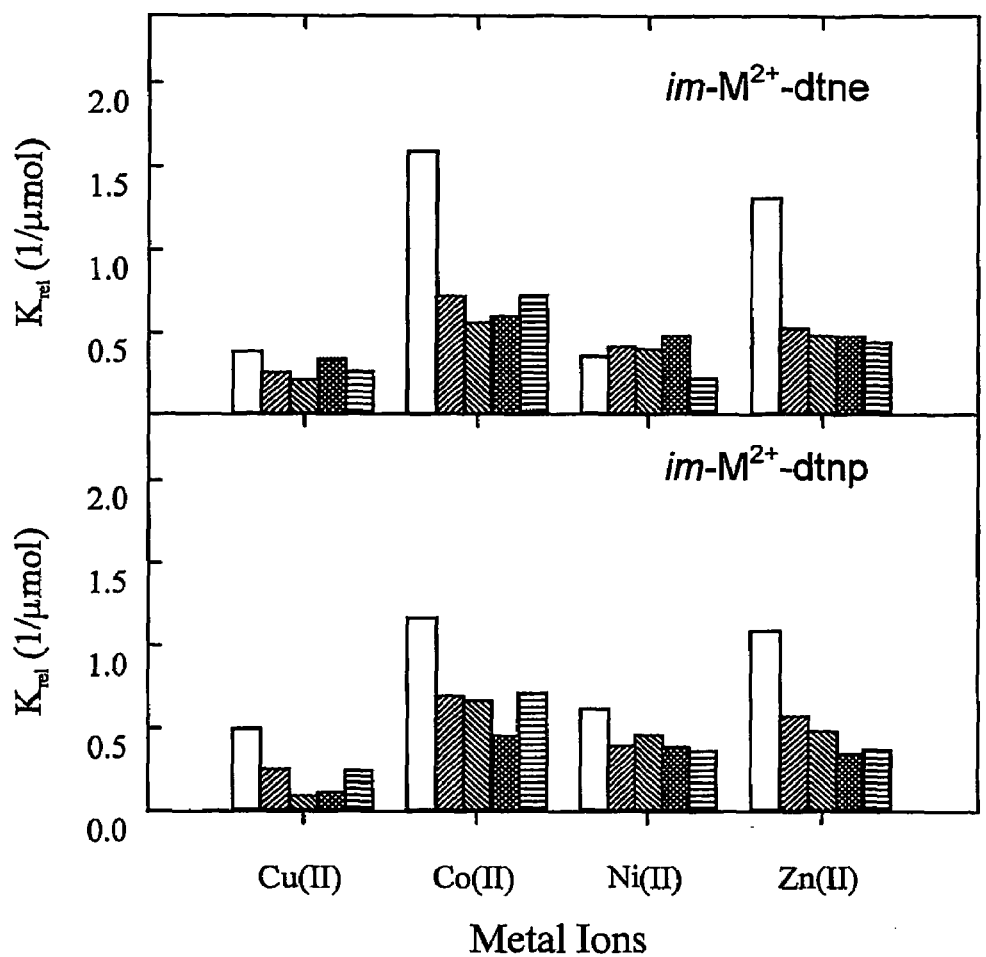

FIG. 28. The binding of horse heart cyclochrome c (HCC) to im-M$^{2+}$-dtne and im-M$^{2+}$-dtnp Sepharose CL-6B adsorbents under different pH conditions. In this study, the buffer conditions used were: ☐---buffer A, 20 mM sodium acetate/500 mM NaCl, pH 4.0; ▨---buffer B, 20 mM potassium phosphate/500 mM NaCl, pH 6.0; ▧---buffer C, 20 mM potassium phosphate/500 mM NaCl, pH 7.0; ▓---buffer D, 20 mM potassium phosphate/500 mM NaCl, pH 8.0; ☰---buffer E, 20 mM sodium bicarbonate/500 mM NaCl, pH 9.5. The Y-axis, relative binding constant, $K_{rel}$ (1/µmol), indicates the relative binding capacity based on per mole of metal ion immobilised in adsorbents at equilibrium.

Figure 29:
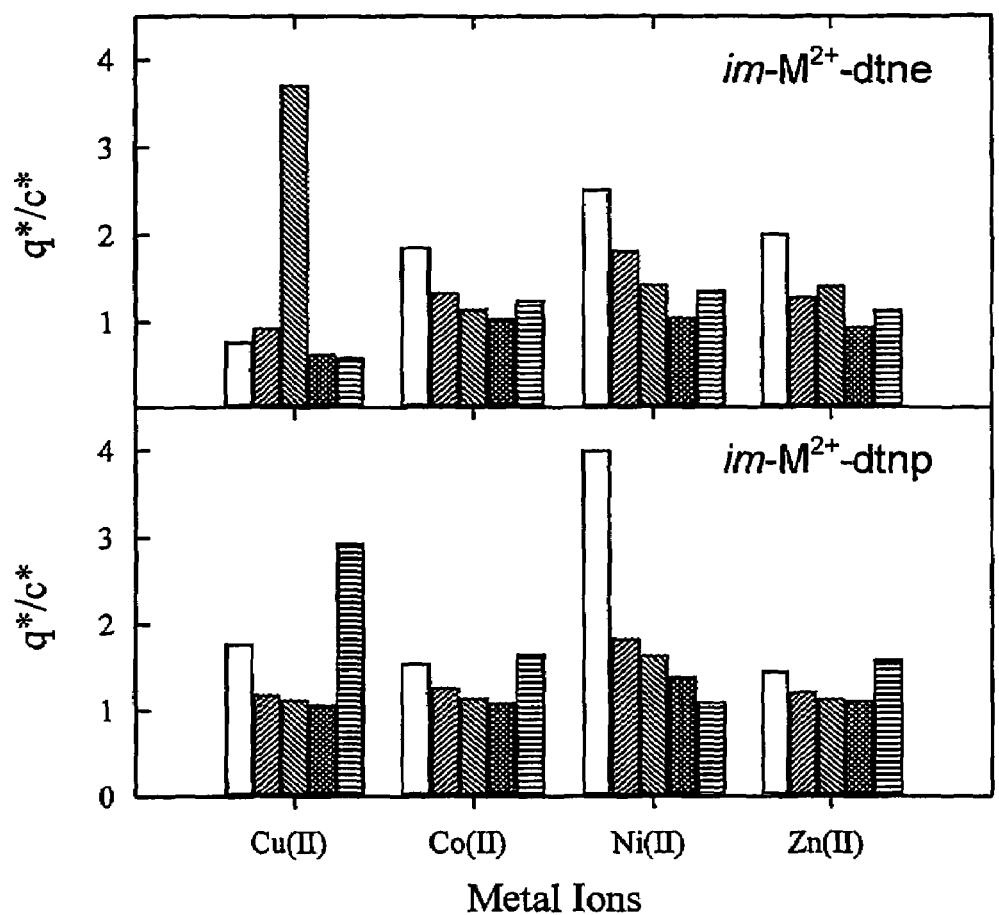

FIG. 29. The binding of hen egg white lysozyme (HEWL) to im-$M^{2+}$-dtne and im-$M^{2+}$-dtnp Sepharose CL-6B adsorbents under different pH conditions. In this study, the buffer conditions were: ☐---buffer A, 20 mM sodium acetate/500 mM NaCl, pH 4.0; ▨---buffer B, 20 mM potassium phosphate/500 mM NaCl, pH 6.0; ▧---buffer C, 20 mM potassium phosphate/500 mM NaCl, pH 7.0; ▓---buffer D, 20 mM potassium phosphate/500 mM NaCl, pH 8.0; ☰---buffer E, 20 mM sodium bicarbonate/500 mM NaCl, pH 9.5. The Y-axis q*/c*, as the capacity factor, indicates the apparent affinity of IMAC adsorbents for proteins based on the ration of the amount of protein bound on the adsorbent and amount of protein in solution at equilibrium.

Figure 30:
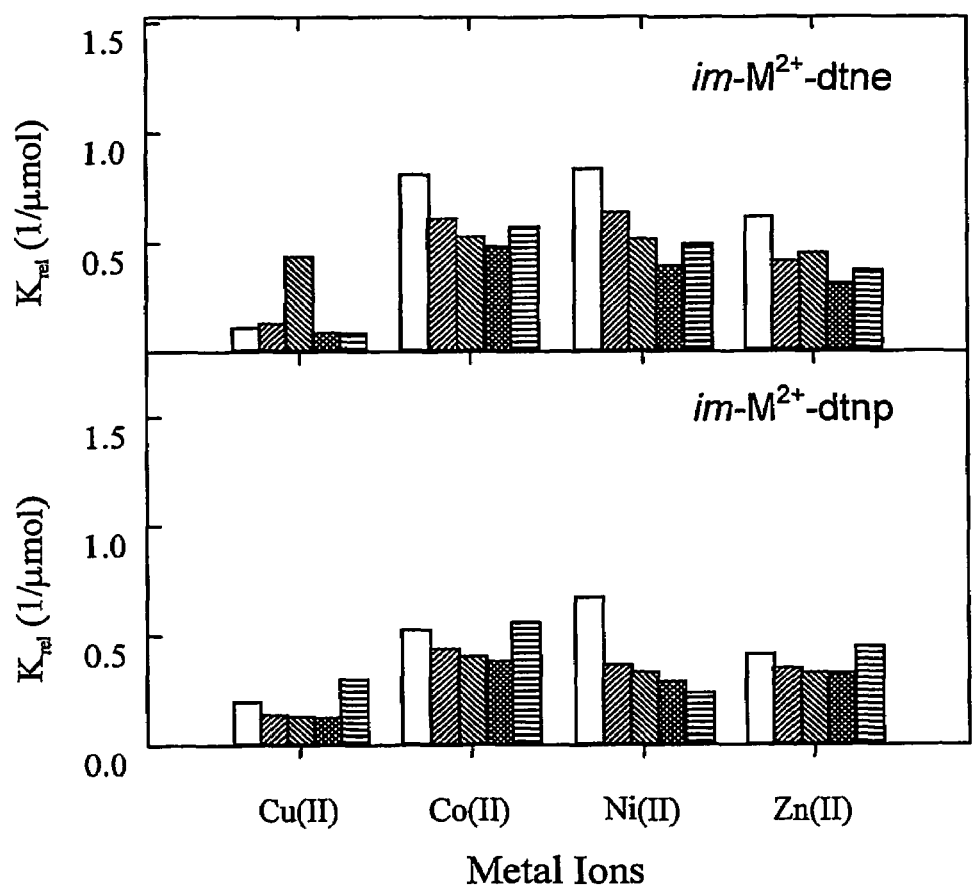

FIG. 30. The binding of hen egg white lysozyme (HEWL) to im-$M^{2+}$-dtne and im-$M^{2+}$-dtnp Sepharose CL-6B adsorbents under different pH conditions. In this study, the buffer conditions were: ☐---buffer A, 20 mM sodium acetate/500 mM NaCl, pH 4.0; ▨---buffer B, 20 mM potassium phosphate/500 mM NaCl, pH 6.0; ▧---buffer C, 20 mM potassium phosphate/500 mM NaCl, pH 7.0; ▓---buffer D, 20 mM potassium phosphate/500 mM NaCl, pH 8.0; ☰---buffer E, 20 mM sodium bicarbonate/500 mM NaCl, pH 9.5. The Y-axis, $K_{rel}$ (1/µmol), indicates the relative binding capacity based on per mole of metal ion immobilised in adsorbents at equilibrium.

Figure 31:
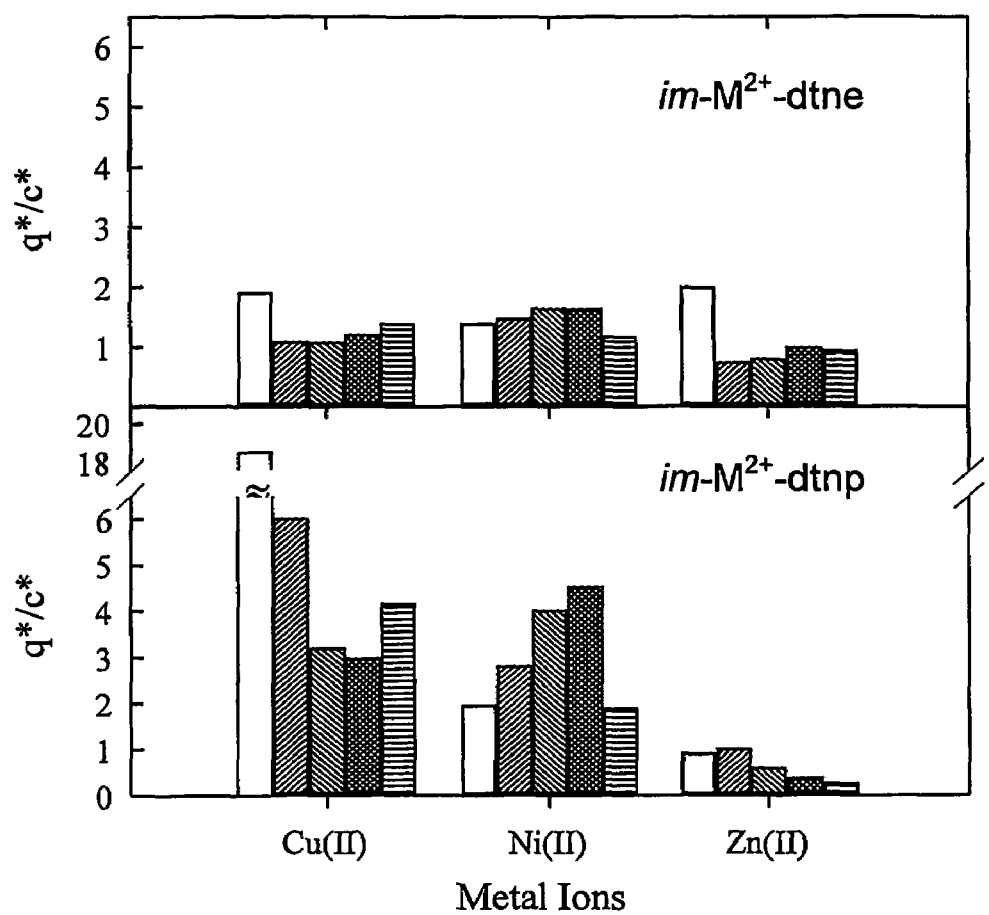

FIG. 31. The binding of bovine a-lactalbumin (αLAC) to im-$M^{2+}$-dtne and im-$M^{2+}$-dtnp Sepharose CL-6B adsorbents under different pH conditions. In this study, the buffer conditions were: ☐---buffer A, 20 mM sodium acetate/500 mM NaCl, pH 4.0; ▨---buffer B, 20 mM potassium phosphate/500 mM NaCl, pH 6.0; ▧---buffer C, 20 mM potassium phosphate/500 mM NaCl, pH 7.0; ▓---buffer D, 20 mM potassium phosphate/500 mM NaCl, pH 8.0; ☰---buffer E, 20 mM sodium bicarbonate/500 mM NaCl, pH 9.5. The Y-axis q*/c*, as the capacity factor, indicates the apparent affinity of IMAC adsorbents for proteins based on the ration of the amount of protein bound on the adsorbent and amount of protein in solution at equilibrium FIG. 32. The binding of bovine a-lactalbumin (αLAC) to im-$M^{2+}$-dtne and im-$M^{2+}$-dtnp Sepharose CL-6B adsorbents under different pH conditions. In this study, the buffer conditions were: ☐---buffer A, 20 mM sodium acetate/500 mM NaCl, pH 4.0; ▨---buffer B, 20 mM potassium phosphate/500 mM NaCl, pH 6.0; ▧---buffer C, 20 mM potassium phosphate/500 mM NaCl, pH 7.0; ▓---buffer D, 20 mM potassium phosphate/500 mM NaCl, pH 8.0; ☰---buffer E, 20 mM sodium bicarbonate/500 mM NaCl, pH 9.5. The Y-axis, $K_{rel}$ (1/µmol), indicates the relative binding capacity based on per mole of metal ion immobilized in adsorbents at equilibrium.

Figure 33:
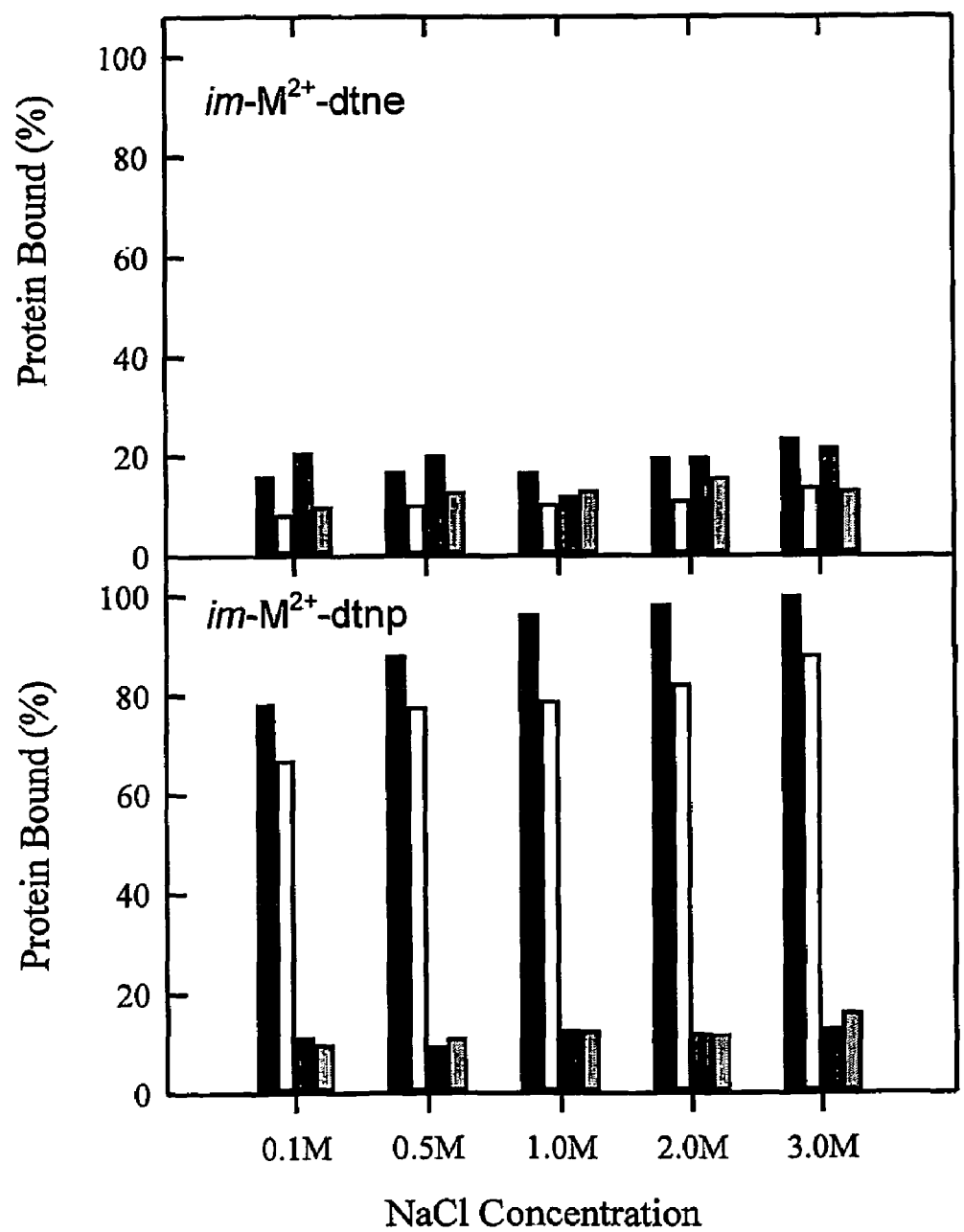

FIG. 33. Influence of ionic strength on binding of the model protein HMYO to im-$M^{2+}$-dtne and im-$M^{2+}$-dtnp Sepharose™ CL-6B adsorbents. Immobilized metal ions were as follows: $Cu^{2+}$ (■), $Ni^{2+}$ (☐), $Zn^{2+}$ (▨), and $Co^{2+}$ (▧). The buffer conditions were: buffer A, 20 mM potassium phosphate buffer/100 mM NaCl, pH 8.0; buffer B, 20 mM potassium phosphate buffer/500 mM NaCl, pH 8.0; buffer C, 20 mM potassium phosphate buffer/1 M NaCl, pH 8.0; buffer D, 20 mM potassium phosphate buffer/2 M NaCl, pH 8.0; buffer E, 20 mM potassium phosphate buffer/3 M NaCl, pH 8.0.

Figure 34:
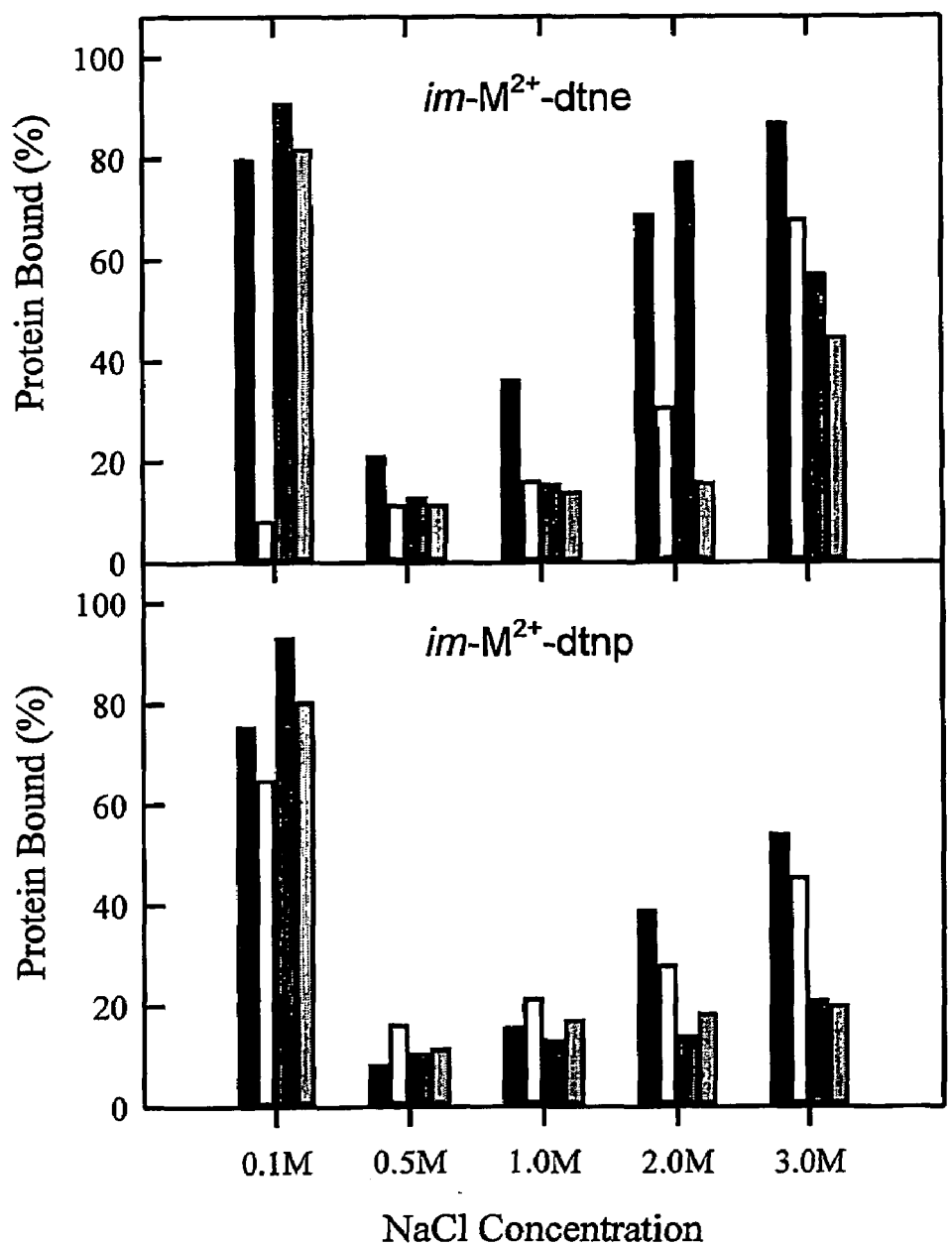

FIG. 34. Influence of ionic strength on binding of the model protein HCC to im-$M^{2+}$-dtne and im-$M^{2+}$-dtnp Sepharose™ CL-6B adsorbents. Immobilized metal ions were as follows: $Cu^{2+}$ (■), $Ni^{2+}$ (☐), $Zn^{2+}$ (▨) and $Co^{2+}$ (▧). The buffer conditions were: buffer A, 20 mM potassium phosphate buffer/100 mM NaCl, pH 8.0; buffer B, 20 mM potassium phosphate buffer/500 mM NaCl, pH 8.0; buffer C, 20 mM potassium phosphate buffer/1 M NaCl, pH 8.0; buffer D, 20 mM potassium phosphate buffer/2 M NaCl, pH 8.0; buffer E, 20 mM potassium phosphate buffer/3 M NaCl, pH 8.0.

Figure 35:
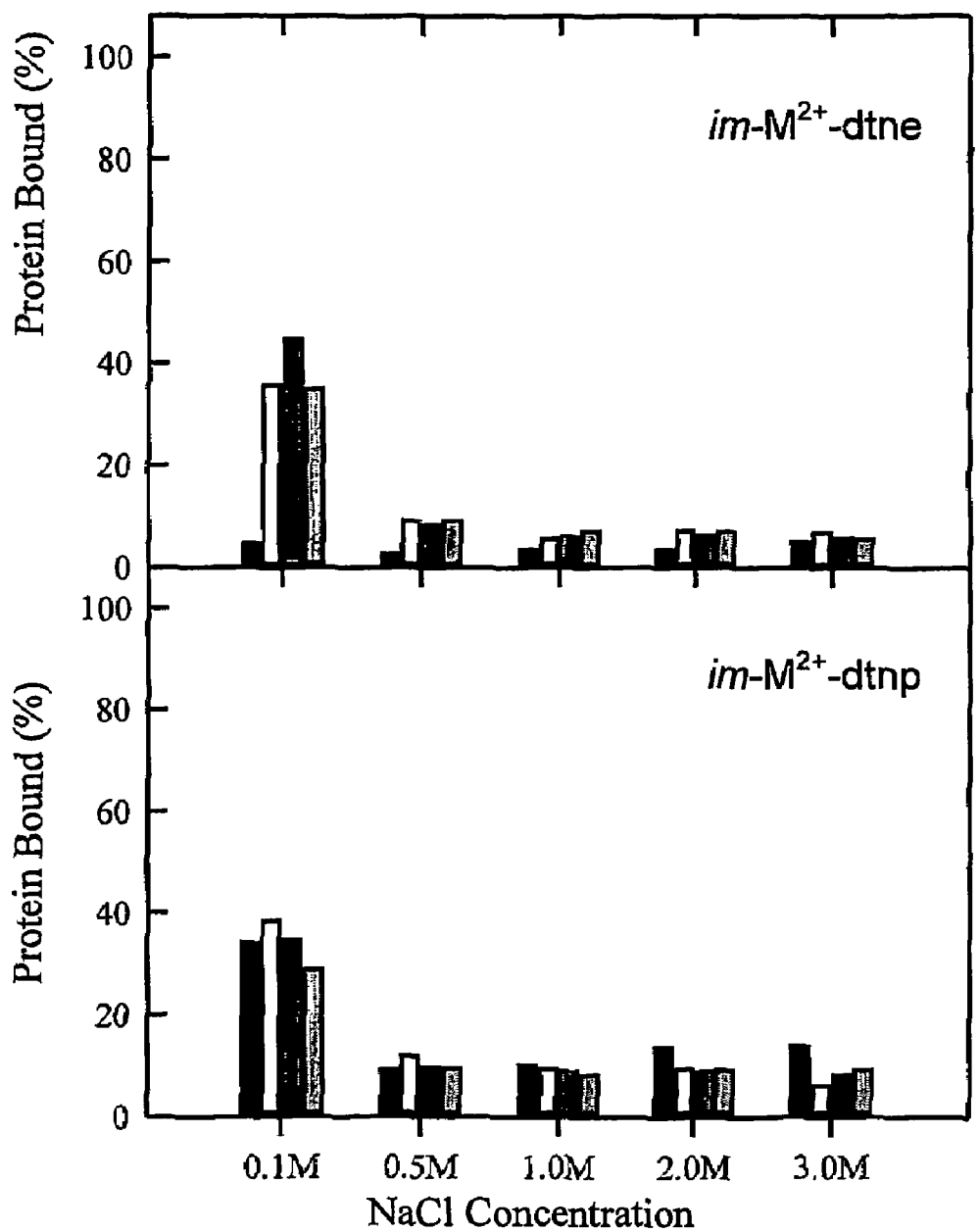

FIG. 35. Influence of ionic strength on binding of the model protein HEWL to im-$M^{2+}$-dtne and im-$M^{2+}$-dtnp Sepharose™ CL-6B adsorbents. Immobilized metal ions were as follows: $Cu^{2+}$ (■), $Ni^{2+}$ (☐), $Zn^{2+}$ (▨), and $Co^{2+}$ (▧). The buffer conditions were: buffer A, 20 mM potassium phosphate buffer/100 mM NaCl, pH 8.0; buffer B, 20 mM potassium phosphate buffer/500 mM NaCl, pH 8.0; buffer C, 20 mM potassium phosphate buffer/1 M NaCl, pH 8.0; buffer D, 20 mM potassium phosphate buffer/2 M NaCl, pH 8.0; buffer E, 20 mM potassium phosphate buffer/3 M NaCl, pH 8.0.

Figure 36:
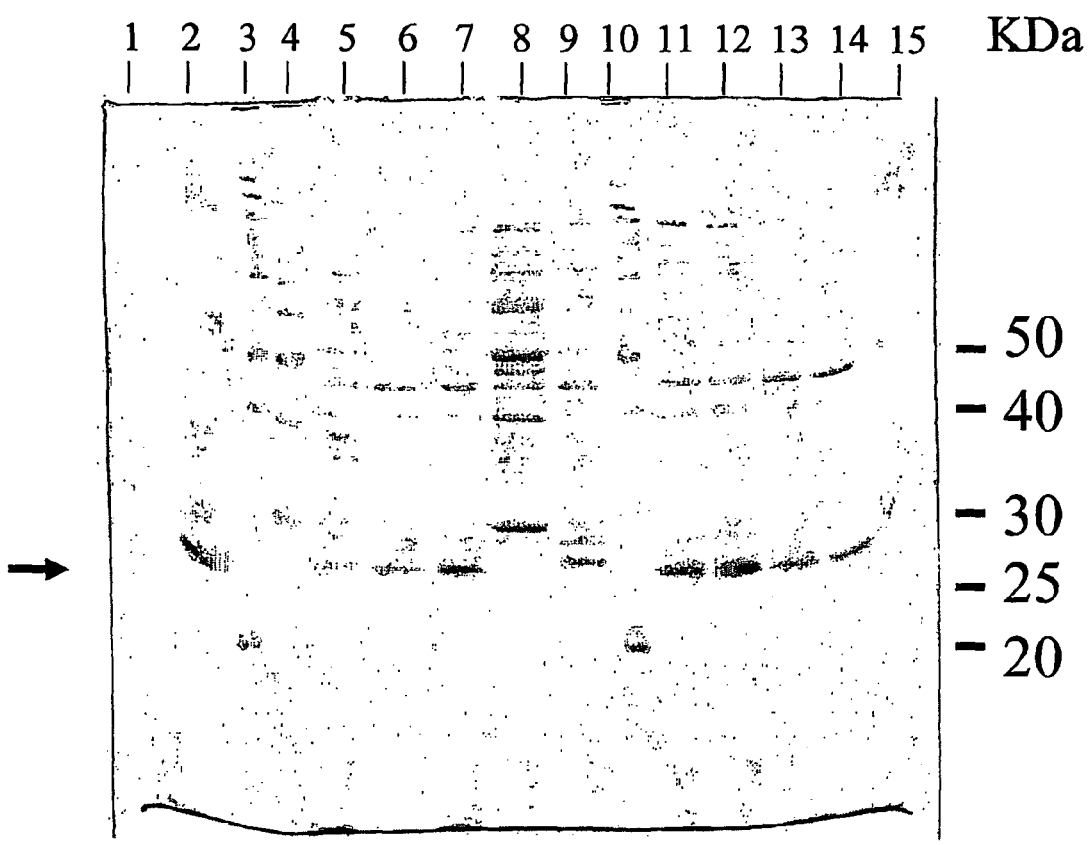

FIG. 36. SDS-PAGE analysis of various clones following small-scale expression of the N-terminally $(His)_6$-tagged tagged recombinant glutathione S-transferase (r-GST) fusion protein GST-CT1. Aliquots of cell lysate (see Example 90 and 105) were mixed with SDS loading buffer (reducing) and heated for 1 min. at 100° C. Samples were then loaded onto a 12% SDS-polyacrylamide gel and run for an appropriate period of time. Approximately 60 µl of cell lysate and 30 µl of the molecular weight markers [BenchMark Protein Ladder (Gibco BRL, Bethesda, Md., U.S.A) and 10 kDa Protein Ladder (Gibco BRL)] were loaded onto the gel. A pGEX3XGST transformant (Amersham Pharmacia, Uppsala, Sweden) served as the positive control. The r-GST component of the N-terminal-tagged r-GST fusion protein is truncated by 1 amino acid at the C-terminal end. The parental GST is expressed as the full-length protein with an additional 14 C-terminal amino acids. Consequently, the parental GST contains an additional 15 amino acids at its C-terminal end and therefore runs approx. 1.65 kDa larger than the GST component of the N-terminal tagged r-GST fusion protein. The *E. coli* strain JM105 cells trans-formed with pTrc served as the negative control. In order to visualize bands, the gel was stained with Coomassie Blue.

Key for Gel 1 shown as FIG. 36: Lane 1, GST-CT1 clone no. 1; Lane 2, GST-CT1 clone no. 2; Lane 5, GST-CT1 clone no. 3; Lane 6, GST-CT1 clone no. 4; Lane 7, GST-CT1 clone no. 5; Lane 11, GST-CT1 clone no. 6; Lane 12, GST-CT1 clone no. 7; Lane 13, GST-CT1 clone no. 8; Lane 14, GST-CT1 clone no. 9; Lane 15, GST-CT1 clone no. 10; Lane 8, negative control consisting of *E. coli* JM105 transformed with pTrc; Lane 9, positive control consisting of *E. coli* JM105 transformed with pGEX3XGST. Molecular weight markers are shown in Lanes 3, 4 and 10.

Figure 37:
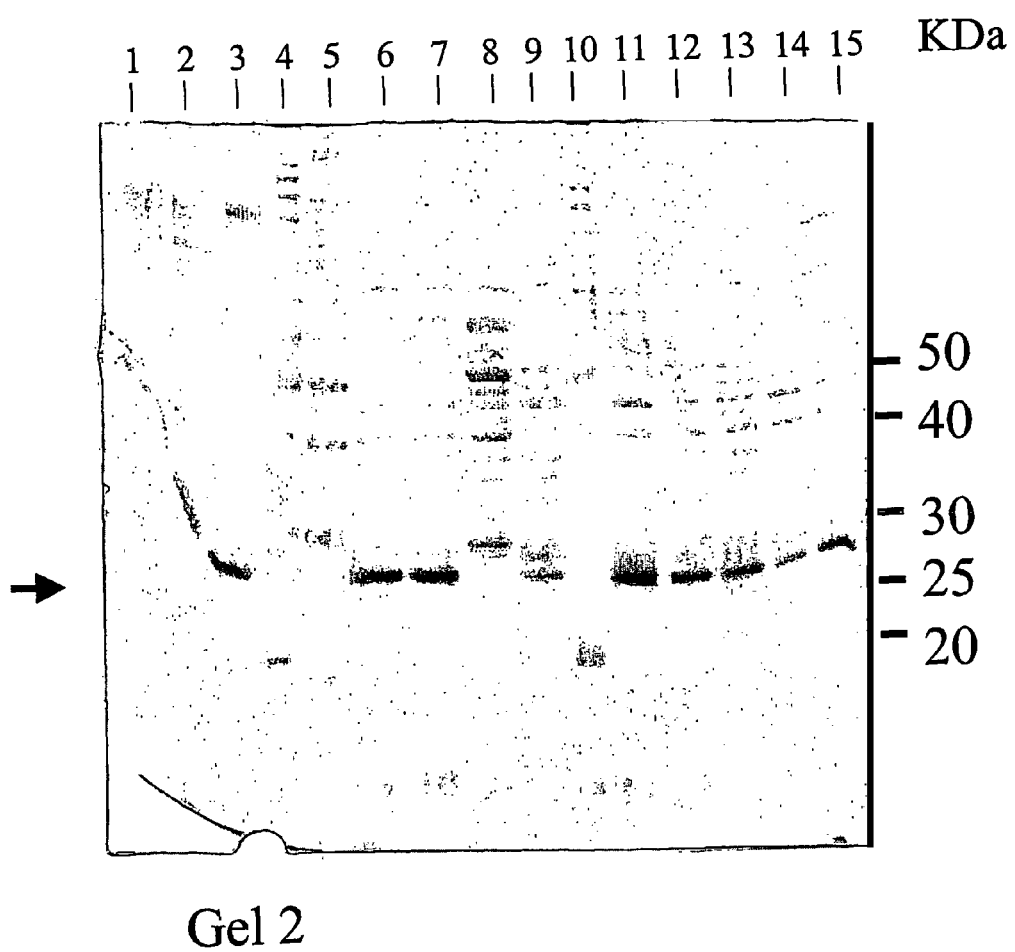

FIG. 37. SDS-PAGE analysis of various clones following small scale expression of the N-terminally (His-Gln)$_6$-tagged recombinant glutathione S-transferase (r-GST) fusion protein GST-CT2. Aliquots of cell lysate (see Example 90 and 105) were mixed with SDS loading buffer (reducing) and heated for 1 min. at 10° C. Samples were then loaded onto a 12% SDS-polyacrylamide gel and run for an appropriate period of time. Approximately 60 μl of cell lysate and 30 μl of the molecular weight markers [BenchMark Protein Ladder (Gibco BRL, Bethesda, Md., U.S.A) and 10 kDa Protein Ladder (Gibco BRL)] were loaded onto the gel. A pGEX3XGST transformant (Amersham Pharmacia, Uppsala, Sweden) served as the positive control. The r-GST component of the N-terminal-tagged r-GST fusion protein is truncated by 1 amino acid at the C-terminal end. The parental GST is expressed as the full-length protein with an additional 14 C-terminal amino acids. Consequently, the parental GST contains an additional 15 amino acids at its C-terminal end and therefore runs approx. 1.65 Kda larger than the GST component of the N-terminal tagged r-GST fusion protein. The *E. coli* strain JM105 cells trans-formed with pTrc served as the negative control. In order to visualize bands, the gel was stained with Coomassie Blue.

Key for Gel 2 shown as FIG. 37: Lane 1, GST-CT2 clone no. 1; Lane 2, GST-CT2 clone no. 2; Lane 3, GST-CT2 clone no. 3; Lane 6, GST-CT2 clone no. 4; Lane 7, GST-CT2 clone no. 5; Lane 11, GST-CT2 clone no. 6; Lane 12, GST-CT2 clone no. 7; Lane 13, GST-CT2 clone no. 8; Lane 14, GST-CT2 clone no. 9; Lane 15, GST-CT2 clone no. 10; Lane 8, negative control consisting of *E. coli* JM105 transformed with pTrc; Lane 9, positive control consisting of *E. coli* JM105 transformed with pGEX3XGST. Molecular weight markers are shown in Lanes 4, 5 and 10.

Figure 38:
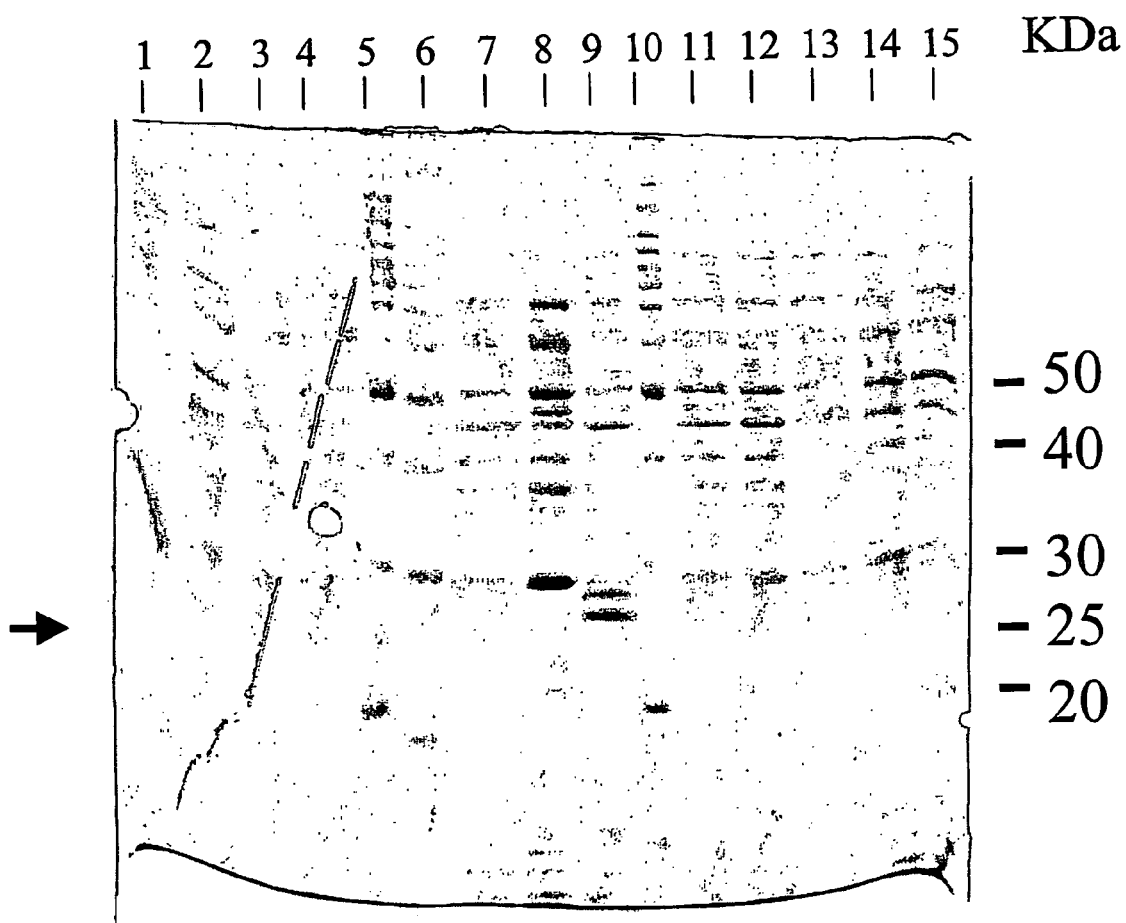

FIG. 38. SDS-PAGE analysis of various clones following small scale expression of the N-terminally tagged recombinant glutathione S-transferase (r-GST) fusion protein GST-NT1. Aliquots of cell lysate (see Example 90 and 107) were mixed with SDS loading buffer (reducing) and heated for 1 min. at 100° C. Samples were then loaded onto a 12% SDS-polyacrylamide gel and run for an appropriate period of time. Approximately 60 μl of cell lysate and 30 μl of the molecular weight markers [BenchMark Protein Ladder (Gibco BRL, Bethesda, Md., U.S.A) and 10 kDa Protein Ladder (Gibco BRL)] were loaded onto the gel. A pGEX3XGST transformant (Amersham Pharmacia, Uppsala, Sweden) served as the positive control. The r-GST component of the N-terminal-tagged r-GST fusion protein is truncated by 1 amino acid at the C-terminal end. The parental GST is expressed as the full-length protein with an additional 14 C-terminal amino acids. Consequently, the parental GST contains an additional 15 amino acids at its C-terminal end and therefore runs approx. 1.65 kDa larger than the GST component of the N-terminal tagged r-GST fusion protein. The *E. coli* strain JM105 cells transformed with pTrc served as the negative control. In order to visualize bands, the gel was stained with Coomassie Blue.

Key for Gel 3 shown as FIG. 38: Lane 1, GST-NT1 clone no. 1; Lane 2, GST-NT1 clone no. 2; Lane 3, GST-NT1 clone no. 3; Lane 4 GST-NT1 clone no. 4; Lane 7, GST-NT1 clone no. 5; Lane 11, GST-NT1 clone no. 6; Lane 12, GST-NT1 clone no. 7; Lane 13, GST-NT1 clone no. 8; Lane 14, GST-NT1 clone no. 9; Lane 15, GST-NT1 clone no. 10; Lane 8, negative control consisting of *E. coli* JM105 transformed with pTrc; Lane 9, positive control consisting of *E. coli* JM105 transformed with pGEX3XGST. Molecular weight markers are shown in Lanes 5, 6 and 10.

Figure 39:
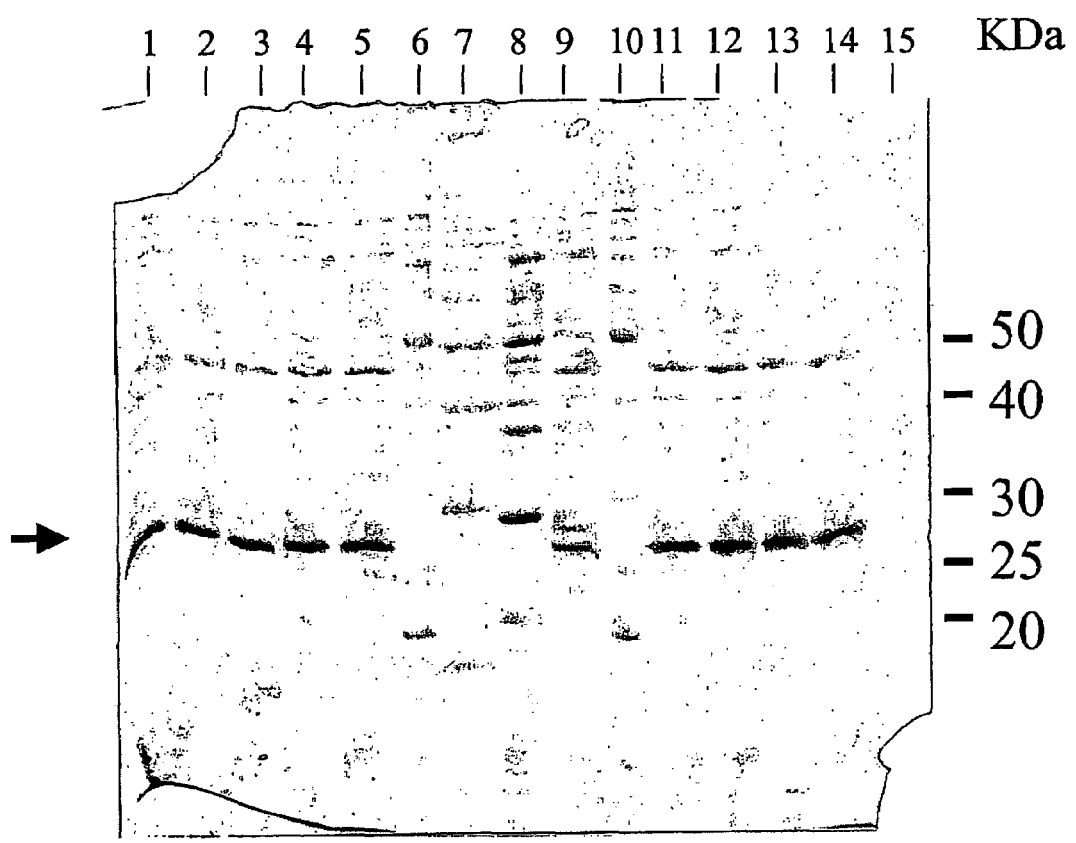

FIG. 39. SDS-PAGE analysis of various clones following small scale expression of the N-terminally tagged recombinant glutathione S-transferase (r-GST) fusion protein GST-NT2. Aliquots of cell lysate (see Example 90 and 108) were mixed with SDS loading buffer (reducing) and heated for 1 min. at 100° C. Samples were then loaded onto a 12% SDS-polyacrylamide gel and run for an appropriate period of time. Approximately 60 μl of cell lysate and 30 μl of the molecular weight markers [BenchMark Protein Ladder (Gibco BRL, Bethesda, Md., U.S.A) and 10 KDa Protein Ladder (Gibco BRL)] were loaded onto the gel. A pGEX3XGST transformant (Amersham Pharmacia, Uppsala, Sweden) served as the positive control. The r-GST component of the N-terminal-tagged r-GST fusion protein is truncated by 1 amino acid at the C-terminal end. The parental GST is expressed as the full-length protein with an additional 14 C-terminal amino acids. Consequently, the parental GST contains an additional 15 amino acids at its C-terminal end and therefore runs approx. 1.65 kDa larger than the GST component of the N-terminal tagged r-GST fusion protein. The *E. coli* strain JM105 cells transformed with pTrc served as the negative control. In order to visualize bands, the gel was stained with Coomassie Blue.

Key for Gel 4 shown as FIG. 39: Lane 1, GST-NT2 clone no. 1; Lane 2, GST-NT2 clone no. 2; Lane 3, GST-NT2 clone no. 3; Lane 4 GST-NT2 clone no. 4; Lane 5, GST-NT2 clone no. 5; Lane 11, GST-NT2 clone no. 6; Lane 12, GST-NT2 clone no. 7; Lane 13, GST-NT2 clone no. 8; Lane 14, GST-NT2 clone no. 9; Lane 8, negative control consisting of *E. coli* JM105 transformed with pTrc; Lane 9, positive control consisting of *E. coli* JM105 transformed with pGEX3XGST. Molecular weight markers are shown in Lanes 6, 7 and 10.

Figure 40:
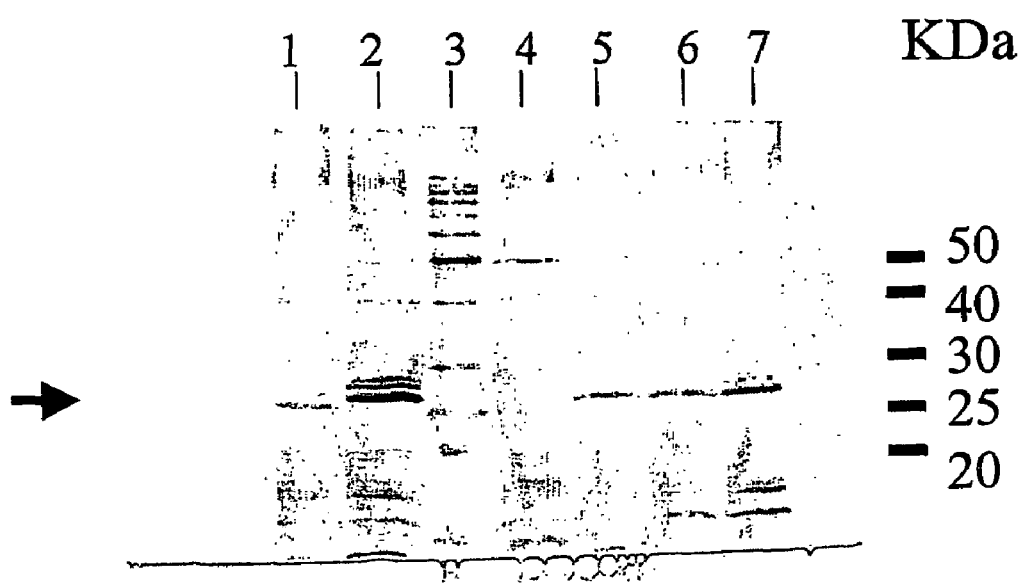

FIG. 40 SDS-PAGE analysis of crude cell lysates following small scale protein expression of the N-terminally tagged recombinant glutathione S-transferase (r-GST) fusion proteins from clones selected for their high expression levels. Aliquots of cell lysate (see Example 90 and 108) were mixed with SDS loading buffer (reducing) and heated for 1 min. at 100° C. Samples were then loaded onto a 12% SDS-polyacrylamide gel and run for an appropriate period of time. Approximately 2 μl of cell lysate and 1 μl of the molecular weight marker [BenchMark Protein Ladder (Gibco BRL, Bethesda, Md., U.S.A)] were loaded onto the gel. A pGEX3XGST transformant (Amersham Pharmacia, Uppsala, Sweden) served as the positive control. The r-GST component of the N-terminal-tagged r-GST fusion protein is truncated by 1 amino acid at the C-terminal end. The parental GST is expressed as the full-length protein with an additional 14 C-terminal amino acids. Consequently, the parental GST contains an additional 15 amino acids at its C-terminal end and therefore runs approx. 1.65 Kda larger than the GST component of the N-terminal tagged r-GST fusion proteins. The *E. coli* strain JM105 cells trans-formed with pTrc served as the negative control. In order to visualize bands, the gel was silver stained. Key for Gel 5 shown as FIG. 40: Lane 1, GST-CT1 clone no. 7; lane 2, GST-CT2 clone no. 6; lane 6, GST-NT1 clone no. 1; lane 7 GST-NT2 clone no. 7; lane 4, negative control consisting of *E. coli* JM105 transformed with pTrc;

lane 5 positive control consisting of E. coli JM105 transformed with pGEX3XGST. The molecular weight marker is shown in lane 3.

Figure 41:
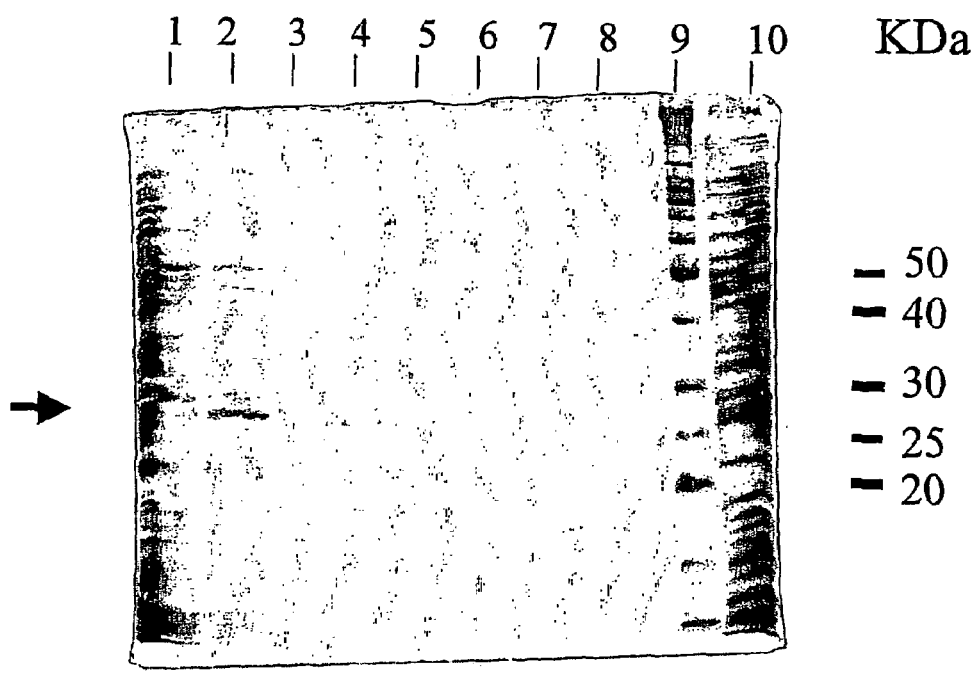

FIG. 41 SDS-PAGE analysis of various fractions collected from the batch purification of the N-terminally (His)$_6$-tagged recombinant glutathione S-transferase (r-GST) fusion protein GST-CT1 obtained from clones selected for their expression levels. Aliquots of cell lysate and fractions collected from the batch purification (see Example 93) were mixed with SDS loading buffer (reducing) and heated at 100° C. for 90 seconds. Approximately 10 µl of purification fraction samples, 5 µl of positive and negative control cell lysate and 1.25 µl of cell lysate containing the recombinant fusion protein and 1 µl of the molecular weight marker [BenchMark Protein Ladder (Gibco BRL, Bethesda, Md., U.S.A)] were loaded onto a 12% SDS-polyacrylamide gel and run for an appropriate period of time. In order to visualize bands, the gel was silver stained. A pGEX3XGST transformant (Amersham Pharmacia, Uppsala, Sweden) served as the positive control. The r-GST component of the N-terminal-tagged r-GST fusion protein is truncated by 1 amino acid at the C-terminal end. The parental GST is expressed as the full-length protein with an additional 14 C-terminal amino acids. Consequently, the parental GST contains an additional 15 amino acids at its C-terminal end and therefore runs approx. 1.65 kDa larger than the GST component of the N-terminal tagged r-GST fusion proteins. The E. coli strain JM105 cells transformed with pTrc served as the negative control.

Key for Gel 6 shown as FIG. 41: Lanes 3-5 contain GST-CT1 samples collected from a Ni$^{2+}$-tacn Sepharose™ CL-6B column whilst lanes 6-8 contain samples from a Ni$^{2+}$-NTA Sepharose™ CL-6B column. Lanes 3 and 6, correspond to the wash 2 step; lanes 4 and 7 correspond to the elution 1 step; Lanes 5 and 8, correspond to the elution 2 step; Lane 1, negative control consisting of E. coli JM105 transformed with pTrc; Lane 2, positive control consisting of E. coli JM105 transformed with pGEX3XGST; Lane 10, crude cell lysate. Molecular weight marker is shown in Lane 9.

Figure 42:
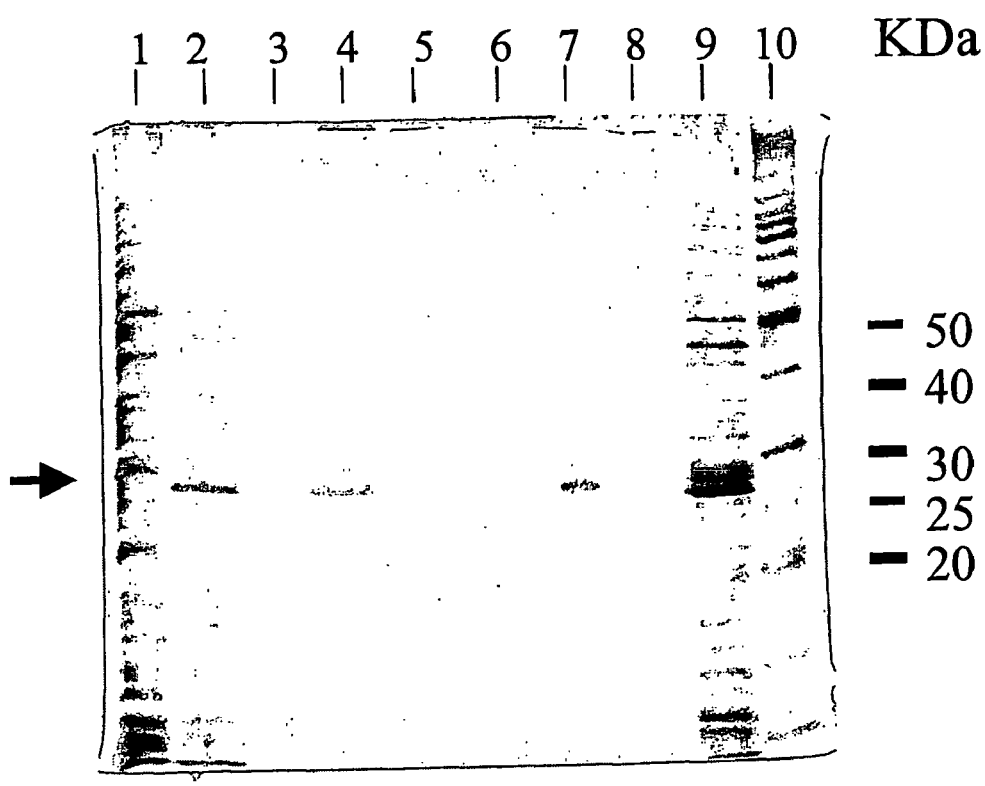

FIG. 42. SDS-PAGE analysis of various fractions collected from the batch purification of the N-terminally (His-Gln)$_6$-tagged recombinant glutathione S-transferase (r-GST) fusion protein GST-CT2 obtained from clones selected for high expression levels Aliquots of cell lysate and fractions collected from the batch purification (see Example 111) were mixed with SDS loading buffer (reducing) and heated at 100° C. for 90 seconds. Approximately 10 µl of purification fraction samples, 5 µl of positive and negative control cell lysate and 1.25 µl of cell lysate containing the recombinant fusion protein and 1 µl of the molecular weight markers [BenchMark Protein Ladder (Gibco BRL, Bethesda, Md., U.S.A)] were loaded onto a 12% SDS-polyacrylamide gel and run for an appropriate period of time. In order to visualize bands, the gel was silver stained. A pGEX3XGST transformant (Amersham Pharmacia, Uppsala, Sweden) served as the positive control. The r-GST component of the N-terminal-tagged r-GST fusion protein is truncated by 1 amino acid at the C-terminal end. The parental GST is expressed as the full-length protein with an additional 14 C-terminal amino acids. Consequently, the parental GST contains an additional 15 amino acids at its C-terminal end and therefore runs approx. 1.65 kDa larger than the GST component of the N-terminal tagged r-GST fusion proteins. The E. coli strain JM105 cells transformed with pTrc served as the negative control.

Key for Gel 7 shown as FIG. 42: Lanes 3-5 contain GST-CT2 samples collected from a Ni$^{2+}$-tacn Sepharose™ CL-6B column whilst Lanes 6-8 contain samples from a Ni$^{2+}$-NTA Sepharose™ CL-6B column. Lanes 3 and 6 correspond to the wash 2 step; Lanes 4 and 7 correspond to the elution 1 step; Lanes 5 and 8, correspond to the elution 2 step; Lane 1, negative control consisting of E. coli JM105 transformed with pTrc; Lane 2, positive control consisting of E. coli JM105 transformed with pGEX3XGST; Lane 9, crude cell lysate. Molecular weight marker is shown in Lane 10.

Figure 43:
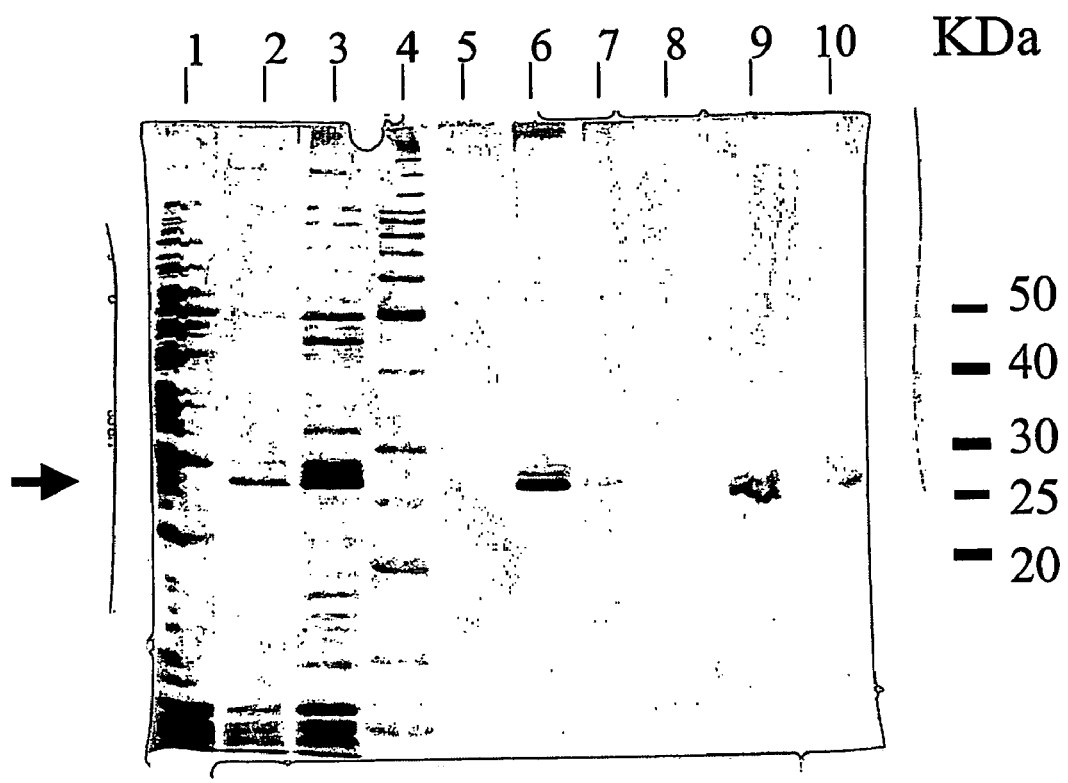

FIG. 43. SDS-PAGE analysis of various fractions collected from the batch purification of the N-terminally tagged recombinant glutathione S-transferase (r-GST) fusion protein GST-NT1 obtained from clones selected for their expression levels. Aliquots of cell lysate and fractions collected from the batch purification (see Example 112) were mixed with SDS loading buffer (reducing) and heated at 100° C. for 90 seconds. Approximately 10 µl of purification fraction samples, 5 µl of positive and negative control cell lysate and 1.25 µl of cell lysate containing the recombinant fusion protein and 1 µl of the molecular weight markers [BenchMark Protein Ladder (Gibco BRL, Bethesda, Md., U.S.A)] were loaded onto a 12% SDS-polyacrylamide gel and run for an appropriate period of time. In order to visualize bands, the gel was silver stained. A pGEX3XGST transformant (Amersham Pharmacia, Uppsala, Sweden) served as the positive control. The r-GST component of the N-terminal-tagged r-GST fusion protein is truncated by 1 amino acid at the C-terminal end. The parental GST is expressed as the full-length protein with an additional 14 C-terminal amino acids. Consequently, the parental GST contains an additional 15 amino acids at its C-terminal end and therefore runs approx. 1.65 kDa larger than the GST component of the N-terminal tagged r-GST fusion proteins. The E. coli strain JM105 cells trans-formed with pTrc served as the negative control.

Key for Gel 8 shown as FIG. 43: Lanes 5-7 contain GST-NT1 samples collected from a Ni$^{2+}$-tacn Sepharose CL-6B column whilst Lanes 8-10 contain samples from a Ni$^{2+}$-NTA Sepharose CL-6B column. Lanes 5 and 8 correspond to the wash 2 step; Lanes 6 and 9 correspond to the elution 1 step; Lanes 7 and 10, correspond to the elution 2 step; Lane 1, negative control consisting of E. coli JM105 trans-formed with pTrc; Lane 2, positive control consisting of E. coli JM105 transformed with pGEX3XGST; Lane 3, crude cell lysate. Molecular weight marker is shown in Lane 4.

Figure 44:
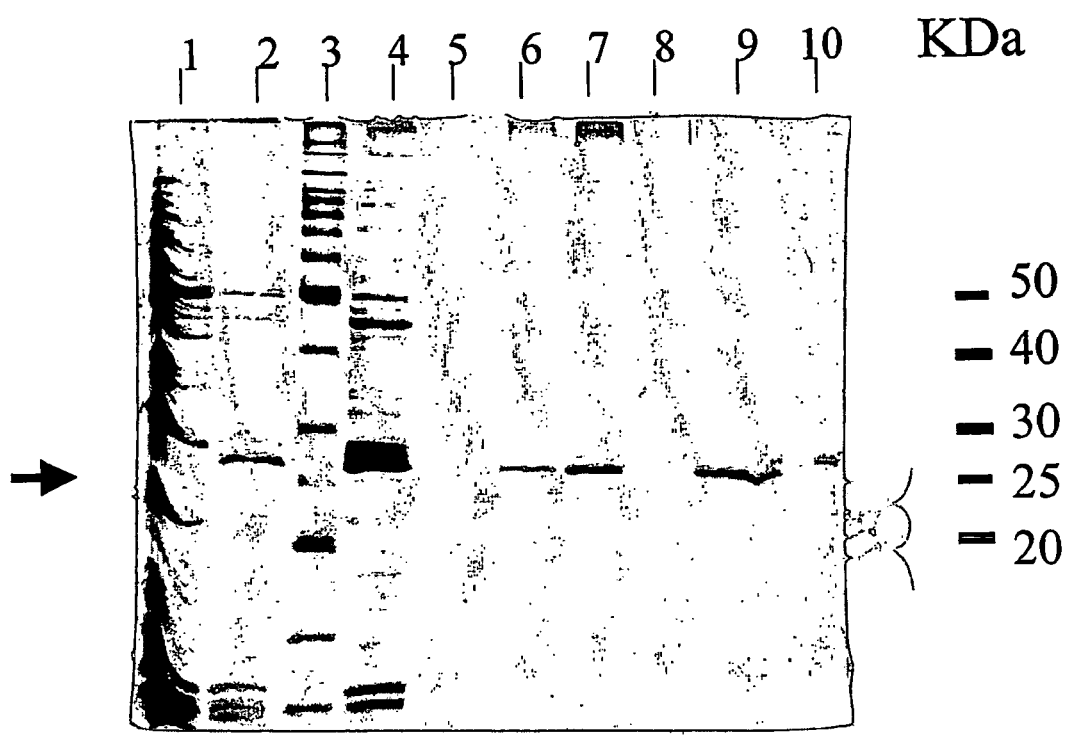

FIG. 44. SDS-PAGE analysis of various fractions collected from the batch purification of the N-terminally tagged recombinant glutathione S-transferase (r-GST) fusion proteins GST-NT2 obtained from clones selected for their expression levels. Aliquots of cell lysate and fractions collected from the batch purification (see Example 113) were mixed with SDS loading buffer (reducing) and heated at 100° C. for 90 seconds. Approximately 10 µl of purification fraction samples, 5 µl of positive and negative control cell lysate and 1.25 µl of cell lysate containing the recombinant fusion protein and 1 µl of the molecular weight markers [BenchMark Protein Ladder (Gibco BRL, Bethesda, Md., U.S.A)] were loaded onto a 12% SDS-polyacrylamide gel and run for an appropriate period of time. In order to visualize bands, the gel was silver stained. A pGEX3XGST transformant (Amersham Pharmacia, Uppsala, Sweden) served as the positive control. The r-GST component of the N-terminal-tagged r-GST fusion protein is truncated by 1 amino acid at the C-terminal end. The parental GST is expressed as the full-length protein with an additional 14 C-terminal amino acids. Consequently, the parental GST contains an additional 15 amino acids at its C-terminal end and therefore runs approx. 1.65 kDa larger than the GST component of the N-terminal tagged r-GST fusion proteins. The E. coli strain JM105 cells trans-formed with pTrc served as the negative control.

Key for Gel 8 shown as FIG. 44: Lanes 5-7 contain GST-NT2 samples collected from a $Ni^{2+}$-tacn Sepharose CL-6B column whilst Lanes 8-10 contain samples from a $Ni^{2+}$-NTA Sepharose CL-6B column. Lanes 5 and 8 correspond to the wash 2 step; Lanes 6 and 9 correspond to the elution 1 step; Lanes 7 and 10, correspond to the elution 2 step; Lane 1, negative control consisting of *E. coli* JM105 trans-formed with pTrc; Lane 2, positive control consisting of *E. coli* JM105 transformed with pGEX3XGST; Lane 4, crude cell lysate. Molecular weight marker is shown in Lane 3.

Figure 45:
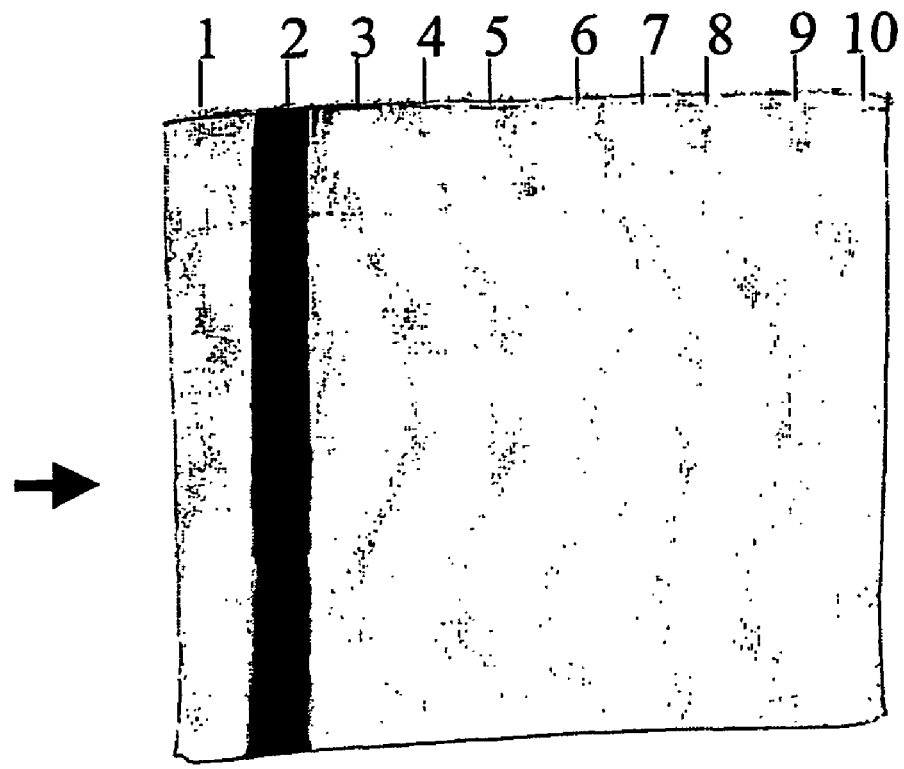

FIG. 45. SDS-PAGE analysis of various fractions collected from the stepwise purification of the N-terminally $(His)_6$-tagged recombinant glutathione S-transferase (r-GST) fusion proteins GST-CT1 obtained from clones selected for their expression levels. Samples from the stepwise elutions of cell lysate containing GST-CT1, as described in Example 97, were mixed with SDS loading buffer (non-reducing) and heated at 100° C. for 90 seconds. 10 µl aliquots from the first 1 ml of the eluted fractions and 2.5 µl of cell lysate were loaded onto a 12.5% SDS-polyacrylamide gel. The gel was run for an appropriate period of time and then silver stained in order to visualize bands as described in the legends to FIGS. 35-44.

Key for Gel 10 shown as FIG. 45: Fractions were recovered using the buffer A system (Table 1) supplemented with the following concentrations of imidazole: Lane 1, 100 mM; Lane 3, 150 mM; Lane 4, 200 mM; Lane 5, 250 mM; Lane 6, 300 mM; Lane 7, 350 mM; Lane 8, 400 mM; Lane 9, 450 mM and Lane 10, 500 mM. Cell lysate is shown in Lane 2.

Figure 46:
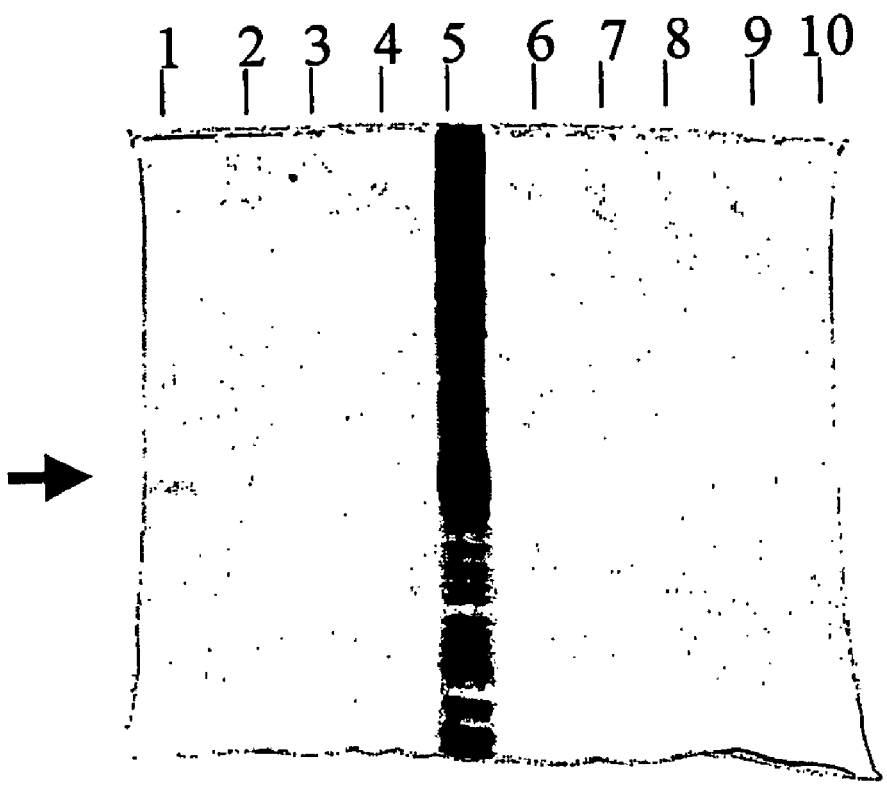

FIG. 46. SDS-PAGE analysis of various fractions collected from the stepwise purification of the N-terminally (His-Gln)-6-tagged recombinant glutathione S-transferase (r-GST) fusion protein GST-CT2 obtained from clones selected for their expression levels. Samples from the stepwise elution of cell lysate containing GST-CT2, as described in Example 98, were mixed with SDS loading buffer (non-reducing) and heated at 100° C. for 90 seconds. 10 µl aliquots from the first 1 ml of the eluted fractions and 2.5 µl of cell lysate were loaded onto a 12.5% SDS-polyacrylamide gel. The gel was run for an appropriate period of time and then silver stained in order to visualize bands as described in the legends to FIGS. 35-44.

Key for Gel 11 shown as FIG. 46: Fractions were recovered using the buffer A system (Table 1) supplemented with the following concentrations of imidazole: Lane 1, 100 mM; Lane 2, 150 mM; Lane 3, 200 mM; Lane 4, 250 mM; Lane 6, 300 mM; Lane 7, 350 mM; Lane 8, 400 mM; Lane 9, 450 mM and Lane 10, 500 mM. Cell lysate is shown in Lane 5.

Figure 47:
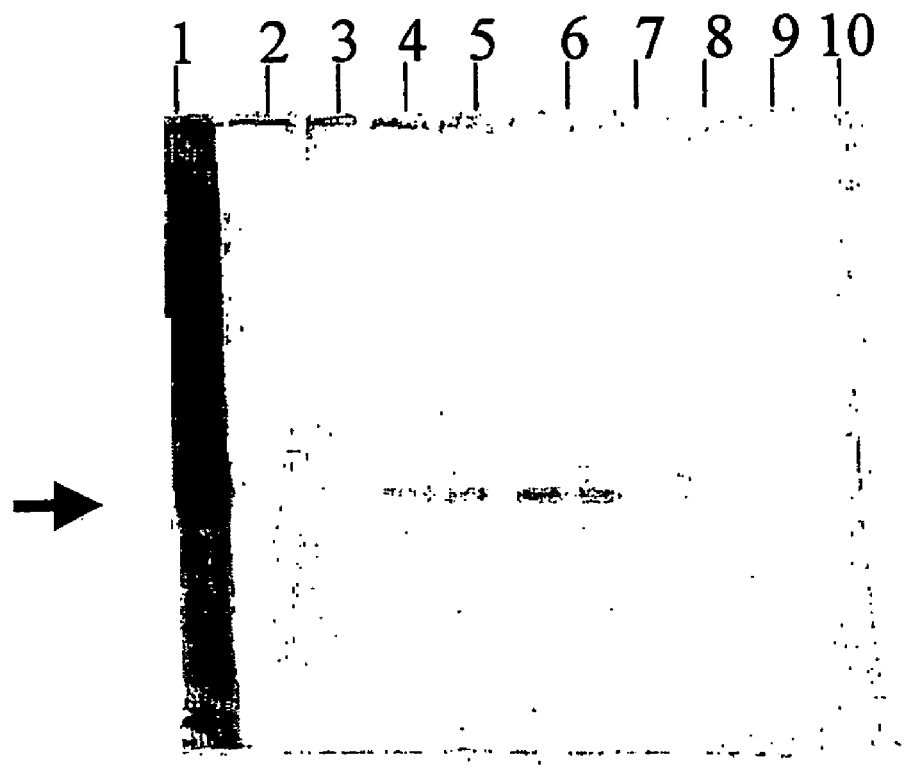

FIG. 47. SDS-PAGE analysis of various fractions collected from the stepwise purification of the N-terminally tagged recombinant glutathione S-transferase (r-GST) fusion protein GST-NT1 obtained from clones selected for their high expression levels. Samples from the stepwise elution of cell lysate containing GST-NT1, as described in Example 99, were mixed with SDS loading buffer (non-reducing) and heated at 100° C. for 90 seconds. 10 µl aliquots from the first 1 ml of the eluted fractions and 2.5 µl of cell lysate were loaded onto a 12.5% SDS-polyacrylamide gel. The gel was run for an appropriate period of time and then silver stained in order to visualize bands as described in the legends to FIGS. 35-44.

Key for Gel 12 shown as FIG. 47: Fractions were recovered using the buffer A system (Table 1) supplemented with the following concentrations of imidazole: Lane 2, 100 mM; Lane 3, 150 mM; Lane 4, 200 mM; Lane 5, 250 mM; Lane 6, 300 mM; Lane 7, 350 mM; Lane 8, 400 mM; Lane 9, 450 mM and Lane 10, 500 mM. Cell lysate is shown in Lane 1.

Figure 48:
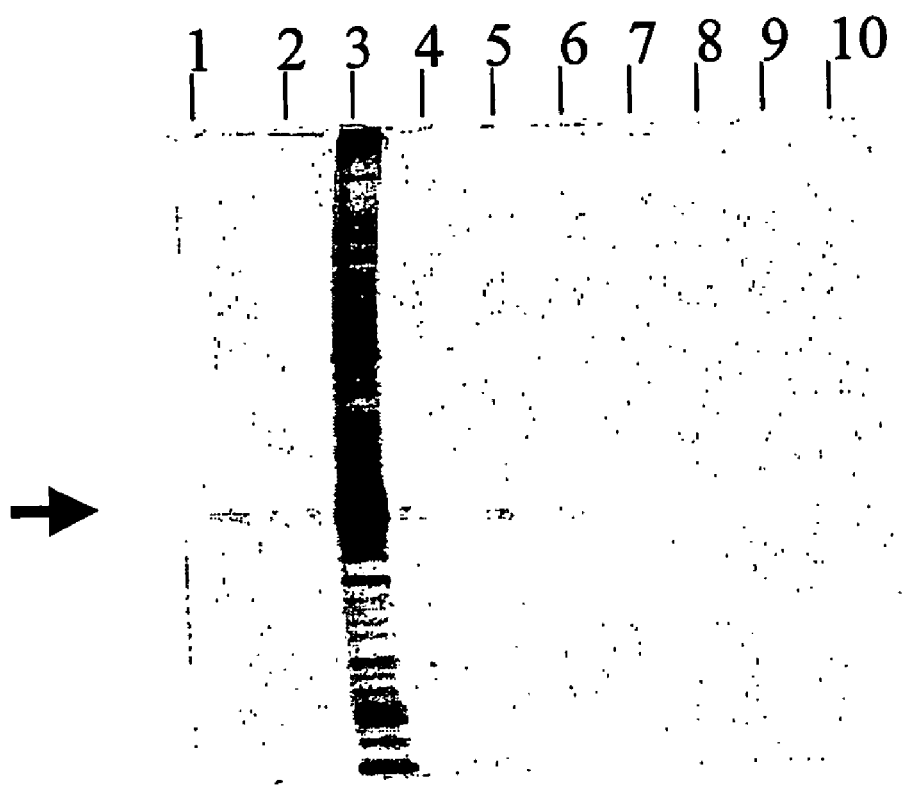

FIG. 48. SDS-PAGE analysis of various fractions collected from the stepwise purification of the N-terminally tagged recombinant glutathione S-transferase (r-GST) fusion protein GST-NT2 obtained from clones selected for their expression levels. Samples from the stepwise elution of cell lysate containing GST-NT2, as described in Example 100, were mixed with SDS loading buffer (non-reducing) and heated at 100° C. for 90 seconds. 10 µl aliquots from the first 1 ml of the eluted fractions and 2.5 µl of cell lysate were loaded onto a 12.5% SDS-polyacrylamide gel. The gel was run for an appropriate period of time and then silver stained in order to visualize bands as described in the legends to FIGS. 35-44.

Key for Gel 13 shown as FIG. 48: Fractions were recovered using the buffer A system (Table 1) supplemented with the following concentrations of imidazole: Lane 1, 100 mM; Lane 2, 150 mM; Lane 4, 200 mM; Lane 5, 250 mM; Lane 6, 300 mM; Lane 7, 350 mM; Lane 8, 400 mM; Lane 9, 450 mM and Lane 10, 500 mM. Cell lysate is shown in Lane 3.

Figure 49:
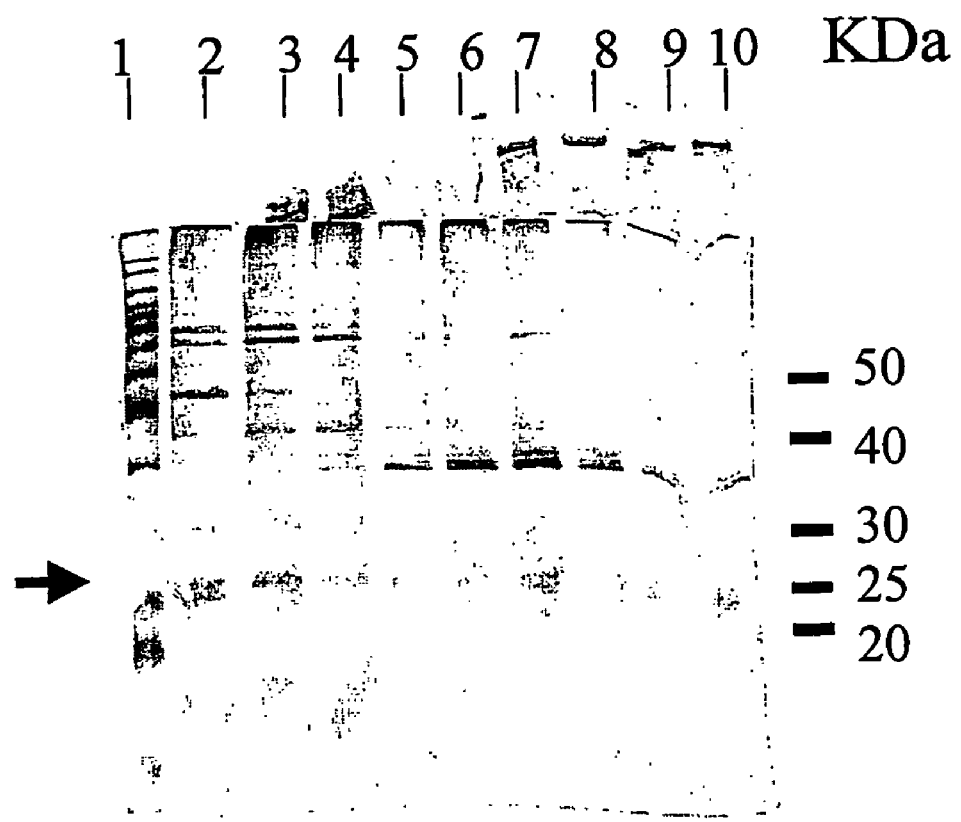

FIG. 49. SDS-PAGE analysis of various fractions collected from the stepwise purification of the N-terminally $(His)_6$-tagged recombinant glutathione S-transferase (r-GST) fusion protein GST-CT1 obtained from clones selected for their expression levels. Samples from the stepwise elution of cell lysate containing GST-CT1, as described in Example 101, were mixed with SDS loading buffer (non-reducing) and heated at 100° C. for 90 seconds. Approximately 16 µl aliquots from the first 1 ml of each eluted fraction and 0.5 µl of molecular weight markers [BenchMark Protein Ladder (Gibco BRL, Bethesda, Md., U.S.A)] were loaded onto a 12.5% SDS-polyacrylamide gel. The gel was run for an appropriate period of time and then silver stained in order to visualize bands as described in the legends to FIGS. 35-44.

Key for Gel 14 shown as FIG. 49: Fractions were recovered using the buffer A system (Table 1) supplemented with the following concentrations of imidazole: Lane 2, 25 mM; Lane 3, 50 mM; Lane 4, 75 mM; Lane 5, 100 mM; Lane 6, 150 mM; Lane 7, 200 mM; Lane 8, 250 mM; Lane 9, 300 mM and Lane 10, 350 mM. Molecular weight marker is shown in Lane 1.

Figure 50:
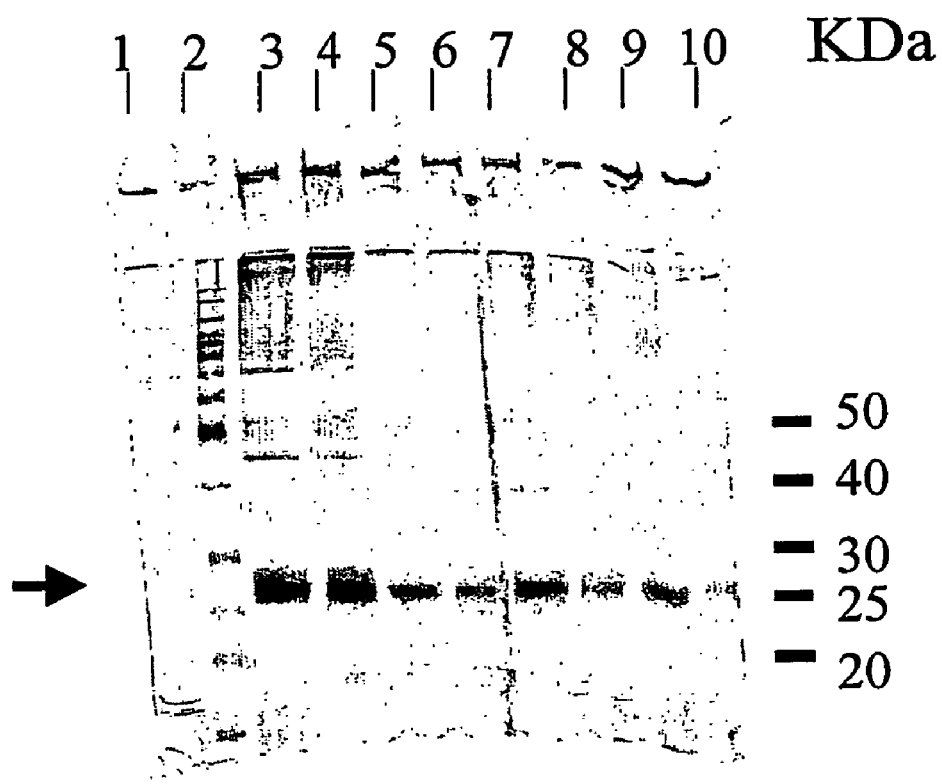

FIG. 50. SDS-PAGE analysis of various fractions collected from the stepwise purification of the N-terminally (His-Gln)$_6$-tagged recombinant glutathione S-transferase (r-GST) fusion protein GST-CT2 obtained from clones selected for their high expression levels. Samples from the stepwise elution of cell lysate containing GST-CT2, as described in Example 102, were mixed with SDS loading buffer (non-reducing) and heated at 100° C. for 90 seconds. Approximately 16 µl aliquots from the first 1 ml of each eluted fraction and 0.5 µl of molecular weight markers [BenchMark Protein Ladder (Gibco BRL, Bethesda, Md., U.S.A)] were loaded onto a 12.5% SDS-polyacrylamide gel. The gel was run for an appropriate period of time and then silver stained in order to visualize bands as described in the legends to FIGS. 35-45.

Key for Gel 15 shown as FIG. 50: Fractions were recovered using the buffer A system (Table 1) supplemented with the following concentrations of imidazole: Lane 1, 25 mM; Lane 3, 50 mM; Lane 4, 75 mM; Lane 5, 100 mM; Lane 6, 150 mM; Lane 7, 200 mM; Lane 8, 250 mM; Lane 9, 300 mM and Lane 10, 350 mM. Molecular weight marker is shown in Lane 2.

Figure 51:
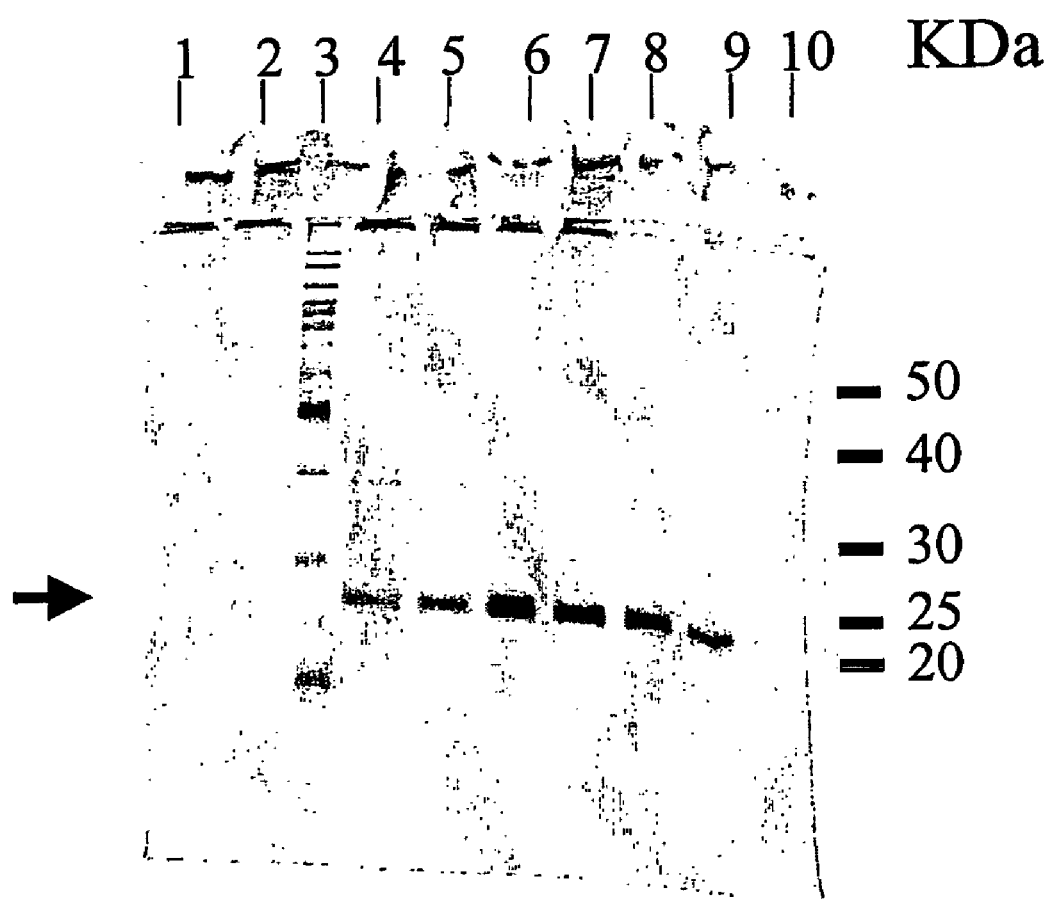

FIG. 51. SDS-PAGE analysis of various fractions collected from the stepwise purification of the N-terminally tagged recombinant glutathione S-transferase (r-GST) fusion protein GST-NT1 obtained from clones selected for their expression levels. Samples from the stepwise elution of cell lysate containing GST-NT1, as described in Example 103, were mixed with SDS loading buffer (non-reducing) and heated at 100° C. for 90 seconds. Approximately 16 µl aliquots from the first 1 ml of each eluted fraction and 0.5 µl of molecular weight markers [BenchMark Protein Ladder (Gibco BRL, Bethesda, Md., U.S.A)] were loaded onto a 12.5% SDS-polyacrylamide gel. The gel was run for an appropriate period of time and then silver stained in order to visualize bands as described in the legends to FIGS. 35-45.

Key for Gel 16 shown as FIG. 51: Fractions were recovered using the buffer A system (Table 1) supplemented with the following concentrations of imidazole: Lane 1, 100 mM; Lane 2, 150 mM; Lane 4, 200 mM; Lane 5, 250 mM; Lane 6, 300 mM; Lane 7, 350 mM; Lane 8, 400 mM; Lane 9, 450 mM and Lane 10, 500 mM. Molecular weight marker is shown in Lane 3.

Figure 52:
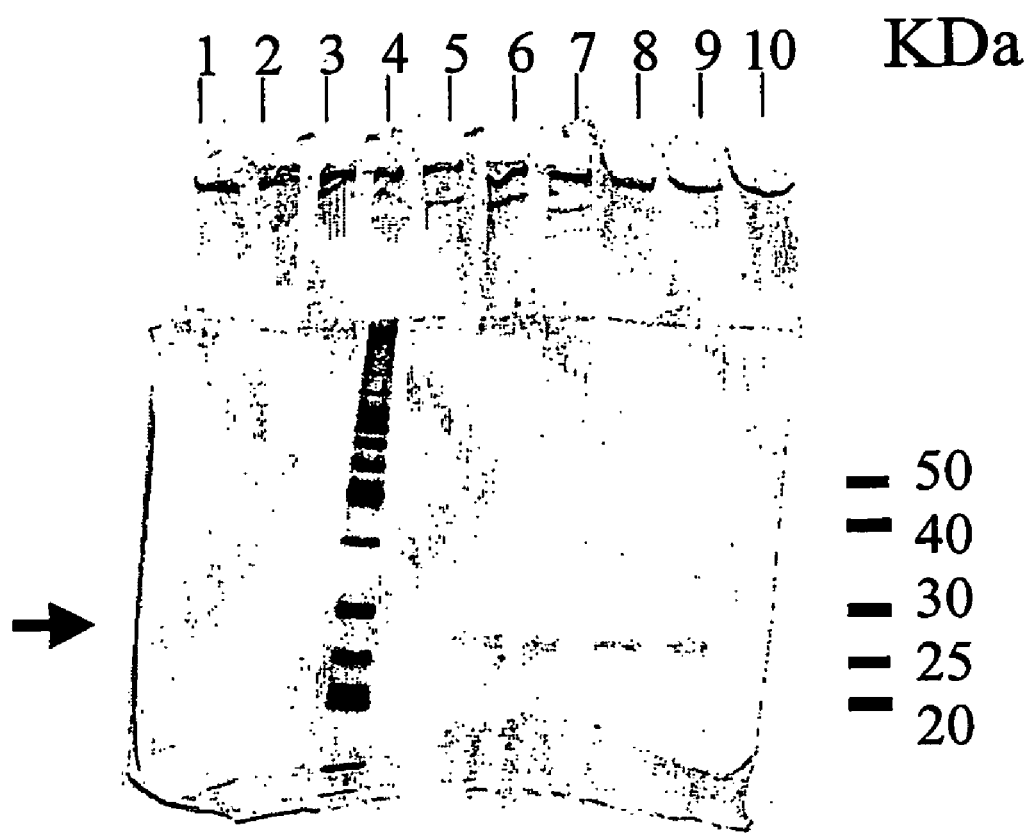

FIG. 52. SDS-PAGE analysis of various fractions collected from the stepwise purification of the N-terminally tagged recombinant glutathione S-transferase (r-GST) fusion protein GST-NT2 obtained from clones selected for their expression levels. Samples from the stepwise elution of cell lysate containing GST-NT2, as described in Example 104, were mixed with SDS loading buffer (non-reducing) and heated at 100° C. for 90 seconds. Approximately 16 µl aliquots from the first 1 ml of each eluted fraction and 0.5 µl of molecular weight markers [BenchMark Protein Ladder] (Gibco BRL, Bethesda, Md., U.S.A) were loaded onto a 12.5% SDS-polyacrylamide gel. The gel was run for an appropriate period of time and then silver stained in order to visualize bands as described in the legends to FIGS. 35-45.

Key for Gel 17 shown as FIG. 52: Fractions were recovered using the buffer A system (Table 1) supplemented with the following concentrations of imidazole: Lane 1, 50 mM; Lane 2, 75 mM; Lane 3, 100 mM; Lane 5, 150 mM; Lane 6, 200 mM; Lane 7, 250 mM; Lane 8, 300 mM; Lane 9, 350 mM and Lane 10, 400 mM. Molecular weight marker is shown in Lane 4.

Figure 53:
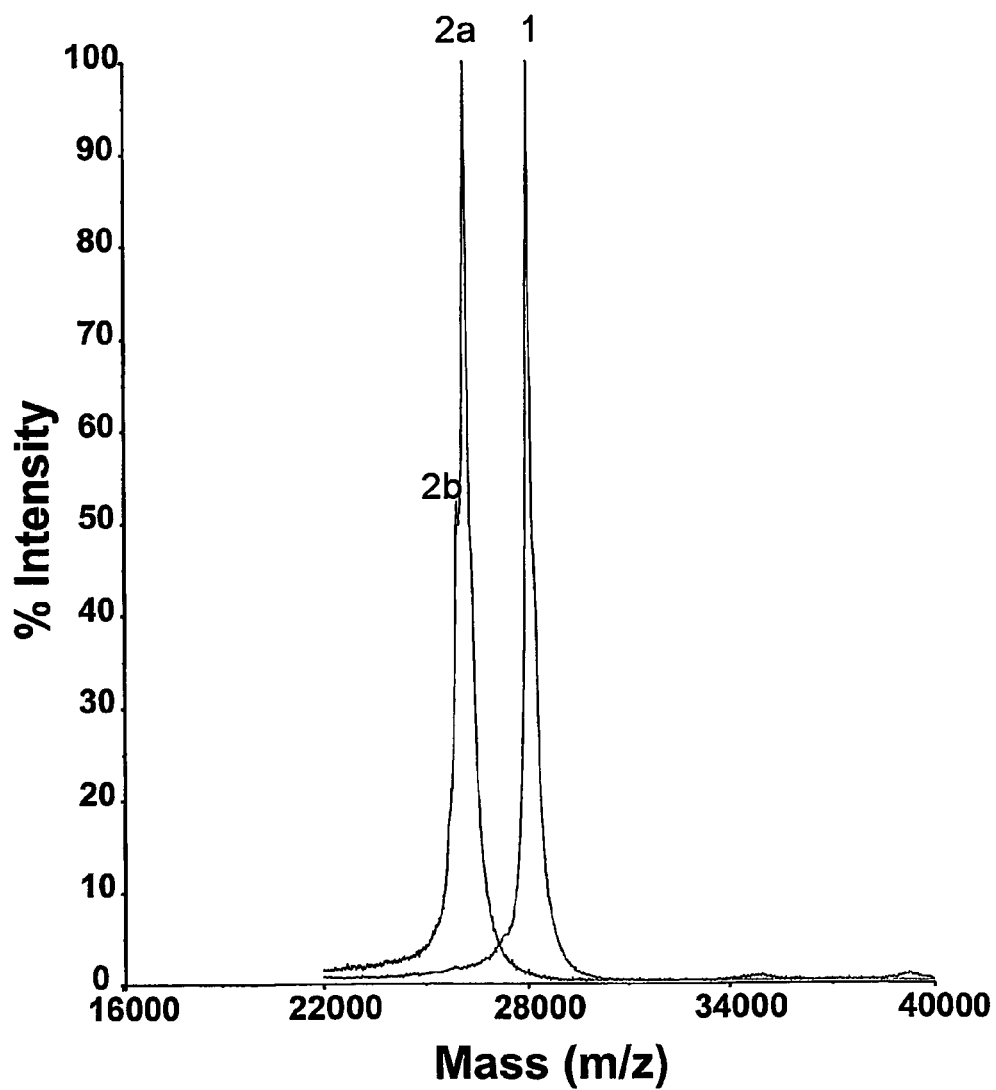

FIG. 53. Spectrum 1: MALDI-TOF MS spectrum for the non-DAP-1-treated GST(FL)-CT2 fusion protein, i.e. the negative control. It shows a single peak (labelled 1) which has a $[M+H]^+$ value of 28,013+3.21 Dalton. The expected theoretical isotopic molecular mass of GST(FL)-CT2 is 28,007.3 Dalton. By comparison herewith, the observed mass is thus consistent with the GST(FL)-CT2 protein being intact.

Spectrum 2: MALDI-TOF MS spectra obtained for DAP-1-digested GST(FL)-CT2; the spectrum demonstrates decreased molecular mass following treatment of the fusion protein with DAP-1 for 2 hours. Spectrum 2 displays a major peak (2a) having an average $[M+H]^+$ value of 26, 154±6 Dalton, and a minor peak (2b) having an average $[M+H]^+$ value of 25,931±7.51 Dalton.

Figure 54:
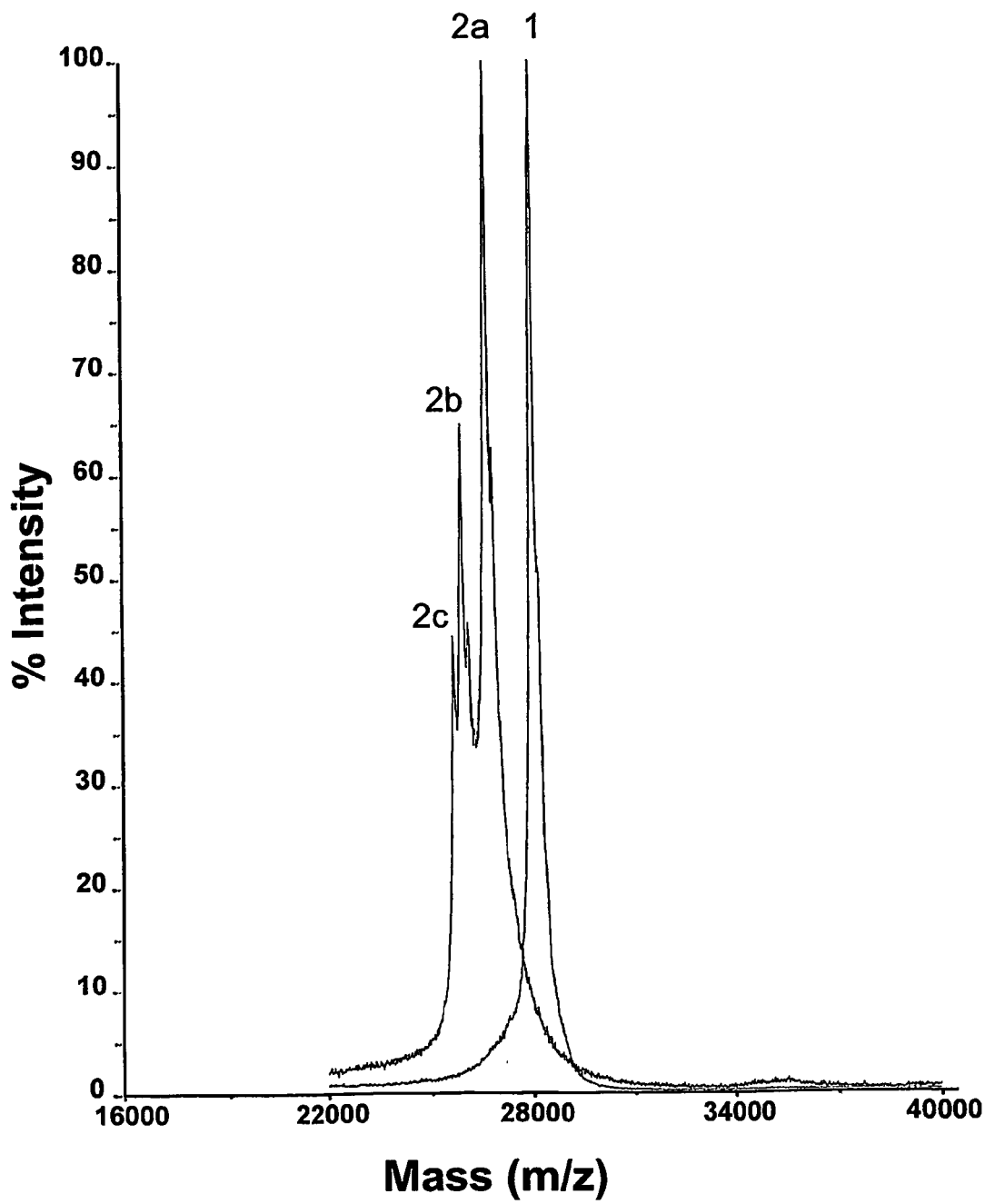

FIG. 54. Spectrum 1: MALDI-TOF MS spectrum for the non-DAP-1-treated GST(FL)-NT1, i.e. the negative control. It shows a single peak (labelled 1) which has a $[M+H]^+$ value of 27,972±3.51 Dalton; by comparison with the expected theoretical molecular mass of 27,965.3 Dalton for GST(FL)-NT1 the observed mass is consistent with the protein being intact. Spectrum 2: MALDI-TOF MS spectra obtained for the DAP-1-digested (2 hr) GST(FL)-NT1; the spectrum demonstrates decreased molecular mass following treatment with DAP-1. Spectrum 2 displays a major peak (2a) having an average $[M+H]^+$ value of 26,659±6.81 Dalton. It also displays a minor peak (2b) having an average $[M+H]^+$ value of 25,934±3.21 Dalton, and a further minor peak (2c) having an average $[M+H]^+$ value of 25,680±6.03 Dalton.

Figure 55:
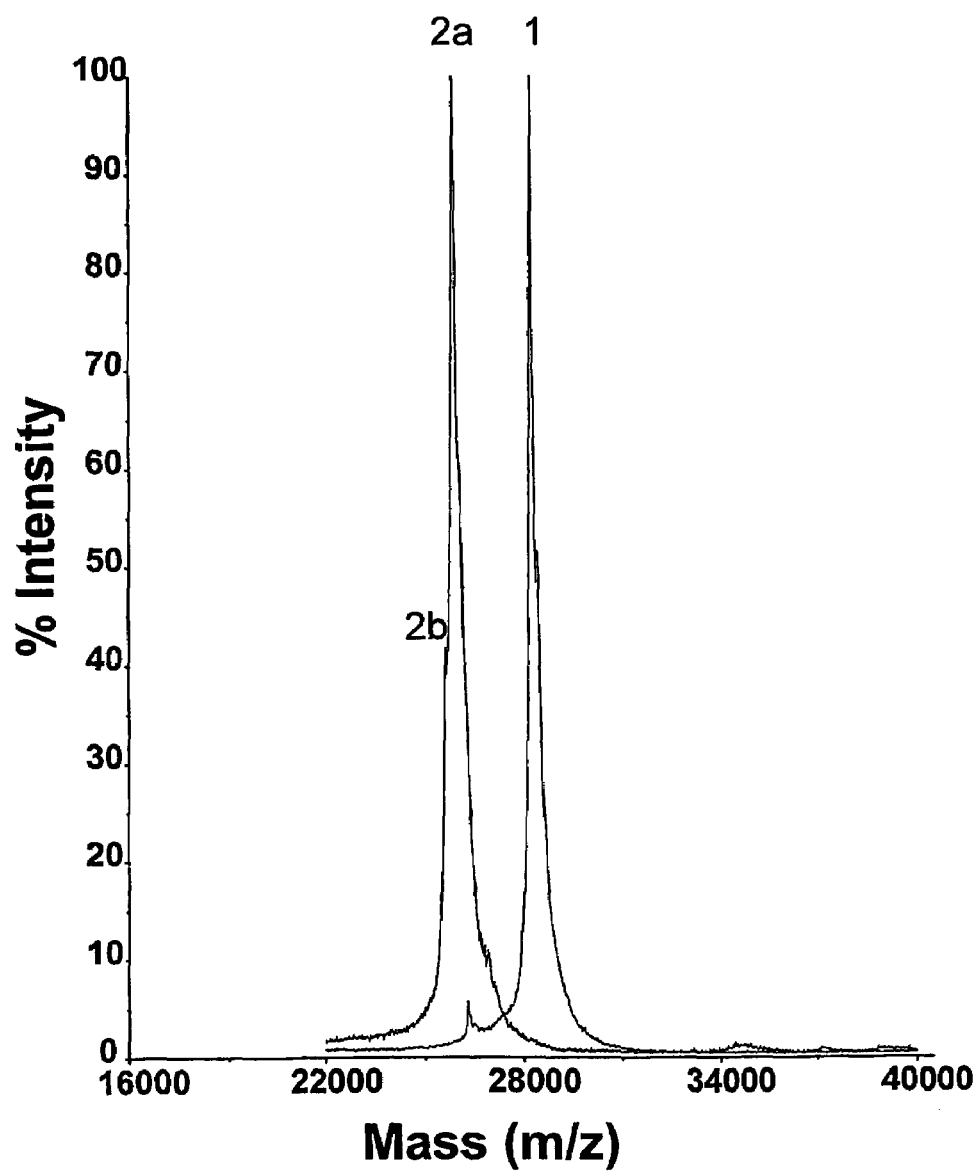

FIG. 55. Spectrum 1: MALDI-TOF MS spectrum for the non-DAP-1-treated GST(FL)-NT2, i.e. the negative control. It shows a single peak (labelled 1) which has a $[M+H]^+$ value of 28,223±2.89 Dalton; by comparison with the expected theoretical molecular mass of 28,218.6 Dalton for GST(FL)-NT2 the observed mass is consistent with the protein being intact. Spectrum 2: MALDI-TOF MS spectra obtained for DAP-1-digested (2 hr) GST(FL)-NT2; the spectrum demonstrates decreased molecular mass following treatment with DAP-1. Spectrum 2 displays a major peak (2a) having an average $[M+H]^+$ value of 25,910±9.16 Dalton, and a minor peak (2b) having an average $[M+H]^+$ value of 25,648±12.86 Dalton.

Figure 56:
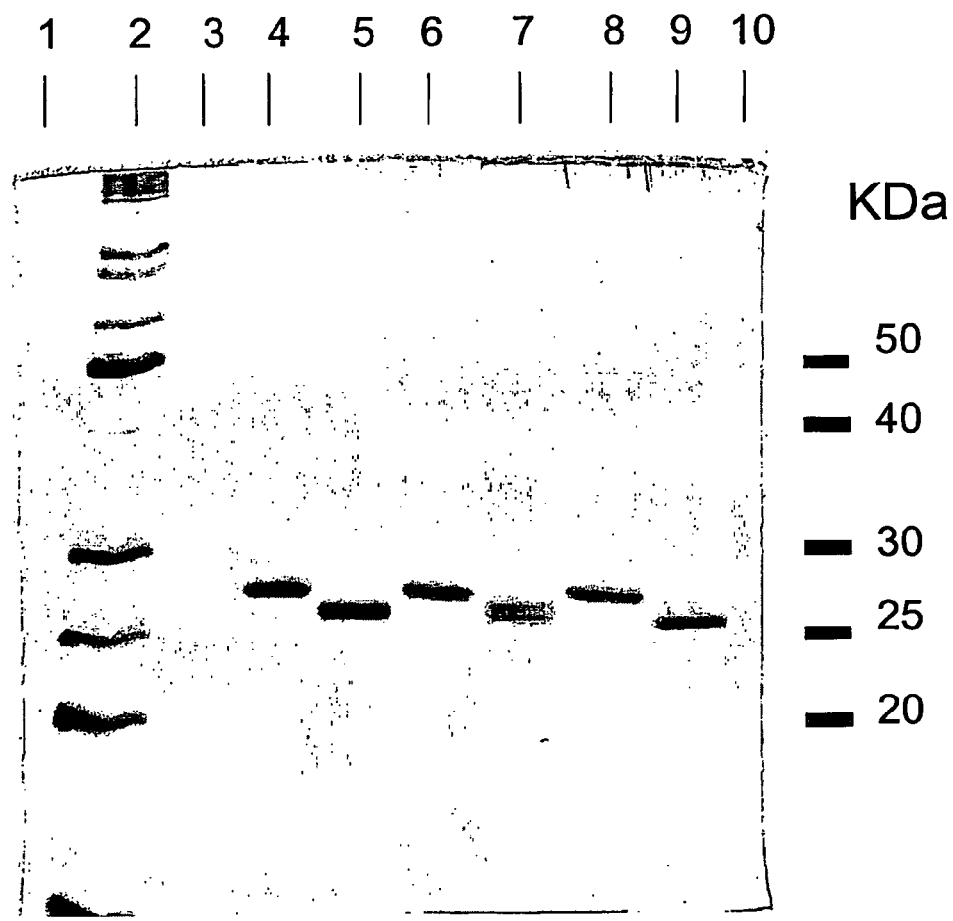

FIG. 56. Key for gel: Lane 4, GST(FL)-CT2 before DAP-1 treatment; Lane 5, GST(FL)-CT2 after DAP-1 treatment; Lane 6, GST(FL)-NT1 before DAP-1 treatment; Lane 7, GST (FL)-NT1 after DAP-1 treatment; Lane 8, GST(FL)-NT2 before DAP-1 treatment; Lane 9, GST(FL)-NT2 after DAP-1 treatment. Lanes 1, 3 and 10 were blank. Molecular weight markers are shown in Lane 2.

Figure 57:
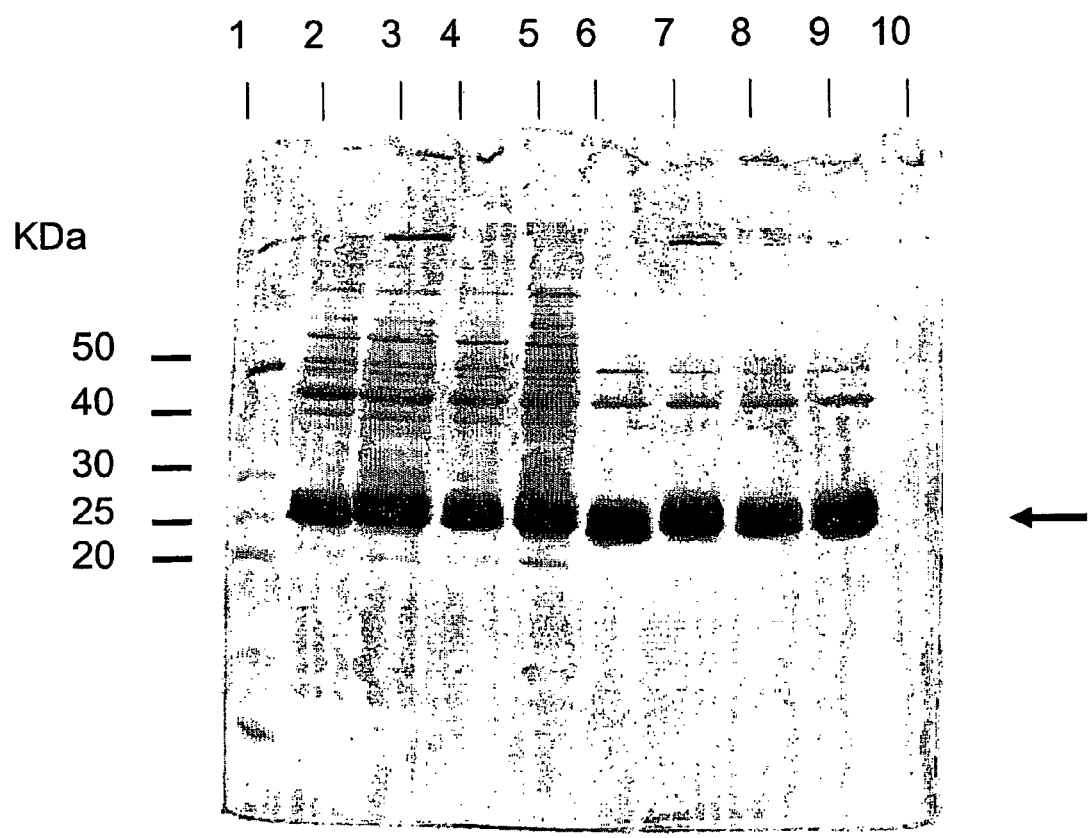

FIG. 57. Key for gel: Lane 2, GST-CT1 purified on $Ni^{2+}$-tacn column; Lane 3, GST-CT2 purified on $Ni^{2+}$-tacn column; Lane 4, GST-NT1 purified on $Ni^{2+}$-tacn column; Lane 5, GST-NT2 purified on $Ni^{2+}$-tacn column; Lane 6, GST-CT1 purified on $Cu^{2+}$-tacn column; Lane 7, GST-CT2 purified on $Cu^{2+}$-tacn column; Lane 8, GST-NT1 purified on $Cu^{2+}$-tacn column; Lane 9, GST-NT2 purified on $Cu^{2+}$-tacn column. Molecular weight marker is shown in Lane 1.

Figure 58:
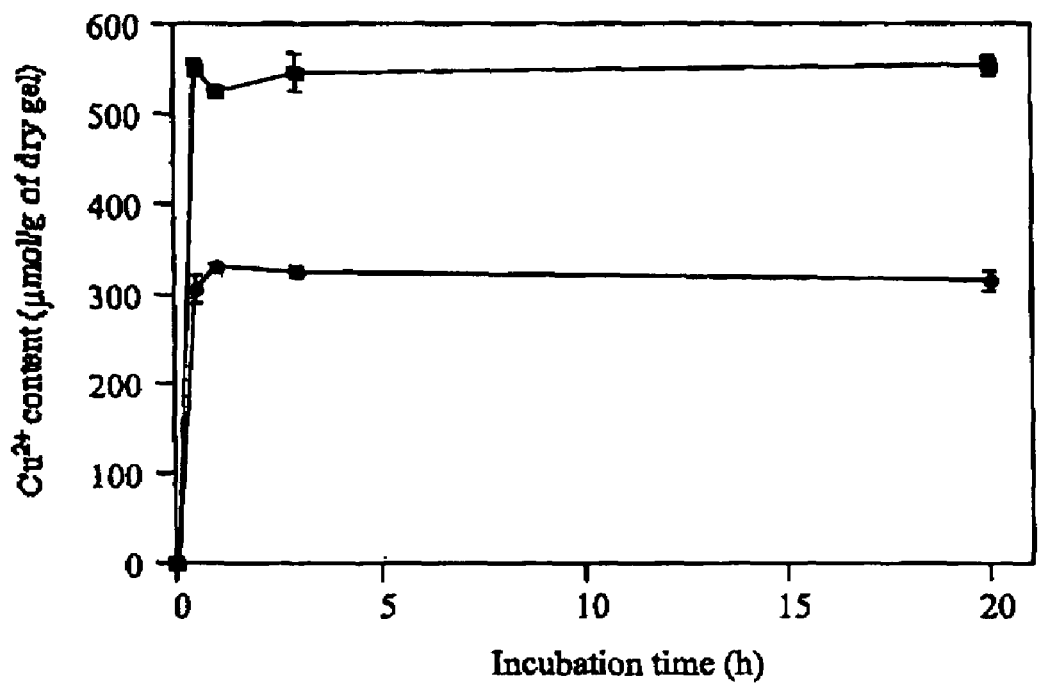

FIG. 58. Uptake of Cu2+ with time for tacn-(o) and LPx (i)-funcUonalized Sepharose TM CL-4B gels.

Figure 59:
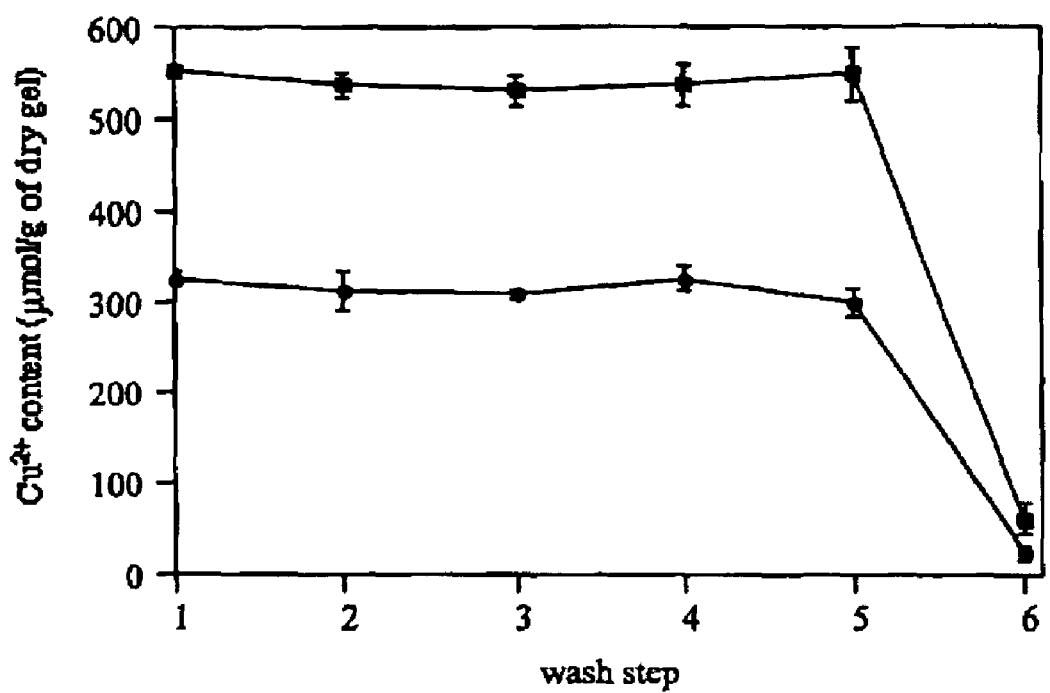

FIG. 59. Cu2+ content of Cu2+-tacn-(e) and -LPX-functionalized (,.) Sepharose TM CL-4B gels after washing with various solutions. Wash 1=20 mM NaOAc/1 M NaCl/pH 5; wash 2=20 mM NaOAc/1 M NaCl/pH 5; wash 3=20 mM Na2HPO4/1 M NaCl/pH 7; wash 4=20 mM Na2B407/1 M NaCl/pH 9; wash 5=200 mM imidazole; 5 wash 6=200 mM Na2EDTA.

FIG. 60 (A) SDS-Page (+_reduction) with colloidal blue staining, and (B) western blot analysis of selected samples. Lanes 1-6: reduced samples; Lanes 7-10 unreduced samples (Lane 1: molecular weight markers; Lane 2: hGH standard; Lane 3: lysed product; Lane 4: isolated tagged hGH; Lane 5: cleaved product; Lane 6: cleaved product after second $Ni^{2+}$-tacn column elution procedure; Lane 7: hGH standard; Lane 8: lysed product; Lane 9: cleaved product; Lane 10: cleaved product after second $NI^{2+}$-tacn elution procedure.

Figure 61:
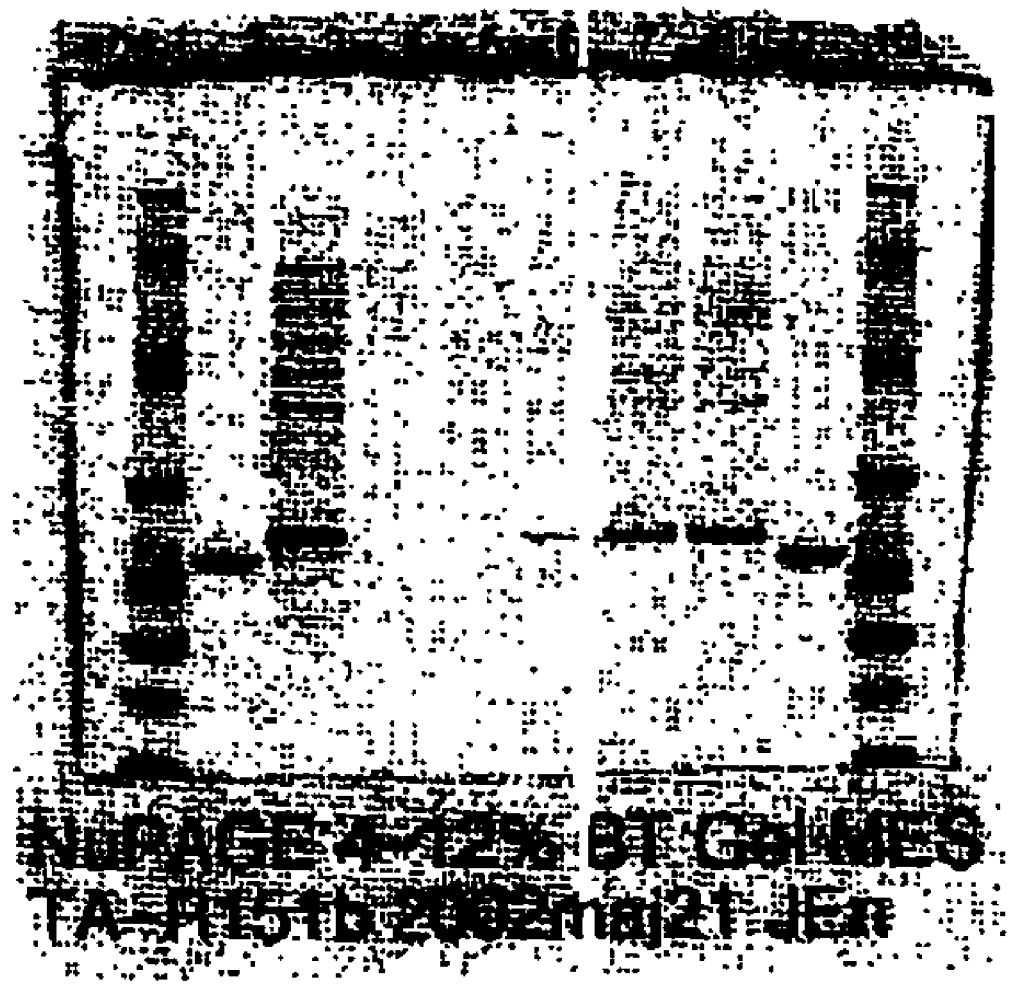

FIG. 61. SDS-Page without reduction. Lane 1: MW markers; Lane 2: hGH standard; Lane 3: dialysed pool from $NI^{2+}$-tacn column purification; Lane 4: throughput after introduction of the pool from $NI^{2+}$-tacn column onto Cu2+-tacn column; Lane 5: wash 1; Lane 6: wash 2: Lane 7: pool of tagged hGH fractions: Lane 8: as for lane 7, but dialysed; Lane 9: hGH standard; Lane 10: MW marker.

EXPERIMENTAL SECTION

Unless otherwise indicated, all reagents employed were of standard laboratory reagent grade purity or higher purity and were obtained from established suppliers. $CH_3CN$ was dried over 4 Å molecular sieves. Sepharose™ CL-4B and other types of Sepharose™, Superose™ and related agarose-based products were purchased from Amersham Pharmacia (Uppsala, Sweden). Distilled or Milli-Q™ water was used throughout.

Metal Ion Coordinating Ligands

The metal ion coordinating ligand 1,4,7-triazacyclononane (abbreviated tacn or TACN) (which can be purchased from Sigma-Aldrich Company, St. Louis, Mo., USA) may be prepared using the Richman-Atkins reaction [J. E. Richman and T. J. Atkins, *Journal of the American Chemical Society*, 96 (1974) 2268; J. E. Richman, W. F. Oettle and T. J. Atkins, *Organic Synthesis* 58 (1978) 86]. The trihydrobromide salt of tacn employed in the following was obtained by crystallization of the free ligand from 5M hydrobromic acid.

1,2-Bis(1,4,7-triazacyclononanyl)ethane (abbreviated dtne, DTNE or $L^{eth}$) and 1,3-bis(1,4,7-triazacyclononanyl) propane (abbreviated dtnp, DTNP or $L^{prop}$) may be prepared as described by Wieghardt et al. [Inorg. Chem. 24 (1985) 1230]. 1,4-Bis(1,4,7-triazacyclononanyl)butane (abbreviated dtnb, DTNB or $L^{but}$) may be prepared as described by Sessler et al [*Inorganic Chemistry*, 29 (1990) 4143] or by Zhang et al. [*Inorganic Chemistry*, 34 (1995) 2883]. The latter three compounds were isolated as the hexakis-hydrobromide salts.

Analogues of the latter bis(1,4,7-triazacyclononanyl) ligands with bridging groups derived from o-, m- or p-xylene, viz.:

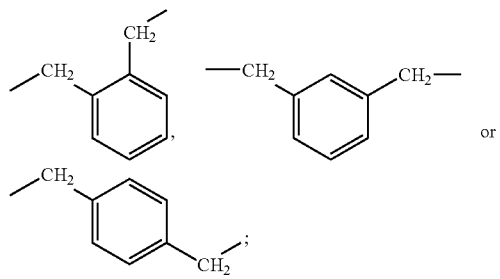

between the two 1,4,7-triazacyclononanyl groups, instead of —(CH$_2$)$_n$— bridges (n=2, 3 or 4), may be prepared, as the hexakis-hydrobromide salts, as described by Graham et al. [*Inorganic Chemistry*, 36 (1997) 6366] or by Farrugia, L. J., Lovatt, P. A. and Peacock, R. D. [*Journal of the Chemical Society, Dalton Transactions* (1997) 911-912]. These ligands are abbreviated herein as $L^{ox}L^{mx}$ and $L^{px}$, respectively.

The corresponding tris(1,4,7-triazacyclononanyl) ligands with three 1,4,7-triazacyclononanyl groups bound to a central mesitylene-derived group, viz.

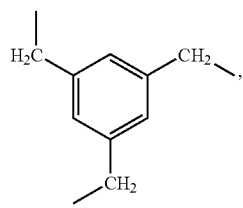

as well as tetrakis(1,4,7-triazacyclononanyl) ligands with four 1,4,7-triazacyclononanyl groups bound to a central durene-derived group, viz.

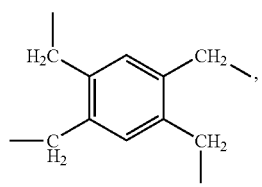

may be prepared, as the nonakis- and dodecakis-hydrobromide salts, respectively, as described by Spiccia et al. [*Journal of the Chemical Society*, Dalton Transactions (1997) 1092] and Graham et al. [*Inorganic Chemistry*, 39 (2000) 1092], respectively.

Analytical Determinations and Physical Measurements

Nitrogen analyses were performed by Dairy Technical Services Ltd., Melbourne, Australia. Copper and nickel analyses were carried out on a Varian AA-1475 atomic absorption spectrometer. Diffuse reflectance electronic spectra were recorded on a Cary 5G spectrophotometer. ESR spectra were recorded at 77K on a Varian E-12 spectrometer operating at ca. 9.6 GHz (X-band) and referenced to α, α'-diphenyl-β-dipicrylhydrazyl (DPPH), which has a g value of 2.0036. Samples were run in normal 3 mm ID tubes and frozen in a liquid nitrogen flow cryostat.

Example 1

Preparation of Adsorbent (Functionalized Substrate) Comprising Immobilized 1,4,7-TRIAZACYCLONONANE (im-TACN)

The first stage in immobilization of the chelating reagent (tacn) on the matrix (substrate) involved covalent activation of the matrix with epichlorohydrin (or another suitable activating compound, such as carbonyl-diimidazole). Thus, Sepharose™ CL-6B gel (10 g, wet weight) was mixed with 10 ml of 2 M NaOH and 37.5 mg of sodium borohydride (98%). After the mixture had been incubated for 2 hours at 25° C., 12 ml of epichlorohydrin was added and the mixture was then gently stirred overnight at 25° C. The resulting epoxy-activated Sepharose™ gel was recovered by suction filtration and then washed thoroughly with Milli-Q™ water to remove any remaining unreacted epichlorohydrin. Volumes of 0.1 M tacn ligand solutions were then prepared by dissolving 5 mmol of the trihydrobromide salt of tacn in water (30 ml), adjusting the pH to 11 by addition of solid NaOH, and then making the final volume up to 50 ml with water. Aliquots of this solution (20 ml) were then added to 10 g (suction dried weight) portions of the epoxy-activated Sepharose™ CL-6B prepared as above. The suspensions were mixed overnight at 25° C. using a shaking water bath. The resulting portions of functionalized gel were collected by suction filtration (using a water pump) and washed extensively with Milli-Q™ water (5×200 ml), 50 mM sodium acetate buffer (50 ml) containing 0.1 M KNO$_3$ (pH 4.0), and finally with Milli-Q™ water (5×200 ml). The portions of im-tacn adsorbent were subsequently suspended in 20 ml of a 20% (v/v) ethanol/water solution and stored at 4° C. until used.

Example 2

Preparation of Adsorbent (Functionalized Substrate) Comprising Immobilized BIS(1,4,7-TRIAZACYCLONONANYL)ETHANE (im-DTN E)

The procedure used was essentially the same as described in Example 1, except that the final volume of 0.1 M dtne ligand solution used was 25 ml.

Example 3

Preparation of Adsorbent (Functionalized Substrate) Comprising Immobilized BIS(1,4,7-TRIAZACYCLONONANYL)PROPAN E (im-DTN P) Adsorbent The procedure used was essentially the same as described in Example 1, except that the final volume of 0.1 M dtnp ligand solution used was 25 ml.

Example 4

Preparation of Immobilized Metal Ion-Tacn Adsorbents

Typically, about 5 g (wet weight) of im-tacn adsorbent was incubated at 25° C. for 30 minutes with 50 ml of a 50 mM solution of a nitrate salt of a metal ion of borderline hardness, viz. $Cu(NO_3)_2$, $Ni(NO_3)_2$, $Zn(NO_3)_2$, $Co(NO_3)_2$, $Mn(NO_3)_2$ or $Cr(NO_3)_3$, respectively, prepared in Milli-Q™water. The various immobilized metal ion adsorbents (gels) were then thoroughly washed with Milli-Q™ water (5×200 ml). To remove loosely bound metal ions from the adsorbents, 50 mM sodium acetate buffer containing 0.1 M $KNO_3$, pH 4.0, was incubated for 10 minutes with the immobilized metal adsorbent gels in a ratio of 5 g (wet weight) of adsorbent to 50 ml buffer. The gels were then washed extensively with Milli-Q™ water. The portions of the various immobilized metal ion adsorbents (gels) were subsequently suspended in 20 ml of a 20% (v/v) solution of ethanol in water and stored at 4° C. until use.

Example 5

Preparation of Immobilized Metal ION-DTNE Adsorbents

The procedure employed was completely analogous to that in Example 4, but using about 5 g (wet weight) portions of im-dtne adsorbent.

Example 6

Preparation of Immobilized Metal ION-DTNP Adsorbents

The procedure employed was completely analogous to that in Example 4, but using about 5 g (wet weight) portions of im-dtnp adsorbent.

Example 7

Separation and Purification of Human Serum Proteins Using Immobilized $Cu^{2+}$-DTNE Adsorbent with Binding Buffer pH 9.5

Preparation of Human Serum

A fresh sample of human blood (20 ml) was allowed to settle for 24 hours at 4° C. to remove the blood cells and the fibrinogen. The serum supernatant was centrifuged at 5000×g and 4° C. for 20 min, using a Sorvall™ RT6000 refrigerated centrifuge (DuPont Co., Newtown, Conn., USA). The supernatant was removed and centrifuged again at 5000×g and 4° C. for 20 min. Aliquots (0.2 ml) of the supernatant were dispensed into 1.5 ml tubes and stored at −20° C.

Isolation of Human Serum Proteins Using Batch Chromatographic Procedures

The im-$Cu^{2+}$-dtne adsorbent (1 ml) was packed into a Bio-Rad™ Econo-column [such as a 4.0 cm (length)×0.8 cm (i.d., i.e. internal diameter) column] (Hercules, Calif., USA) and equilibrated with an equilibration buffer containing 20 mM sodium carbonate and 0.1 M NaCl, pH 9.5 (cf.Table 1). An aliquot of human serum (200 μl), diluted five fold with the equilibration buffer, was added to the equilibrated column. After loading the human serum sample over a period of 5 minutes, equilibration buffer (300 μl) was added to wash any sample from the walls of the columns into the gel. After a further 5 minutes equilibration buffer (5 ml) was introduced into the column reservoir to elute unbound proteins. The collected fractions (ca. 5.5 ml) were denoted the unbound fractions. Bound human serum proteins were eluted from the adsorbent using a series of elution buffers (5 ml) listed in Table 1. The collected fractions were denoted the eluted fractions.

Figure 1:
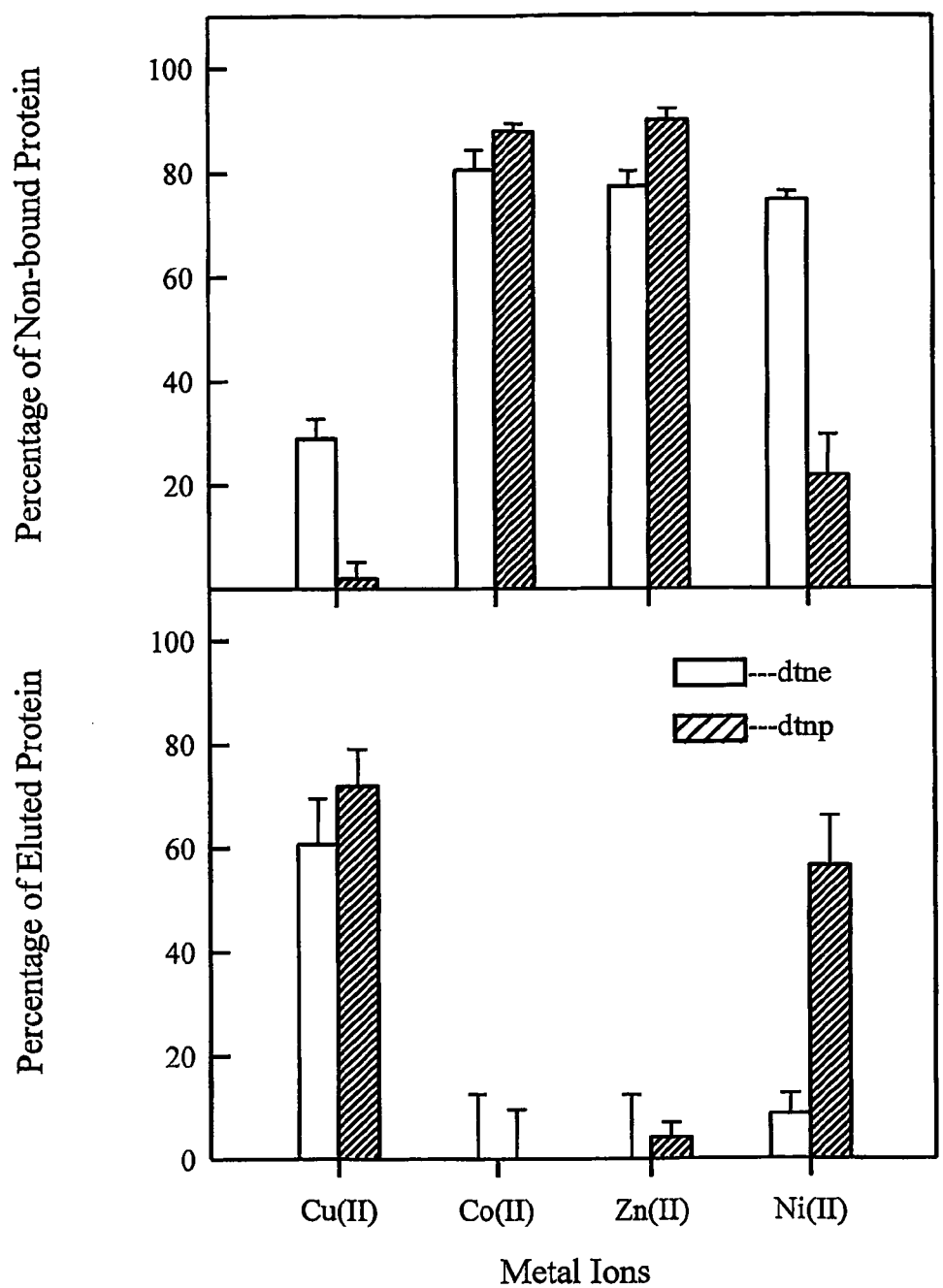
FIG. 1. The binding behaviour of human serum proteins on the im-$M^{n+}$-dtne and im-$Mn^{n+}$-dtnp Sepharose™ CL-6B columns using a binding buffer of 20 mM sodium carbonate buffer/0.1 M NaCl, pH 9.5 and different metal ions, where $M^{n+}=Cu^{2+}$, $Co^{2+}$, $Zn^{2+}$ and $Ni^{2+}$, respectively. The elution was performed using the procedure summarized in Table 1 in the working examples herein (vide infra). The percentage of eluted protein=(total amount of eluted protein/total amount of protein loaded)×100%.
Figure 2:
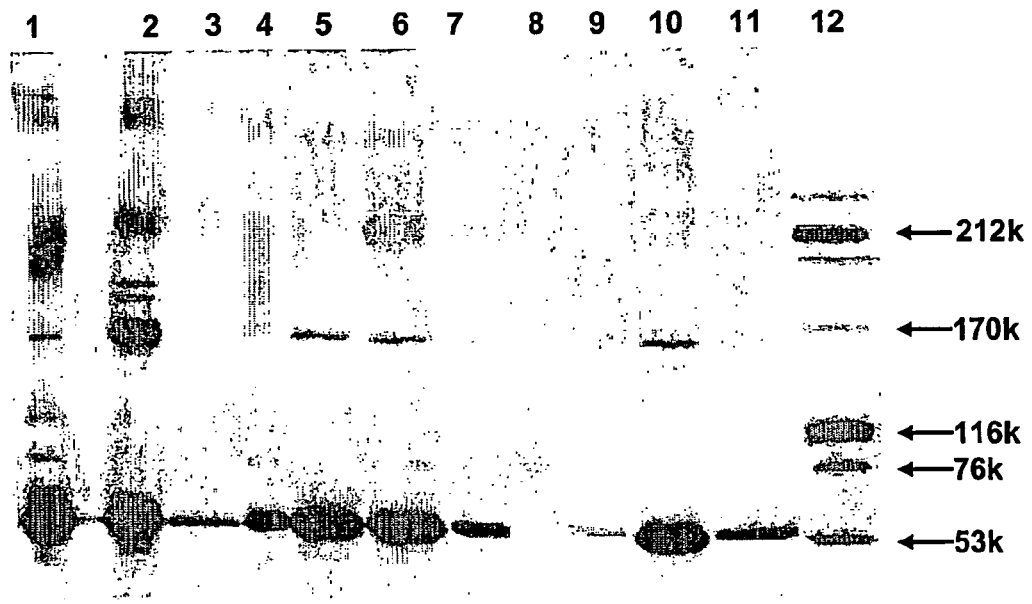
FIG. 2. SDS-PAGE profile of the selected fractions collected from im-$Cu^{2+}$-dtne and im-$Cu^{2+}$-dtnp Sepharose™ CL-6B batch columns under different loading conditions. Lane 1=human serum sample; Lane 2 and 3=breakthrough/wash and eluted fractions from im-$Cu^{2+}$-dtne Sepharose™ CL-6B column when the loading pH was pH 4.0; Lane 4 and 5=breakthrough/wash and eluted fractions from imCu$^{2+}$-dtne Sepharose™ CL-6B column when the loading pH was pH 9.5; Lane 6 and 7=breakthrough/wash and eluted fractions from im-$Cu^{2+}$-dtnp Sepharose™ CL-6B column when the loading pH was pH 4.0; Lane 8 to 11=breakthrough/wash and eluted fractions from im-$Cu^{2+}$-dtnp Sepharose™ CL-6B column when the loading pH was pH 9.5. Elution was achieved with an increase in concentration of NaCl and a decrease in pH; Lane 9=1 M NaCl and pH 9.5, Lane 10=pH 4.0, Lane 11=pH 4.0 and 250 mM imidazole; Lane 12 represents the molecular weight standards, myosin 212 kDa, reduced $\alpha_2$-macroglobulin 170 kDa, β-galactosidase 116 kDa, transferrin 76 kDa, and glutamine dehydrogenase 53 kDa.

The protein content in the unbound fractions and eluted fractions was analyzed using Bio-Rad™ Dye and bicinchoninic acid (BCA) assays (FIG. 1). Proteins in these fractions were identified by SDS-PAGE (FIG. 2). All the adsorption and desorption procedures were performed at room temperature.

Example 8

Separation and Purification of Human Serum Proteins Using Immobilized $Cu^{2+}$-DTNE Adsorbent with Binding Buffer pH 7.0

Figure 3:
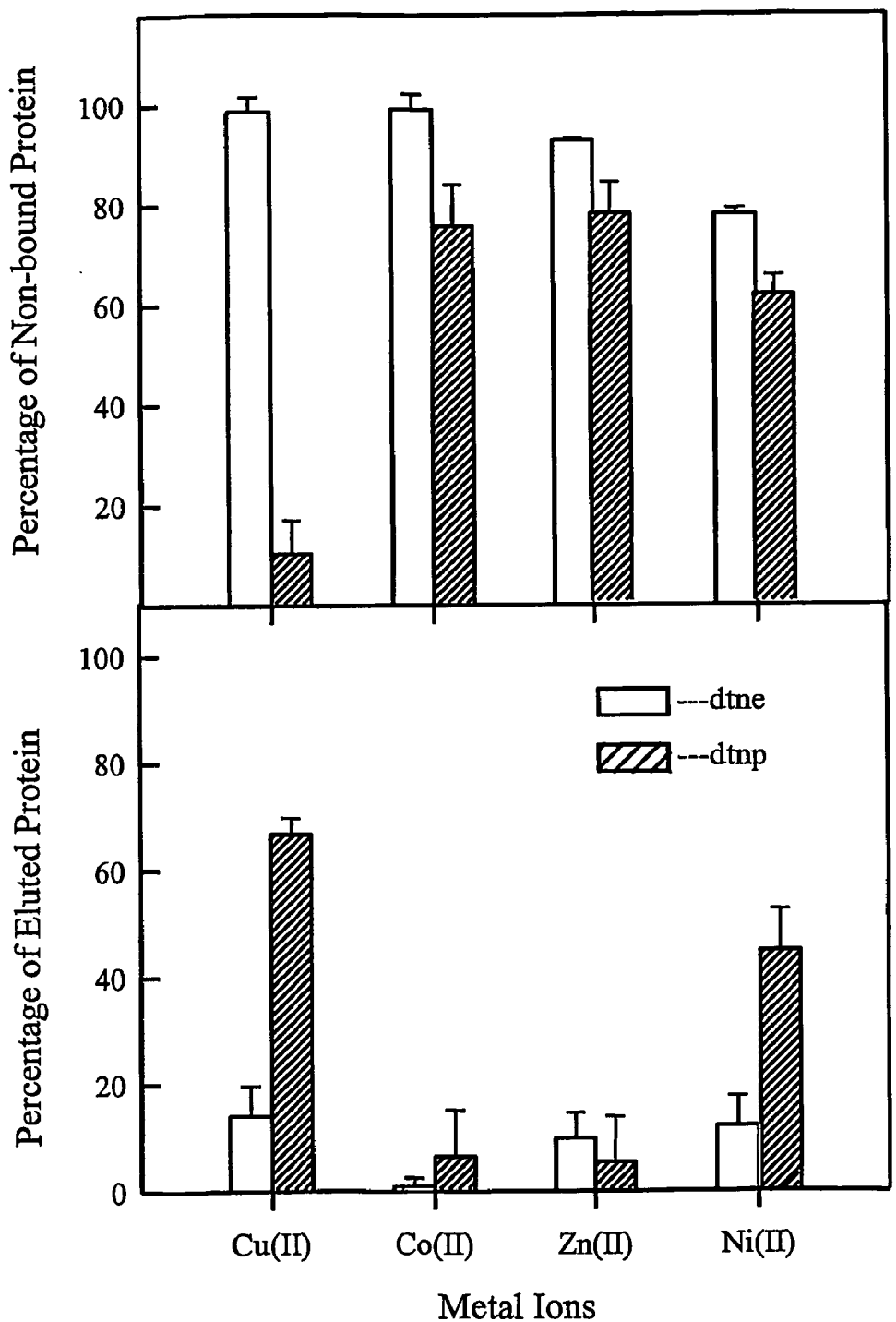
FIG. 3. The binding behaviour of human serum on the im-$M^{n+}$-dtne and im-$M^{n+}$-dtnp Sepharose™ CL-6B columns with different metal ions, where $M^{n+}=Cu^{2+}$, $Co^{2+}$, $Zn^{2+}$ and $Ni^{2+}$, respectively, and when binding buffer was 20 mM potassium phosphate buffer/0.1 M NaCl, pH 7.0. The elution was performed using the procedure in Table 2. The percentage of eluted protein=(total amount of eluted protein/total amount of protein loaded)×100%.
Figure 4:
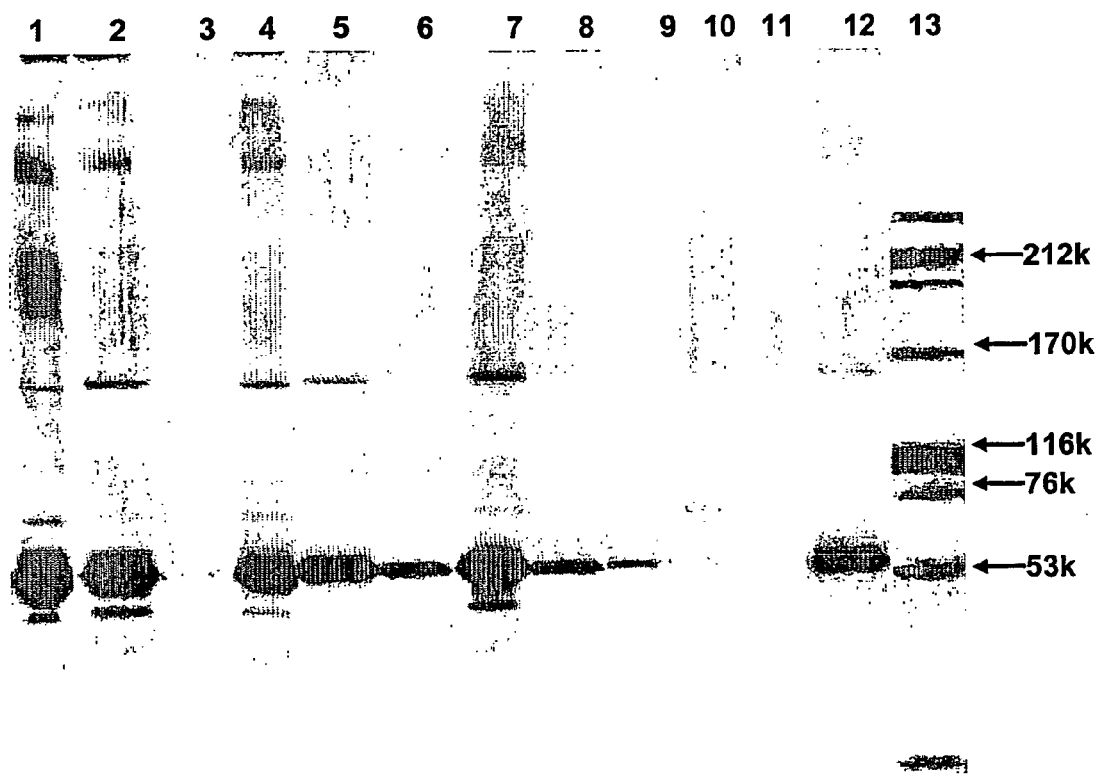
FIG. 4. SDS-PAGE profile of the selected fractions collected from im-$Cu^{2+}$-dtne and im-$Cu^{2+}$-dtnp and im-$Ni^{2+}$-dtne and im-$Ni^{2+}$-dtnp Sepharose™ CL-6B batch columns when the binding pH was 7.0. Elution was achieved with an increasing concentration of NaCl to 1.0 M and an application of 0.2 M EDTA, pH 4.2. Lane 1=human serum sample; Lane 2 and 3=breakthrough/wash and eluted fractions from im-$Ni^{2+}$-dtne Sepharose™ CL-6B column; Lane 4=breakthrough/wash fraction from im-$Ni^{2+}$-dtnp column; Lane 5 and 6=eluted fractions from im-$Ni^{2+}$-dtnp Sepharose™ CL-6B column using pH 7.0 buffer with 1 M NaCl or 0.2 M EDTA pH 4.2; Lane 7=breakthrough/wash fraction from im-$Cu^{2+}$-dtne column; Lane 8 and 9=eluted fractions from im-$Cu^{2+}$-dtne Sepharose™ CL-6B column using pH 7.0 buffer with 1 M NaCl or 0.2 M EDTA pH 4.2; Lane 10=breakthrough/wash fraction from im-$Cu^{2+}$-dtnp column; Lane 11 and 12=eluted fractions from im-$Cu^{2+}$-dtnp Sepharose™ CL-6B column using pH 7.0 buffer with 1 M NaCl or 0.2 M EDTA pH 4.2; Lane 13 represents the molecular weight standards, Myosin 212 kDa, reduced $\alpha_2$-Macroglobulin 170 kDa, β-galactosidase 116 kDa, transferrin 76 kDa, and glutamine dehydrogenase 53 kDa.

The procedure used was essentially the same as described in Example 7, except that the equilibration buffer used was 20 mM potassium phosphate buffer containing 0.1 M NaCl, pH 7.0 (cf.Table 2), and that the bound human serum proteins were eluted from the adsorbents with a series of elution buffers (5 ml) that are listed in Table 2. The results are shown in FIG. 3 and FIG. 4.

Example 9

Separation and purification of Human Serum Proteins Using Immobilized $Cu^{2+}$-DTNE Adsorbent with Binding Buffer pH 4.0

Figure 5:
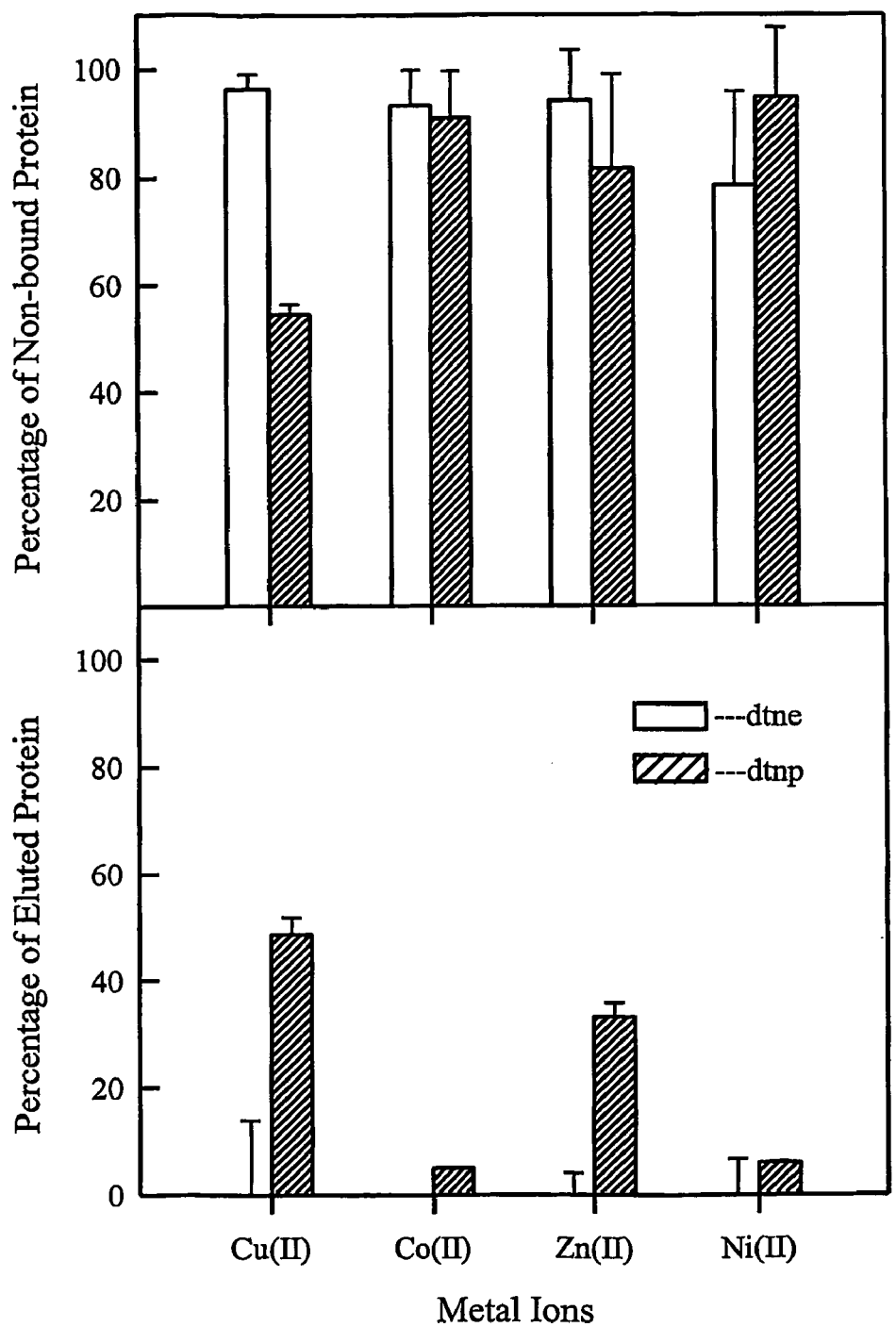
FIG. 5. The binding behaviour of human serum on the im-$M^{n+}$-dtne and im-$M^{n+}$-dtnp Sepharose™ CL-6B columns when binding buffer was 20 mM sodium acetate buffer/0.1 M NaCl, pH 4.0 and with different metal ions, where $M^{n+}=Cu^{2+}$, $CO^{2+}$, $Zn^{2+}$ and $Ni^{2+}$, respectively. The elution was performed using the procedure in Table 3. The percentage of eluted protein=(total amount of eluted protein/total amount of protein loaded)×100%.

The procedure used was essentially the same as described in Example 7, except that the equilibration buffer used was 20 mM sodium acetate buffer containing 0.1 M NaCl, pH 4.0 (cf.Table 3), and that the bound human serum proteins were eluted from the adsorbents with a series of elution buffers (5 ml) that are listed in Table 3. The results are shown in FIG. 5 and FIG. 2.

Example 10

Separation and Purification of Human Serum Proteins Using Immobilized $Cu^{2+}$-DTNP Adsorbent with Binding Buffer pH 9.5

The procedure used was essentially the same as described in Example 7, except that the adsorbent used was im-$Cu^{2+}$-dtnp on Sepharose™ CL-6B. The results are shown in FIG. 1 and FIG. 2.

Example 11

Separation and Purification of Human Serum Proteins Using Immobilized $Cu^{2+}$-DTNP Adsorbent with Binding Buffer pH 7.0

The procedure used was essentially the same as described in Example 8, except that the adsorbent used was im-$Cu^{2+}$-dtnp on Sepharose™ CL-6B. The results are shown in FIG. 3 and FIG. 4.

Example 12

Separation and Purification of Human Serum Proteins Using Immobilized $Cu^{2+}$-DTNP Adsorbent with Binding Buffer pH 4.0

The procedure used was essentially the same as described in Example 9, except that the adsorbent used was im-$Cu^{2+}$-dtnp on Sepharose™ CL-6B. The results are shown in FIG. 5 and FIG. 2.

Example 13

Separation and Purification of Human Serum Proteins Using Immobilized $Ni^{2+}$-DTNE Adsorbent with Binding Buffer pH 9.5

Figure 6:
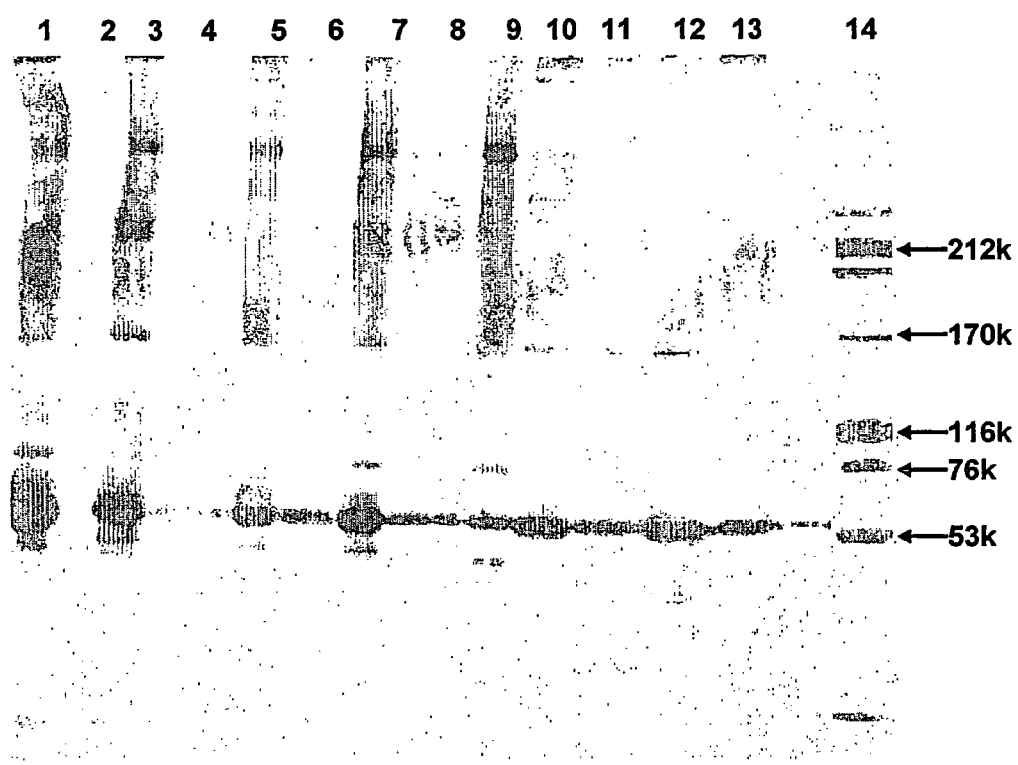
FIG. 6. SDS-PAGE profile of the fractions collected from im-$Ni^{2+}$-dtne and im-$Ni^{2+}$-dtnp Sepharose™ CL-6B batch columns under different loading conditions. Lane 1=human serum sample; Lane 2 and 3=breakthrough/wash and elution fractions from im-$Ni^{2+}$-dtne column when the loading pH was pH 4.0; Lane 4 and 5=breakthrough/wash and eluted fractions from im-$Ni^{2+}$-dtne Sepharose™ CL-6B column when the loading pH was pH 9.5; Lane 6 and 7=breakthrough/wash and eluted fractions from im-$Ni^{2+}$-dtnp column when the loading pH was pH 4.0; Lane 8 to 13=breakthrough/wash and eluted fractions from im-$Ni^{2+}$-dtnp Sepharose™ CL-6B column when the loading pH was pH 9.5. Elution was achieved with an increase concentration of NaCl and a decreasing pH; Lane 9=1 M NaCl and pH 9.5, Lane 10=pH 8.0, Lane 11=pH 7.0, Lane 12=pH 6.0, Lane 13=pH 4.0 and 250 mM imidazole; Lane 14 represents the molecular weight standards, myosin: 212 kDa, reduced $\alpha_2$-macroglobulin: 170 kDa, β-galactosidase: 116 kDa, transferrin: 76 kDa, and glutamine dehydrogenase 53 kDa.

The procedure used was essentially the same as described in Example 7, except that the adsorbent used was im-$Ni^{2+}$-dtne on Sepharose™ CL-6B. The results are shown in FIG. 1 and FIG. 6.

Example 14

Separation and Purification of Human Serum Proteins Using Immobilized $Ni^{2+}$-DTNE Adsorbent with Binding Buffer pH 7.0

The procedure used was essentially the same as described in Example 8, except that the adsorbent used was im-$Ni^{2+}$-dtne on Sepharose™ CL-6B. The results are shown in FIG. 3 and FIG. 4.

Example 15

Separation and Purification of Human Serum Proteins Using Immobilized $Ni^{2+}$-DTNE Adsorbent with Binding Buffer pH 4.0

The procedure used was essentially the same as described in Example 9, except that the adsorbent used was im-$Ni^{2+}$-dtne on Sepharose™ CL-6B. The results are shown in FIG. 5 and FIG. 6.

Example 16

Separation and Purification of Human Serum Proteins Using Immobilized $Ni^{2+}$-DTNP Adsorbent with Binding Buffer pH 9.5

The procedure used was essentially the same as described in Example 7, except that the adsorbent used was im-$Ni^{2+}$-dtnp on Sepharose™ CL-6B. The results are shown in FIG. 1 and FIG. 6.

Example 17

Separation and Purification of Human Serum Proteins Using Immobilized $Ni^{2+}$-DTNP Adsorbent with Binding Buffer pH 7.0

The procedure used was essentially the same as described in Example 8, except that the adsorbent used was im-$Ni^{2+}$-dtnp on Sepharose™ CL-6B. The results are shown in FIG. 3 and FIG. 4.

Example 18

Separation and Purification of Human Serum Proteins Using Immobilized $Ni^{2+}$-DTNP Adsorbent with Binding Buffer pH 4.0

The procedure used was essentially the same as described in Example 9, except that the adsorbent used was im-$Ni^{2+}$-dtnp on Sepharose™ CL-6B. The results are shown in FIG. 5 and FIG. 6.

Example 19

Separation and Purification of Human Serum Proteins Using Immobilized $Co^{2+}$-DTNE Adsorbent with Binding Buffer pH 9.5

The procedure used was essentially the same as described in Example 7, except that the adsorbent used was im-$Co^{2+}$-dtne on Sepharose CL-6B. The results are shown in FIG. 1.

Example 20

Separation and Purification of Human Serum Proteins Using Immobilized $Co^{2+}$-DTNE Adsorbent with Binding Buffer pH 7.0

The procedure used was essentially the same as described in Example 8, except that the adsorbent used was im-$Co^{2+}$-dtne on Sepharose™ CL-6B. The results are shown in FIG. 3.

Example 21

Separation and Purification of Human Serum Proteins Using Immobilized $Co^{2+}$-DTNE Adsorbent with Binding Buffer pH 4.0

The procedure used was essentially the same as described in Example 9, except that the adsorbent used was im-$Co^{2+}$-dtnp on Sepharose™ CL-6B. The results are shown in FIG. 5.

Example 22

Separation and Purification of Human Serum Proteins Using Immobilized $Co^{2+}$-DTNP Adsorbent with Binding Buffer pH 9.5

The procedure used was essentially the same as described in Example 7, except that the adsorbent used was im-$Co^{2+}$-dtnp on Sepharose™ CL-6B. The results are shown in FIG. 1.

Example 23

Separation and Purification of Human Serum Proteins Using Immobilized $Co^{2+}$-DTNP Adsorbent with Binding Buffer pH 7.0

The procedure used was essentially the same as described in Example 8, except that the adsorbent used was im-$Co^{2+}$-dtnp on Sepharose™ CL-6B. The results are shown in FIG. 3.

Example 24

Separation and Purification of Human Serum Proteins Using Immobilized $Co^{2+}$-DTNP Adsorbent with Binding Buffer pH 4.0

The procedure used was essentially the same as described in Example 9, except that the adsorbent used was im-$Co^{2+}$-dtnp on Sepharose™ CL-6B. The results are shown in FIG. 5.

Example 25

Separation and Purification of Human Serum Proteins Using Immobilized $Zn^{2+}$-DTNE Adsorbent with Binding Buffer pH 9.5

Figure 7:
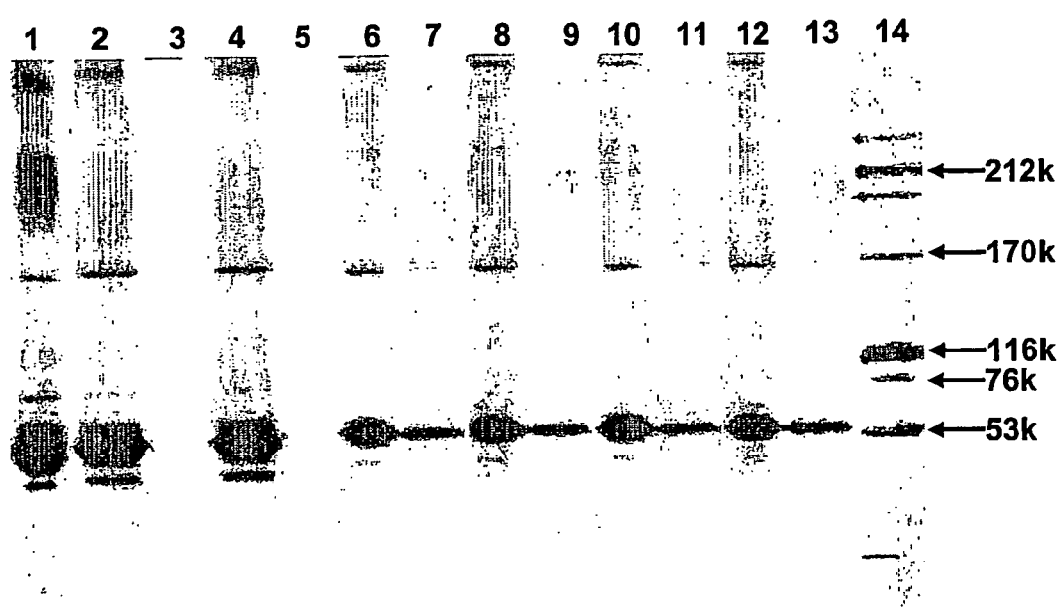
FIG. 7. SDS-PAGE profile of the fractions collected from im-$Zn^{2+}$-dtne and im-$Zn^{2+}$-dtnp Sepharose™ CL-6B batch columns under different loading conditions. Lane 1=human serum sample; Lane 2 and 3=breakthrough/wash and eluted fractions from im-$Zn^{2+}$-dtne Sepharose™ CL-6B column when the loading pH was pH 4.0; Lane 4 and 5=breakthrough/wash and eluted fractions from im-$Zn^{2+}$-dtnp Sepharose™ CL-6B columns when the loading pH was pH 9.5; Lane 6 and 7=breakthrough/wash and eluted fractions from im-$Zn^{2+}$-dtnp Sepharose™ CL-6B column when the loading pH was pH 4.0; Lane 8 and 9=breakthrough/wash and eluted fractions from im-$Zn^{2+}$-dtnp Sepharose™ CL-6B column when the loading pH was pH 9.5; Lane 10 and 11=breakthrough/wash and eluted fractions from im-$Zn^{2+}$-dtne Sepharose™ CL-6B column when the loading pH was pH 7.0; Lane 12 and 13=breakthrough/wash and eluted fractions from im-$Zn^{2+}$-dtnp Sepharose™ CL-6B column when the loading pH was pH 7.0; Lane 14=the molecular weight standards, Myosin 212 kDa, reduced $\alpha_2$-Macroglobulin 170 kDa, β-galactosidase 116 kDa, Transferrin 76 kDa, and glutamine dehydrogenase 53 kDa.

The procedure used was essentially the same as described in Example 7, except that the adsorbent used was im-$Zn^{2+}$-dtne on Sepharose™ CL-6B. The results are shown in FIG. 1 and FIG. 7.

Example 26

Separation and Purification of Human Serum Proteins Using Immobilized $Zn^{2+}$-DTNE Adsorbent with Binding Buffer pH 7.0

The procedure used was essentially the same as described in Example 8, except that the adsorbent used was im-$Zn^{2+}$-dtne on Sepharose™ CL-6B. The results are shown in FIG. 3 and FIG. 7.

Example 27

Separation and Purification of Human Serum Proteins Using Immobilized $Zn^{2+}$-DTNE Adsorbent with Binding Buffer pH 4.0

The procedure used was essentially the same as described in Example 9, except that the adsorbent used was im-$Zn^{2+}$-dtne on Sepharose™ CL-6B. The results are shown in FIG. 5 and FIG. 7.

Example 28

Separation and Purification of Human Serum Proteins Using Immobilized $Zn^{2+}$-DTNP Adsorbent with Binding Buffer pH 9.5

The procedure used was essentially the same as described in Example 7, except that the adsorbent used was im-$Zn^{2+}$-dtnp on Sepharose™ CL-6B. The results are shown in FIG. 1 and FIG. 7.

Example 29

Separation and Purification of Human Serum Proteins Using Immobilized $Zn^{2+}$-DTNP Adsorbent with Binding Buffer pH 7.0

The procedure used was essentially the same as described in Example 8, except that the adsorbent used was im-$Zn^{2+}$-dtnp on Sepharose™ CL-6B. The results are shown in FIG. 3 and FIG. 7.

Example 30

Separation and Purification of Human Serum Proteins Using Immobilized $Zn^{2+}$-DTNP Adsorbent with Binding Buffer pH 4.0

The procedure used was essentially the same as described in Example 9, except that the adsorbent used was im-$Zn^{2+}$-dtnp Sepharose™ CL-6B. The results are shown in FIG. 5 and FIG. 7.

Example 31

Figure 8:
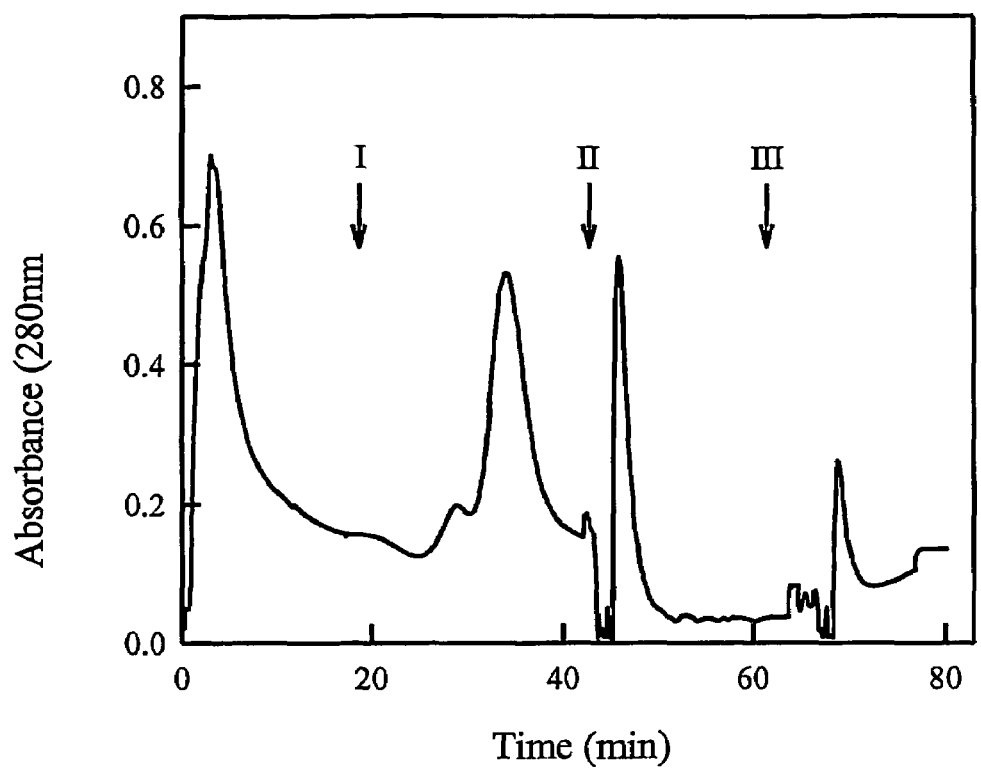
FIG. 8. Elution profile for human serum proteins separated on im-$Cu^{2+}$-dtne Sepharose™ CL-6B column (50 mm×5 mm i.d.) using following elution procedures: (I) a pH gradient from pH 9.5 to pH 4.0, (II) a NaCl concentration gradient from 100 mM to 1000 mM, and (III) a gradient of imidazole concentration from 0 to 250 mM. The flow rate was 0.5 ml/min. Equilibrium buffer was 20 mM sodium carbonate buffer containing 100 mM NaCl, pH 9.5.
Figure 9:
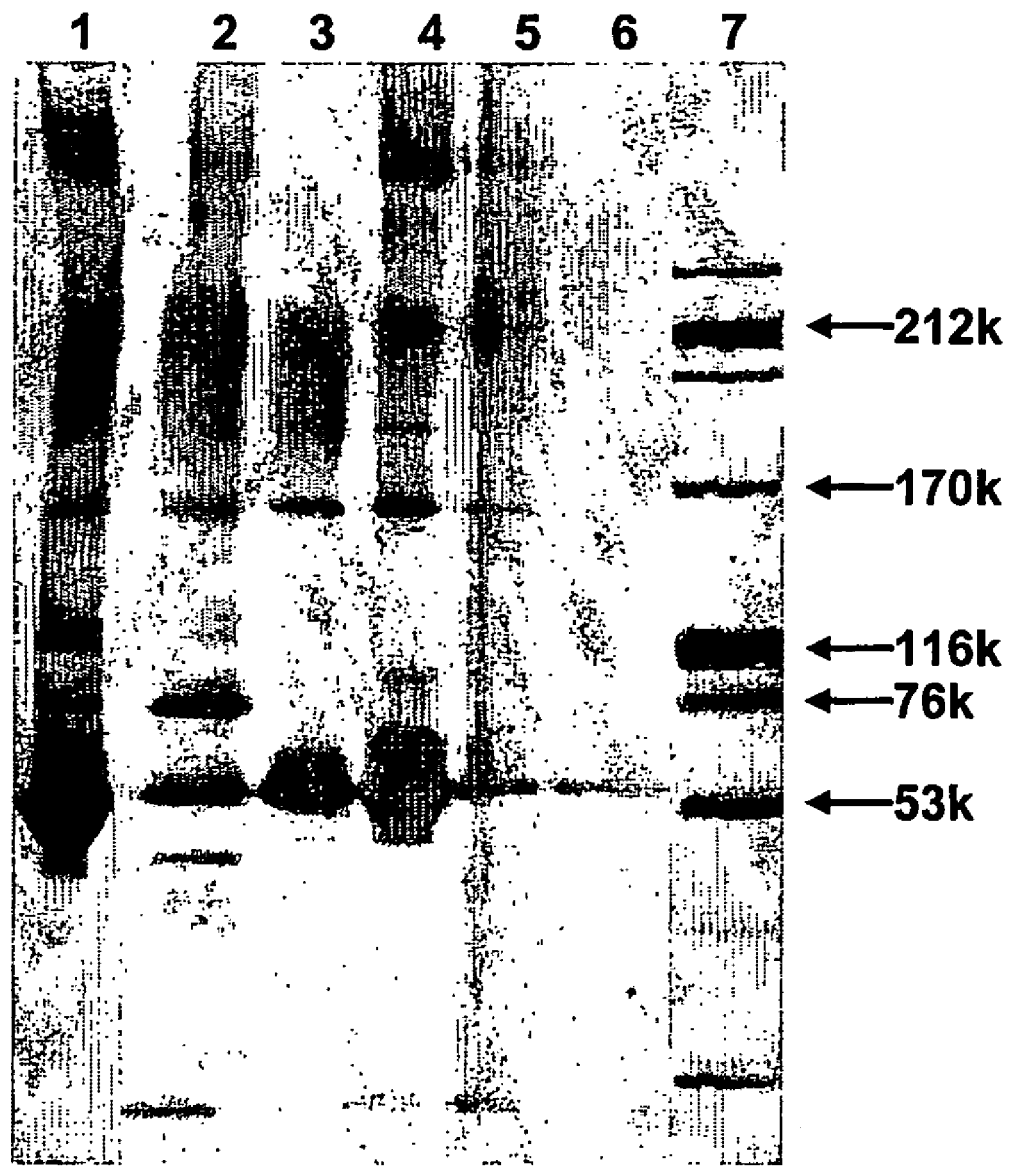
FIG. 9. The SDS-PAGE profile of the selected fractions in FIG. 8. Lane 1 represents human serum sample; Lane 2 represents breakthrough/washing fractions; Lane 3 and 4 represent the elution peaks under pH gradient elution via pH from pH 9.5 to pH 4.0; Lane 5 represents the elution peak under NaCl gradient elution; Lane 6 represents the elution peak under imidazole gradient elution; Lane 7 represents the molecular weight standards, Myosin 212 kDa, reduced $\alpha_2$-Macroglobulin 170 kDa, galactosidase 116 kDa, Transferrin 76 kDa, and glutamine dehydrogenase 53 kDa.

Separation of Human Serum Proteins Using Immobilized $Cu^{2+}$-DTNE Adsorbent with the FPLC™ System A programmed FPLC system (Pharmacia Fine Chemicals, Uppsala, Sweden) was used throughout for these separation procedures. The im-$Cu^{2+}$-dtne/Sepharose™ CL-6B adsorbent (1 ml) was packed into Amersham Pharmacia™ HR5/10 columns (packed volume 5 cm×0.5 cm i.d.). A flow rate of 0.5 ml/min was employed throughout the chromatographic procedures. The column was equilibrated using equilibration buffer (see below). The human serum solution (200 µl), diluted five times with equilibration buffer, was loaded onto the packed column through a 200 µl injection loop. All the washing and gradient elution procedures are described below. A Pharmacia™ UV-1 single path monitor (280 nm), REC-482 two-channel recorder and a computerised data-logger were employed to monitor and record chromatographic profiles of the human serum proteins. All the fractions were collected with a FRAC-100 fraction collector as 1 ml fractions, and analyzed using Bio-Rad™ Dye and bicinchoninic acid (BCA) methods. The peak fractions were analysed by SDS-PAGE. The results are shown in FIG. 8 and FIG. 9.

Elution Protocol for the im-$Cu^{2+}$-dtne Column

| | |
|---|---|
| Equilibration buffer: | 20 mM sodium carbonate buffer/0.1 M NaCl, pH 9.5. |
| Washing buffer: | 15 ml of equilibration buffer. |
| Elution Procedures: | 1) 10 ml of linear pH gradient over 20 min, from 20 mM sodium carbonate buffer/100 mM NaCl, pH 9.5, to 20 mM sodium acetate buffer/100 mM NaCl, pH 4.0; |
| | 2) 10 ml of linear salt concentration gradient over 20 min, from 0.1 M to 1.0 M NaCl in 20 mM sodium acetate buffer, pH 4.0; |
| | 3) 10 ml of linear imidazole concentration gradient over 20 min, from 0 to 250 mM imidazole in 20 mM sodium acetate buffer/1.0 M NaCl, pH 4.0. |

Example 32

Figure 10:
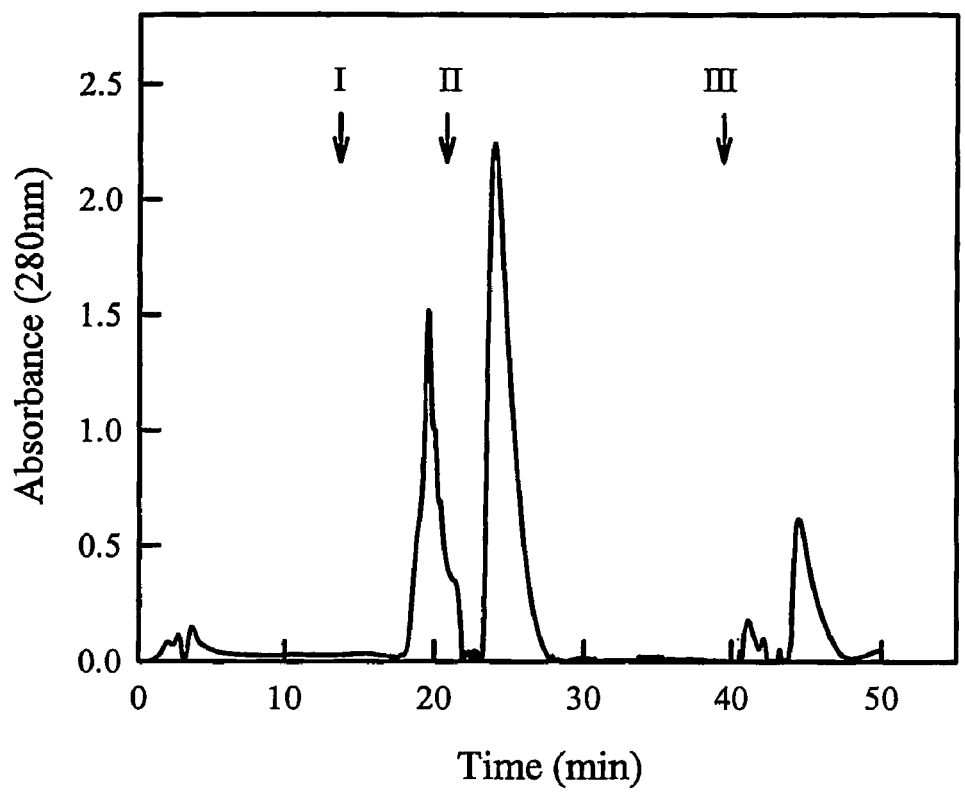
FIG. 10. Elution profile for human serum proteins separated on im-$Cu^{2+}$-dtnp Sepharose™ CL-6B column (50 mm×5 mm i.d.) using following elution procedures: (I) a pH gradient form pH 9.5 to pH 4.0, (II) a NaCl concentration gradient from 100 mM to 1000 mM, and (III) a gradient of imidazole concentration from 0 to 250 mM. The flow rate was 0.5 ml/min. equilibrium buffer was 20 mM sodium carbonate buffer containing 100 mM NaCl, pH 9.5.
Figure 11:
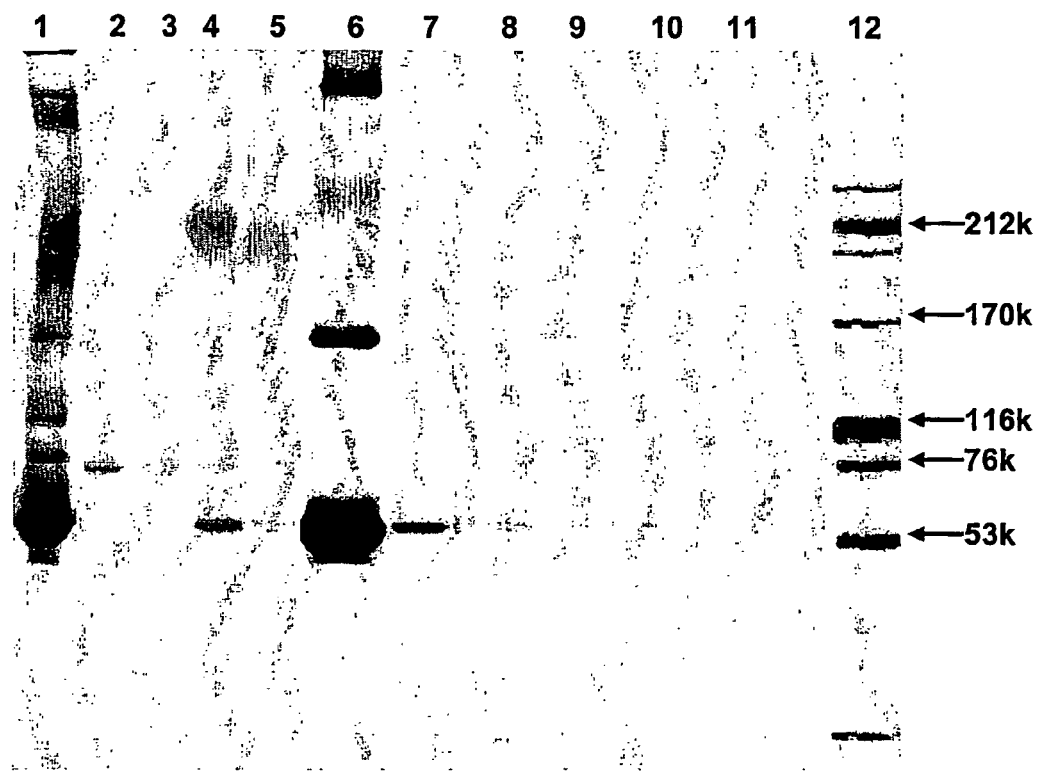
FIG. 11. SDS-PAGE profile of the selected fractions in FIG. 10. Lane 1 represents human serum sample; Lane 2 and 3 represent breakthrough/washing fractions; Lane 4 and 5 represent the elution peaks under pH gradient elution via pH from pH 9.5 to pH 4.0; Lane 6 to 8 represent the elution peak under NaCl gradient elution; Lane 9 to 11 represent the elution peak under imidazole gradient elution; Lane 12 represents the molecular weight standards, Myosin 212 kDa, reduced $\alpha_2$-Macroglobulin 170 kDa, β-galactosidase 116 kDa, Transferrin 76 kDa, and glutamine dehydrogenase 53 kDa.

Separation of Human Serum Proteins Using Immobilized $Cu^{2+}$-DTNP Adsorbent with the FPLC™ System The procedure used was essentially the same as described in Example 31, except that the adsorbent used was im-$Cu^{2+}$-dtnp/Sepharose™ CL-6B and that the following elution protocol was used. The results are shown in FIG. 10 and FIG. 11.

Elution Protocol for im-Cu$^{2+}$-dtnp Column

| | |
|---|---|
| Equilibration buffer: | 20 mM sodium carbonate buffer/0.1 M NaCl, pH 9.5. |
| Washing buffer: | 5 ml of equilibration buffer. |
| Elution Procedures: | 1) 5 ml of linear pH gradient over 10 min, from 20 mM sodium carbonate buffer/0.1 M NaCl, pH 9.5, to 20 mM sodium acetate buffer/0.1 M NaCl, pH 4.0; |
| | 2) 2 ml of 20 mM sodium acetate buffer/0.1 M NaCl, pH 4.0; |
| | 3) 7 ml of linear salt concentration gradient over 14 min, from 0.1 M to 1.0 M NaCl in 20 mM sodium acetate buffer, pH 4.0; |
| | 4) 1 ml of 20 mM sodium acetate buffer/1.0 M NaCl, pH 4.0; |
| | 5) 5 ml of linear imidazole gradient over 10 min, from 0 to 250 mM imidazole in 20 mM sodium acetate buffer/1.0 M NaCl, pH 4.0; |
| | 6) 1 ml of 20 mM sodium acetate buffer/1.0 M NaCl and 250 mM imidazole, pH 4.0. |

Example 33

Figure 12:
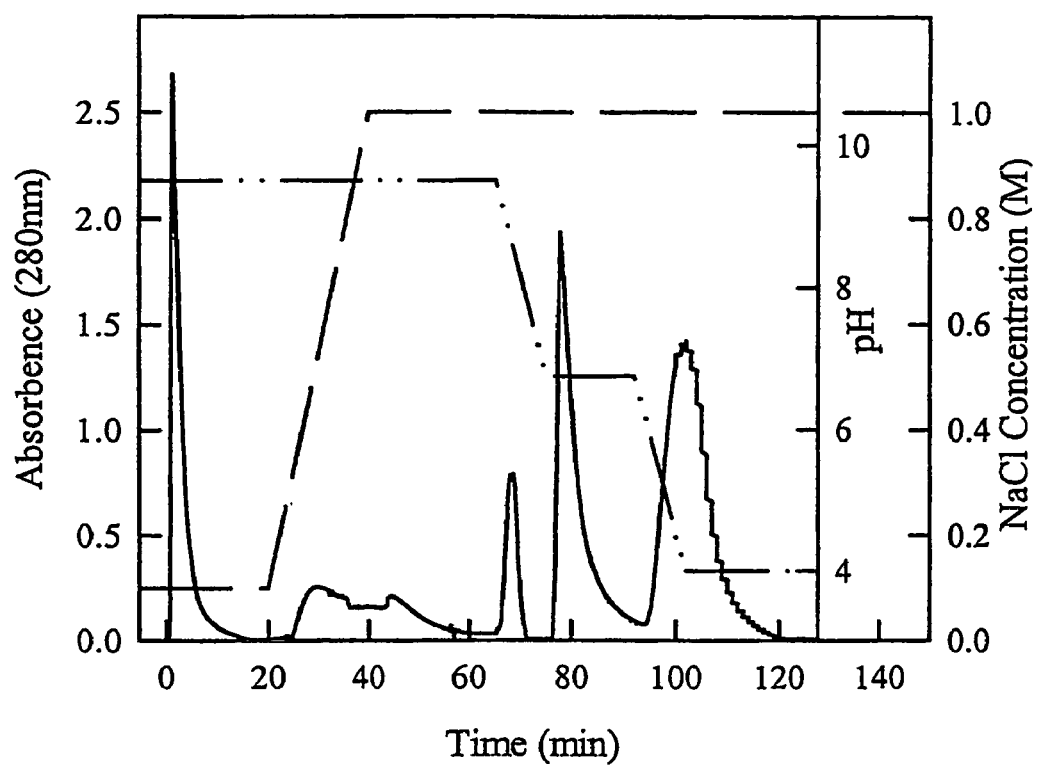
FIG. 12. Elution profile for human serum proteins separated on im-$Cu^{2+}$-dtne Sepharose™ CL-6B column (50 mm×5 mm i.d.) using a combined elution of a NaCl concentration gradient and pH gradient. The full line (—) indicates the UV absorbance of the fractions at a wavelength of 280 nm. The dashed line ( - - - ) indicates NaCl concentration. The dash-dot-dot-dash line (- • • - • • -) indicates the pH. The flow rate was 0.5 ml/min. Equilibrium buffer was 20 mM sodium carbonate buffer containing 100 mM NaCl, pH 9.5.
Figure 13:
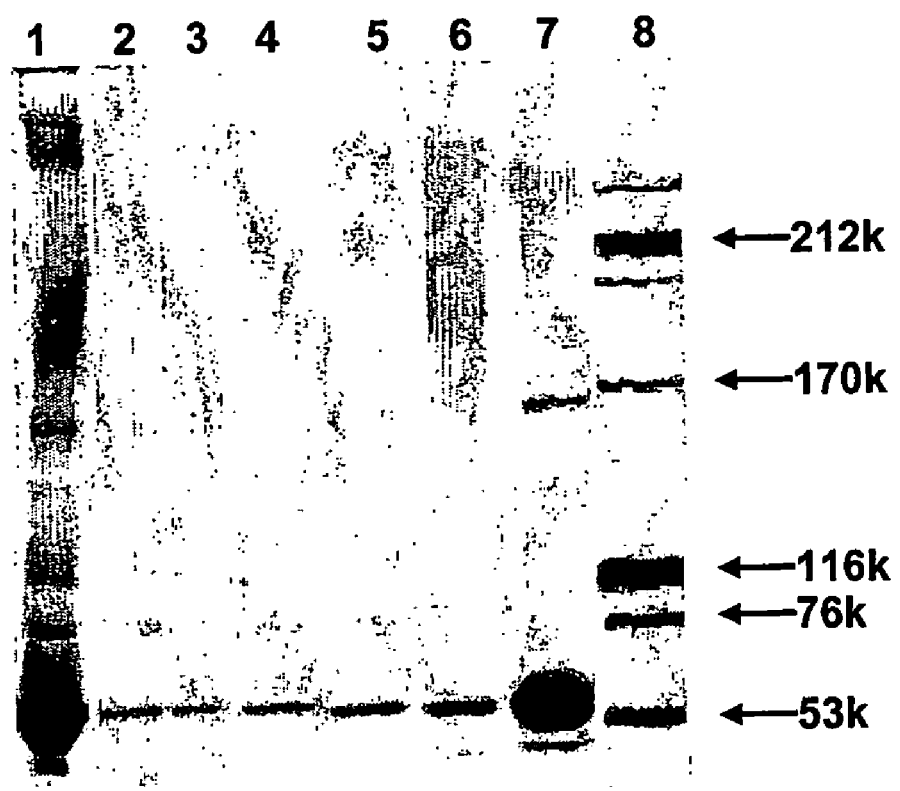
FIG. 13. SDS-PAGE profile of selected fractions in FIG. 12. Lane 1 represents human serum sample; Lane 2 represents breakthrough/washing fraction; Lane 3 represents the elution peak under NaCl gradient elution; Lane 4 represents the elution peak under elution with pH 9.5 buffer containing 1 M NaCl; Lane 5 represents the elution peak under pH gradient elution from pH 9.5 to pH 6.75 with an NaCl concentration of 1 M; Lane 6 represents the elution peak under elution with pH 6.75 buffer containing 1 M NaCl; Lane 7 represents the elution peak under pH gradient from pH 6.75 to pH 4.0, and isocratic elution with pH 4.0 buffer containing 1 M NaCl; Lane 8 represents the molecular weight standards, Myosin 212 kDa, reduced $\alpha_2$-Macroglobulin 170 kDa, β-galactosidase 116 kDa, Transferrin 76 kDa, and glutamine dehydrogenase 53 kDa.

Separation of Human Serum Proteins Using Immobilized Cu$^{2+}$-DTNP Adsorbent with the FPLC™ System The procedure used was essentially the same as described in Example 31, except that the adsorbent used was im-Cu$^{2+}$-dtnp/Sepharose™ CL-6B and that the following elution protocol was used. The results are shown in FIG. 12 and FIG. 13.

Elution Protocol for im-Cu$^{2+}$-dtnp Column

| | |
|---|---|
| Equilibration buffer: | 20 mM sodium carbonate buffer/0.1 M NaCl, pH 9.5. |
| Washing buffer: | 10 ml of equilibration buffer. |
| Elution Buffers: | buffer A: 20 mM sodium carbonate buffer/1.0 M NaCl, pH 9.5; buffer B: 20 mM sodium acetate buffer/1.0 M NaCl, pH 4.0. |
| Elution procedures: | 1) 10 ml of linear salt concentration gradient over 20 min, from 0.1 M to 1.0 M NaCl in 20 mM sodium carbonate buffer, pH 9.5; |
| | 2) 1 ml of buffer A; |
| | 3) 5 ml of linear gradient over 10 min, from buffer A to buffer B; final buffer composition: 50% buffer A and 50% buffer B; |
| | 4) 8 ml of a 50:50 v/v mixture of buffer A and buffer B; |
| | 5) 5 ml of linear gradient over 10 min, from 50/50 v/v buffer A + buffer B to 100% buffer B; |
| | 6) 10 ml of 20 mM sodium acetate buffer/1.0 M NaCl, pH 4.0. |

Example 34

Screening of the im-Cu$^{2+}$-TACN Adsorbent for Binding of Recombinant GST-δATPASE-HIS$_6$ Protein A Bio-Rad™ Econo-column [typically a column of size from 4.0 cm (length)×0.8 cm (i.d.) to 12 cm (length)×1.5 cm (i.d.)] (Hercules, Calif., USA) containing from 0.5 ml to 20 ml of the im-Cu$^{2+}$-tacn/Sepharose™ CL-6B gel was equilibrated with an equilibration buffer comprising 50 mM sodium phosphate buffer, 300 mM sodium chloride and 10% glycerol, pH 8.0. An aliquot of a partially purified fusion protein, GST-δATPase-His$_6$ (produced in E. coli strain K12 DH5alphaF'. The origin of the DH5alphaF'strain and genotype is as follows: F', 80dlacZΔM15, endA1, recA1, hsdR17 (rk$^-$,mk$^+$), supE44, thi-1, gyrA96, relA1, Δ(lacZYA-argF) U169, deoR, λ$^-$. [see http://wheat.pw.usda.gov/qqpages/probes/strains.html]. The crude E. coli cell lysate, containing the target recombinant protein GST-δATPAse-His$_6$ produced by cell disruption of the collected E. coli cell pellet from the cell expression system (0.3 ml for a 4.0 cm×0.8 cm column, and proportionately larger aliquots for larger columns), was loaded onto the column. The equilibration buffer (5 ml for a 4.0 cm×0.8 cm column, and proportionately larger volumes for larger columns) was used to elute unbound or weakly bound proteins. When no further protein was eluted, volumes of equilibration buffer containing 20 mM imidazole, 40 mM imidazole and 250 mM imidazole, respectively (2 ml volumes for a 4.0 cm×0.8 cm column, and proportionately larger volumes for larger columns) were then applied sequentially to elute the bound proteins, with fractions of 1 ml being collected. The protein concentration of unbound and eluted fractions was determined by the bicinchoninic acid (BCA) reagent (Pierce Chemical Co., Rockford, Ill., USA) and Bio-Rad™ Dye (BioRad, Richmond, Calif., USA) methods, and the enzymatic activity was determined using the GST substrate 1-chloro-2,4-dinitrobenzene (CDNB). The percentage of the fusion protein GST-δATPase-His$_6$ bound to the adsorbent is given in Table 4.

Example 35

Screening of the im-Ni$^{2+}$-TACN Adsorbent for Binding of Recombinant GST-δATPASE-HIS$_6$ Protein The procedure used was essentially the same as described in Example 34, except that the adsorbent used was im-Ni$^{2+}$-tacn on Sepharose™ CL-6B. The percentage of the fusion protein GST-δATPaseHis$_6$ bound to the adsorbent is given in Table 4.

Example 36

Screening of the im-Zn$^{2+}$-TACN Adsorbent for Binding of Recombinant GST-δATPASE-HIS$_6$ Protein The procedure used was essentially the same as described in Example 34, except that the adsorbent used was im-Zn$^{2+}$-tacn on Sepharose™ CL-6B. The percentage of the fusion protein GST-δATPaseHis$_6$ bound to the adsorbent is given in Table 4.

Example 37

Screening of the im-Co$^{2+}$-TACN Adsorbent for Binding of Recombinant GST-δATPASE-HIS$_6$ Protein The procedure used was essentially the same as described in Example 34, except that the adsorbent used was im-Co$^{2+}$-tacn on Sepharose™ CL-6B. The percentage of the fusion protein GST-δATPaseHis$_6$ bound to the adsorbent is given in Table 4.

Example 38

Screening of the im-$Mn^{2+}$-TACN Adsorbent for Binding to Recombinant GST-δATPASE-$HIS_6$ Protein The procedure used was essentially the same as described in Example 34, except that the adsorbent used was im-$Mn^{2+}$-tacn on Sepharose™ CL-6B. The percentage of the fusion protein GST-δATPaseHis$_6$ bound to the adsorbent is given in Table 4.

Example 39

Screening of the im-$Cr^{3+}$-TACN Adsorbents for Binding of Recombinant GST-δATPASE-$HIS_6$ Protein The procedure used was essentially the same as described in Example 34, except that the adsorbent used was im-$Cr^{3+}$-tacn on Sepharose™ CL-6B. The percentage of the fusion protein GST-δATPaseHis$_6$ bound to the adsorbent is given in Table 4.

Example 40

Screening of the im-$Cu^{2+}$-DTNE Adsorbents for Binding of Recombinant GST-δATPASE-$HIS_6$ Protein The procedure used was essentially the same as described in Example 34, except that the adsorbent used was im-$Cu^{2+}$-DTNE on Sepharose™ CL-6B. The percentage of the fusion protein GST-δATPaseHis$_6$ bound to the adsorbent is given in Table 4.

Example 41

Screening of the im-$Ni^{2+}$-DTNE Adsorbents for Binding of Recombinant GST-δATPASE-$HIS_6$ Protein The procedure used was essentially the same as described in Example 34, except that the adsorbent used was im-$Ni^{2+}$-DTNE on Sepharose™ CL-6B. The percentage of the fusion protein GST-δATPaseHis$_6$ bound to the adsorbent is given in Table 4.

Example 42

Screening of the im-$Zn^{2+}$-DTNE Adsorbents for Binding of Recombinant GST-δATPASE-$HIS_6$ Protein The procedure used was essentially the same as described in Example 34, except that the adsorbent used was im-$Zn^{2+}$-DTNE on Sepharose™ CL-6B. The percentage of the fusion protein GST-δATPaseHis$_6$ bound to the adsorbent is given in Table 4.

Example 43

Screening of the im-$Co^{2+}$-DTNE Adsorbents for Binding of Recombinant GST-δATPASE-$HIS_6$ Protein The procedure used was essentially the same as described in Example 34, except that the adsorbent used was im-$Co^{2+}$-DTNE on Sepharose™ CL-6B. The percentage of the fusion protein GST-δATPaseHis$_6$ bound to the adsorbent is given in Table 4.

Example 44

Screening of the im-$Mn^{2+}$-DTNE Adsorbents for Binding of Recombinant GST-δATPASE-$HIS_6$ Protein The procedure used was essentially the same as described in Example 34, except that the adsorbent used was im-$Mn^{2+}$-DTNE on Sepharose™ CL-6B. The percentage of the fusion protein GST-δATPaseHis$_6$ bound to the adsorbent is given in Table 4.

Example 45

Screening of the im-$Cr^{3+}$-DTNE Adsorbents for Binding of Recombinant GST-δATPASE-$HIS_6$ Protein The procedure used was essentially the same as described in Example 34, except that the adsorbent used was im-$Cr^{3+}$-DTNE on Sepharose™ CL-6B. The percentage of the fusion protein GST-δATPaseHis$_6$ bound to the adsorbent is given in Table 4.

Example 46

Screening of the im-$Cu^{2+}$-DTNP Adsorbents for Binding of Recombinant GST-δATPASE-$HIS_6$ Protein The procedure used was essentially the same as described in Example 34, except that the adsorbent used was im-$Cu^{2+}$-DTNP on Sepharose™ CL-6B. The percentage of the fusion protein GST-δATPaseHis$_6$ bound to the adsorbent is given in Table 4.

Example 47

Screening of the im-$Ni^{2+}$-DTNP Adsorbents for Binding of Recombinant GST-δATPASE-$HIS_6$ Protein The procedure used was essentially the same as described in Example 34, except that the adsorbent used was im-$Ni^{2+}$-DTNP on Sepharose™ CL-6B. The percentage of the fusion protein GST-δATPaseHis$_6$ bound to the adsorbent is given in Table 4.

Example 48

Screening of the im-$Zn^{2+}$-DTNP Adsorbents for Binding of Recombinant GST-δATPASE-$HIS_6$ Protein The procedure used was essentially the same as described in Example 34, except that the adsorbent used was im-$Zn^{2+}$-DTNP on Sepharose™ CL-6B. The percentage of the fusion protein GST-δATPaseHis$_6$ bound to the adsorbent is given in Table 4.

Example 49

Screening of the im-$Co^{2+}$-DTNP Adsorbents for Binding of Recombinant GST-δATPASE-$HIS_6$ Protein The procedure used was essentially the same as described in Example 34, except that the adsorbent used was im-$Co^{2+}$-DTNP on Sepharose™ CL-6B. The percentage of the fusion protein GST-δATPaseHis$_6$ bound to the adsorbent is given in Table 4.

Example 50

Screening of the im-$Mn^{2+}$-DTNP Adsorbents for Binding of Recombinant GST-δATPASE-$HIS_6$ Protein The procedure used was essentially the same as described in Example 34, except that the adsorbent used was im-$Mn^{2+}$-DTNP on Sepharose™ CL-6B. The percentage of the fusion protein GST-δATPaseHis$_6$ bound to the adsorbent is given in Table 4.

Example 51

Screening of the im-$Cr^{3+}$-DTNP Adsorbents for Binding of Recombinant GST-δATPASE-$HIS_6$ Protein The procedure used was essentially the same as described in Example 34, except that the adsorbent used was im-$Cr^{3+}$-DTNP on Sepharose™ CL-6B. The percentage of the fusion protein GST-δATPaseHis$_6$ bound to the adsorbent is given in Table 4.

Example 52

Figure 14:
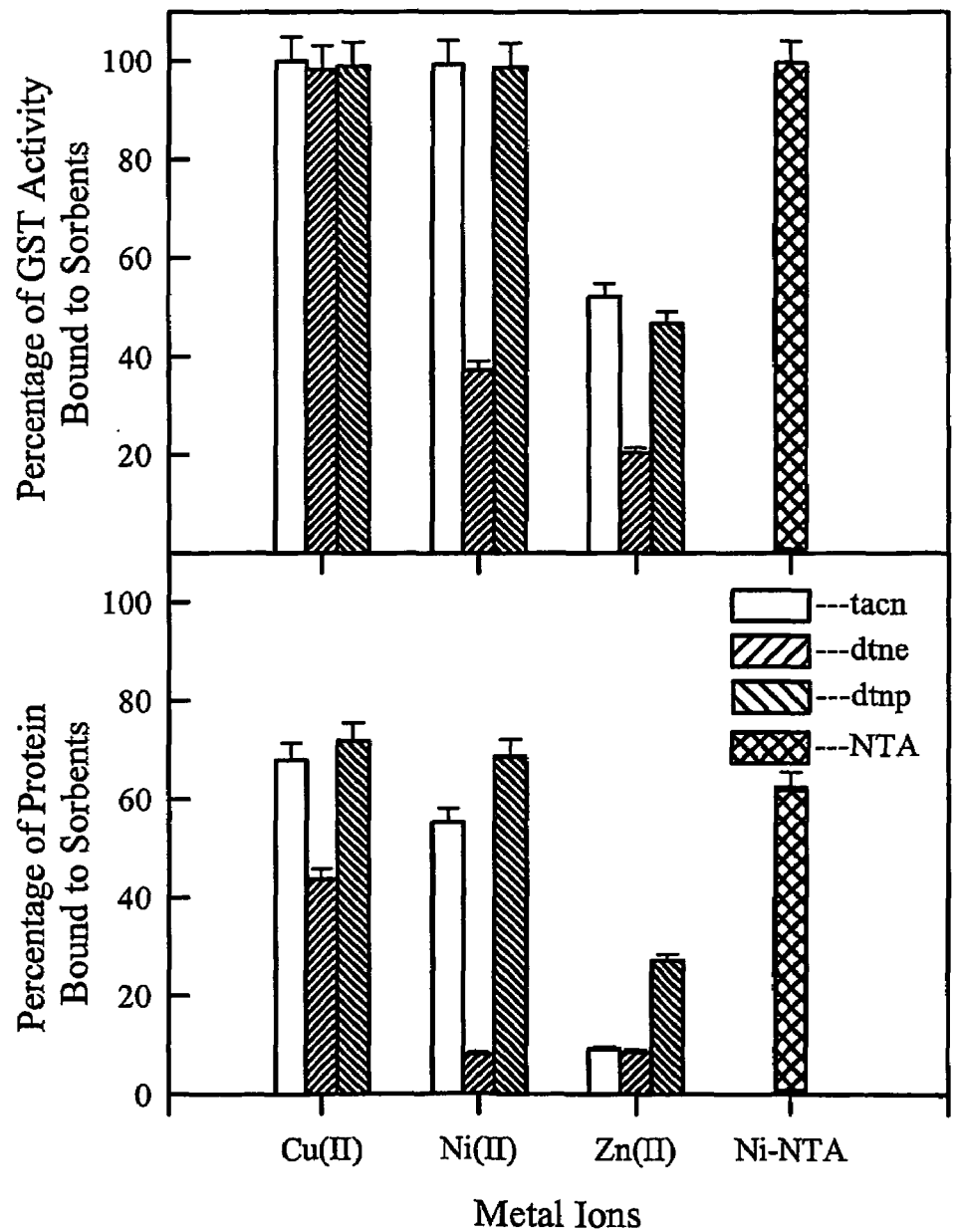
FIG. 14. The percentage of total protein and enzymatic activity present in the recovered fractions of an E. coli cell extract from the expression of recombinant glutathione S-transferase (r-GST) that bound to different columns prepared from the im-$Cu^{2+}$-, im-$Ni^{2+}$- and im-$Zn^{2+}$-tacn, -dtne and -dtnp Sepharose™ CL-6B adsorbents and the im-$Ni^{2+}$-NTA Sepharose™ CL-6B adsorbent using batch adsorption procedures. The equilibration buffer for these binding studies was 50 mM $Na_2HPO_4$/300 mM NaCl and 10% glycerol, pH 8.0.
Figure 15:
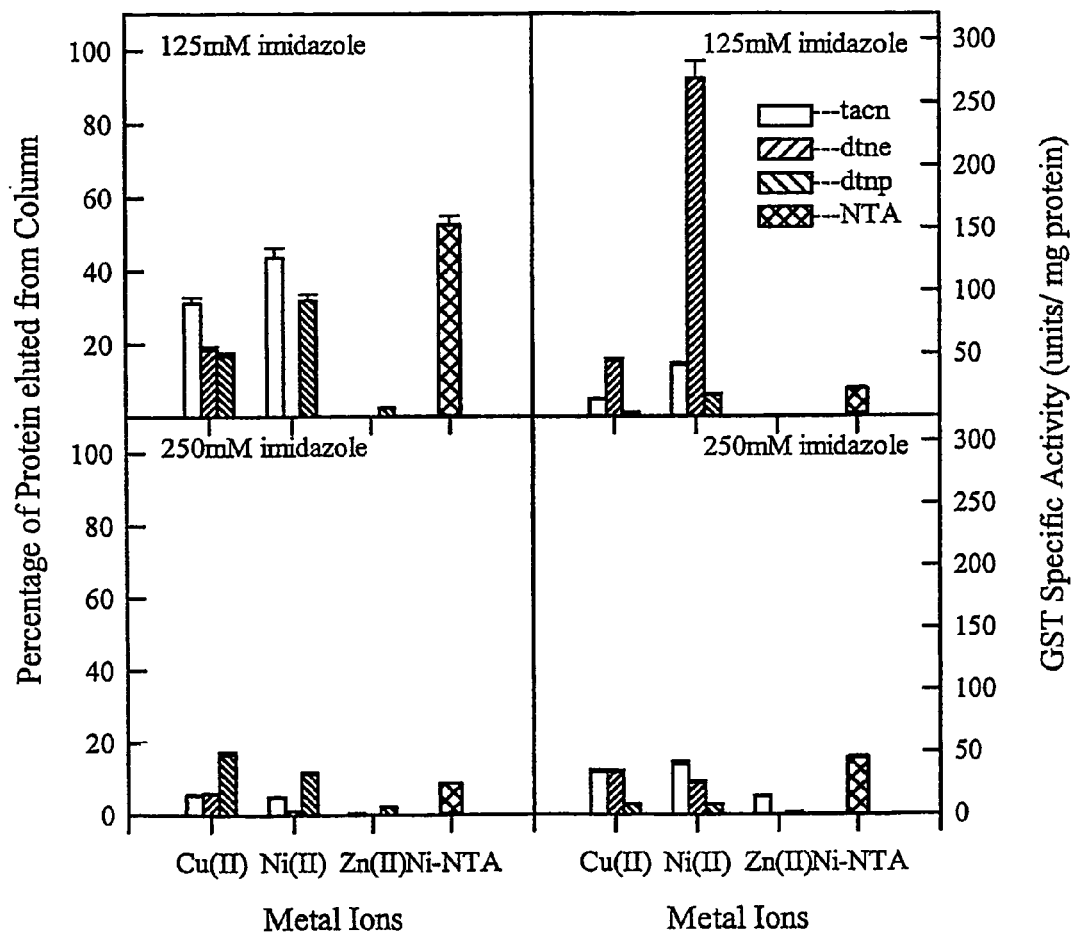
FIG. 15. This figure shows the amount of bound protein (as a percentage of the total protein loaded onto the column) that could be eluted from the im-$Cu^{2+}$-, im-$Ni^{2+}$- and im-$Zn^{2+}$-tacn, -dtne and -dtnp Sepharose™ CL-6B columns and im-$Ni^{2+}$-NTA Sepharose™ CL-6B column with 125 mM and 250 mM imidazole in the elution buffer (50 mM $Na_2HPO_4$/300 mM NaCl and 10% glycerol, pH 7.0) and the corresponding GST specific activities of the recovered fractions from the fractionation of an *E. coli* cell extract from the expression of recombinant glutathione S-transferase (r-GST).

Separation of the Recombinant GST-δATPASE-$HIS_6$ Protein from *E. coli* Lysate Using a Batch Adsorption Procedure with im-$Cu^{2+}$-TACN SEPHAROSE™ CL-6B as Adsorbent The crude *E. coli* extract (3 ml) obtained as in Example 34 was mixed with 1 ml of im-$Cu^{2+}$-tacn Sepharose™ CL-6B gel that was equilibrated in the presence of 50 mM sodium phosphate buffer containing 300 mM sodium chloride and 10% glycerol, pH 8.0 (equilibration buffer). After incubation at 4° C. for 30 min, the mixtures were centrifuged at 3,000×g, 4° C. for 5 min and the supernatant removed. The gel pellet was washed twice with 5 ml of equilibration buffer to remove unbound or weakly bound proteins. The washed gel was then packed into a Bio-Rad™ Econo-column (10 ml) (Hercules, Calif., USA). The equilibration buffer (20 ml) was further used to elute any unbound or weakly bound proteins. Elution of the retained proteins was achieved by using 10 ml of the equilibration buffer containing 125 mM imidazole, pH 7.0 (elution buffer A) and by using 5 ml of the equilibration buffer containing 250 mM imidazole, pH 7.0 (elution buffer B). All fractions (1 ml) were collected and analysed for protein content and enzyme activity. The protein concentration of unbound and eluted fractions was determined by the bicinchoninic acid (BCA) reagent (Pierce Chemical Co., Rockford, Ill., USA) and Bio-Rad™ Dye (BioRad, Richmond, Calif., USA) methods, and the enzymatic activity was determined using the GST substrate 1-chloro-2,4-dinitrobenzene (CDNB). The results are shown in FIGS. 14-16.

Example 53

Separation of the Recombinant GST-δATPASE-$HIS_6$ Protein from *E. coli* Lysate Using a Batch Adsorption Procedure with im-$Ni^{2+}$-TACN Sepharose™ CL-6B as Adsorbent The procedure used was essentially the same as described in Example 52, except that the adsorbent used was im-$Ni^{2+}$-tacn Sepharose™ CL-6B. The results are shown in FIGS. 14-16.

Example 54

Separation of the Recombinant GST-δATPASE-$HIS_6$ Protein from *E. coli* Lysate Using a Batch Adsorption Procedure with im-$Zn^{2+}$-TACN Sepharose™ CL-6B as Adsorbent The procedure used was essentially the same as described in Example 52, except that the adsorbent used was im-$Zn^{2+}$-tacn Sepharose™ CL-6B. The results are shown in FIGS. 14-16.

Example 55

Separation of the Recombinant GST-δATPASE-$HIS_6$ Protein from *E. coli* Lysate Using a Batch Adsorption Procedure with im-$Cu^{2+}$-DTNE Sepharose™ CL-6B as Adsorbent The procedure used was essentially the same as described in Example 52, except that the adsorbent used was im-$Cu^{2+}$-dtne Sepharose™ CL-6B. The results are shown in FIGS. 14-16.

Example 56

Separation of the Recombinant GST-δATPASE-$HIS_6$ Protein from *E. coli* Lysate Using a Batch Adsorption Procedure with im-$Ni^{2+}$-DTNE Sepharose™ CL-6B as Adsorbent The procedure used was essentially the same as described in Example 52, except that the adsorbent used was im-$Ni^{2+}$-dtne Sepharose™ CL-6B. The results are shown in FIGS. 14-16.

Example 57

Separation of the Recombinant GST-δATPASE-$HIS_6$ Protein from *E. coli* Lysate Using a Batch Adsorption Procedure with im-$Zn^{2+}$-DTNE SEPHAROSE™ CL-6B as Adsorbent The procedure used was essentially the same as described in Example 52, except that the adsorbent used was im-$Zn^{2+}$-dtne Sepharose™ CL-6B. The results are shown in FIGS. 14-16.

Example 58

Separation of the Recombinant GST-δATPASE-HIS$_6$ Protein from *E. coli* Lysate Using a Batch Adsorption Procedure with im-Cu$^{2+}$-DTNP Sepharose™ CL-6B as Adsorbent The procedure used was essentially the same as described in Example 52, except that the adsorbent used was im-Cu$^{2+}$-dtnp Sepharose™ CL-6B. The results are shown in FIGS. 14-16.

Example 59

Separation of the Recombinant GST-δATPASE-HIS$_6$ Protein from *E. coli* Lysate Using a Batch Adsorption Procedure with im-Ni$^{2+}$-DTNP Sepharose™ CL-6B as Adsorbent The procedure used was essentially the same as described in Example 52, except that the adsorbent used was im-Ni$^{2+}$-dtnp Sepharose™ CL-6B. The results are shown in FIGS. 14-16.

Example 60

Separation of the Recombinant GST-δATPASE-HIS$_6$ Protein from *E. coli* Lysate Using a Batch Adsorption Procedure with im-Zn$^{2+}$-DTNP Sepharose™ CL-6B as Adsorbent The procedure used was essentially the same as described in Example 52, except that the adsorbent used was im-Zn$^{2+}$-dtnp Sepharose™ CL-6B. The results are shown in FIGS. 14-16.

Example 61

Figure 17:
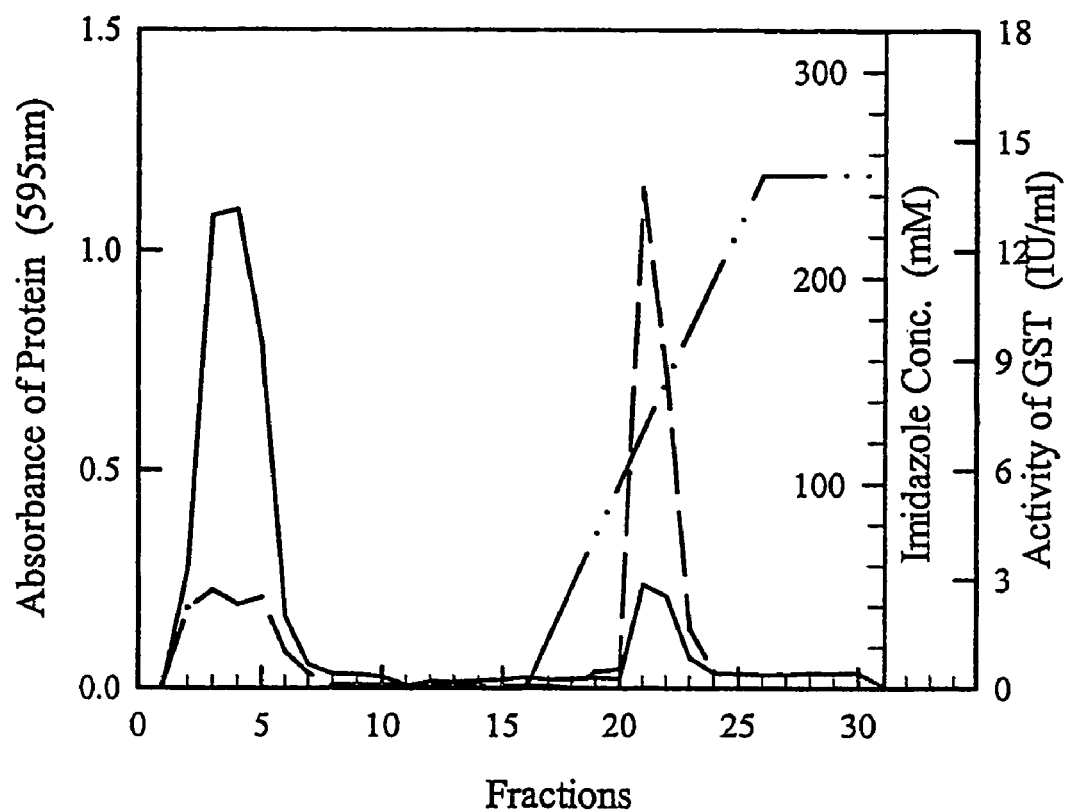
FIG. 17. Chromatographic separation of the recombinant GST-δATPase-$His_6$ protein from other proteins in the crude *E. coli* extract using the im-$Ni^{2+}$-tacn Sepharose™ CL-6B adsorbent equilibrated with 50 mM $Na_2HPO_4$/300 mM NaCl and 10% glycerol, pH 8.0, at a flow rate of 0.5 ml/min. The crude *E. coli* extract (2 ml crude *E. coli* extract per ml adsorbent) containing the recombinant GST-δATPase-$His_6$ protein was loaded onto the packed column. Unbound or weakly bound proteins were washed off with 15 volumes of the equilibration buffer. Bound proteins were then eluted using a linear gradient of 0 to 250 mM imidazole in the equilibration buffer over 20 minutes. Following completion of the gradient elution, the column was flushed with a 200 mM solution of EDTA in the elution buffer. The GST activity in the recovered fractions was determined and is indicated by the dashed line (- - -). The dash-dot-dot-dash line (- • • - • • -) and solid line (—) indicate the gradient of the imidazole and the UV absorbance of the protein in the fractions at a wavelength of 280 nm, respectively.
Figure 18:
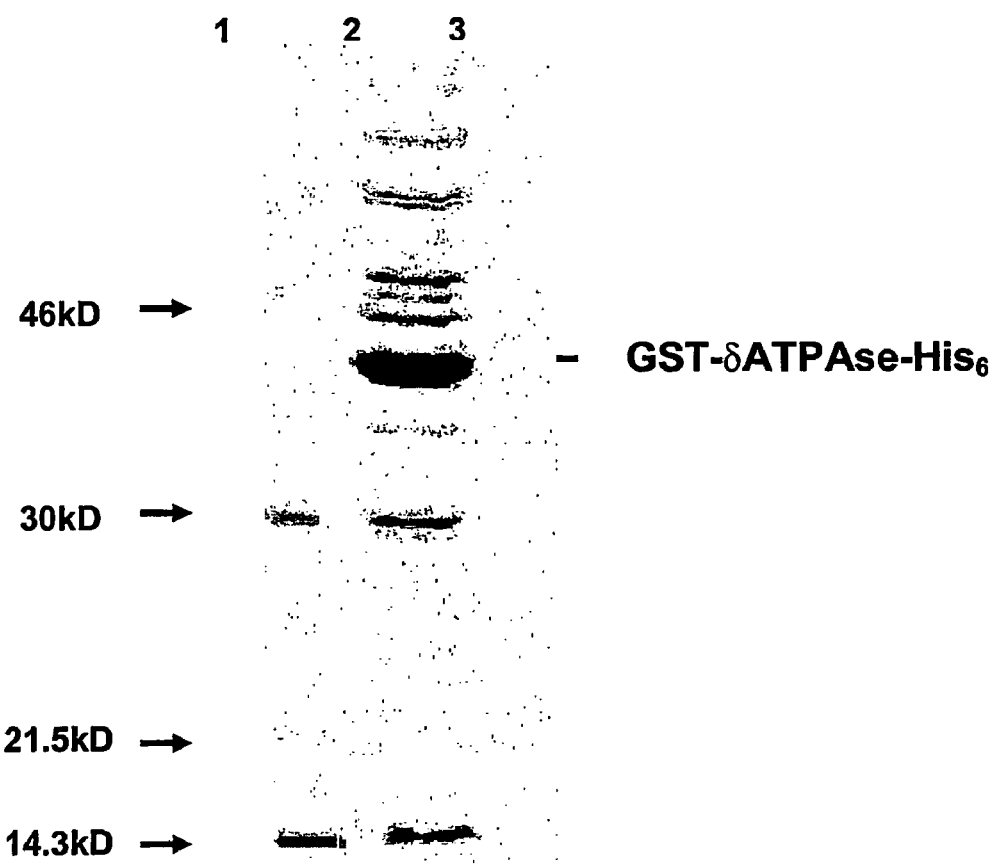
FIG. 18. SDS-PAGE profile of the crude *E. coli* extract (Lane 2) and the eluted fraction containing the recombinant GST-δATPase-$His_6$ protein (Lane 3) which was collected from the chromatographic separation of the crude *E. coli* extract on the im-$Ni^{2+}$-tacn Sepharose™ CL-6B column (shown in FIG. 17). The molecular weight standards (Lane 1) were as follows: ovalbumin, 46 kDa, carbonic anhydrase, 30 kDa, trypsin inhibitor, 21.5 kDa, lysozyme, 14.3 kDa.

Separation of the Recombinant GST-δATPASE-HIS$_6$ Protein from *E. coli* Lysate Using a Chromatographic Procedure with im-Ni$^{2+}$-TACN Sepharose™ CL-6B as Adsorbent The im-Ni$^{2+}$-tacn adsorbent (1 ml) was packed into Pharmacia HR5/10 columns to a height of 5 cm (packed volume 5 cm×0.5 cm i.d.). A flow rate of 0.5 ml/min was employed throughout the chromatographic procedures. After the gel had been equilibrated in Bio-Rad™ Econo-columns (10 ml) with the equilibration buffer (50 mM sodium phosphate buffer containing 300 mM sodium chloride and 10% glycerol, pH 8.0), 2 ml of the *E. coli* extract obtained as described in Example 52 was loaded onto the packed column via a 2 ml injection loop. The gel was then eluted with 15 ml of the equilibration buffer. A linear gradient increasing from 0 mM to 250 mM imidazole in equilibration buffer (10 ml) over a period of 20 minutes was used for this elution procedure, followed by isocratic elution with 5 ml of equilibration buffer containing 250 mM imidazole. A Pharmacia™ UV-1 single path monitor (280 nm), REC-482 two channel recorder and a computerized data logger were used to monitor and record the chromatographic curve for the eluted proteins. All fractions (1 ml) were collected with a FRAC™-100 fraction collector. The protein concentration of unbound and eluted fractions was determined by the bicinchoninic acid (BCA) reagent (Pierce Chemical Co., Rockford, Ill., USA) and Bio-Rad™ Dye (BioRad, Richmond, Calif., USA) methods, and the enzymatic activity was determined using the GST substrate 1-chloro-2,4-dinitrobenzene (CDNB). The peak fractions were characterised by SDS-PAGE. The results are shown in FIGS. 17-18.

Example 62

Figure 19:
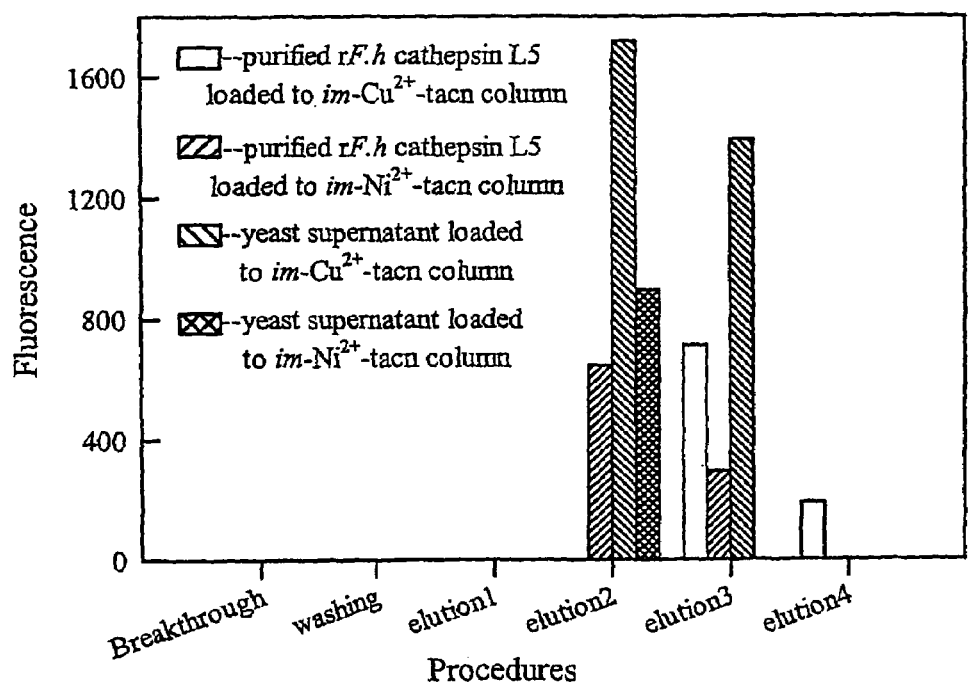
FIG. 19. Enzymatic activity of the recombinant C-terminal hexahistidine-tagged *Fasciola hepatica* cathepsin L5 (rF.h cathepsin L5) indicated by fluorescence read out using the fluorescent substrate N-carbobenzoxy-Phe-Arg-7-amino-4-methylcoumarin, in the fractions collected from the chromatographic separation of the purified rF.h cathepsin L5 from the im-$Ni^{2+}$-NTA Sepharose™ CL-6B column and the crude yeast supernatant using the im-$Cu^{2+}$-tacn and im-$Ni^{2+}$-tacn Sepharose™ CL-6B columns. The washing procedure was performed with the equilibration buffer of 50 mM $Na_2HPO_4$/150 mM NaCl, pH 8.0. Elution procedures 1 to 4 were carried out with an elution buffer of 50 mM $Na_2HPO_4$/500 mM NaCl, pH 6.0 containing 0 mM, 125 mM, 250 mM or 500 mM imidazole.

Separation of rF.h Cathepsin L5 from Yeast Broth Using a Batch Adsorption Procedure with im-Cu$^{2+}$-TACN Sepharose™ CL-6B as Adsorbent The im-Cu$^{2+}$-tacn Sepharose™ CL-6B adsorbent (1 ml), packed in Bio-Rad™ Econo-columns (10 ml), was equilibrated with an equilibration buffer (50 mM sodium phosphate buffer containing 150 mM sodium chloride, pH 8.0). The crude yeast broth supernatant (30 ml) obtained from the transfected Saccharomyces cerevisiae yeast cells grown in culture and containing the expression system for the specific recombinant C-terminal hexahistidine-tagged Fasciola hepatica cathepsin L5 (rF.h cathepsin L5) was loaded onto the im-Cu$^{2+}$-tacn Sepharose™ column. The breakthrough fractions (unbound fractions) were collected for subsequent determination of protein content and enzyme activity. The column was then washed with 10 ml of equilibration buffer to remove unbound or weakly bound proteins. A washing step, using 10 ml of 50 mM sodium phosphate containing 150 mM NaCl, pH 6.0, was then employed to elute any contaminating proteins. Thereafter, three aliquots of 5 ml of this wash buffer further containing 125 mM imidazole (elution buffer A), 250 mM imidazole (elution buffer B) and 500 mM imidazole (elution buffer C), respectively, were used to elute the bound proteins. All fractions collected in the breakthrough, wash and elution procedures were analyzed for protein content by BCA and Bio-Rad™ Dye assays and SDS-PAGE. The enzyme activity was determined by a fluorescence assay as described by Barrett, A. J. [Biochemical Journal, 187 (1980) 909-912] and by Anastati, A., Brown, M. A., Kembhavi, A. A., Nicklin, M. J. H., Sayers, C. A., Sunter, D. C. and Barrett, A. J. [Biochemical Journal, 211 (1983) 129-138]. The results are shown in FIG. 19.

Example 63

Separation of rF.h Cathepsin L5 From Yeast Broth Using a Batch Adsorption Procedure with im-Ni$^{2+}$-TACN Sepharose™CL-6B as Adsorbent The procedure used was essentially the same as described in Example 62, except that the adsorbent used was im-Ni$^{2+}$-tacn Sepharose™ CL-6B. The results are shown in FIG. 19.

Example 64

Figure 20:
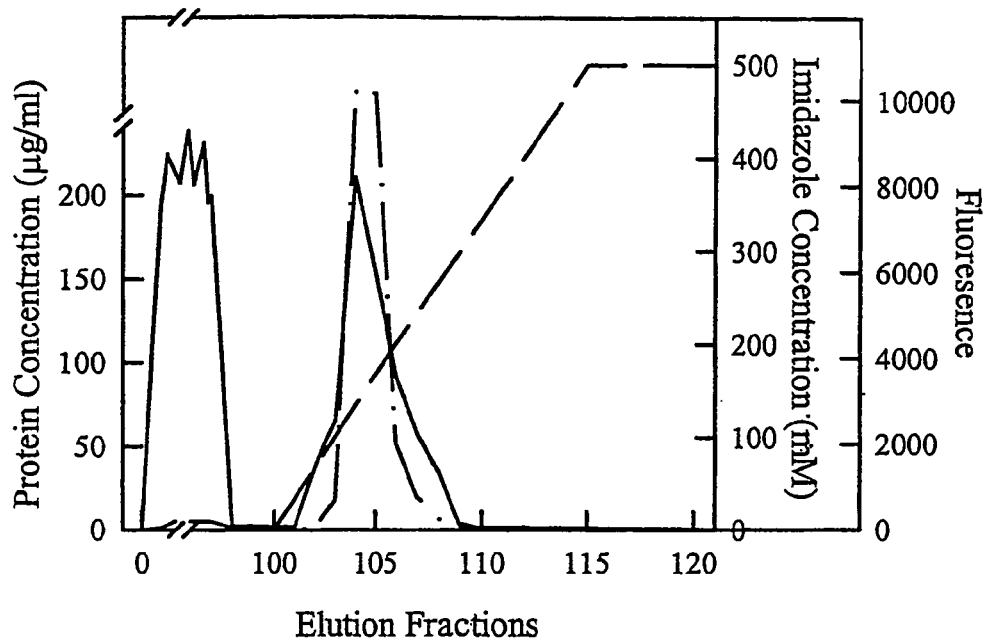
FIG. 20. Elution profile of the separation of the recombinant C-terminal hexahistidine-tagged Fasciola hepatica cathepsin L5 (rF.h cathepsin L5) from other proteins in the crude *S. cerevisiae* supernatant using the im-$Cu^{2+}$-tacn Sepharose™ CL-6B adsorbent. The crude yeast supernatant was loaded onto the packed column equilibrated with 50 mM $Na_2HPO_4$/150 mM NaCl, pH 8.0 at a flow rate of 0.2 ml/min for overnight. Unbound or weakly bound proteins were washed off with 50 volumes of the equilibration buffer and wash buffer (50 mM $Na_2HPO_4$/500 mM NaCl, pH 6.0), respectively. Then the bound proteins were eluted with a linear gradient at 0.5 ml/min from 0 to 500 mM imidazole in the wash buffer (50 mM $Na_2HPO_4$/500 mM NaCl, pH 6.0). Following completion of the gradient elution, the column was washed with 200 mM EDTA in the elution buffer. The activity of rF.h cathepsin L5 in the recovered fractions was determined by fluorescence assay and indicated by the dash-dot-dash line (- • • - • • -). The dashed line (- - -) and the solid line (—) indicate the gradient of imidazole concentration and protein concentration in the fractions, respectively.
Figure 21:
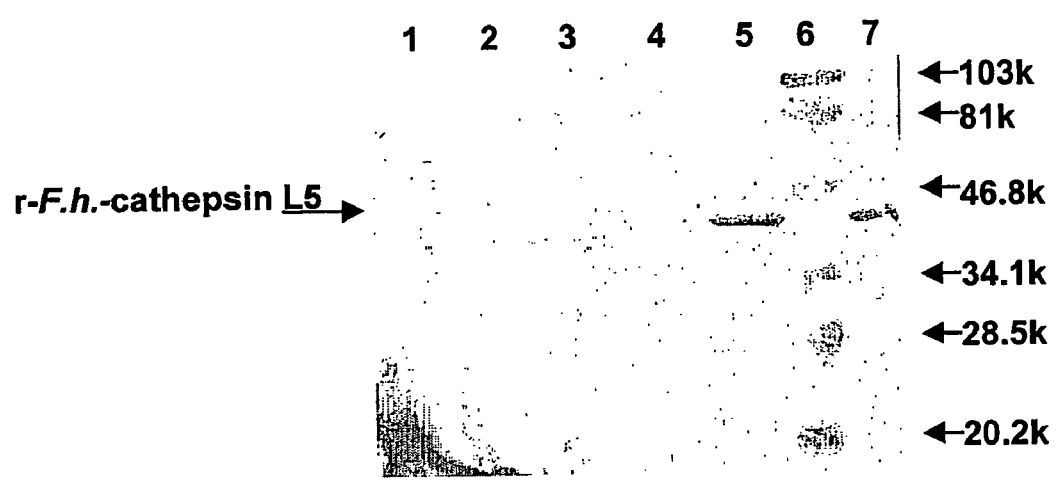
FIG. 21. SDS-PAGE profile of the fractions of the recombinant C-terminal hexahistidine-tagged *Fasciola hepatica* cathepsin L5 (rF.h cathepsin L5) purified on a im-$Cu^{2+}$-tacn Sepharose™ CL-6B column as shown in FIG. 20. Lane 1=crude sample, supernatant of yeast; Lane 2=breakthrough fraction; Lane 3=wash fraction using equilibrium buffer (50 mM $Na_2HPO_4$/150 mM NaCl, pH 8.0); Lane 4=wash fraction using wash buffer (50 mM $Na_2HPO_4$/500 mM NaCl, pH 6.0); Lane 5=elution fraction using a concentration gradient of imidazole from 0 to 500 mM in the wash buffer, where the minor bands in the molecular range from ca. 28.5 kDa to ca. 34.1 kDa were the fragment bands due to autolysis of rF.h cathepsin L5. At low protein concentration, these bands cannot be identified in the SDS-PAGE. Lane 6=molecular weight standards, phosphorylase B 103 kDa, bovine serum albumin 81 kDa, ovalbumin 46.9 kDa, carbonic anhydrase 34.1 kDa, soybean trypsin inhibitor 28.5 kDa, and lysozyme 20.2 kDa; Lane 7=fraction of the rF.h Cathepsin L5 obtained from im-$Ni^{2+}$-NTA Sepharose™ CL-6B column.

Separation of rF.h Cathepsin L5 from Yeast Broth Using a Chromatographic Procedure with im-Cu$^{2+}$-TACN Sepharose™ CL-6B as Adsorbent The im-Cu$^{2+}$-tacn Sepharose™ CL-6B adsorbent (0.5 ml) was packed into a Pharmacia HR5/5 column to a height of 2.5 cm (packed volume 2.5 cm×0.5 cm i.d.). The yeast supernatant (containing the recombinant C-terminal hexahistidine tagged Fasciola hepatica cathepsin L5 (rF.h cathepsin L5)) (246 ml) was loaded onto the packed column at a flow rate of 0.2 ml/min. A washing procedure was performed with 30 ml of equilibration buffer (50 mM sodium phosphate buffer containing 150 mM NaCl, pH 8.0) and 21 ml of the elution buffer A (50 mM sodium phosphate containing 150 mM NaCl, pH 6.0). The column was then eluted with a linear gradient (15 ml, over 30 min) from buffer A to buffer B, followed by an isocratic elution of 5 ml of buffer B. Elution buffer B was 50 mM sodium phosphate containing 150 mM NaCl and 500 mM imidazole, pH 6.0. All fractions (1 ml) were collected with a FRAC-100 fraction collector. Protein content was analysed by the Bio-Rad assay. The enzyme activity was determined by a fluorescence assay as in Example 62. The peak fractions were characterised by SDS-PAGE. The results are shown in FIG. 20 and FIG. 21.

Example 65

Separation of the Hexahistidine-Tagged Recombinant Malarial Antigen Apical Membrane Antigen-1 (AMA-1) From Yeast Broth Using im-Cu$^{2+}$-TACN Sepharose™ CL-6B as Adsorbent The crude supernatant from the transfected *Saccharomyces cerevisiae* yeast cells containing the AMA-1 was dialysed at 4° C. overnight with a dialysis buffer (50 mM sodium phosphate containing 150 mM NaCl and 10% glycerol, pH 8.0), and then re-dialysed twice with fresh dialysis buffer at 4° C. for 4 hours.

Figure 22:
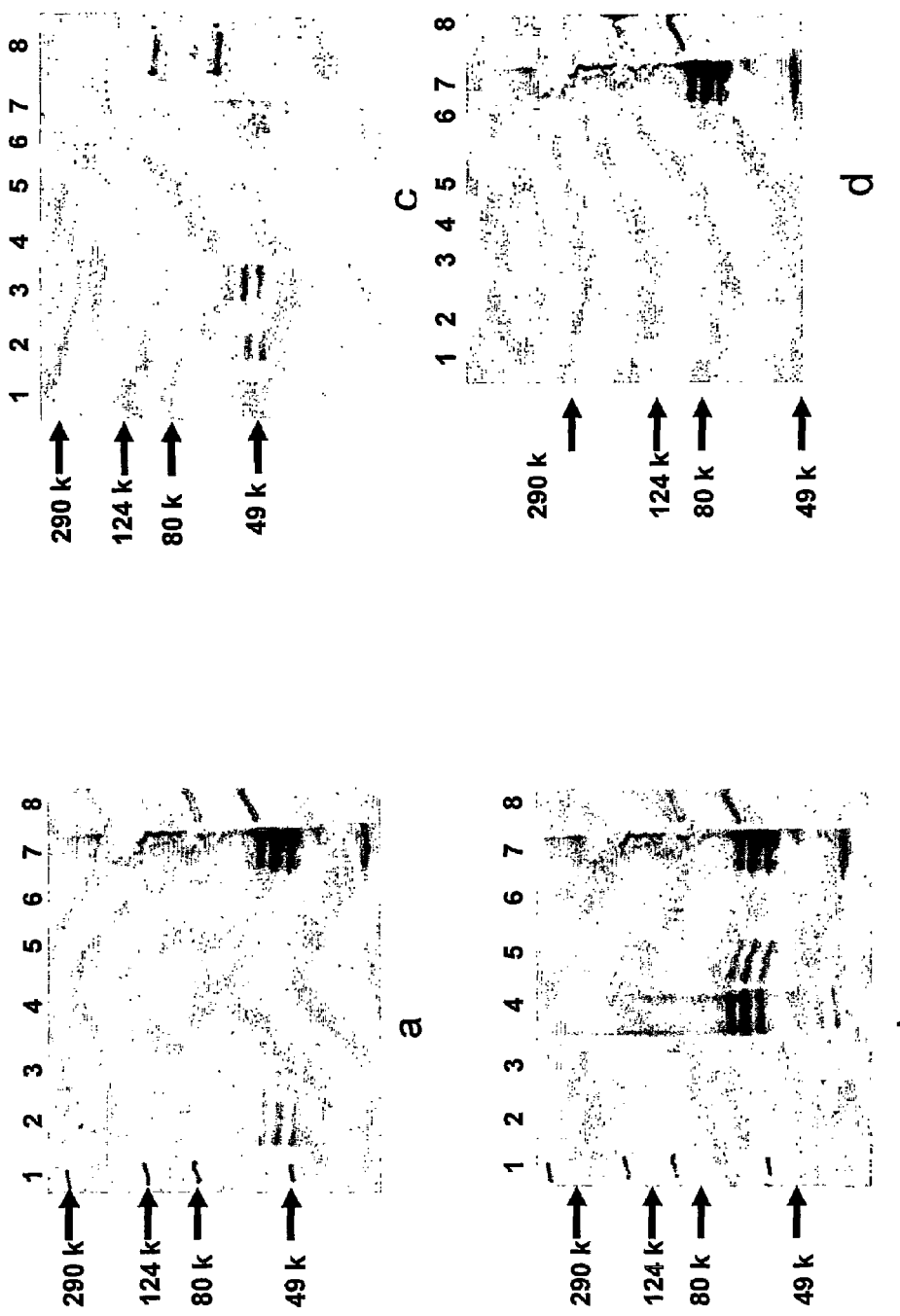
FIG. 22. Western blot profile of the fractions containing the hexahistidine tagged apical membrane antigen-1 (AMA-1) protein collected from im-$Ni^{2+}$-tacn (a), im-$Cu^{2+}$-tacn (b), im-$Cu^{2+}$-dtnp (c), and im-$Ni^{2+}$-dtnp (d) Sepharose™ CL-6B columns. Lane 1=molecular weight, Myosin 209 kDa, β-galactosidase 124 kDa, Bovine serum albumin 80 kDa, and ovalbumin 49 kDa; Lane 2=wash fraction using equilibrium buffer (50 mM $Na_2HPO_4$/150 mM NaCl, pH 8.0); Lane 3=eluted fraction using buffer containing 50 mM $Na_2HPO_4$/500 mM NaCl, pH 6.0; Lane 4=eluted fraction using buffer containing 50 mM $Na_2HPO_4$/500 mM NaCl and 125 mM imidazole, pH 6.0; Lane 5=eluted fraction using buffer containing 50 mM $Na_2HPO_4$/500 mM NaCl and 250 mM imidazole, pH 6.0; Lane 6=eluted fraction using buffer containing 50 mM Na$_2$HPO$_4$/500 mM NaCl and 500 mM imidazole, pH 6.0; Lane 7=loaded sample, yeast supernatant; Lane 8=control sample, *Plasmodium chabaudi adami* lysate. The recombinant AMA-1 protein was expressed in the yeast *Saccharomyces cerevisiae*.

The im-Cu$^{2+}$-tacn Sepharose™ CL-6B adsorbent (1 ml) was packed in a Bio-Rad™ Econo-column (10 ml). The column was equilibrated with an equilibration buffer of 50 mM sodium phosphate buffer containing 150 mM sodium chloride, pH 8.0. The dialysed yeast supernatant (45 ml) was loaded onto this column. The breakthrough (unbound) fractions were collected for protein assay. The column was then washed with 25 ml of the equilibration buffer to remove unbound and weakly bound proteins. A total of 20 ml of wash buffer (50 mM sodium phosphate containing 150 mM NaCl, pH 6.0) was then passed through the column twice to elute any contaminating proteins. Three 5 ml aliquots of 50 mM sodium phosphate containing 150 mM NaCl and 125 mM imidazole, pH 6.0 (elution buffer A), 50 mM sodium phosphate containing 150 mM NaCl and 250 mM imidazole, pH 6.0 (elution buffer B) and 50 mM sodium phosphate containing 150 mM NaCl and 500 mM imidazole, pH 6.0 (elution buffer C), respectively, were used sequentially to elute the bound proteins. The breakthrough fractions and the fractions from the wash and elution procedures were collected for western-blot analysis. The results are shown in FIG. 22.

Example 66

Separation of the Hexahistidine-Tagged Recombinant Malarial Antigen Apical Membrane Antigen-1 (AMA-1) From Yeast Broth Using im-Cu$^{2+}$-DTNP Sepharose™ CL-6B as Adsorbent The procedure used was essentially the same as described in Example 65, except that the adsorbent used was im-Cu$^{2+}$-dtnp Sepharose™ CL-6B. The results are shown in FIG. 22.

Example 67

Separation of the Hexahistidine-Tagged Recombinant Malarial Antigen Apical Membrane Antigen-1 (AMA-1) From Yeast Broth Using im-Ni$^{2+}$-TACN Sepharose™ CL-6B as Adsorbent The procedure used was essentially the same as described in Example 65, except that the adsorbent used was im-Ni$^{2+}$-tacn Sepharose™ CL-6B. The results are shown in FIG. 22.

Example 68

Separation of the Hexahistidine-Tagged Recombinant Malarial Antigen Apical Membrane Antigen-1 (AMA-1) From Yeast Broth Using im-Ni$^{2+}$-DTNP Sepharose™ CL-6B as Adsorbent The procedure used was essentially the same as described in Example 65, except that the adsorbent used was im-Ni$^{2+}$-dtnp Sepharose™ CL-6B. The results are shown in FIG. 22.

Example 69

Purification of the Hexahistidine-Tagged Recombinant Protein Glutamic Acid Decarboxylase (GAD67/65) Isolated From the Recombinant *Saccharomyces cerevisiae* BJ3505 Strain Using im-Cu$^{2+}$-TACN Sepharose™ CL-6B as Adsorbent The Buffers Used in this Study Included:

| | |
|---|---|
| Equilibration buffer: | 50 mM potassium phosphate buffer containing 300 mM potassium chloride, 20 mM imidazole and 0.12% Triton ™ X-100, pH 8.0; |
| Washing buffer: | 50 mM potassium phosphate buffer containing 1 M potassium chloride, 40 mM imidazole and 0.12% Triton ™ X-100, pH 8.0; and |
| Elution buffers: | A. 50 mM potassium phosphate buffer containing 500 mM potassium chloride, 125 mM imidazole and 0.12% Triton ™ X-100, pH 8.0; B. 50 mM potassium phosphate buffer containing 500 mM potassium chloride, 250 mM imidazole and 0.12% Triton ™ X-100, pH 8.0; and C. 50 mM potassium phosphate buffer containing 500 mM potassium chloride, 500 mM imidazole and 0.12% Triton ™ X-100, pH 8.0. |

Figure 23:
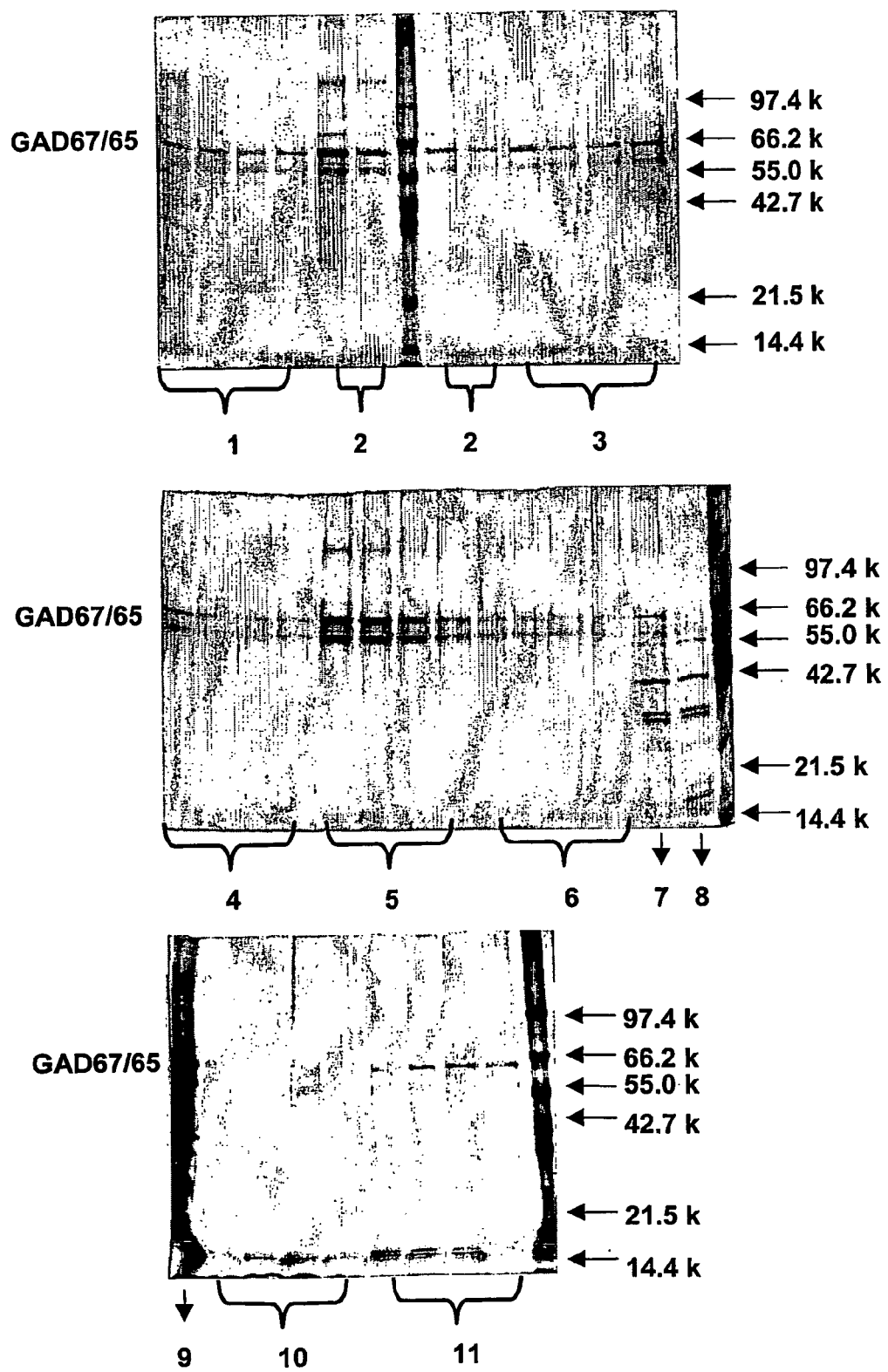
FIG. 23. SDS-PAGE profile of the recovered fractions of hexahistidine tagged recombinant protein glutamic acid decarboxylase (GAD67/65) isolated from the *Saccharomyces cerevisiae* BJ3505 strain using the im-Ni$^{2+}$-tacn and im-Cu$^{2+}$-tacn Sepharose™ CL-6B columns. The SDS-PAGE profile involved the analysis of the following fractions.

The im-Cu$^{2+}$-tacn Sepharose™ CL-6B adsorbent was equilibrated with equilibration buffer, after which a 0.2 ml portion was dispensed into a 1.8 ml Eppendorf tube. The semi-purified protein solution (500 μl), which had been previously separated by using an im-Ni$^{2+}$-NTA column (Chelating Sepharose™ Fast Flow, Amersham Pharmacia, Uppsala, Sweden) and the crude protein mixture obtained following expression in the *Saccharomyces cerevisiae* BJ3505 strain, was added to the Eppendorf tube and incubated at 4° C. for 90 min. After the mixture had been centrifuged at 1000×g for 1 min, the supernatant was removed. The adsorbent was washed with 1 ml of equilibration buffer, followed by 5×1 ml of the washing buffer to remove contaminating proteins. Elution of the bound proteins was achieved using 4×0.5 ml of elution buffer A, elution buffer B and elution buffer C sequentially. The unbound fractions, wash fractions and elution fractions were collected for SDS-PAGE analysis. The results are shown in FIG. 23.

Example 70

Purification of the Hexahistidine-Tagged Recombinant Protein Glutamic Acid Decarboxylase (GAD67/65) Isolated from the *Saccharomyces cerevisiae* BJ3505 Strain Using im-Ni$^{2+}$-TACN Sepharose™ CL-6B as Adsorbent The procedure used was essentially the same as described in Example 69, except that the adsorbent used was im-Ni$^{2+}$- tacn Sepharose™ CL-6B. The results of the SDS-PAGE analysis are shown in FIG. 23.

Example 71

Purification of the Hexahistidine-Tagged Recombinant Protein Glutamic Acid Decarboxylase (GAD67/65) Isolated from the Recombinant *Pichia pastoris* Using imCu$^{2+}$-TACN Sepharose™ CL-6B as Adsorbent The im-Cu$^{2+}$-tacn Sepharose CL-6B gel (1 ml) packed into a Bio-Rad™ Econo-column was equilibrated with equilibration buffer (50 mM potassium phosphate buffer containing 300 mM potassium chloride, 0.1 mM 2-aminoethylisothiouronium bromide, 1 mM glutamine, 0.2 mM phenylmethysulfonyl fluoride, 20 µM pyridoxal-L-phosphate, and 2 mM β-mercaptoethanol, pH 8.0, denoted "Ni-buffer"). The expression vectors for the production, in *S. cerevisiae* BJ3505 strain and in a *Pichia pastoris* strain, of the recombinant glutamic acid decarboxylase containing C-terminal hexahistidine "tag" (GAD67/65) were generated using established methods [Law, R. H. P., Rowley, M. J., MacKay, I. R. and Corner, B., *Journal of Biotechnology* 61 (1998) 57-68; Papakonstantinou, T., Law, R. H. P., Gardiner, P., Rowley, M. J. and MacKay, I, *Enzyme and Microbial Technology* 26 (2000) 645-652]. The crude fusion protein GAD67/65 from *P. pastoris* lysate was semi-purified using an im-Ni$^{2+}$-NTA Chelating Sepharose™ Fast Flow column (Amersham Pharmacia, Uppsala, Sweden). Despite, extensive attempts at optimization, the fusion protein GAD67/65 could not be obtained in a homogeneous form using the im-Ni$^{2+}$-NTA Chelating Sepharose™ Fast Flow sorbent. In the separation procedure using the im-Ni$^{2+}$-NTA column, the elution of the bound GAD67/65 was achieved by further including 250 mM imidazole in the Ni-buffer. The imidazole concentration in the solution of semi-purified fusion protein GAD67/65 was then adjusted to 20 mM by dilution with Ni-buffer. This solution was then loaded onto the im-Cu$^{2+}$-tacn column at a flow rate of 0.2 ml/min. The breakthrough (unbound) fraction was collected for protein content determination. The column was washed with 20 ml of washing buffer (40 mM imidazole in Ni-buffer, pH 8.0) to remove the unbound or weakly bound contaminating proteins. The bound proteins were eluted with 250 mM imidazole in Ni-buffer, pH 8.0, and fractions (0.5 ml) were collected. The breakthrough fractions, wash fractions and elution fractions were collected for determination of protein content using the Bio-Rad™ assay, SDS-PAGE analysis, and the enzymatic activity was determined according to the methods of Papakonstantinou, T., Law, R. H. P., Gardiner, P., Rowley, M. J. and MacKay, I, *Enzyme and Microbial Technology* 26 (2000) 645-652. The SDS-PAGE results are shown in FIG. 24.

Example 72

Binding of Myoglobin to im-M$^{2+}$-DTNE Sepharose™ CL-6B Adsorbents Under Different pH Conditions Aliquots containing 1.0 mg/ml of horse skeletal muscle myoglobin (HMYO) were prepared by accurately weighing the protein on a Mettler™ AE50 five-figure balance and diluting in the following equilibration buffers:

| Buffer A: | 20 mM sodium acetate buffer containing 0.5 M sodium chloride, pH 4.0; |
|---|---|
| Buffer B: | 20 mM potassium phosphate buffer containing 0.5 M sodium chloride, pH 6.0; |

-continued

| Buffer C: | 20 mM potassium phosphate buffer containing 0.5 M sodium chloride, pH 7.0; |
|---|---|
| Buffer D: | 20 mM potassium phosphate buffer containing 0.5 M sodium chloride, pH 8.0; and |
| Buffer E: | 20 mM sodium carbonate buffer containing 0.5 M sodium chloride, pH 9.5. |

Suction-dried im-M$^{2+}$-dtne Sepharose™ CL-6B gel (ca. 0.05 g) (where M$^{2+}$ represents Cu$^{2+}$, Ni$^{2+}$, Zn$^{2+}$ or Co$^{2+}$) was incubated in Durapore™ membrane tube (Ultrafree™-CL, 0.1 µm, Nihon Millipore, Kogyo K. K, Japan) containing 0.5 ml of the protein solution, by gently swirling with a clockwise rotator (RATEK™ Instruments, Mitcham, VIC, Australia) at 25° C. for 90 min. The supernatant was then recovered following centrifugation of the mixture at 3000×g with a Sorvall™ RT6000 refrigerated centrifuge (DuPont Co., Newtown, Conn., USA) and the sample immediately analysed for free protein concentration using the analytical reversed phase (RP)HPLC method. The results are shown in FIG. 25 and FIG. 26.

Example 73

Binding of Myoglobin to im-M$^{2+}$-DTNP Sepharose™ CL-6B Adsorbents Under Different pH Conditions The procedure used was essentially the same as described in Example 72, except that im-Mn$^{2+}$-dtnp Sepharose™ CL-6B adsorbents were used. The results are shown in FIG. 25 and FIG. 26.

Example 74

Binding of Lysozyme to im-M$^{2+}$-DTNE Sepharose™ CL-6B Adsorbents Under Different pH Conditions The procedure used was essentially the same as described in Example 72, except that the protein was hen egg white lysozyme (HEWL). The results are shown in FIG. 27 and FIG. 28.

Example 75

Binding of Lysozyme to im-M$^{2+}$-DTNP Sepharose™ CL-6B Adsorbents Under Different pH Conditions The procedure used was essentially the same as described in Example 74, except that im-Mn$^{2+}$-dtnp Sepharose™ CL-6B adsorbents were used. The results are shown in FIG. 27 and FIG. 28.

Example 76

Binding of Cytochrome C To im-M$^{2+}$-DTNE Sepharose™ CL-6B Adsorbents Under Different pH Conditions The procedure used was essentially the same as described in Example 72, except that the protein was horse heart cytochrome C (HHCC). The results are shown in FIG. 29 and FIG. 30.

Example 77

Binding of Cytochrome C To im-M$^{2+}$-DTNP Sepharose™ CL-6B Adsorbents Under Different pH Conditions The procedure used was essentially the same as described in Example 76, except that im-Mn$^{2+}$-dtnp Sepharose™ CL-6B adsorbents were used. The results are shown in FIG. 29 and FIG. 30.

Example 78

Figure 32:
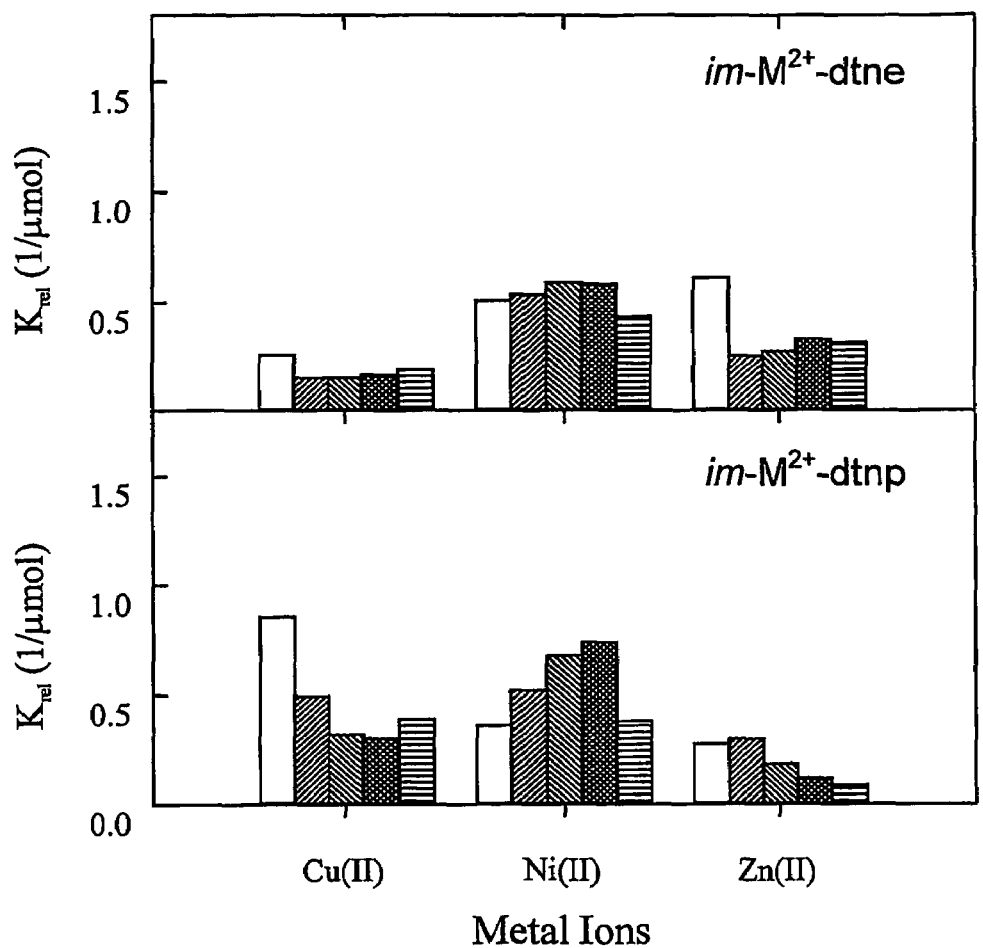

Binding of α-Lactalbumin to im-M$^{2+}$-DTNE Sepharose™ CL-6B Adsorbents Under Different pH Conditions The procedure used was essentially the same as described in Example 72, except that the protein was cow milk α-lactalbumin (αLAC). The results are shown in FIG. 31 and FIG. 32.

Example 79

Binding of α-Lactalbumin to im-M$^{2+}$-DTNP Sepharose™ CL-6B Adsorbents Under Different pH Conditions The procedure used was essentially the same as described in Example 78, except that im-Mn$^{2+}$-dtnp Sepharose™ CL-6B adsorbents were used. The results are shown in FIG. 31 and FIG. 32.

Example 80

Binding of Myoglobin to im-M$^{2+}$-DTNE Sepharose™ CL-6B Adsorbents at Different Salt Concentrations The procedure used was essentially the same as described in Example 72, except that the following equilibration buffers were used.

| | |
|---|---|
| Buffer F: | 20 mM potassium phosphate buffer containing 0.1 M sodium chloride, pH 8.0; |
| Buffer G: | 20 mM potassium phosphate buffer containing 0.5 M sodium chloride, pH 8.0; |
| Buffer H: | 20 mM potassium phosphate buffer containing 1.0 M sodium chloride, pH 8.0; |
| Buffer I: | 20 mM potassium phosphate buffer containing 2.0 M sodium chloride, pH 8.0; and |
| Buffer J: | 20 mM potassium phosphate buffer containing 3.0 M sodium chloride, pH 8.0. |

The results are shown in FIG. 33.

Example 81

Binding of Myoglobin to im-M$^{2+}$-DTNP Sepharose™ CL-6B Adsorbents at Different Salt Concentrations The procedure used was essentially the same as described in Example 80, except that im-Mn$^{2+}$-dtnp Sepharose™ CL-6B adsorbents were used. The results are shown in FIG. 33.

Example 82

Binding of Lysozyme to im-M$^{2+}$-DTNE Sepharose™ CL-6B Adsorbents at Different Salt Concentrations The procedure used was essentially the same as described in Example 80, except that the protein was hen egg white lysozyme (HEWL). The results are shown in FIG. 34.

Example 83

Binding of Lysozyme to im-M$^{2+}$-DTNP Sepharose™ CL-6B Adsorbents at Different Salt Concentrations The procedure used was essentially the same as described in Example 82, except that im-Mn$^{2+}$-dtnp Sepharose™ CL-6B adsorbents were used. The results are shown in FIG. 34.

Example 84

Binding of Cytochrome C to im-M$^{2+}$-DTNE Sepharose™ CL-6B Adsorbents at Different Salt Concentrations The procedure used was essentially the same as described in Example 80, except that the protein was horse heart cytochrome C(HHCC). The results are shown in FIG. 35.

Example 85

Binding of Cytochrome C to im-M$^{2+}$-DTNP Sepharose™ CL-6B Adsorbents at Different Salt Concentrations The procedure used was essentially the same as described in Example 84, except that im-Mn$^{2+}$-dtnp Sepharose™ CL-6B adsorbents were used. The results are shown in FIG. 35.

TABLE 1

Equilibration buffer and elution buffers used in Examples 7, 10, 13, 16, 19, 22, 25 and 28.

| | |
|---|---|
| Equilibration buffer | 20 mM sodium carbonate buffer with 0.1 M NaCl, pH 9.5 |
| Elution buffer | 20 mM sodium carbonate buffer with 1.0 M NaCl, pH 9.5 |
| | 20 mM potassium phosphate buffer with 1.0 M NaCl, pH 8.0 |
| | 20 mM potassium phosphate buffer with 1.0 M NaCl, pH 7.0 |
| | 20 mM potassium phosphate buffer with 1.0 M NaCl, pH 6.0 |
| | 20 mM sodium acetate buffer with 1.0 M NaCl, pH 4.0 |
| | 20 mM sodium acetate buffer with 1.0 M NaCl and 250 mM imidazole, pH 4.0 |
| | 200 mM EDTA, pH 4.2 |

TABLE 2

Equilibration buffer and elution buffers used in Examples 8, 11, 14, 17, 20, 23, 26 and 29.

| | |
|---|---|
| Equilibration buffer | 20 mM potassium phosphate buffer with 0.1 M NaCl, pH 7.0 |
| Elution buffer | 20 mM potassium phosphate buffer with 1.0 M NaCl, pH 7.0 |

TABLE 2-continued

Equilibration buffer and elution buffers used in
Examples 8, 11, 14, 17, 20, 23, 26 and 29.

20 mM potassium phosphate buffer
with 0.1 M EDTA, pH 7.0

TABLE 3

Equilibration buffer and elution buffers used in
Examples 9, 12, 15, 18, 21, 24, 27 and 30.

| | |
|---|---|
| Equilibration buffer | 20 mM sodium acetate buffer with 0.1 M NaCl, pH 4.0 |
| Elution buffer | 20 mM sodium acetate buffer with 1.0 M NaCl, pH 4.0 |
| | 20 mM potassium phosphate buffer with 0.5 M NaCl, pH 6.0 |
| | 20 mM potassium phosphate buffer with 0.5 M NaCl, pH 7.0 |
| | 20 mM potassium phosphate buffer with 0.5 M NaCl, pH 8.0 |
| | 20 mM sodium carbonate buffer with 0.5 M NaCl, pH 9.5 |
| | 20 mM sodium carbonate buffer with 1.0 M NaCl and 250 mM imidazole, pH 9.5 |
| | 200 mM EDTA, pH 4.2 |

TABLE 4

Percentage of the fusion protein GST-δATPase-His$_6$ bound to the different im-M$^{n+}$-tacn Sepharose ™ CL-6B, im-M$^{n+}$-dtne Sepharose ™ CL-6B and im-M$^{n+}$-dtnp Sepharose ™ CL-6B adsorbents under binding conditions with 50 mM sodium phosphate buffer containing 300 mM NaCl and 10% glycerol, pH 8.0.

| Metal-binding ligand | Metal Ion | | | | | |
|---|---|---|---|---|---|---|
| | $Cu^{2+}$ | $Ni^{2+}$ | $Zn^{2+}$ | $Co^{2+}$ | $Mn^{2+}$ | $Cr^{3+}$ |
| Tacn | 100 ± 3 | 100 ± 3 | 100 ± 3 | 41 ± 3 | 0 ± 4 | 0 ± 3 |
| Dtne | 100 ± 3 | 51 ± 3 | 0 ± 2 | 0 ± 1 | 0 ± 1 | 20 ± 1 |
| Dtnp | 100 ± 3 | 97 ± 3 | 33 ± 3 | 13 ± 1 | 0 ± 2 | 0 ± 1 |

Example 86

Construction of an Expression Plasmid which can be Used to Express Glutathione S-Transferase (GST) Fused at the N-Terminus to the Oligopeptide "TAG" Denoted NT1

PCR Template Digestion:

The source of the GST was pGEX3XGST. This was digested with the restriction endonucleases EcoRV and BamHI. The conditions were: approx. 3.45 µg plasmid, 20 units of BamHI, 20 units of EcoRV, 10 mM Tris-HCl, pH 8.0, 5 mM MgCl$_2$, 100 mM NaCl and 1 mM 2-Mercaptoethanol in a volume of 50 µl. The mixture was incubated at 37° C. for 2 hours. The two DNA fragments were separated on a 1% agarose gel and the desired fragment was isolated.

PCR Procedures:

50 and 25 ng amounts of the DNA fragment encoding GST were added to a mixture containing: 60 µmol forward primer, 60 µmol reverse primer, 2.5 units of DNA polymerase, 0.5 mM dNTP's, 10 mM Tris-HCl, pH 8.3, 1.5 mM MgCl$_2$ and 50 mM KCl. The volume of the reaction mixtures was 50 µl. The GST cDNA was amplified by PCR. Briefly, this involved applying the reaction mixtures to a thermo-cycler using the following conditions: an initial denaturation step at 95° C. for 5 minutes, then 2 cycles of 94° C., 50° C. and 72° C. for 1, 2 and 3 minutes respectively, followed by 40 cycles of 94° C., 55° C. and 72° C. for 1, 2 and 3 minutes, followed by a final extension step at 72° C. for 5 minutes. The reaction mixtures were run on a 1% agarose gel and the PCR products were isolated.

```
The forward primer had the sequence:
5' - TTAATCATGAAACACCACCACAACTCCTGGGA
CCACGACATCAACCGTGTCGACCAGATGTCCCCTATACTAGGT-3'

The reverse primer had the sequence:
5' - TAAAAGCTTTTACAGATCCGATTAAGG-3'
```

Modification of the Ends of the PCR Products:

Approx. 300 ng of the isolated PCR products sample described above was added to a 100 µl reaction mixture containing: 3 units of T4 DNA polymerase, 10 units of T4 polynucleotide kinase, 1 mM rATP, 0.5 mM dNTP's, 50 mM Tris, pH 7.5, 10 mM MgCl$_2$, 1 mM dithiothreitol (DTT) and 5 µg BSA. The reaction was carried out for 1 hour at 37° C. Following this, 0.5 µl of 0.5M EDTA was added to the mixture, which was then incubated at 75° C. for 10 mins. and then cooled on ice. The DNA was recovered by performing a phenol/chloroform extraction followed by an ethanol precipitation.

Ligation to the Shuttle Vector:

10 µl reactions containing various amounts of the modified PCR products (approx. 36 ng, 12 ng and 4 ng) were mixed with: 50 ng of the shuttle vector pBluescript II SK+ (which was SmaI cut and dephosphorylated), 2.5 units of T4 DNA ligase, 40 mM Tris-HCl, pH 7.8, 10 mM MgCl$_2$, 10 mM DTT and 0.5 mM ATP. The ligation reactions were incubated at room temperature overnight.

Transformation of DH5α:

Rubidium chloride treated E. coli DH5α cells were transformed with 5 µl of the above ligation reaction mixtures using standard techniques. Different dilutions of the transformation mixtures were plated onto LB Amp plates (tryptone 10 g/l, yeast extract 5 g/l, NaCl 10 g/l with agar 15 g/l added and autoclaved, then supplemented with ampicillin 100 mg/l) that had been spread with 800 µg amounts of Preparation of the Expression Vector:

The expression plasmid pTrc 99A (Pharmacia Biotech) was incubated with the restriction endonucleases NcoI and HindIII. The conditions were: approx. 4.25 µg plasmid, 20 units of NcoI, 20 units of HindIII, 10 mM Tris-HCl, pH 8.0, 5 mM MgCl$_2$, 100 mM NaCl and 1 mM 2-mercaptoethanol. in a volume of 200 µl. The temperature was 37° C. and the reaction time was 2 hours. The 2 DNA fragments were separated on a 1% agarose gel and the desired fragment was isolated.

In order to check that the plasmid had been fully digested by both enzymes, the isolated fragment was ligated and then used to transform E. coli DH5α cells. Briefly, this was performed as follows: a 10 µl reaction was prepared, containing: approx. 50 ng isolated fragment, 2.5 units of T4 DNA ligase, 40 mM Tris-HCl, pH 7.8, 10 mM MgCl$_2$, 10 mM DTT and 0.5 mM ATP. The ligation reactions were incubated at 16° C. overnight. Rubidium chloride treated E. coli DH5α cells were transformed with 5 µl of the ligation reaction using standard techniques. Different dilutions of the transformations were plated onto LB Amp plates. The plates were incubated at 37° C. overnight. An absence of transformed colonies confirmed that the expression plasmid had been fully digested by both enzymes.

Ligation to the NcoI/HinDIII Cut Vector PTRC99A:

10 µl reactions were prepared, containing various amounts of the insert prep DNA (approx. 25 ng, 8.3 ng and 2.75 ng) mixed with: approx. 50 ng of expression plasmid pTrc 99A (NcoI/HindIII cut), 2.5 units of T4 DNA ligase, 40 mM Tris-HCl, pH 7.8, 10 mM MgCl$_2$, 10 mM DTT and 0.5 mM ATP. The temperature was 16° C. and the reaction time was at least 1 day. 5 µl of this reaction mixture was used for the transformation of E. coli DH5α cells. The modified expression plasmid was isolated and identified by performing an enzyme screen using the restriction endonucleases EcoRV/HindIII.

Transformation of Expression Cells:

Rubidium chloride treated E. coli cells, strain JM105, were transformed with approx. 100 ng of the modified expression plasmid, using standard techniques. Different dilutions of the transformed cells were plated onto LB Amp plates for selection of plasmid-containing cells.

Example 87

Construction of an Expression Plasmid Which can be Used to Express Glutathione S-Transferase (GST) Fused at the N-Terminus to a Control Oligopeptide "TAG" Denoted CT1 (Having the Amino Acid Sequence: MKHHHHHH)

The procedure was essentially the same as described in example 86, with the exception that the forward primer had the sequence: 5'-TAAATCATGAAACATCACCATCAC-CATCACCAGATGTCCCCTATACTAGGT-3'.

Identification of Positive Clones:

Plasmid DNA from a number of clones was incubated with the restriction endonuclease PvuII. The conditions were: approx. 150 µg of plasmid, 10 units of PvuII, 10 mM Tris-HCl, pH 7.5, 10 mM MgCl$_2$, 50 mM NaCl and 1 mM DTE in a volume of 20 µl. The temperature was 37° C. and the reaction time was 1 hour. The 2 DNA fragments were separated on a 1% agarose gel, enabling identification of plasmids containing fragments of the correct size. A second enzyme screen was then performed on these selected plasmids with the restriction endonucleases HindIII and SalI. The conditions of this double digestion were: approx. 150 µg of plasmid, 20 units of HindIII, 20 units of Sa/l, 50 mM Tris-HCl, pH 7.5, 10 mM MgCl$_2$, 100 mM NaCl and 1 mM DTE in a volume of 40 µl. The temperature was 37° C. and the reaction time was 4 hours. The digested DNA was run on a 1% agarose gel and plasmids containing fragments of the correct size were identified. Approx. 300 ng of the uncut DNA from the selected plasmids was used as the template from which DNA sequencing was performed. Other sequencing conditions were the same as described in Example 86.

A clone containing the desired plasmid insert encoding GST-CT1 was identified. The sequence was verified as correct with the following exceptions: A point mutation of GST at base 28 from A to G which resulted in a conservative substitution of isoleucine with valine at amino acid 10 of GST (AAT to GTT). A point mutation of GST at base 342 from C to T, resulting in a silent mutation of aspartic acid (GAC to GAU). A possible point mutation of GST at base 645 from T to C, resulting in a silent mutation of histidine (CAT to CAC).

Insert Preparation:

Plasmid DNA from the positive clone was incubated with the restriction endonucleases BspHI and HindIII. The conditions were: approx. 150 ng plasmid, 30 units of BspHI, 60 units of HindIII, 50 mM potassium acetate, 20 mM Tris-acetate, pH 7.9, 10 mM magnesium acetate and 1 mM DTT, in a volume of 100 µl. The temperature was 37° C. and the reaction time was 22 hours.

Example 88

Construction of an Expression Plasmid which can be Used to Express Glutathione S-Transferase (GST) Fused at the N-Terminus to a Control Oligopeptide "TAG" Denoted CT2 (Having the Amino Acid Sequence: MKHQHQHQHQHQHQ)

The procedure was essentially as described in Example 86, with the exception that the forward primer encoding the CT2 had the sequence:

5'-TAAATCATGAAACACCAACACCAACATCAACATCAACATCAACATCA
AGTCGACCAGATGTCCCCTATACTAGGT-3'.

Identification of Positive Clones:

Modified plasmid DNA from different clones was digested only with the restriction endonuclease PvuII. The conditions were: approx. 300 µg of plasmid, 20 units of PvuII, 10 mM Tris-HCl, pH 7.5, 10 mM MgCl$_2$, 50 mM NaCl and 1 mM DTE in a volume of 30 µl. The temperature was 37° C. and the reaction time was 3 hours. The 2 DNA fragments were separated on a 1% agarose gel enabling identification of plasmids containing fragments of the correct size. The desired fragment was isolated, and approx. 100 ng was used as the template, which was DNA sequenced.

A clone containing the desired plasmid insert encoding GST-CT2 was identified. DNA sequencing verified that the sequence was correct.

Insert Preparation:

Plasmid DNA from the positive clone was incubated with the restriction endonucleases BspHI and HindIII. The conditions were: approx. 150 ng plasmid, 30 units of BspHI, 60 units of HindIII, 50 mM potassium acetate, 20 mM Tris-acetate, pH 7.9, 10 mM magnesium acetate and 1 mM DTT in a volume of 100 µl. The temperature was 37° C. and the reaction time was ca. 22 hours.

Example 89

Construction of an Expression Plasmid which can be Used to Express Glutathione S-Transferase (GST) Fused at the N-Terminus to the Oligopeptide "TAG" Denoted NT2

The procedure used was essentially the same as described in Example 86, with the exception that the forward primer encoding the NT2 had the sequence:

5'-TAAATCATGAAACACACCAACATCCACCAGGACCAGCACAACCACTT
CCACCGTGTCGACCAGATGTCCCCTATACTAGGT-3'.

Identification of Positive Clones:

A clone containing the desired plasmid insert encoding GST-NT2 was identified. DNA sequencing verified that the sequence was correct.

Example 90

Small Scale Expression of the N-Terminal-Tagged GST Fusion Proteins

*E. coli* cells strain JM105 were transformed as described for Examples 86-89, as well as with unmodified expression vector pTrc 99A and with the parental GST vector pGEX3XGST. Transformed cells were propagated on petri-plates containing LB Amp medium at 37° C. overnight. LB medium (tryptone 10 g/l, yeast extract 5 g/l, NaCl 10 g/l and autoclaved) supplemented with 100 μg/ml ampicillin was inoculated with single colonies from the petri-plates and incubated at 37° C. with shaking overnight. 5 ml of 2×YT medium (tryptone 16 g/l, yeast extract 10 g/l, NaCl 5 g/l, pH 7.0 and autoclaved) supplemented with 100 μg/ml ampicillin (2×YTA) was inoculated with a 1/10 dilution of the overnight cultures and then incubated at 37° C. with shaking until an absorbance at 600 nm ($A_{600}$) of 0.6-1.0 for pTrc transformants or 0.6-0.8 for pGEX3XGST transformants was attained. Gene expression was induced by the addition of IPTG to a final concentration of 1 mM (pTrc transformants) or 0.1 mM (pGEX3XGST transformant). Cells from 1.5 ml of culture were harvested 5 hours (pTrc transformants) or 1 hour (pGEX3XGST transformants) post-induction. Cells were resuspended in 300 μl of ice-cold 1×PBS (140 mM NaCl, 2.7 mM KCl, 10 mM $Na_2HPO_4$, 1.8 mM $KH_2PO_4$, pH 7.3) and lysed by sonication. Following pelleting, the cell lysate was collected and frozen.

Example 91

Larger Scale Expression of the N-Terminal-Tagged GST Fusion Proteins

Individual clones of each of the tagged GST fusion proteins were selected for use in larger scale protein expression. This was performed essentially as described in Example 90, with the following exceptions: 100 ml media (2×YTA) was inoculated with a 1/100 dilution of overnight culture. Following induction, the cultures were incubated for a further 6 hours prior to harvesting of cells. Cells were then resuspended in 5 ml 1×PBS (except for those containing GST-CT2, which were resuspended in 10 ml) and lysed by sonication. Triton X-100 was added to a final concentration of 1%, followed by incubation for 30 min. to aid in solubilization of fusion proteins. Following pelleting, cell lysate was collected and frozen.

Example 92

Evaluation of Activity

A reliable assay for functional GST activity is the CDNB (1-chloro-2,4-dinitrobenzene) assay, in which GST catalyzes the derivatization of CDNB with glutathione; this complex can be monitored by optical density measurements at a wavelength of 340 nm. The assay was performed as outlined in the information booklet *GST Gene Fusion System*, $3^{rd}$ edn., Revision 1, from Pharmacia Biotech. Briefly, 10 μl of cell lysate samples from each of the recombinant GST fusion proteins, as described in Example 90 and 91, were added to 190 μl of a reaction mixture containing 100 mM $KH_2PO_4$, pH 6.5, 1 mM 1-chloro-2,4-dinitrobenzene (CDNB) and 1 mM reduced glutathione in a 96-well plate, and the absorbance at 340 nm was measured in a plate reader for 5 min. at 1 minute intervals. All four recombinant fusion proteins exhibited functional GST activity as determined by this assay.

Example 93

Batch Purification of the Met-Lys-(His)$_6$-Tagged Recombinant Glutathione S-Transferase Fusion Protein GST-CT1

Crude cell lysate (see Example 91) was purified using $Ni^{2+}$-tacn and $Ni^{2+}$-NTA columns. Each column had a bed volume of 0.5 ml, and was equilibrated with Buffer B (Buffer B=Buffer A supplemented with 10 mM imidazole pH 8.4; Buffer A=445 mM NaCl, 7.5 mM $Na_2HPO_4$ and 2.5 mM $NaH_2PO_4.2H_2O$, pH 7.2). Columns were loaded with 125 μl of crude cell lysate (which was diluted 1 in 4 with Buffer B to a total volume of 0.5 ml.). Columns were then washed twice with Buffer B prior to elution. Two elution procedures were used: elution with Buffer 1 (Buffer 1=Buffer A supplemented with 500 mM imidazole, pH 9.71) (1 ml) followed by a second elution with 200 mM sodium malonate solution (1 ml) which had been adjusted to pH 8.0 with 10 M sodium hydroxide.

Example 94

Batch Purification of the Met-Lys-(His-Gln)$_6$-Tagged Recombinant Glutathione S-Transferase Fusion Protein GST-CT2

The procedure was the same as described in Example 93.

Example 95

Batch Purification of the N-Terminally Tagged Recombinant Glutath-ione S-Transferase (r-GST) Fusion Protein GST-NT1

The procedure was the same as described in Example 93

Example 96

Batch Purification of the N-Terminally Tagged Recombinant Glutath-ione S-Transferase (r-GST) Fusion Protein GST-NT2

The procedure was the same as described in Example 93

Example 97

Stepwise (Isocratic) Elution of the Met-Lys-(His)$_6$-Tagged Recombinant Glutathione S-Transferase Fusion Protein GST-CT1

Crude cell lysate (see Example 91) was applied to a $Ni^{2+}$-tacn column. The column had a bed volume of 0.5 ml, and was equilibrated with Buffer C (Buffer C=Buffer B+50 mM imidazole, pH 9.0). The column was loaded with 0.5 ml of sample containing 125 μl of crude cell lysate diluted 1 in 4 with Buffer C. After the sample had passed through the column, the column was washed with Buffer C (5 ml). A series of stepwise (isocratic) elutions was performed, each consisting of 3 applications of 1 ml aliquots of Buffer A supplemented with various concentrations of imidazole. The initial elution was carried out using Buffer A supplemented with 100 mM imidazole, pH 9.3. The concentration of imidazole was increased by 50 mM increments with each successive elution. Aliquots from the first round of the various elution conditions were then applied to SDS-polyacrylamide gels for analysis.

Example 98

Stepwise (Isocratic) Elution of the Met-Lys-(His-Gln)$_6$-Tagged Recombinant Glutathione S-Transferase Fusion Protein GST-CT2

The procedure was the same as described in Example 97

Example 99

Stepwise (Isocratic) Elution of the N-Terminally Tagged Recombinant Glutathione S-Transferase (r-GST) Fusion Protein GST-NT1

The procedure was the same as described in Example 97

Example 100

Stepwise (Isocratic) Elution of the N-Terminally Tagged Recombinant Glutathione S-Transferase (r-GST) Fusion Protein GST-NT2

The procedure was the same as described in Example 97

Example 101

Second Stepwise (Isocratic) Elution of the Met-Lys-(His)$_6$-Tagged Recombinant Glutathione S-Transferase Fusion Protein GST-CT1

A second series of stepwise (isocratic) elutions was performed. A Ni$^{2+}$-tacn column with a bed volume of 0.5 ml was equilibrated with Buffer B. The column was loaded with a 2.5 ml sample containing 500 µl of crude cell lysate, as described in Example 90 and 91, diluted 1 in 5 with Buffer D (Buffer D=Buffer A+12.5 mM imidazole, pH 8.5). The flow-through fraction was reapplied to the column twice. Buffer B (5 ml) was then applied to the column. A series of stepwise (isocratic) elutions was then performed, each consisting of 3 applications of 1 ml. aliquots of Buffer A supplemented with various concentrations of imidazole. The initial elution was carried out using Buffer A+25 mM imidazole. The concentration of imidazole was increased by 25 mM increments with each successive elution until a concentration of 100 mM was reached, and was thereafter increased by 50 mM increments. Aliquots from the first round of the various elution conditions were then applied to SDS-polyacrylamide gels for analysis.

Example 102

Second Stepwise (Isocratic) Elution of the Met-Lys-(His-Gln)$_6$-Tagged Recombinant Glutathione S-Transferase Fusion Protein GST-CT2

The procedure used was essentially the same as described in Example 101, except that the column was loaded with a 5 ml sample containing 1 ml of crude cell lysate diluted 1 in 5 with Buffer D.

Example 103

Second Stepwise (Isocratic) Elution of the N-Terminally Tagged Recombinant Glutath-ione S-Transferase (r-GST) Fusion Protein GST-NT1

The procedure used was essentially the same as described in Example 101, except that the column was loaded with a 1.5 ml sample containing 300 µl of crude cell lysate diluted 1 in 5 with Buffer D.

Example 104

Second Stepwise (Isocratic) Elution of the N-Terminally Tagged Recombinant Glutath-ione S-Transferase (r-GST) Fusion Protein GST-NT2

The procedure used was essentially the same as described in Example 101, except that the column was loaded with a 0.5 ml sample containing 100 µl of crude cell lysate diluted 1 in 5 with Buffer D.

Example 105

SDS-Page Analysis of Various Clones Following Small-Scale Expression of the N-Terminally Met-Lys-(His)$_6$-Tagged Recombinant Glutathione S-Transferase Fusion Protein GST-CT1

Aliquots of cell lysate (see Example 90) were mixed with SDS loading buffer (reducing) and heated for 1 min. at 100° C. Samples were then loaded onto a 12% SDS-polyacrylamide gel and run for an appropriate period of time. 60 µl of cell lysate and 30 µl of the molecular weight markers [BenchMark Protein Ladder (Gibco BRL) and 10 KDa Protein Ladder (Gibco BRL)] were loaded onto the gel. The pGEX3XGST transformant served as the positive control. The GST component of the N-terminal-tagged GST fusion proteins is truncated by 1 amino acid at the C-terminal end. The parental GST is expressed as the full-length protein with an additional 14 C-terminal amino acids. Consequently, the parental GST contains an additional 15 amino acids at its C-terminal end and therefore runs approx. 1.65 Kda larger than the GST component of the N-terminal-tagged GST fusion proteins. The *E. coli* strain JM105 transformed with pTrc served as the negative control. In order to visualize bands, the gel was stained with Coomassie Blue.

Key for Gel 1, Shown in FIG. 36:
Lane 1, GST-CT1 clone no. 1; Lane 2, GST-CT1 clone no. 2; Lane 5, GST-CT1 clone no. 3; Lane 6, GST-CT1 clone no. 4; Lane 7, GST-CT1 clone no. 5; Lane 11, GST-CT1 clone no. 6; Lane 12, GST-CT1 clone no. 7; Lane 13, GST-CT1 clone no. 8; Lane 14, GST-CT1 clone no. 9; Lane 15, GST-CT1 clone no. 10; Lane 8, negative control consisting of *E. coli* JM105 transformed with pTrc; Lane 9, positive control consisting of *E. coli* JM105 transformed with pGEX3XGST. Molecular weight markers are shown in Lanes 3, 4 and 10.

Example 106

SDS-Page Analysis of Various Clones Following Small-Scale Expression of the N-Terminally Met-Lys-(His-Gln)$_6$-Tagged Recombinant Glutathione S-Transferase Fusion Protein GST-CT2

The procedure used was essentially the same as described in Example 105.

Key for Gel 2, Shown in FIG. 37:

Lane 1, GST-CT2 clone no. 1; Lane 2, GST-CT2 clone no. 2; Lane 3, GST-CT2 clone no. 3; Lane 6, GST-CT2 clone no. 4; Lane 7, GST-CT2 clone no. 5; Lane 11, GST-CT2 clone no. 6; Lane 12, GST-CT2 clone no. 7; Lane 13, GST-CT2 clone no. 8; Lane 14, GST-CT2 clone no. 9; Lane 15, GST-CT2 clone no. 10; Lane 8, negative control consisting of *E. coli* JM105 transformed with pTrc; Lane 9, positive control consisting of *E. coli* JM105 transformed with pGEX3XGST. Molecular weight markers are shown in Lanes 4, 5 and 10.

Example 107

SDS-Page Analysis of Various Clones Following Small-Scale Expression of the N-Terminally Tagged Recombinant Glutathione S-Transferase Fusion Protein GST-NT1

The procedure used was essentially the same as described in Example 105.

Key for Gel 3, Shown in FIG. 38:

Lane 1, GST-NT1 clone no. 1; Lane 2, GST-NT1 clone no. 2; Lane 3, GST-NT1 clone no. 3; Lane 4, GST-NT1 clone no. 4; Lane 7, GST-NT1 clone no. 5; Lane 11, GST-NT1 clone no. 6; Lane 12, GST-NT1 clone no. 7; Lane 13, GST-NT1 clone no. 8; Lane 14, GST-NT1 clone no. 9; Lane 15, GST-NT1 clone no. 10; Lane 8, negative control consisting of *E. coli* JM105 transformed with pTrc; Lane 9, positive control consisting of *E. coli* JM105 transformed with pGEX3XGST. Molecular weight markers are shown in Lanes 5, 6 and 10.

Example 108

SDS-Page Analysis of Various Clones Following Small-Scale Expression of the N-Terminally Tagged Recombinant Glutathione S-Transferase Fusion Protein GST-NT2

The procedure used was essentially the same as described in Example 105.

Key for Gel 4, Shown in FIG. 39:

Lane 1, GST-NT2 clone no. 1; Lane 2, GST-NT2 clone no. 2; Lane 3, GST-NT2 clone no. 3; Lane 4, GST-NT2 clone no. 4; Lane 5, GST-NT2 clone no. 5; Lane 11, GST-NT2 clone no. 6; Lane 12, GST-NT2 clone no. 7; Lane 13, GST-NT2 clone no. 8; Lane 14, GST-NT2 clone no. 9; Lane 8, negative control consisting of *E. coli* JM105 transformed with pTrc; Lane 9, positive control consisting of *E. coli* JM105 transformed with pGEX3XGST. Molecular weight markers are shown in Lanes 6, 7 and 10.

Example 109

SDS-Page Analysis of Crude Cell Lysate Following Small-Scale Protein Expression of GST Fusion Protein Clones Selected for their High Expression Levels The procedure used was essentially the same as described in Example 105, with the exception that 5 µl of cell lysate and 1 µl of molecular weight marker [BenchMark Protein Ladder (Gibco BRL)] were loaded onto the gel. In order to visualize bands, the gel was silver stained.

Key for Gel 5, Shown in FIG. 40:

Lane 1, GST-CT1 clone no. 7; Lane 2, GST-CT2 clone no. 6; Lane 6, GST-NT1 clone no. 1; Lane 7, GST-NT2 clone no. 7; Lane 4, negative control consisting of *E. coli* JM105 transformed with pTrc; Lane 5, positive control consisting of *E. coli* JM105 transformed with pGEX3XGST. Molecular weight marker is shown in Lane 3.

Example 110

SDS-Page Analysis of Various Fractions Collected from the Batch Purification of the N-Terminally Met-Lys-(His)$_6$-Tagged Recombinant Glutathione S-Transferase Fusion Protein GST-CT1

Aliquots of cell lysate and fractions collected from the batch purification (see Example 93) were mixed with SDS loading buffer (reducing) and heated at 100° C. for 90 seconds. 10 µl of purification fraction samples, 5 µl of positive and negative control cell lysate and 1.25 µl of cell lysate containing the recombinant fusion protein and 1 µl of molecular weight markers [BenchMark Protein Ladder (Gibco BRL)] were loaded onto a 12% SDS-polyacrylamide gel and run for an appropriate period of time. In order to visualize bands, the gel was silver stained.

Key for Gel 6, Shown in FIG. 41:

Lanes 3-5 contain samples collected from a $Ni^{2+}$-tacn column, whilst Lanes 6-8 contain samples from a $Ni^{2+}$-NTA column. Lanes 3 and 6, wash 2; Lanes 4 and 7, elution 1; Lanes 5 and 8, elution 2. Lane 1, negative control consisting of *E. coli* JM105 transformed with pTrc; Lane 2, positive control consisting of *E. coli* JM105 transformed with pGEX3XGST; Lane 10, crude cell lysate. Molecular weight marker is shown in Lane 9.

Example 111

SDS-Page Analysis of Various Fractions Collected from the Batch Purification of the N-Terminally Met-Lys-(His-Gln)$_6$-Tagged Recombinant Glutathione S-Transferase Fusion Protein GST-CT2

The procedure used was essentially the same as described in Example 110, with the exception that aliquots of cell lysate and fractions collected from the batch purification as described in Example 94 were applied to the gel.

Key for Gel 7, Shown in FIG. 42:

Lanes 3-5 contain samples collected from a $Ni^{2+}$-tacn column whilst Lanes 6-8 contain samples from a $Ni^{2+}$-NTA column. Lanes 3 and 6, wash 2; Lanes 4 and 7, elution 1; Lanes 5 and 8, elution 2. Lane 1, negative control consisting of *E. coli* JM105 transformed with pTrc; Lane 2, positive control consisting of *E. coli* JM105 transformed with pGEX3XGST; Lane 9, crude cell lysate. Molecular weight marker is shown in Lane 10.

Example 112

SDS-Page Analysis of Various Fractions Collected from the Batch Purification of the N-Terminally Tagged Recombinant Glutathione S-Transferase Fusion Protein GST-NT1

The procedure used was essentially the same as described in Example 110, with the exception that aliquots of cell lysate and fractions collected from the batch purification as described in Example 95 were applied to the gel.

Key for Gel 8, Shown in FIG. 43:

Lanes 5-7 contain samples collected from a $Ni^{2+}$-tacn column whilst Lanes 8-10 contain samples from a $Ni^{2+}$-NTA column. Lanes 5 and 8, wash 2; Lanes 6 and 9, elution 1; Lanes 7 and 10, elution 2. Lane 1, negative control consisting of E. coli JM105 transformed with pTrc; Lane 2, positive control consisting of E. coli JM105 transformed with pGEX3XGST; Lane 3, crude cell lysate. Molecular weight marker is shown in Lane 4.

Example 113

SDS-Page Analysis of Various Fractions Collected from the Batch Purification of the N-Terminally Tagged Recombinant Glutathione S-Transferase Fusion Protein GST-NT2

The procedure used was essentially the same as described in Example 110, with the exception that aliquots of cell lysate and fractions collected from the batch purification as described in Example 96 were applied to the gel.

Key for Gel 9, Shown as FIG. 44:

Lanes 5-7 contain samples collected from a $Ni^{2+}$-tacn column whilst Lanes 8-10 contain samples from a $Ni^{2+}$-NTA column. Lanes 5 and 8, wash 2; Lanes 6 and 9, elution 1; Lanes 7 and 10, elution 2. Lane 1, negative control consisting of E. coli JM105 transformed with pTrc; Lane 2, positive control consisting of E. coli JM105 transformed with pGEX3XGST; Lane 4, crude cell lysate. Molecular weight marker is shown in Lane 3.

Example 114

SDS-Page Analysis of Various Fractions Collected from Stepwise (Isocratic) Elution of the N-Terminally Met-Lys-$(His)_6$-Tagged Recombinant Glutathione S-Transferase Fusion Protein GST-CT1

Samples from the first series of stepwise isocratic elutions of cell lysate containing GST-CT1, as described in Example 97, were mixed with SDS loading buffer (non-reducing) and heated at 100° C. for 90 seconds. 10 µl aliquots from the first 1 ml of the eluted fractions and 2.5 µl of cell lysate were loaded onto a 12.5% SDS-polyacrylamide gel. The gel was run for an appropriate period of time and then silver stained in order to visualize bands.

Key for Gel 10, Shown in FIG. 45:

Elutions were performed with Buffer A supplemented with the following concentrations of imidazole: Lane 1, 100 mM; Lane 3, 150 mM; Lane 4, 200 mM; Lane 5, 250 mM; Lane 6, 300 mM; Lane 7, 350 mM; Lane 8, 400 mM; Lane 9, 450 mM and Lane 10, 500 mM. Cell lysate is shown in Lane 2.

Example 115

SDS-Page Analysis of Various Fractions Collected from the Stepwise (Isocratic) Elution of the N-Terminally Met-Lys-$(His-Gln)_6$-Tagged Recombinant Glutathione S-Transferase Fusion Protein GST-CT2

The procedure used was essentially the same as described in Example 114, with the exception that aliquots of cell lysate and fractions collected from the stepwise (isocratic) elution as described in Example 98 were applied to the gel.

Key for Gel 11, Shown as FIG. 46:

Elutions were performed with Buffer A supplemented with the following concentrations of imidazole:

Lane 1, 100 mM; Lane 2, 150 mM; Lane 3, 200 mM; Lane 4, 250 mM; Lane 6, 300 mM; Lane 7, 350 mM; Lane 8, 400 mM; Lane 9, 450 mM and Lane 10, 500 mM. Cell lysate is shown in Lane 5.

Example 116

SDS-Page Analysis of Various Fractions Collected from the Stepwise (Isocratic) Elution of the N-Terminally Tagged Recombinant Glutathione S-Transferase Fusion Protein GST-NT1

The procedure used was essentially the same as described in Example 114, with the exception that aliquots of cell lysate and fractions collected from the stepwise (isocratic) elution as described in Example 99 were applied to the gel.

Key for Gel 12, Shown in FIG. 47:

Elutions were performed with Buffer A supplemented with the following concentrations of imidazole: Lane 2, 100 mM; Lane 3, 150 mM; Lane 4, 200 mM; Lane 5, 250 mM; Lane 6, 300 mM; Lane 7, 350 mM; Lane 8, 400 mM; Lane 9, 450 mM and Lane 10, 500 mM. Cell lysate is shown in Lane 1.

Example 117

SDS-Page Analysis of Various Fractions Collected from the Stepwise (Isocratic) Elution of the N-Terminally Tagged Recombinant Glutathione S-Transferase fusion Protein GST-NT2

The procedure used was essentially the same as described in Example 114, with the exception that aliquots of cell lysate and fractions collected from the stepwise (isocratic) elution as described in Example 100 were applied to the gel.

Key for Gel 13, Shown in FIG. 48:

Elutions were performed with Buffer A supplemented with the following concentrations of imidazole: Lane 1, 100 mM; Lane 2, 150 mM; Lane 4, 200 mM; Lane 5, 250 mM; Lane 6, 300 mM; Lane 7, 350 mM; Lane 8, 400 mM; Lane 9, 450 mM and Lane 10, 500 mM. Cell lysate is shown in Lane 3.

Example 118

SDS-Page Analysis of Various Fractions Collected from the Second Stepwise (Isocratic) Elution of the N-Terminally Met-Lys-$(His)_6$-Tagged Recombinant Glutathione S-Transferase Fusion Protein GST-CT1

Samples from the second series of stepwise (isocratic) elutions of cell lysate containing GST-CT1, as described in example 101, were mixed with SDS loading buffer (non-reducing) and heated at 100° C. for 90 seconds. 16 µl aliquots from the first 1 ml of the eluted fractions and 0.5 µl of molecular weight markers [BenchMark Protein Ladder (Gibco BRL)] were loaded onto a 12.5% SDS-polyacrylamide gel. The gel was run for an appropriate period of time and then silver stained in order to visualize bands.

Key for Gel 14, Shown in FIG. 49:

Elutions were performed using Buffer A supplemented with the following concentrations of imidazole:

Lane 2, 25 mM; Lane 3, 50 mM; Lane 4, 75 mM; Lane 5, 100 mM; Lane 6, 150 mM; Lane 7, 200 mM; Lane 8, 250 mM; Lane 9, 300 mM and Lane 10, 350 mM. Molecular weight marker is shown in Lane 1.

Example 119

SDS-Page Analysis of Various Fractions Collected from the Second Stepwise (Isocratic) Elution of the N-Terminally Met-Lys-(His-Gln)$_6$-Tagged Recombinant Glutathione S-Transferase Fusion Protein, GST-CT2

The procedure used was essentially the same as described in Example 118, with the exception that aliquots of fractions collected from the stepwise (isocratic) purification as described in Example 102 were applied to the gel.

Key for Gel 15, Shown in FIG. 50:
Elutions were performed using Buffer A supplemented with the following concentrations of imidazole: Lane 1, 25 mM; Lane 3, 50 mM; Lane 4, 75 mM; Lane 5, 100 mM; Lane 6, 150 mM; Lane 7, 200 mM; Lane 8, 250 mM; Lane 9, 300 mM and Lane 10, 350 mM. Molecular weight marker is shown in Lane 2.

Example 120

SDS-Page Analysis of Various Fractions Collected from the Second Stepwise (Isocratic) Elution of the N-Terminally Tagged Recombinant Glutathione S-Transferase Fusion Protein GST-NT1

The procedure used was essentially the same as described in Example 118, with the exception that aliquots of fractions collected from the stepwise (isocratic) purification as described in Example 103 were applied to the gel.

Key for Gel 16, Shown in FIG. 51:
Elutions were performed using Buffer A supplemented with the following concentrations of imidazole: Lane 1, 100 mM; Lane 2, 150 mM; Lane 4, 200 mM; Lane 5, 250 mM; Lane 6, 300 mM; Lane 7, 350 mM; Lane 8, 400 mM; Lane 9, 450 mM and Lane 10, 500 mM. Molecular weight marker is shown in Lane 3.

Example 121

SDS-Page Analysis of Various Fractions Collected from the Stepwise (Isocratic) Elution of the N-Terminally Tagged Recombinant Glutathione S-Transferase Fusion Protein GST-NT2

The procedure used was essentially the same as described in Example 118, with the exception that aliquots of fractions collected from the stepwise (isocratic) purification as described in Example 104 were applied to the gel.

Key for Gel 17, Shown in FIG. 52:
Elutions were performed using Buffer A supplemented with the following concentrations of imidazole: Lane 1, 50 mM; Lane 2, 75 mM; Lane 3, 100 mM; Lane 5, 150 mM; Lane 6, 200 mM; Lane 7, 250 mM; Lane 8, 300 mM; Lane 9, 350 mM and Lane 10, 400 mM. Molecular weight marker is shown in Lane 4.

Example 122

Immobilization of BIS(1,4,7-TRIAZACYCLONONANE) Ligands onto Sepharose™ CL-4B

This example teaches methodologies for the immobilization of preconstructed ligands onto the surface of Sepharose™ CL-4B. The ligand tacn (=1,4,7-triazacyclononane), as well as various bis(tacn) ligands (denoted $L^{eth}$, $L^{prop}$, $L^{but}$, $L^{ox}$, $L^{mx}$ and $L^{px}$) that have been immobilized are shown below in Scheme 7. The attachment (covalent attachment) of these macrocycles and bis(macrocycles) to Sepharose™ CL-4B employed techniques which are of rather general applicability for attachment of molecules containing one or more amino groups to the surface of a hydroxylic polymer substrate, such as a polysaccharide-type substrate (exemplified here by Sepharose™ CL-4B). The first stage in the process in question involves treatment of the substrate (in this case Sepharose™ CL-4B gel) with epichlorohydrin, under basic conditions, to produce an epoxy-activated polymer substrate (in this case epoxy-activated Sepharose™ CL-4B gel). Covalent attachment of the ligands may then be achieved via reaction of nucleophilic secondary amine groups present in their structures with the electrophilic epoxide surface groups. Scheme 8 (below) shows a schematic representation of the surface of the polymer substrate in question (e.g Sepharose™ CL-4B), with attachment of the ligands occurring via a single spacer group in each case. Given the presence of more than one secondary amine group within the ligands, multiple immobilization linkages may form to some extent, i.e. a small percentage of the ligands may attach to the polymer substrate surface by reaction with two or more epoxide groups.

Scheme 7. Ligands immobilized on Sepharose™ CL-4B.

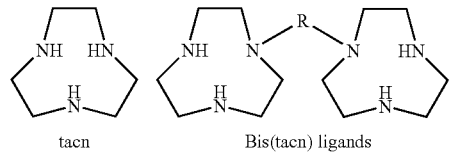

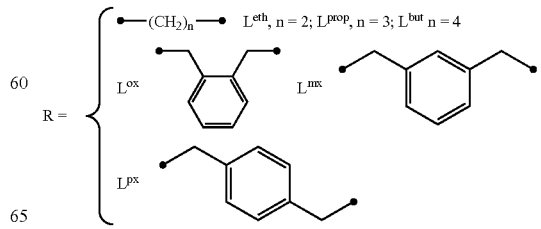

Scheme 8. Covalent attachment of ligands via a single spacer group.

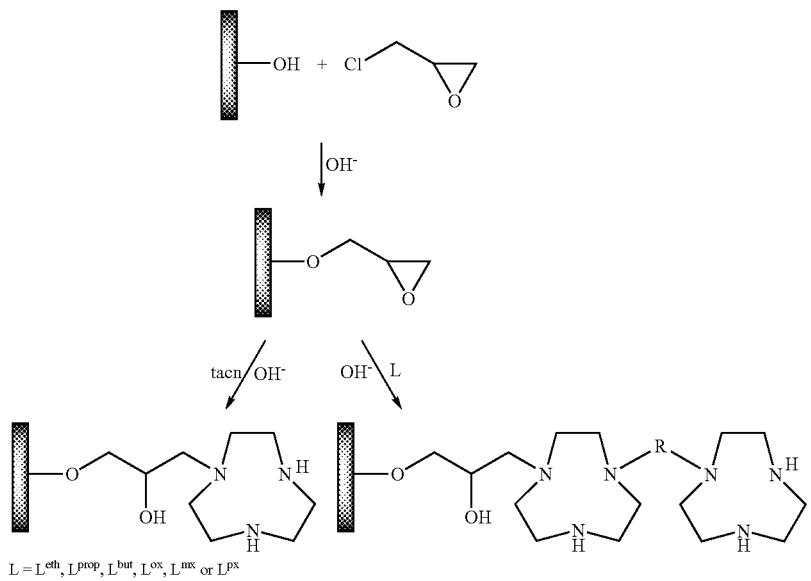

L = L$^{eth}$, L$^{prop}$, L$^{but}$, L$^{ox}$, L$^{mx}$ or L$^{px}$

Since the ligands are the only nitrogen-containing component of the sorbents, the extent of ligand immobilization could be determined via nitrogen analysis (Table 5, below). A higher surface coverage (ligand surface density) was observed for the immobilized tacn sorbent when compared with the bis(tacn) ligands. This is in spite of the availability of a greater number of secondary amine groups within the bis (tacn) ligands, which would be expected to statistically favour reaction with the electrophilic surface epoxide groups. The lower surface coverages for the bis(tacn) ligands may be due to the greater span of the bis(tacn) ligands permitting increased numbers of ligands to react with multiple epoxide groups, enhancing the levels of cross-linking within the gel structure. In addition, the bulkier bis(tacn) ligands may not be able to access as many epoxide groups as the sterically more compact tacn ligand.

TABLE 5

Nitrogen content and calculated surface densities of ligands for tacn- and bis(tacn)-Sepharose ™ CL-4B gels

| Immobilized ligand | % N (w/w) (±0.01) | Ligand surface density (μmol/g dry gel) |
|---|---|---|
| tacn | 1.88 | 447 |
| L$^{but}$ | 2.97 | 353 |
| L$^{ox}$ | 3.05 | 363 |
| L$^{mx}$ | 3.20 | 381 |
| L$^{px}$ | 3.13 | 372 |

Example 123

Assembly of a BIS(TACN) Ligand on the Surface of Sepharose™ CL-4B

This example teaches a methodology—which is believed to be of broad generality—for assembling a bis(tacn) ligand on the surface of a hydroxylic polymer substrate, such as a polysaccharide-type substrate (exemplified here by Sepharose™ CL-4B). The strategy is believed to be of broad generality since other bis(tacn), tris(tacn), tetrakis(tacn) . . . etc, derivatives and structural analogues thereof can be assembled through attachment to an appropriate poly(electrophile) on the surface of the polymer support. For a bis(tacn) ligand the synthetic strategy involves treatment of an aminated polymer substrate surface with one of the electrophilic groups of a tris(electrophile), followed by reaction of the two remaining electrophilic groups with tacn macrocycles (see Scheme 9, below). The polymer substrate in question (in this case Sepharose™ CL-4B gel) is first epoxy-activated as described earlier (see, e.g., Example 122, above) and reacted with an excess of methylamine to yield an aminated surface. The activated polymer substrate is then treated with a large excess (abbreviated XS) of 1,3,5-tris(bromomethyl)benzene with the aim of producing reaction between only one of the electrophilic groups of this molecule and the aminated gel surface, leaving two electrophilic groups available for subsequent reaction with tacn to yield an immobilized bis(tacn) ligand assembly. The attachment of the highly reactive benzylic derivative may be performed without the addition of base (which is consistent with the expectation that the proton liberated upon condensation between the bromomethyl group and an immobilized secondary amine group will protonate the resulting tertiary amine, providing a certain degree of protection from further reaction to yield a quaternary nitrogen center). Nitrogen analyses performed on Sepharose™ CL-4B gels which had been first aminated and then fully functionalized in this manner revealed successful coupling of tacn to the gel surface, as seen by a three-fold increase in the nitrogen content of the material (Table 6).

Scheme 9. Synthesis of C-linked L$^{mx}$-functionalized hydroxylic polymer substrate (e.g. Sepharose™ CL-4B gel).

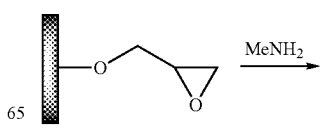

-continued

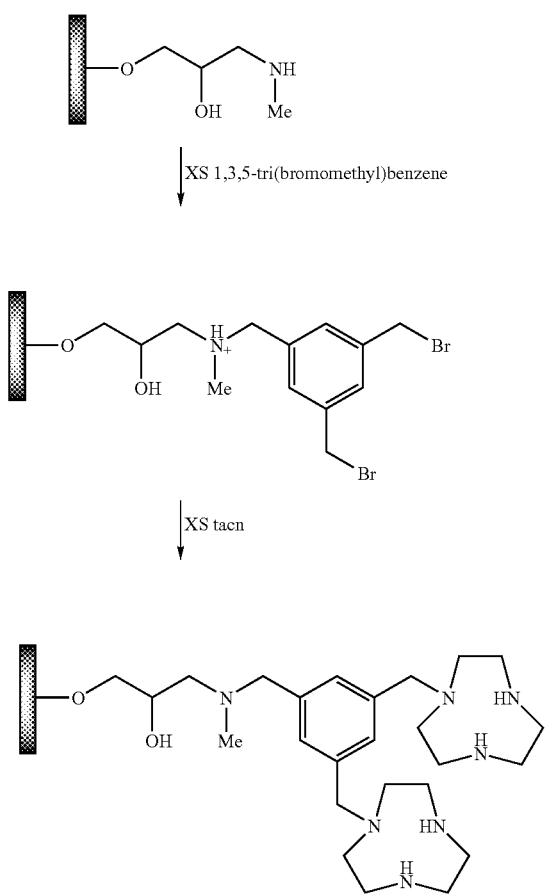

TABLE 6

Nitrogen content and calculated ligand density for immobilized MeNH$_2$- and C-linked L$^{mx}$-Sepharose ™ CL-4B gels.

| Immobilized ligand | % N (w/w) (±0.01) | Ligand surface density (μmol/g dry gel) |
|---|---|---|
| MeNH$_2$ | 1.39 | 992 |
| C-linked L$^{mx}$ | 4.27 | 343[§§] |

[§§]Calculated from the difference between the N content of the two gels. The actual surface density of bis(tacn) ligands may be lower due to cross-linking (vide supra).

According to the immobilization scheme presented in Scheme 9 (vide supra), the nitrogen content of the final gel would be expected to be approximately seven times that of the simple aminated gel. There are two conceivable explanations for the lower nitrogen content. Firstly, it is possible that incomplete reaction occurred in either one or both of the two synthetic steps following amination of the gel surface with methylamine. Consequently, the final gel may possess a number of unreacted methylamine and/or bromomethyl groups on its surface. Secondly, cross-linking could have occurred during any one of the three synthetic steps shown in Scheme 9, leading to cross-linked species such as those shown in Scheme 10, below. Interestingly, the immobilized ligand surface density matches well those determined for all the gels prepared from pre-assembled bis(tacn) ligands.

Scheme 10. Two examples of possible cross-linked species formed during the synthesis of C-linked L$^{mx}$ Sepharose™ CL-4B gel.

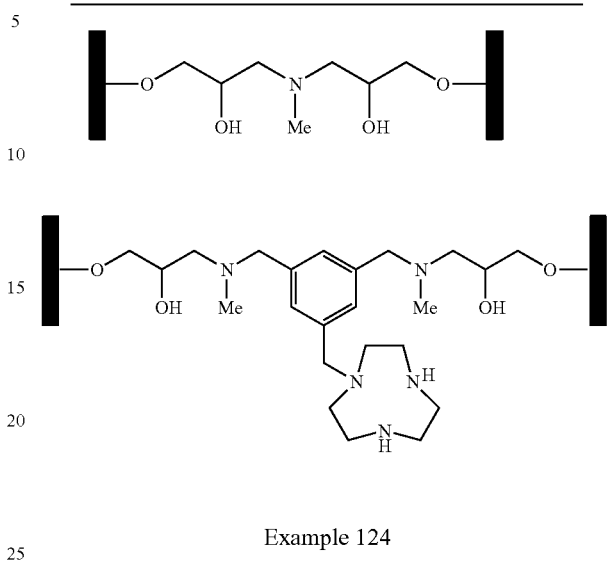

Example 124

Documentation of Metal Ion Binding

This example describes the immobilization of $Cu^{2+}$ and $Ni^{2+}$ ions onto the new functionalized gels, and characterization of the products. Immobilization was achieved by mixing the gel in question with a solution of the appropriate metal nitrate salt, followed by washing with acetate buffer (pH 5) in order to remove any loosely bound ions. The rapid uptake of $Cu^{2+}$ ions by the gels was immediately apparent from a change of the colour of the gel to blue, whilst for binding of $Ni^{2+}$, incubation at elevated temperatures was found to be necessary in order to impart a light purple-blue colouration to the gels within a reasonable length of time. Thus, the reaction between $Ni^{2+}$ ions and the immobilized ligands in question appears to be quite slow. After incubation at 60° C. for 1 h, the levels of uptake of $Cu^{2+}$ and $Ni^{2+}$ by the gels were found to be ca. 70% and 40%, respectively, of the maximum uptake predicted on the basis of the corresponding ligand surface densities (Table 7, vide infra). In the case of the $Ni^{2+}$-treated gels, the presence of non-coordinated ligand donor atoms was confirmed by the fact that samples of the gels became blue when mixed with a solution of $Cu^{2+}$ ions; the known kinetic inertness of nickel(II) tacn complexes precludes the possibility that this is due to displacement of the $Ni^{2+}$ ions by $Cu^{2+}$ ions [see, e.g.: Yang, R. and Zompa, L. J., *Inorganic Chemistry*, 15 (1976) 1499; and Murphy, L. J. and Zompa, L. J. *Inorganic Chemistry*, 18 (1979) 3278]. Given that only low levels of immobilized binuclear nickel(II) complex species would be expected to have formed under such low loadings, and that one important motivation for studying the application of bis(tacn) ligands to IMAC (in the manner according to the present invention) was to explore protein binding to binuclear complexes, it appears that the $Ni^{2+}$-loaded supports are less advantageous than corresponding $Cu^{2+}$-loaded sorbents; moreover, from a practical point of view, maximal uptake of metal ions by an IMAC sorbent needs to be achieved fairly rapidly so that excessive amounts of time are not spent preparing the sorbent for use. Based on such observations and considerations, greater experimental focus was therefore placed on the higher-capacity $Cu^{2+}$-loaded sorbents.

TABLE 7

Uptake of $Cu^{2+}$ and $Ni^{2+}$ by tacn- and bis(tacn)-functionalized Sepharose ™ CL-4B gels as determined by atomic absorption spectroscopy

| Immobilized Ligand | Ni content (μmol/g dry gel)* (±5%) | Cu content (μmol/g dry gel)* (±5%) | Cu content (μmol/mL wet gel)* (±5%) |
|---|---|---|---|
| tacn | 185 (41%) | 305 (68%) | 11.1 |
| $L^{but}$ | 293 (42%) | 506 (72%) | 18.3 |
| $L^{ox}$ | 246 (34%) | 510 (70%) | 20.9 |
| $L^{mx}$ | 267 (35%) | 552 (72%) | 20.4 |
| $L^{px}$ | 246 (33%) | 553 (74%) | 21.2 |
| C-linked $L^{mx}$ | 284 (41%) | 496 (72%) | 21.6 |

*Values in parentheses are metal ion contents expressed as a percentage of the maximum theoretical uptake calculated from the ligand surface densities.

In order to confirm the apparent rapid uptake of $Cu^{2+}$ ions by the functionalized gels, a series of small-scale experiments were performed to establish the incubation time necessary to achieve equilibrium. The results indicated that equilibrium was reached quickly, with little or no detectable increase in uptake occurring after 30 min mixing at room temperature. Representative uptake curves are shown in FIG. 58. Based on the results of this study, a standard adsorption time of 30 minutes was chosen for subsequent preparations of $Cu^{2+}$-loaded supports.

It is of interest to consider the possible reasons for the observed sub-maximal degrees of binding of $Cu^{2+}$, which, in contrast to $Ni^{2+}$ uptake, do not appear to be due to slow attainment of equilibrium. Whilst metal ion:ligand ratios of approximately 1:1 have been reported for $Cu^{2+}$-binding to IDA-agarose supports [see, e.g., Porath, J. and Belew, M. Journal of Chromatography, 516 (1990) 333; and Jiang, W. and Hearn, M. T. W. Analytical Biochemistry, 242 (1996) 45], the observed degrees of binding of ca. 70% are consistent with those observed for various supports incorporating immobilized ligands with solely N-donors or N-donors in combination with ether-type O-donors [see, e.g., Gros, C., Rabiet, F., Denat, F., Brandès, S., Chollet, H. and Guilard, R. Journal of the Chemical Society, Dalton Transactions, (1996) 1209; van Berkel, P. M., Driessen, W. L., Kodhaas, G. J. A. A., Reedijk, J. and Sherrington, D. C. Journal of the Chemical Society., Chemical Communications, (1995) 147; and Dudler, V., Lindoy, L. F., Sallin, D. and Schlaepfer, C. W. Australian Journal of Chemistry, 40 (1987) 1557]. A dependence of the binding on the metal ion for some of these immobilized systems has been taken to reflect differential steric effects associated with the three-dimensional polymeric network (see van Berkel, P. M. et al. and Dudler, V. et al./oc cit.). Such steric hindrance may reduce the ability of some sites to bind certain metal ions when unfavourable conformational changes are induced, or may restrict access of metal ions to particular sites. For the sorbents reported here, the lowered $Cu^{2+}$:ligand ratios could also be due in part to the formation of $CuL_2^{2+}$ species, in which $Cu^{2+}$ ions are sandwiched between pairs of tacn rings from neighbouring ligands (L) on the gel surface (Scheme 12). The relatively high degrees of binding achieved, however, indicate that the main species are likely to be $CuL^{2+}$ and $Cu_2L^{2+}$ for the tacn- and bis(tacn)-functionalized sorbents, respectively. It is important to note that the uptake of $Cu^{2+}$ ions, expressed as a percentage of the maximum extent of binding predicted from the ligand surface density, is virtually identical in all cases.

Scheme 12. Possible sandwich structure, involving neighboring immobilized ligands, which may form on the surface of $Cu^{2+}$-loaded tacn- and bis(tacn)-functionalized Sepharose™ CL-4B gels.

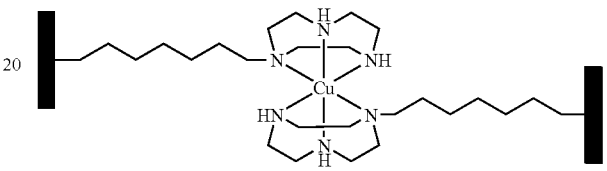

In order to further assess the suitability of the novel $Cu^{2+}$-loaded sorbents according to the invention for use in IMAC, the resistance of the systems to metal ion leaching was examined under a variety of different equilibrating conditions to be used in later protein/peptide binding studies. After washing the metal-ion-loaded supports with water and 20 mM acetate buffer (pH 5) to remove loosely bound metal ions, the sorbents were further washed with one of the following media: 20 mM acetate buffer, 20 mM phosphate buffer (pH 7), 20 mM borate buffer (pH 9), 200 mM imidazole or 200 mM $Na_2EDTA$ solution. Results are presented in FIG. 59. With the exception of the $Na_2EDTA$ medium, negligible metal-ion leakage was found to occur with these media, confirming the high stability of the immobilized complexes. Prolonged treatment with $Na_2EDTA$, however, led to elution of greater than 80% of the immobilized $Cu^{2+}$ ions.

FIG. 59 $Cu^{2+}$ content of $Cu^{2+}$-tacn-(●) and -$L^{px}$-functionalized (■) Sepharose™-4B gels after washing with various solutions. Wash 1=20 mM NaOAc/1 M NaCl/pH 5; wash 2=20 mM NaOAc/1 M NaCl/pH 5; wash 3=20 mM $Na_2HPO_4$/1 M NaCl/pH 7; wash 4=20 mM $Na_2B_4O_7$/1 M NaCl/pH 9; wash 5=200 mM imidazole; wash 6=200 mM $Na_2EDTA$.

Equilibrium data of relevance and importance to the disclosure herein concerning aspects of the pre-sent invention are summarized in Table 8 and Table 9, below.

TABLE 8

Summary of stability constant data for tacn, bis(tacn) and related ligands employed in IMAC

| Ligand | Reaction | | | | | Constant | Free ligand | Ligand immobilised on Sepharose ™ CL-4B |
|---|---|---|---|---|---|---|---|---|
| | $H_3-L^{3+}$ | ⇌ | $H_2-L^{2+}$ | + | $H^+$ | | | |
| | $H_2-L^{2+}$ | ⇌ | $H-L^+$ | + | $H^+$ | | | |
| tacn | $H-L^+$ | ⇌ | L | + | $H^+$ | $pK_{a1}$ | $<2^{a,b}$ | $<2^a$ |
| | | | | | | $pK_{a2}$ | $6.80^{a,b}$ | $5.40^a$ |
| | L + $Cu^{2+}$ | ⇌ | $CuL^{2+}$ | | | $pK_{a3}$ | $10.4^{a,b}$ | $10.30^a$ |
| | | | | | | $pK_{CuL}$ | $15.0^a, 15.5^b$ | $14.1^a$ |
| | L + $Ni^{2+}$ | ⇌ | $NiL^{2+}$ | | | $pK_{NiL}$ | $16.2^b$ | — |
| | L + $Zn^{2+}$ | ⇌ | $ZnL^{2+}$ | | | $pK_{ZnL}$ | $11.6^{a,b}$ | $10.3^a$ |

TABLE 8-continued

| | | | | | | | |
|---|---|---|---|---|---|---|---|
| IDA | $H_3$—$L^+$ | ⇌ | $H_2$—L + $H^+$ | $pK_{a1}$ | 1.79[c] | N.D.[c] | |
| | $H_2$—L | ⇌ | H—$L^-$ + $H^+$ | $pK_{a2}$ | 2.55[c] | 2.67[c] | |
| | H—$L^-$ | ⇌ | $L^{2-}$ + $H^+$ | $pK_{a3}$ | 9.26[c] | 8.67[c] | |
| | L + $Cu^{2+}$ | ⇌ | $CuL^{2+}$ | $pK_{CuL}$ | 10.63[d] | 8.05[c] | |
| | L + $Ni^{2+}$ | ⇌ | $NiL^{2+}$ | $pK_{NiL}$ | 8.07[e] | N.D. | |
| | L + $Zn^{2+}$ | ⇌ | $ZnL^{2+}$ | $pK_{ZnL}$ | 7.00[f] | N.D. | |
| NTA | $H_3$—L | ⇌ | $H_2$—$L^-$ + $H^+$ | $pK_{a1}$ | ~1.6[g] | N.D. | |
| | $H_2$—$L^-$ | ⇌ | H—$L^{2-}$ + $H^+$ | $pK_{a2}$ | 2.40[g] | N.D. | |
| | H—$L^{2-}$ | ⇌ | $L^{3-}$ + $H^+$ | $pK_{a3}$ | 9.56[g] | N.D. | |
| | L + $Cu^{2+}$ | ⇌ | $CuL^{2+}$ | $pK_{CuL}$ | 12.96[d] | N.D. | |
| | L + $Ni^{2+}$ | ⇌ | $NiL^{2+}$ | $pK_{NiL}$ | 11.54[h] | N.D. | |
| | L + $Zn^{2+}$ | ⇌ | $ZnL^{2+}$ | $pK_{ZnL}$ | 10.44[i] | N.D. | |

[a]T. W. Hearn et al., this work;
[b]R. Yang and L. J. Zompa, Inorg. Chem., 15, 1499, 1976;
[c]M. Zachariou, I. Traverso, L. Spiccia, M. T. W. Hearn, J. Phys. Chem., 100, 12680, 1996.
[d]A. Hulanicki, and T. Krawczyk, Anal. Chim. Acta, 158, 343, 1984.
[e]G. Arena and V. Cucinotta, Inorg. Chim. Acta, 52, 275, 1981.
[f]L. Anderegg, Helv. Chim. Acta, 47, 1801, 1964.
[g]D. Sanna, I. Bodi, S Bouhsina and G. Micera, Dalton Trans, 3275, 1999.
[h]G. Anderegg, Pure Appl. Chem., 54, 2693, 1982.
[i]H Irving and M. Miles, J. Chem. Soc. (A), 727, 1966.
N.D. = not determined.

| Bis-(tacn) derivatives | Linker group | Reaction | | Constant | Free ligand[a] |
|---|---|---|---|---|---|
| $L^{eth}$ | —$CH_2$—$CH_2$— | L + $Cu^{2+}$ ⇌ $CuL^{2+}$ | | $pK_{CuL}$ | 27.82 |
| | | L + $2Cu^{2+}$ ⇌ $Cu_2L^{4+}$ | | $pK_{Cu2L}$ | N.D. |
| $L^{prop}$ | —$CH_2$—$CH_2$—$CH_2$— | L + $Cu^{2+}$ ⇌ $CuL^{2+}$ | | $pK_{CuL}$ | 24.90 |
| | | L + $2Cu^{2+}$ ⇌ $Cu_2L^{4+}$ | | $pK_{Cu2L}$ | 29.08 |
| $L^{but}$ | —$CH_2$—$CH_2$—$CH_2$—$CH_2$— | L + $Cu^{2+}$ ⇌ $CuL^{2+}$ | | $pK_{CuL}$ | 23.02 |
| | | L + $2Cu^{2+}$ ⇌ $Cu_2L^{4+}$ | | $pK_{Cu2L}$ | 29.61 |
| $L^{pent}$ | —$CH_2$—$CH_2$—$CH_2$—$CH_2$—$CH_2$— | L + $Cu^{2+}$ ⇌ $CuL^{2+}$ | | $pK_{CuL}$ | 21.6 |
| | | L + $2Cu^{2+}$ ⇌ $Cu_2L^{4+}$ | | $pK_{Cu2L}$ | 29.64 |
| $L^{hex}$ | —$CH_2$—$CH_2$—$CH_2$—$CH_2$—$CH_2$—$CH_2$— | L + $Cu^{2+}$ ⇌ $CuL^{2+}$ | | $pK_{CuL}$ | 21.3 |
| | | L + $2Cu^{2+}$ ⇌ $Cu_2L^{4+}$ | | $pK_{Cu2L}$ | 29.69 |
| $L^{hept}$ | —$CH_2$—$CH_2$—$CH_2$—$CH_2$—$CH_2$—$CH_2$—$CH_2$— | L + $Cu^{2+}$ ⇌ $CuL^{2+}$ | | $pK_{CuL}$ | 21.2 |
| | | L + $2Cu^{2+}$ ⇌ $Cu_2L^{4+}$ | | $pK_{Cu2L}$ | 29.48 |
| $L^{oct}$ | —$CH_2$—$CH_2$—$CH_2$—$CH_2$—$CH_2$—$CH_2$—$CH_2$—$CH_2$— | L + $Cu^{2+}$ ⇌ $CuL^{2+}$ | | $pK_{CuL}$ | 21.7 |
| | | L + $2Cu^{2+}$ ⇌ $Cu_2L^{4+}$ | | $pK_{Cu2L}$ | 29.33 |
| $L^{ox}$ | ortho-xylyl (—$CH_2$—$C_6H_4$—$CH_2$—) | L + $Cu^{2+}$ ⇌ $CuL^{2+}$ | | $pK_{CuL}$ | 22.19 |
| | | L + $2Cu^{2+}$ ⇌ $Cu_2L^{4+}$ | | $pK_{Cu2L}$ | N.D. |
| $L^{mx}$ | meta-xylyl (—$CH_2$—$C_6H_4$—$CH_2$—) | L + $Cu^{2+}$ ⇌ $CuL^{2+}$ | | $pK_{CuL}$ | 19.8 |
| | | L + $2Cu^{2+}$ ⇌ $Cu_2L^{4+}$ | | $pK_{Cu2L}$ | 27.7 |

TABLE 8-continued

| | | | | | |
|---|---|---|---|---|---|
| $L^{px}$ | (−CH₂−C₆H₄−CH₂−) | L + Cu²⁺ ⇌ CuL²⁺ | | p$K_{CuL}$ | N.D. |
| | | L + 2Cu²⁺ ⇌ Cu₂L⁴⁺ | | p$K_{Cu2L}$ | 28.23 |

[a]Data taken from: B. DasGupta, C. Katz, T. Israel,
M. Watson and L.J. Zompa, Inorg. Chim. Acta. 292, 172, 1999; M.T.W. Hearn et al., this work.
N.D. = not determined.

TABLE 9

Comparative association constants representative of the binding behaviour of model proteins to immobilized Cu(ll) tacn ligand systems at pH = 7.0.

| | Linker group | Metal ion | Model protein | Affinity constant ($M^{-1}$) |
|---|---|---|---|---|
| Ligand | | | | |
| Tacn | | Cu(II) | Myoglobin | $2.2 \times 10^5$ |
| IDA | | Cu(II) | Myoglobin | $2.6 \times 10^4$ |
| | | | Lysozyme | $8.9 \times 10^5$ |
| Bis(tacn) derivatives | | | | |
| $L^{eth}$ | −CH₂−CH₂− | Cu(II) | Myoglobin | $6.6 \times 10^4$ |
| | | Cu(II) | Lysozyme | $2.8 \times 10^4$ |
| $L^{prop}$ | −CH₂−CH₂−CH₂− | Cu(II) | Myoglobin | $9.0 \times 10^5$ |
| | | Cu(II) | Lysozyme | $4.5 \times 10^5$ |
| $L^{but}$ | −CH₂−CH₂CH₂CH₂− | Cu(II) | Myoglobin | $2.7 \times 10^5$ |
| | | Cu(II) | Lysozyme | $1.1 \times 10^5$ |
| $L^{ox}$ | ortho-xylyl (−CH₂−C₆H₄−CH₂−) | Cu(II) | Myoglobin | $7.9 \times 10^5$ |
| | | Cu(II) | Lysozyme | $0.25 \times 10^5$ |
| $L^{mx}$ | meta-xylyl (−CH₂−C₆H₄−CH₂−) | Cu(II) | Myoglobin | $38 \times 10^5$ |
| | | Cu(II) | Lysozyme | $0.30 \times 10^5$ |
| $L^{px}$ | para-xylyl (−CH₂−C₆H₄−CH₂−) | Cu(II) | Myoglobin | $78 \times 10^5$ |
| | | Cu(II) | Lysozyme | $0.28 \times 10^5$ |
| N-(2-pyridyl-methyl)-amino | pyridine-2,6-diyl-bis(methylene) with NH₂ and NH− | Cu(II) | Myoglobin | $1.8 \times 10^5$ |

Example 125

Documentation of Spectral Characterisation of Cu²⁺-Loaded Gels

To obtain information about the coordination environment of the Cu²⁺ ions immobilized on the sorbent surfaces, diffuse reflectance and ESR spectra of the Cu²⁺-loaded supports were recorded. The diffuse reflectance spectra each showed a very broad band centred at ca. 640 nm in the visible region, similar to that observed for the copper(II) complexes of the non-immobilized bis(tacn) ligands in solution and indicative of copper(II) residing in a square-pyramidal or tetragonally-distorted octahedral coordination environment. The low intensity bands observed at ca. 1100 nm for the "free" complexes were not resolved in the diffuse reflectance spectra of the gels.

X-band ESR spectra of the Cu²⁺-loaded gels, measured at 77 K, showed a strong signal at ca. 3200 G in each case, typical of that found for mononuclear copper(II) complexes with nuclear spin 3/2; three of the four expected hyperfine signals were visible, with the fourth being hidden under the gi line [see Hathaway, B. J. In *Comprehensive Coordination Chemistry*; Wilkinson, G., Gillard, R. D. and McCleverty, J. A. (Eds.), Pergamon Press, Oxford, 1987, Vol. 5, p 533]. The signal for the tacn gel was well resolved. Those for the bis (tacn) gels were somewhat broader, reflecting the fact that the two halves of the ligand become inequivalent upon immobilization to the gel surface. Hence the coordination environments of the two copper(II) centres bound by each ligand would be expected to be slightly different. The ESR spectra of the sorbents are very similar to those of the "free" copper(II) complexes with parameters ($g_∥$=2.24, $g_⊥$=2.05–2.07, $A∥$170× $10^{-4}$ cm$^{-1}$) characteristic for $Cu^{2+}$ ions residing in a SP or tetragonally-distorted octahedral coordination environment (see Hathaway, B. J., loc cit.). The complex species existing on the gel surfaces are therefore similar in nature to the copper(II) complexes formed by the ligands in solution.

Example 126

In addition to the information provided in the introduction to the Experimental Section (vide supra), the following provides further details regarding, in particular, various materials, reagents and procedures employed in relation to the present invention.

Larger Scale Immobilization of TACN and BIS(TACN) Ligands onto Sepharose™ CL-4B

Suction-dried Sepharose™ CL-4B (300 g), thoroughly washed with water (5×300 ml), was placed in a round-bottom flask and mixed with 1 M NaOH (300 ml) and NaBH$_4$ (1.2 g) at room temperature for 1 h by means of an overhead mechanical stirrer. Epichlorohydrin (100 ml) was then added and the suspension stirred for a further 6 h. The resulting epoxy-activated gel was collected by vacuum filtration and washed extensively with water (5×300 ml), 20% EtOH/water (5×300 ml), and water once more (5×300 ml). 75 mM solutions of the ligands [tacn and the bis(tacn) ligands $L^{eth}$, $L^{prop}$, $L^{but}$, $L^{ox}$, $L^{mx}$ and $L^{px}$] were prepared by dissolving 3.75 mmol quantities of the hydrobromide salts of each ligand in water (40 ml), adjusting the pH to 11 with 6 M NaOH, and then making up to 50 ml with water. The solutions were added to 60 g portions of the suction-dried epoxy-activated gel, and the suspensions mixed at 60° C. for 15 h using a shaking water bath. The resulting functionalized gels were collected by vacuum filtration, washed with water (5×200 ml), 50 mM acetic acid/0.1 M KNO$_3$ (pH 4) (2×200 ml) and once more with water (5×200 ml). The gels were stored at 4° C. in 20% EtOH/water until required.

Assembly of a BIS(TACN) Ligand on Sepharose™ CL-4B

Suction-dried epoxy-activated Sepharose CL-4B gel (80 g) (prepared as described above) was suspended in 24% aqueous methylamine solution, and the mixture stirred for 15 h at 60° C. The resulting aminated gel was then filtered off by vacuum filtration and washed with water (10×200 ml), 50 mM acetic acid/0.1 M KNO$_3$/pH 4 buffer (4×100 ml) and once more with water (10×200 ml). A portion of the aminated gel (15 g) was set aside for nitrogen analysis. The remainder was washed successively with three 100 ml portions of 5% triethylamine/water, 20% acetonitrile/5% triethylamine/water, 40% acetonitrile/5% triethylamine/water, 60% acetonitrile/5% triethylamine/water, 80% acetonitrile/5% triethylamine/water, 95% acetonitrile/5% triethylamine, and finally acetonitrile (6×100 ml). Acetonitrile was then added to the gel to give a suspension of total volume 170 ml. A solution of 1,3,5-tris(bromomethyl)benzene (10 g, 28 mmol) in acetonitrile (30 ml) was added, and the mixture stirred rapidly for 18 h at room temperature. The gel was then filtered off and washed with acetonitrile (5×100 ml). Acetonitrile was added to the gel to give a suspension of total volume 130 ml. A solution of the free base form of tacn (6.5 g, 50 mmol) in acetonitrile (40 ml) was then added, and the mixture stirred vigorously for 22 h at room temperature. The gel was filtered off and washed successively with two 50 ml portions of acetonitrile, 75% acetonitrile/water, 50% acetonitrile/water, 25% acetonitrile/water, water, 50 mM acetic acid/0.1 M KNO$_3$/pH 4 buffer, and once more with water. The gel was stored at 4° C. in 20% EtOH/water.

Nitrogen Analysis of Ligand-Functionalized Sepharose™ CL-4B Sorbents

The functionalized gels were analysed for nitrogen content to determine the extent of ligand immobilization. For each gel, approximately 20 g of suction-dried material was suspended in 20% acetone/water (50 ml) for 2 min. The bulk of the solvent was then removed by gentle vacuum filtration, taking care not to allow the gels to dry out (desiccation of the gels at this stage having been found to lead to aggregation of the sorbents). The gels were washed with a further portion of 20% acetone/water in exactly the same manner. This double-washing procedure was repeated using solutions of increasing acetone content (20% increments) until the gels had been passaged into neat acetone. The gels were then washed once more with acetone (50 ml) before being thoroughly suction-dried and then dried under high vacuum for 24 h. The dried sorbents were analysed for their total nitrogen content using the Kjeldahl procedure.

Loading of $Cu^{2+}$ and $Ni^{2+}$ Ions onto Functionalized Sepharose™ CL-4B Sorbents Portions (0.5 g) of suction-dried sorbents were added to 10 ml scintillation vials containing 50 mM aqueous solutions of the appropriate metal nitrate (5 ml) and mixed by inversion for 60° C. for 1 h. For $Cu^{2+}$ loading, this procedure was performed as a series of runs at room temperature for periods of time varying from 0.5 h to 20 h in order to establish the variation in $Cu^{2+}$ uptake with time. The gels were then collected by vacuum filtration and washed successively with water (3×50 m), 20 mM NaOAc/1 M NaCl/pH 5 buffer (2×25 ml) and water (3×50 ml), allowing 3 min equilibration time between addition of the solutions and their removal by vacuum filtration.

Standard Conditions for the Loading of $Cu^{2+}$ and $Ni^{2+}$ Ions onto Functionalized Sepharose™ CL-4B Sorbents Large-scale loading (binding) of $Cu^{2+}$ ions onto the functionalized sorbents was achieved by incubating 4 g portions of the suction-dried gels with 50 mM Cu(NO$_3$)$_2$.3H$_2$O (50 ml) in 50 ml scintillation vials at room-temperature for 30 min, since preliminary uptake experiments (Example 124; vide supra) had shown this to be a sufficient length of time. The metal ion-loaded sorbents were then collected by vacuum filtration, washed with water (5×100 ml) and suspended in 20 mM NaOAc/1 M NaCl/pH 5 buffer (50 ml) for 15 min. The gels were filtered off, washed with a further aliquot (50 ml) of the pH 5 buffer and then with water (3×100 ml), maintaining a 3 min washing equilibration time.

Further Details Relating to the Choice of the Buffer Equilibration Experiments

Portions (0.5 g) of suction-dried $Cu^{2+}$-loaded sorbents were incubated in 20 mL scintillation vials at room temperature with the solutions specified below (10 ml) for the specified times; the gels were then isolated by vacuum filtration before being washed with a further aliquot of 20 mM Na$_2$HPO$_4$/1 M NaCl/pH 7 buffer (10 mL) and then water (3×50 ml), with 3 min equilibrations between washings.

Solutions: 1) 20 mM Na$_2$HPO$_4$/1 M NaCl/pH 7 buffer, 10 min.

2) 20 mM Na$_2$B407/1 M NaCl/pH 9 buffer, 10 min.

3) 200 mM imidazole, 10 min.

4) 200 mM Na$_2$EDTA, 30 min.

Metal Analysis of $Cu^{2+}$- and $Ni^{2+}$-Loaded Sepharose™ CL-4B Sorbents

For each metal ion-loaded sorbent sample, approximately 0.5 g of suction-dried material was passaged into neat acetone and dried under high vacuum using the procedure described above for the metal-ion free gels. Approximately 20 mg of dried sorbent was then accurately weighed into a sealable 20 ml scintillation vial and digested in 4 M HCl (4 ml) at 50° C. for 4 h with frequent inversion. The resulting light yellow-brown solution was diluted with water to a volume of 8 ml and then analysed for copper content by atomic absorption spectrophotometry. In order to determine the metal content of the sorbents in terms of the swollen gel volume, the analysis was repeated using aliquots (1 ml) of 50% (v/v) gel/water suspension, prepared by settling the gels in water and adjusting the volume of liquid above the gel to equal the bed volume.

Diffuse Reflectance and ESR Spectroscopy of $Cu^{2+}$-Loaded Sepharose™ CL-4B Sorbents Diffuse reflectance spectra were recorded using gel samples that had been dried under high vacuum according to the procedure described above. ESR spectra were recorded using suction-dried samples of gels that had been washed with 20 mM NaOAc/1 M NaCl/pH 5 buffer.

Example 127

Construction of an Expression Plasmid that can be Used to Express the Full-Length Recombinant Glutathione S-Transferase [r-GST(FL)] Fused at The N-Terminus to the Oligopeptide "TAG" Denoted NT1 (SEQ, ID NO. 1) [Fusion Protein Denoted GST(FL)-NT1]

Site-directed mutagenesis (SDM) of the plasmid constructed to express GST-NT1, as described in Example 86, was performed in order to modify the C-terminal end of the sequence encoding GST to achieve a full-length construct. A single base change was introduced by SDM, which altered the stop codon (TAA), of the GST to encode a lysine residue (codon AAA). Removal of this stop codon in the N-terminally tagged recombinant GST fusion protein (GST-NT1) expression plasmid resulted in a plasmid that can be used to express the N-terminally tagged recombinant GST fusion protein, GST-NT1, in which the GST is C-terminally extended by the four amino acids Lys-Ser-Asp-Leu, respectively. This resultant expression plasmid has been named full-length Glutathione S-transferase [GST(FL)], as the restoration of the C-terminal lysine residue encodes the full-length GST sequence plus an additional three C-terminal residues that can be derived, for example, from the pGEX3XGST vector, which was used to create the original construct.

The SDM procedures were performed as outlined in the *QuickChange™ Site-Directed Mutagenesis kit Instruction Manual*, Catalog #200518, Revision # 1000007, from Stratagene.

Site-Directed Mutagenesis Reactions:

The expression plasmid that was constructed to express the N-terminally tagged GST fusion protein GST-NT1 as described in Example 86 was used as the template DNA. The oligonucleotides that were used to incorporate the desired base change, as underlined, were as follows:

```
Oligonucleotide No. 1:
5' GGCGACCATCCTCCTAAATCGGATCTGTAAAAGC 3'

Oligonucleotide No. 2:
5' GCTTTTACAGATCCGATTTAGGAGGATGGTCGCC 3'
```

Approximately 25 ng of the dsDNA template was added to a mixture containing 125 ng of oligonucleotide No. 1, 125 ng of oligonucleotide No. 2, 5 µL of 10× reaction buffer and 1 µL of dNTP's. The volume of the reaction mixture was adjusted to 50 µL with doubly distilled $H_2O$. To this mixture 2.5 U of Pfu Turbo DNA polymerase was added, and the reaction mixture was overlaid with mineral oil.

The reaction mixture was then placed in a thermo-cycler using the following conditions: (a) an initial denaturation step at 95° C. for 30 sec followed by (b) 12 cycles of 95° C. for 30 sec, (c) 55° C. for 1 min then (d) 68° C. for 10 min. At the cessation of the temperature cycling the reaction was removed and cooled on ice for 2 min. 10 U of the restriction enzyme DpnI was then applied to the amplification reaction, and the mixture was then gently but thoroughly agitated. The mixture was then spun down in a microcentrifuge for 1 min and immediately incubated at 37° C. for 1 hour.

Transformation into XL-1-Blue Supercompetent Cells:

5 µL of the DpnI-treated DNA from the preceding reaction was added to a 50 µL aliquot of XL-1 Blue supercompetent cells, and the mixture was incubated on ice for 30 min. This mixture was then heat-pulsed for 45 sec at 42° C. and then chilled on ice for 2 min. Following the addition of 0.5 ml of SOC media [5 ml of SOB (tryptone 20 g/L, yeast extract 5 g/L, 2.5 mM NaCl and 625 µM KCl and autoclaved) supplemented with 5 mM $MgCl_2$, 5 mM $MgSO_4$ and 20 mM glucose and filter-sterilised], the transformation reaction was incubated at 37° C. for 1 hour. Different dilutions of the transformation mixture were plated onto LB Amp plates (tryptone 10 g/L, yeast extract 5 g/L, NaCl 10 g/L with agar 15 g/L added and autoclaved, then supplemented with ampicillin 100 mg/L). The plates were incubated at 37° C. overnight.

Identification of Positive Clones:

Modified plasmid DNA was isolated from XL-1 Blue transformants described above using standard techniques. DNA sequencing of the isolated plasmid DNA was performed as follows: Approximately 200 ng of the modified plasmid DNA, 5 µmol primer and 6 µL of terminator premix in a volume of 15 µL. Duplicate mixtures of the above reactions were prepared, one set containing the (a) pTrc forward primer: 5 TTGACAATTAATCATCCGGC 3 and the other set containing the (b) pTrc reverse primer 5 CCAGGCAAATTCTGTTTTATCAG 3'.

The reaction mixtures were applied to a thermo-cycler using the following conditions: (a) an initial denaturation step at 96° C. for 1 min, then 25 cycles consisting of (b) 96° C. for 30 sec, (c) 45° C. for 15 sec and (d) 60° C. for 4 min, respectively. The extension products were recovered by performing an ethanol/sodium acetate precipitation using standard techniques, and the pellets were dried and subjected to DNA sequencing. A clone containing the desired plasmid encoding GST(FL)-NT1 was identified and verified as correct.

Transformation of Expression Cells:

Rubidium chloride treated *E. coli* cells, strains JM105, BL21 and TOP10, were each transformed with approx. 100 ng of the modified expression plasmid, using standard techniques. Different dilutions of the transformed cells were plated onto LB Amp plates for selection of plasmid-containing cells.

Example 128

Construction of an Expression Plasmid that can be Used to Express the Full-Length Recombinant Glutathione S-Transferase [r-GST(FL)] Fused at the N-Terminus to the Oligopeptide "TAG" Met-Lys-(His-Gln)$_6$ Denoted CT2 [Fusion Protein Denoted GST(FL)-CT2]

The procedure used was essentially the same as described in Example 127, except that site-directed mutagenesis (SDM) of the plasmid constructed to express GST-CT2, as described in Example 88, was performed in order to modify the C-terminal end of the sequence encoding GST.

Example 129

Construction of an Expression Plasmid that can be Used to Express the Full-Length Recombinant Glutathione S-Transferase [r-GST(FL)] Fused at the N-Terminus to the Oligopeptide "TAG" Denoted NT2 (SEQ. ID NO. 2) [Fusion Protein Denoted GST (FL)-NT2]

The procedure used was essentially the same as described in Example 127, except that site-directed mutagenesis (SDM) of the plasmid constructed to express GST-NT2, as described in Example 89, was performed in order to modify the C-terminal end of the sequence encoding GST.

Example 130

Large-Scale Expression of the N-Terminally Met-Lys-(His-Gln)$_6$-Tagged Recombinant Glutathione S-Transferase Full-Length Fusion Protein, GST(FL)-CT2, in E. coli Cells Strain JM105

E. coli cells strain JM105 were transformed with the GST(FL)-CT2 expression plasmid, as described in Example 128. Transformed cells were propagated on petri-plates containing LB Amp medium at 37° C. overnight. LB medium (tryptone 10 g/l, yeast extract 5 g/l, NaCl 10 g/l and autoclaved) supplemented with 100 µg/ml ampicillin was inoculated with single colonies from the petri-plates and incubated at 37° C. with shaking overnight. 500 ml of 2×YT medium (tryptone 16 g/l, yeast extract 10 g/l, NaCl 5 g/l, pH 7.0 and autoclaved) supplemented with 100 µg/ml ampicillin (2×YTA) was inoculated with a 1/100 dilution of the overnight cultures and then incubated at 37° C. with shaking until an absorbance at 600 nm ($A_{600}$) of 0.6-1.0 was reached. Gene expression was induced by the addition of IPTG to a final concentration of 1 mM. Cells from the culture were harvested 6-7 hours post-induction. Cells were resuspended in 25 ml of ice-cold 1×PBS (140 mM NaCl, 2.7 mM KCl, 10 mM $Na_2HPO_4$, 1.8 mM $KH_2PO_4$, pH 7.3) and lysed by sonicating. Following pelleting, the cell lysate was collected.

Example 131

Large-Scale Expression of the N-Terminally Tagged Recombinant Glutathione S-Transferase Full-Length [r-GST(FL)] (SEQ. ID NO. 1) Fusion Protein, GST (FL)-NT1, in E. coli Cells Strain JM105

The procedure used was essentially the same as described in Example 130, except that E. coli cells strain JM105 were transformed with the GST(FL)-NT1 expression plasmid as described in Example 127.

Example 132

Large-Scale Expression of the N-Terminally Tagged Recombinant Glutathione S-Transferase Full-Length [r-GST(FL)] (SEQ. ID NO. 2) Fusion Protein, GST (FL)-NT2, in E. coli Cells Strain JM105

The procedure used was essentially the same as described in Example 130, except that E. coli cells strain JM105 were transformed with the GST(FL)-NT2 expression plasmid as described in Example 129.

Example 133

Large-Scale Expression of the N-Terminally Met-Lys-(His-Gln)$_6$-Tagged Recombinant Glutathione S-Transferase Full-Length Fusion Protein, GST(FL)-CT2, IN E. coli Cells Strain BL21

The procedure used was essentially the same as described in Example 130, except that E. coli cells strain BL21 were transformed with the GST(FL)-CT2 expression plasmid.

Example 134

Large-Scale Expression of the N-Terminally Tagged Recombinant Glutathione S-Transferase Full-Length [r-GST(FL)] (SEQ. ID NO. 1) Fusion Protein, GST (FL)-NT1, in E. coli Cells Strain BL21

The procedure used was essentially the same as described in Example 131, except that E. coli cells strain BL21 were transformed with the GST(FL)-NT1 expression plasmid.

Example 135

Large-Scale Expression of the N-Terminally Tagged Recombinant Glutathione S-Transferase Full-Length [r-GST(FL)] (SEQ. ID NO. 2) Fusion Protein, GST (FL)-NT2, in E. coli Cells Strain BL21

The procedure used was essentially the same as described in Example 132, except that E. coli cells strain BL21 were transformed with the GST(FL)-NT2 expression plasmid.

Example 136

Large-Scale Expression of the N-Terminally Met-Lys-(His-Gln)$_6$-Tagged Recombinant Glutathione S-Transferase Full-Length Fusion Protein, GST(FL)-CT2, in *E. coli* Cells Strain TOP10

The procedure used was essentially the same as described in Example 130, except that *E. coli* cells strain TOP10 were transformed with the GST(FL)-CT2 expression plasmid.

Example 137

Large-Scale Expression of the N-Terminally Tagged Recombinant Glutathione S-Transferase Full-Length [r-GST(FL)] (SEQ. ID NO. 1) Fusion Protein, GST(FL)-NT1, in *E. coli* Cells Strain TOP10

The procedure used was essentially the same as described in Example 131, except that *E. coli* cells strain TOP10 were transformed with the GST(FL)-NT1 expression plasmid.

Example 138

Large-Scale Expression of the N-Terminally Tagged Recombinant Glutathione S-Transferase Full-Length [r-GST(FL)] (SEQ. ID NO. 2) Fusion Protein, GST(FL)-NT2, in *E. coli* Cells Strain TOP10

The procedure used was essentially the same as described in Example 132, except that *E. coli* cells strain TOP10 were transformed with the GST(FL)-NT2 expression plasmid.

Example 139

Purification of the N-Terminally Met-Lys-(His-Gln)$_6$-Tagged Recombinant Glutathione S-Transferase Full-Length Fusion Protein, GST(FL)-CT2, Expressed in *E. coli* Cells Strain JM105

The N-terminally tagged GST(FL) fusion protein GST(FL)-CT2 expressed as described in Example 128 (above) can be purified by batch or column chromatographic methods essentially as described in Example 93 using immobilised Ni$^{2+}$-tacn, Cu$^{2+}$-tacn, Ni$^{2+}$-dtne, Cu$^{2+}$-dtne, Ni$^{2+}$-dtnp, Cu$^{2+}$-dtnp or other metal ion chelated macrocyclic tris- or tetrakis-tacn systems as an appropriate chromatographic sorbent. Each column was incubated with Buffer B (Buffer B=Buffer A supplemented with 10 mM imidazole, pH 8.4; Buffer A=445 mM NaCl, 7.5 mM Na$_2$HPO$_4$ and 2.5 mM NaH$_2$PO$_4$.2H$_2$O, pH 7.2). Columns were loaded with 250 µl of the crude lysate (which was diluted 1 in 4 with Buffer B) per ml of gel. Columns were then washed twice with Buffer B prior to elution. Two elution procedures were used: elution with Buffer 1 (Buffer 1=Buffer A supplemented with 50 mM imidazole, pH 9.7) followed by a second elution with 200 mM sodium malonate, which had been adjusted to pH 8.0 with 10 M sodium hydroxide. Alternatively, these GST fusion proteins can be purified using Glutathione Sepharose™ 4B (GS4B). In this case, batch purification was performed as outlined in the information booklet GST Gene Fusion System, 3rd edn., Revision 1, from Pharmacia Biotech. Briefly, 24 ml of cell lysate, as described in Example 130, was applied to 0.75 ml bed volume of GS4B which had been washed and equilibrated with 1×PBS (140 mM NaCl, 2.7 mM KCl, 10 mM Na$_2$HPO$_4$, 1.8 mM KH$_2$PO$_4$, pH 7.3). The resultant mixture was incubated with end-on-end rotation for approximately 1 hour at room temperature. The mixture was centrifuged at 500×g for 5 min. The supernatant was collected and the gel was extensively washed with 1×PBS. The fusion protein was eluted with elution buffer (50 mM Tris-HCl pH 8, 10 mM reduced glutathione).

The eluate was collected and then applied to a 10 ml Econo-column (Bio-Rad™) in order to remove any residual buffer salts or GS4B. The eluate was incubated with 4.7 mM ethylenediaminetetraacetic acid (EDTA) for 20 min at room temperature and then extensively dialyzed at 4° C. against a buffer (20 mM sodium phosphate, 150 mM NaCl, pH 6.9). Following dialysis, the protein was passed through a 0.45 µm sterile filter (Millipore™). The protein concentrations pre- and post-filtering were determined employing the bichinchoninic acid (BCA) reagent (Pierce Chemical Co., Rockford, Ill., USA) using Bovine serum albumin (BSA) as a standard. The purified fusion protein was then stored at 4° C.

Example 140

Batch Purification of the N-Terminally Tagged Recombinant Glutathione S-Transferase Full-Length [r-GST(FL)] (SEQ. ID NO. 1) Fusion Protein, GST(FL)-NT1, Expressed in *E. coli* Cells Strain JM105

The procedure used was essentially the same as described in Example 139, except that the crude cell lysate as described in Example 131 was purified.

Example 141

Batch Purification of the N-Terminally Tagged Recombinant Glutathione S-Transferase Full-Length [r-GST(FL)] (SEQ. ID NO. 2) Fusion Protein, GST(FL)-NT2, Expressed in *E. coli* Cells Strain JM105

The procedure used was essentially the same as described in Example 139, except that the crude cell lysate as described in Example 132 was purified.

Example 142

Batch Purification of the N-Terminally Met-Lys-(His-Gln)$_6$-Tagged Recombinant Glutathione S-Transferase Full-Length Fusion Protein, GST(FL)-CT2, Expressed in *E. coli* Cells Strain BL21

The procedure used was essentially the same as described in Example 139, except that the crude cell lysate as described in Example 133 was purified.

Example 143

Batch Purification of the N-Terminally Tagged Recombinant Glutathione S-Transferase Full-Length [r-GST(FL)] (SEQ. ID NO. 1) Fusion Protein, GST(FL)-NT1, Expressed in *E. coli* Cells Strain BL21

The procedure used was essentially the same as described in Example 139, except that the crude cell lysate as described in Example 134 was fractionated with the purified protein not being incubated with EDTA.

Example 144

Batch Purification of the N-Terminally Tagged Recombinant Glutathione S-Transferase Full-Length [r-GST(FL)] (SEQ. ID NO. 2) Fusion Protein, GST (FL)-NT2, Expressed in *E. coli* Cells Strain BL21

The procedure used was essentially the same as described in Example 139, except that the crude cell lysate as described in Example 135 was fractionated with the purified protein not being incubated with EDTA.

Example 145

Batch Purification of the N-Terminally Met-Lys-(His-Gln)$_6$-Tagged Recombinant Glutathione S-Transferase Full-Length Fusion Protein, GST(FL)-CT2, Expressed in *E. coli* Cells Strain TOP10

The procedure used was essentially the same as described in Example 139, except that the crude cell lysate as described in Example 136 was fractionated with the purified protein not being incubated with EDTA.

Example 146

Batch Purification of the N-Terminally Tagged Recombinant Glutathione S-Transferase Full-Length [r-GST(FL)] (SEQ. ID NO. 1) Fusion Protein, GST (FL)-NT1, Expressed in *E. coli* Cells Strain TOP10

The procedure used was essentially the same as described in Example 139, except that the crude cell lysate as described in Example 137 was fractionated with the purified protein not being incubated with EDTA.

Example 147

Batch Purification of the N-Terminally Tagged Recombinant Glutathione S-Transferase Full-Length [r-GST(FL)] (SEQ. ID NO. 2) Fusion Protein, GST (FL)-NT2, Expressed in *E. coli* Cells Strain TOP10

The procedure used was essentially the same as described in Example 139, except that the crude cell lysate as described in Example 138 was fractionated with the purified protein not being incubated with EDTA.

Example 148

Molecular Mass Measurement of the N-Terminally Met-Lys-(His-Gln)$_6$-Tagged Recombinant Glutathione S-Transferase Full-Length Fusion Protein, GST(FL)-CT2, Expressed in Various Strains of *E. coli* Cells, by MALDI-TOF MS.

The molecular masses of the purified, dialyzed N-terminal tagged GST(FL)-CT2 fusion proteins, which had been expressed in various strains of *E. coli* cells and purified as described in Examples 139, 142 and 145, were measured by Matrix-Assisted Laser Desorption/Ionisation-Time Of Flight mass spectrometry (MALDI-TOF-MS). Non-reduced protein samples arising from the Glutathione Sepharose™ 4B (GS4B) purification procedure resulted in experimental [M+H]$^+$ values higher than the expected theoretical molecular masses, consistent with the GST proteins having been S-thiolated by the reduced glutathione (GSH) during the glutathione purification, described in Examples 136, 142 and 145. However, reduction of the protein samples by the addition of β-mercaptoethanol, followed by desalting, resulted in experimental [M+H]$^+$ values which were in accordance with the expected theoretical masses. Accordingly, all the samples analysed by MALDI-TOF MS were prepared in this manner.

Protein samples that had not previously been incubated with 4.7 mM EDTA were treated in this fashion for 20 min at room temperature. The protein was then incubated with β-mercaptoethanol (at a final concentration of 50 mM) and then desalted using a $C_{18}$ ZipTip™ (Millipore™) and stored at −20° C. until analysis. The sample was applied to a sinapinic acid matrix using the crushed-crystal method. Spectra were recorded using a Voyager-DE STR BioSpectrometry Workstation. Samples were analysed in positive ion linear mode with an acceleration potential of 25 kV, a pulse delay time of 250 ns, a low mass gate of 5 KDa and a grid voltage of 85%. 100 shots per spectrum were taken, and 5 spectra were accumulated.

GST(FL)-CT2 has a theoretical molecular mass of 28,007.3 Dalton.

Molecular Mass Measurement of GST(FL)-CT2, Expressed in *E. coli* Cell Strain JM105, by MALDI-TOF MS The spectra of GST(FL)-CT2 which had been expressed in the *E. coli* cell strain JM105, as described in Example 139, showed a single peak which had an average [M+H]$^+$ value of 28,006±5.57 Dalton. The experimental data were consistent with the protein being intact.

Molecular Mass Measurement of GST(FL)-CT2, Expressed in *E. coli* Cell Strain BL21, by MALDI-TOF MS The spectra of GST(FL)-CT2 which had been expressed in the *E. coli* cell strain BL21, as described in Example 142, showed a single peak which had an average [M+H]$^+$ value of 28,008.10±5.29 Dalton. The experimental data were consistent with the protein being intact.

Molecular Mass Measurement of GST(FL)-CT2, Expressed in *E. coli* Cell Strain TOP10, by MALDI-TOF MS The spectra of GST(FL)-CT2 which had been expressed in the *E. coli* cell strain TOP10, as described in Example 145, showed a single peak which had an average [M+H]$^+$ value of 28,003.00±3.46 Dalton. The experimental data were consistent with the protein being intact.

Example 149

Molecular Mass Measurement of the N-Terminally Tagged Recombinant Glutathione S-Transferase Full-Length [r-GST(FL)] (SEQ. ID NO. 1) Fusion Protein, GST(FL)-NT1, Expressed in Various Strains OF *E. coli* Cells, by MALDI-TOF MS The procedure used was essentially the same as described in Example 148, with the following exceptions:

GST(FL)-NT1 has a theoretical molecular mass of 27,965.3 Dalton.

Molecular Mass Measurement of GST(FL)-NT1, Expressed in *E. coli* Cell Strain JM105, by MALDI-TOF MS The spectra of GST(FL)-NT1 which had been expressed in the *E. coli* cell strain JM105, as described in Example 140, showed a single peak which had an average [M+H]$^+$ value of 27,953.00±2.65 Dalton. The experimental data were consistent with the protein being intact.

Molecular Mass Measurement of GST(FL)-NT1, Expressed in E. coli Cell Strain BL21, by MALDI-TOF MS The spectra of GST(FL)-NT1 which had been expressed in the E. coli cell strain BL21, as described in Example 143, showed a single peak which had an average [M+H]$^+$ value of 27,951.00±4.36 Dalton. The experimental data were consistent with the protein being intact.

Molecular Mass Measurement of GST(FL)-NT1, Expressed in E. coli Cell Strain TOP10, by MALDI-TOF MS The spectra of GST(FL)-NT1 which had been expressed in the E. coli cell strain TOP10, as described in Example 146, showed a single peak which had an average [M+H]$^+$ value of 27,954.67±6.66 Dalton. The experimental data were consistent with the protein being intact.

Example 150

Molecular Mass Measurement of the N-Terminally Tagged Recombinant Glutathione S-Transferase Full-Length [r-GST(FL)] (SEQ. ID NO. 2) Fusion Protein, GST(FL)-NT2, Expressed in Various Strains OF E. coli Cells, by MALDI-TOF MS The procedure used was essentially the same as described in Example 148, with the following exceptions:

GST(FL)-NT2 has a theoretical molecular mass of 28,218.6 Dalton.

Molecular Mass Measurement of GST(FL)-NT2, Expressed in E. coli Cell Strain JM105, by MALDI-TOF MS The spectra of GST(FL)-NT2 which had been expressed in the E. coli cell strain JM105, as described in Example 141, showed a single peak which had an average [M+H]$^+$ value of 28,208.00±8.44 Dalton. The experimental data were consistent with the protein being intact.

Molecular Mass Measurement of GST(FL)-NT2, Expressed in E. coli Cell Strain BL21, by MALDI-TOF MS The spectra of GST(FL)-NT2 which had been expressed in the E. coli cell strain BL21, as described in Example 144, showed a single peak which had an average [M+H]$^+$ value of 28,214.33±5.86 Dalton. The experimental data were consistent with the protein being intact.

Molecular Mass Measurement of GST(FL)-NT2, Expressed in E. coli Cell Strain TOP10, by MALDI-TOF MS The MALDI-MS spectra of GST(FL)-NT2 which had been expressed in the E. coli cell strain TOP10, as described in Example 147, showed:
 (a) a major peak (100% intensity) which had an average [M+H]$^+$ value of 28,213.83±6.05Dalton;
 (b) a minor peak (~25% relative intensity) which had an average [M+H]$^+$ value of 27,815.83±8.04 Dalton;
 (c) a minor peak (~13% relative intensity) which had an average [M+H]$^+$ value of 26,301.0±6.90 Dalton.

The experimental data were consistent with the purified sample containing predominantly the intact protein and small amounts of the protein that had been N-terminally truncated by the first 3 and the first 15 residues, respectively. These species correspond to truncated forms of GST(FL)-NT2 missing the following N terminal amino acids as italicised:

Minor peak   *MKH*                $^1$TNIHQDQHNHFHR-[GST]
 This species has a theoretical molecular mass of 27,822.11 Dalton
Minor peak   *MKHTNIHQDQHNHFH*    $^1$R-[GST]
 This species has a theoretical molecular mass of 26,312.55 Dalton Example 151

Dipeptidyl Aminopeptidase I (DAP-1) Digestion of the N-Terminally Met-Lys-(His-Gln)-6-Tagged Recombinant Glutathione S-Transferase Full-Length Fusion Protein, GST(FL)-CT2

The N-terminal cleavage enzyme dipeptidyl aminopeptidase I [DAP-1 (E.C. 3.4.14.1); obtainable from, e.g., Aldrich-Sigma, St Louis, Mo., USA, or Unizyme Laboratories, Horsholm, Denmark] (10 U/ml) was activated by adding an equal volume of DTT (20 mM) and incubating the mixture for 4-6 min at room temperature. The digest reaction mixture contained 50 µg of the N-terminally tagged GST(FL)-CT2 protein expressed in E. coli cell strain JM105, as described in Example 139, and 12.5 mU of the activated DAP-1. The reaction mixture was adjusted to a volume of 70 Pl by the addition of the buffer in which the protein was suspended (20 mM sodium phosphate, 150 mM NaCl, pH 6.9). The digest reaction mixture was then incubated at 37° C. in a water bath for time periods of from 5 min to approximately 23 hours.

At the end of the incubation time an aliquot of the DAP-1 digest reaction mixture was removed and the reaction stopped by the addition of SDS loading buffer (reducing). The sample was heated at 100° C. for 90 sec and then stored at –20° C. for subsequent SDS-polyacrylamide gel analysis.

In addition, at the completion of the incubation period, a second aliquot of the DAP-1 digest reaction mixture was removed and incubated with guanidine-HCl (added to a final concentration of 1 M) for 5 min at room temp. in order to stop the digestion reaction. This mixture was then further prepared, as described in Example 148, for later analysis by MALDI-TOF MS. Briefly, this involved the addition of β-mercaptoethanol (to a final concentration of 50 mM) to the stopped digest reaction mixture which was then incubated for 15 min at room temp. prior to being desalted using a $C_{18}$ ZipTip™ and then stored at –20° C.

In order to assess the protein sample at the time of the DAP-1 digestion, and to serve as a negative control therefor, a sample of the undigested (i.e. non-DAP-1-treated) protein, GST(FL)-CT2, as described in Example 139, was also prepared for subsequent molecular mass measurement by MALDI-TOF MS. This involved supplementing the protein sample with β-mercaptoethanol (to a final concentration of 50 mM) prior to being desalted using a $C_{18}$ ZipTip™. The sample was then stored at –20° C. until subsequent MALDI-TOF MS analysis.

A sample of the undigested (i.e. non-DAP-1-treated) protein, GST(FL)-CT2, as described in Example 139, was also supplemented with SDS loading buffer (reducing) and heated at 100° C. for 90 sec prior to being stored at –20° C. for subsequent SDS-polyacrylamide gel analysis.

Example 152

DAP-1 Digestion of the N-Terminally Tagged Recombinant Glutathione S-Transferase Full-Length [r-GST(FL)] (SEQ. ID NO. 1) Fusion Protein, GST (FL)-NT1

The procedure was essentially the same as described in Example 151, with the following exceptions:

The purified N-terminally tagged GST(FL) fusion protein GST(FL)-NT1, which had been expressed in E. coli cell strain JM105, as described in Example 140, was further dialyzed against the buffer (20 mM sodium acetate, 150 mM NaCl, pH 5.5). Following dialysis, the protein concentration was determined employing the bichinchoninic acid (BCA) reagent (Pierce Chemical Co., Rockford, Ill., USA) using bovine serum albumin (BSA) as a standard. The DAP-1 digest reaction mixture was incubated for time periods of from 5 min to approximately 24 hours.

Example 153

DAP-1 Digestion of the N-Terminally Tagged Recombinant Glutathione S-Transferase Full-Length [r-GST(FL)] (SEQ. ID NO. 2) Fusion Protein, GST (FL)-NT2

The procedure for the DAP-1 digestion of the N-terminally tagged GST(FL) fusion protein GST(FL)-NT2 was essentially the same as described in Example 151, with the following exceptions:

The purified N-terminally tagged GST(FL) fusion protein GST(FL)-NT2, which had been expressed in *E. coli* cell strain JM105, as described in Example 141, was further dialyzed against the buffer (20 mM sodium phosphate, 150 mM NaCl, pH 6.3). Following dialysis, the protein concentration was determined employing the bichinchoninic acid (BCA) reagent (Pierce Chemical Co., Rockford, Ill., USA) using bovine serum albumin (BSA) as a standard. The digest reaction mixture was incubated for time periods of from 5 min to approximately 24 hours.

Example 154

Molecular Mass Measurement of the N-Terminally Met-Lys-(His-Gln)$_6$-Tagged Re-Combinant Glutathione S-Transferase Full-Length Fusion Protein, GST(FL)-CT2, Before and After Digestion with DAP-1

GST(FL)-CT2 was treated with DAP-1, the conditions of the digestion reaction being as described in Example 151. At the end of incubation time periods ranging from 5 min to approximately 23 hours, an aliquot of the digest reaction was removed and incubated with guanidine-HCl (added to a final concentration of 1 M) for 5 min at room temp. in order to stop the digest reaction. This mixture was then further prepared, as described in Example 148, for later analysis by MALDI-TOF MS. Briefly, this involved the addition of β-mercaptoethanol (to a final concentration of 50 mM) to the stopped digest reaction mixture, which was then incubated for 15 min at room temp prior to being desalted using a C$_{18}$ ZipTip™, and then stored at −20° C.

A sample of the undigested (i.e. non-DAP-1-treated) protein, GST(FL)-CT2, as described in Example 139, was also prepared at the time of the DAP-1 digestion for subsequent molecular mass measurement by MALDI-TOF MS, in order to assess the protein sample at the time of digestion and to serve as a negative control therefor. As previously described in Example 151, this involved supplementing the protein sample with β-mercaptoethanol (to a final concentration of 50 mM) prior to being desalted using a C$_{18}$ ZipTip™. The sample was then stored at −20° C. until subsequent MALDI-TOF MS analysis.

The above-mentioned samples were analysed by MALDI-TOF-MS. Each sample was applied to a sinapinic acid matrix using the crushed-crystal method. Spectra were recorded using a Voyager-DE STR BioSpectrometry Workstation. Samples were analyzed in positive ion linear mode with an acceleration potential of 25 kV, a pulse delay time of 250 ns, a low mass gate of 5 KDa and a grid voltage of 85%. 100 shots per spectrum were taken, and 5 spectra were accumulated.

The spectra are shown in FIG. 53. The spectrum for the non-DAP-1-treated GST(FL)-CT2 fusion protein, i.e. the negative control, shows a single peak (labelled 1) which has a [M+H]$^+$ value of 28,013±3.21 Dalton; by comparison with the theoretical isotopic molecular mass of GST(FL)-CT2 (28,007.3 Dalton) the observed mass is consistent with the GST(FL)-CT2 protein being intact. The spectrum for the DAP-1-digested GST(FL)-CT2 (labelled 2) shows decreased molecular mass following treatment of the fusion protein with DAP-1 for 2 hours.

Spectrum 2 displays a major peak (2a) having an average [M+H]$^+$ value of 26,154±6 Dalton, and a minor peak (2b) having an average [M+H]$^+$ value of 25,931±7.51 Dalton. These species correspond to truncated forms of GST(FL)-CT2 missing the N-terminal amino acids as italicised:

Peak (2a)   *MKHQHQHQHQHQHQ*   $^1$VDQMSP-[GST]
(this species has a theoretical molecular mass of 26,156.3 Dalton)
Peak (2b)   *MKHQHQHQHQHQHQVD*   $^1$QMSP-[GST]
(this species has a theoretical molecular mass of 25,942.1 Dalton)

where $^1$V and $^1$Q correspond to the N-terminal amino acid residue of the truncated variants of GST(FL)-CT2 following DAP-1 digestion. Based on the apparent specificity of DAP-1, further cleavage occurs up to the DAP-1 stop position $^1$SP - - - [GST], where 1S is the N-terminal amino acid residue.

Example 155

Molecular Mass Measurement of the N-Terminally Tagged Recombinant Glutathione S-Transferase Full-Length [r-GST(FL)] (SEQ. ID NO. 1) Fusion Protein, GST(FL)-NT1, Before and After Digestion WITH DAP-1

The procedure was essentially the same as described in Example 154, with the following exceptions:

GST(FL)-NT1 was treated with DAP-1, the conditions of the digest reaction being as described in Example 152. The digestion reaction mixture was incubated for time periods ranging from 5 min to approximately 24 hours.

A sample of the undigested (i.e. non-DAP-1-treated) protein, GST(FL)-NT1, as described in Example 140, was also prepared at the time of the DAP-1 digestion.

The spectra are shown in FIG. 54. The spectrum for the non-DAP-1-treated GST(FL)-NT1, i.e. the negative control, shows a single peak (labelled 1) which has a [M+H]$^+$ value of 27,972±3.51 Dalton; by comparison with the expected theoretical molecular mass of 27,965.3 Dalton for GST(FL)-NT1 the observed mass is consistent with the protein being intact. The spectrum for the DAP-1-digested (2 hr) GST(FL)-NT1 (labelled 2) shows decreased molecular mass following treatment with DAP-1.

Spectrum 2 displays a major peak (2a) having an average [M+H]$^+$ value of 26,659±6.81 Dalton. It also displays a minor peak (2b) having an average [M+H]$^+$ value of 25,934±3.21 Dalton, and a further minor peak (2c) having an average [M+H]$^+$ value of 25,680±6.03 Dalton. These species correspond to truncated forms of GST(FL)-NT1 missing the following N-terminal amino acids as italicised:

Peak (2a)   MKHHHNSWDH   $^1$DINRVDQMSP-[GST]
   (this species has a theoretical molecular mass of 26,654.9 Dalton)
Peak (2b)   MKHHHNSWDHDINRVD   $^1$QMSP-[GST]
   (this species has a theoretical molecular mass of 25,942.1 Dalton)
Peak (2c)   MKHHHNSWDHDINRVDQM   $^1$SP-[GST]
   (this species has a theoretical molecular mass of 25,682.80 Dalton)

where $^1$D . . . $^1$Q and $^1$S . . . correspond to the N-terminal amino acid residue of the truncated variants of GST(FL)-NT1 following DAP-1 digestion. Based on the apparent specificity of DAP-1, cleavage up to the DAP-1 stop position $^1$SP - - - [GST] has occurred. Subsidiary peaks in the spectrum corresponding to adducts of sinapinic acid (of additional molecular mass of 224.2 Da) and β-mercaptoethanol (MW 78.13) are also evident.

Example 156

Molecular Mass Measurement of the N-Terminally Tagged Recombinant Glutathione S-Transferase Full-Length [r-GST(FL)] (SEQ. ID NO. 2) Fusion Protein, GST(FL)-NT2, Before and After DAP-1 Treatment The procedure was essentially the same as described in Example 154, with the following exceptions:

GST(FL)-NT2 was treated with DAP-1, the conditions of the digestion reaction being as described in Example 153. The digest reaction mixture was incubated for time periods ranging from 5 min to approximately 24 hours.

A sample of the undigested (i.e. non-DAP-1-treated) protein, GST(FL)-NT2, as described in Example 141, was also prepared at the time of the DAP-1 digestion.

The spectra are shown in FIG. 55. The spectrum for the non-DAP-1-treated GST(FL)-NT2, i.e. the negative control, shows a single peak (labelled 1) which has a [M+H]$^+$ value of 28,223±2.89 Dalton; by comparison with the expected theoretical molecular mass of 28,218.6 Dalton for GST(FL)-NT2 the observed mass is consistent with the protein being intact. The spectrum for the DAP-1-digested (2 hr) GST(FL)-NT2 (labelled 2) shows decreased molecular mass following treatment with DAP-1.

Spectrum 2 displays a major peak (2a) having an average [M+H]$^+$ value of 25,910±9.16 Dalton, and a minor peak (2b) having an average [M+H]$^+$ value of 25,648±12.86 Dalton. These species correspond to truncated forms of GST(FL)-NT2 missing the N-terminal amino acids as italicised: IPTG (isopropyl-o-D-thiogalactoside) and X-gal (5-bromo-4-chloro-3-indolyl-o-D-galactoside) The plates were incubated at 37° C. overnight.

Identification of Positive Clones:

Modified plasmid DNA was isolated from the DH5α transformants described above using standard techniques. Plasmid DNA from different clones was digested with various restriction endonucleases to identify those clones likely to contain plasmids having the desired insert. Plasmid DNA from a number of clones was digested with the restriction endonuclease PvuII. The conditions were: appr. 300 μg DNA. 10 units of PvuII,10 mM Tris-HCl, pH 7.5, 10 mM MgCl$_2$, 50 mM NaCl and 1 mM DTE in a volume of 20 μl. The temperature was 37° C. and the reaction time was 3 hours. The DNA fragments were separated on a 1% agarose gel enabling identification of plasmids containing fragments of the correct size. Plasmids selected from the PvuII enzyme screen were screened a second time using the restriction endonuclease BspHI. The conditions were: approx. 300 μg DNA, 10 units of BspHI, 50 mM Potassium acetate, 20 mM Tris-acetate, 10 mM magnesium acetate and 1 mM DTT, pH 7.9 in a volume of 20 μl. The temperature was 37° C. and the reaction time was 2 hours. The digested DNA was run on a 1% agarose gel, and plasmids containing fragments of the correct size were identified.

DNA sequencing of the plasmid inserts, of the clones selected from both enzyme screens, was performed as follows. Approx. 100 ng of the desired plasmid fragment isolated from the PvuII digestion of the selected clones was used as the template for DNA sequencing reactions. The sequencing reactions were: 100 ng plasmid DNA, 5 μmol primer and 8 μl of terminator premix in a volume of 20 PI.

Duplicate mixtures of the above reactions were prepared, one set containing the pBluescript T3 primer with the sequence 5'-AATTAACCCTCACTAAAGGG-3', and the other containing the pBluescript T7 primer, which has the sequence 3'-CGGGATATCACTCAGC ATAATG-5'. The reaction mixtures were applied to a thermo-cycler using the following conditions: an initial denaturation step at 96° C. for 1 minute, then 25 cycles of 96° C., 50° C. and 60° C. for 30 seconds, 15 seconds and 4 minutes, respectively. The extension products were recovered by performing an ethanol/sodium acetate precipitation using standard techniques, and the pellets were dried and subjected to DNA sequencing.

A clone containing the desired plasmid insert encoding GST-NT1 was identified. DNA sequencing verified that the sequence was correct.

Insert Preparation:

Plasmid from the positive clone (pBluescript with the desired insert) was incubated with the restriction endonucleases BspHI and HindIII. The conditions were: approx. 500 ng plasmid DNA, 20 units of BspHI, 40 units of HindIII, 50 mM potassium acetate, 20 mM Tris-acetate, 10 mM magnesium acetate and 1 mM DTT, pH 7.9 in a volume of 70 μl. The temperature was 37° C. and the reaction time was 2.5 hours. The DNA fragments were separated on a 2% agarose gel and the desired fragment isolated.

Peak (2a)   MKHTNIHQDQHNHFHRVD   $^1$QMSP-[GST]
   (this species has a theoretical molecular mass of 25,942.1 Dalton)
Peak (2b)   MKHTNIHQDQHNHFHRVDQM   $^1$SP-[GST]
   This species has a theoretical molecular mass of 25,682.8 Da where $^1$Q . . . and $^1$S . . . correspond to the N-terminal amino acid residue of the truncated variants of GST(FL)-NT2 following DAP-1 digestion. Based on the apparent specificity of DAP-1, cleavage up to the DAP stop position $^1$SP - - - [GST] has occurred.

Example 157

SDS-Page Analysis of the Various Recombinant Full-Length Glutathione S-Transferase Fusion Proteins N-Terminally Tagged with the Various Oligopeptide Constructs [e.g. GST(FL)-CT2, GST(FL)-NT1 AND GST(FL)-NT2] BEFORE AND AFTER DAP-1 DIGESTION Aliquots of the various N-terminally tagged recombinant glutathione S-transferase full-length fusion proteins, before and after DAP-1 digestion, were mixed with SDS loading buffer (reducing) and heated for 90 sec at 100° C., as described in Examples 151, 152 and 153. Samples were then loaded onto an 18% SDS-polyacrylamide gel and run for an appropriate period of time. 0.4 μl of the undigested (i.e. non-DAP-1-treated) proteins, 0.6 μl of the DAP digest reaction mixtures and 8 μl of the molecular weight marker [BenchMark Protein Ladder (Gibco BRL)] were loaded onto the gel.

In order to visualize bands, the gel was silver stained. The stained gel is shown in FIG. 56.

Example 158

Evaluation of the Activity of the Recombinant Full-Length Glutathione S-Transferase [r-GST(FL)] (SEQ. ID NO. 1) Fusion Protein, N-Terminally Tagged with the Oligopeptide Construct Designated NT1, i.e. GST(FL)-NT1, Before and After DAP-1 Digestion A DAP-1 digestion reaction mixture was prepared, the procedure being essentially as described in Examples 92 and 152. Briefly, DAP-1 [EC 3.4.14.1] (10 U/ml) was activated by adding an equal volume of DTT (20 mM) and incubating the mixture for 4-6 min at room temperature. The digest reaction mixture contained 50 µg of the N-terminally tagged GST (FL)-NT1 protein expressed in $E.$ $coli$ cell strain JM105, as described in Examples 140 and 152, and 12.5 mU of the activated DAP-1. The reaction mixture was adjusted to a volume of 70 µl by the addition of the buffer in which the protein was suspended (20 mM sodium acetate, 150 mM NaCl, pH 5.5). The digest reaction mixture was then incubated at 37° C. in a water bath for approximately 24 hours.

A non-DAP-1-treated, negative control reaction mixture was also prepared. The procedure was essentially as described above, except that DAP-1 was omitted.

At the cessation of the incubation period, both reactions were assessed for activity. A reliable assay for functional GST activity is the CDNB (1-chloro-2,4-dinitrobenzene) assay in which GST catalyzes the derivatisation of CDNB with glutathione; this complex can be monitored by optical density measurements at a wavelength of 340 nm. This assay was performed as outlined in the information booklet GST Gene Fusion System, 3rd edn., Revision 1, from Pharmacia Biotech. Briefly, 10 µl of a 1 in 100 dilution of each of the pre- and post-DAP-1-digestion reaction mixtures was added to 100 µl of assay reaction mixture containing 100 mM $KH_2PO_4$, pH 6.5, 1 mM 1-chloro-2,4-dinitrobenzene (CDNB) and 1 mM reduced glutathione in a cuvette, and the absorbance at 340 nm was measured for 5 min at 1 minute intervals. Both the pre- and post-DAP-1-digestion reaction mixtures containing GST(FL)-NT1 exhibited functional GST activity as determined by this assay.

Example 159

Evaluation of the Activity of the Recombinant Full-Length Glutathione S-Transferase [r-GST(FL)] (SEQ. ID NO. 1) Fusion Protein, N-Terminally Tagged with the Oligopeptide Construct Designated NT2, i.e. GST(FL)-NT2, Before and After DAP-1 Digestion The procedure was essentially the same as described in Example 158, with the following exceptions:

The digestion reaction mixture contained 50 µg of the N-terminally tagged GST(FL)-NT2 protein expressed in $E.$ $coli$ cell strain JM105, as described in Examples 141 and 153, and 12.5 mU of the activated DAP-1. The reaction mixture was adjusted to a volume of 70 p by the addition of the buffer in which the protein was suspended (20 mM sodium phosphate, 150 mM NaCl, pH 6.3). The digest reaction mixture was then incubated at 37° C. in a water bath for approximately 12 hours.

A non-DAP-1-treated, negative control reaction mixture was also prepared. The procedure was essentially as described above, except that DAP was omitted.

Both the pre- and post-DAP-1-digestion reaction mixtures containing GST(FL)-NT2 exhibited functional GST activity as determined by this assay.

Example 160

Single-Step Isocratic Elution of Various N-Terminally Tagged GST Fusion Proteins Crude cell lysate (CCL) obtained from the large scale expression of glutathione S-transferase (GST) fused at the N-terminus to the following various affinity tags: hexa-histidine (GST-CT1), alternating His-Gln repeats (GST-CT2), new tag 1 (GST-NT1) and NT2 (GST-NT2), as described in Example 91, were purified by single-step isocratic elution procedures. Crude cell lysate was applied to both $Ni^{2+}$-tacn and $Cu^{2+}$-tacn columns. Each column (10 mL Econo-columns, Bio-Rad™) had a bed volume of 0.5 mL, and was equilibrated with Buffer A1 [Buffer A11=Buffer A (20 mM phosphate buffer, 500 mM NaCl, pH 8)+10 mM imidazole, pH 8]. The columns were loaded with 5 ml of sample containing 0.5 ml (CCL)+4.5 ml Buffer A1. After the sample had passed through the column, the column was washed with Buffer A1 (5 ml). A second wash (5 ml) was performed using Buffer A2 (Buffer A2=Buffer A+20 mM imidazole, pH 8). Elution was performed by applying 3×1 ml volumes of elution buffer (BA+500 mM imidazole, pH 8) to the columns.

xample 161

SDS-Page Analysis of the First Elution Fractions Collected from the Purification Of Various N-Terminally Tagged GST Fusion Proteins, Using Single-Step Isocratic Elution Aliquots of the first elution fraction collected from the single step isocratic elution of various N-terminally tagged GST fusion proteins which had each been applied to $Ni^{2+}$-tacn and $Cu^{2+}$-tacn columns as described in Example 160 were mixed with SDS loading buffer (reducing) and heated for 90 sec at 100° C. Samples were then loaded onto a 15% SDS-polyacrylamide gel and run for an appropriate period of time. 16 µl of the elution fractions and 2 µl of molecular weight marker [Benchmark protein ladder (Gibco, BRL)] were loaded onto the gel. In order to visualize bands, the gels were silver stained. The stained gel is shown in FIG. 57.

Example 162

Purification of N-Terminally NT2-VD-Tagged Human Growth Hormone (NT2-VD-hGH; MKHTNIHQDQHNHFHRVD-hGH). Cleavage of the tag by DAP-1 and Isolation of Mature hGH The N-terminally tagged fusion protein NT2-VD-hGH, i.e. MKHTNIHQDQHNHFHRVD-hGH, was expressed in a 1 liter shaking bottle using a plasmid construct produced essentially as described in Example 127. The pellet was collected and washed with water. The pellet from 250 ml was then lysed in lysis buffer (20 ml 20 mM $Na_2HPO_4$, 500 mM NaCl, pH 8) by addition of 250 µl Lysozyme (30 mg/ml) and 1.25 µl Benzonase. The suspension was left for 1 hour at 5° C. followed by centrifugation. The supernatant was collected and diluted with 80 ml lysis buffer, and was then introduced onto a 15 ml immobilised $Ni^{2+}$-tacn column at a rate 3 ml/min, followed by 150 ml buffer. The column was then washed with 150 ml lysis buffer with a content of 2% elution buffer (20 mM $Na_2HPO_4$, 500 mM NaCl, 500 ml imidazole, pH 8), and then with 150 ml lysis buffer with a content of 4% elution buffer. Gradient elution using from 4% to 100% elution buffer over a total volume of 75 ml was then performed, followed by elution with 75 ml 100% elution buffer.

Eluted fractions containing the desired product were identified by electrophoresis, and were pooled and desalted against 20 mM $Na_2HPO_4$, 150 mM NaCl, pH 6.3, followed by heating to 37° C. Activated DAP-1 (125 µl DAP-1+25 µl 100 mM DTT, incubated for 5 minutes at room temperature) was added to the desalted fractions, and the pH of the medium was then varied a number of times between approx. 6.3 and 5.1 during a period of 270 minutes. The medium was then left at 5° C. and at a pH of 5 over the weekend. The cleaved pool was then centrifuged, and the supernatant was collected, adjusted to pH 8 and introduced onto a 1 ml immobilised $Ni^{2+}$-tacn column. The column was then eluted essentially as described above with a flow of 0.18 ml/min, and the peak containing hGH was collected. Selected samples were analysed by SDS-Page and western blot as shown in FIG. 60 below.

In addition, a number of samples were analysed by MALDI-TOF MS with an estimated accuracy of 50 Dalton, and the molecular mass of the isolated tagged product was determined to be 24,444 Dalton (theoretical value 24,402 Dalton). After cleavage and a second $Ni^{2+}$-tacn column elution, a molecular mass of 22,156 Dalton was determined (theoretical value 24,125 Dalton). A molecular mass of 22,147 Dalton was obtained for a hGH standard sample.

Example 163

Purification of CT2-VD-hGH (MKHQHQHQHQHQHQVD-hGH) BY $Ni^{2+}$-tacn Column Elution Followed by $Cu^{2+}$-tacn Column Elution The N-terminally tagged fusion protein CT2-VD-hGH, i.e. MKHQHQHQHQHQHQVD-hGH, was expressed in a 1 liter shaking bottle using a plasmid construct produced essentially as described in Example 127. The pellet was collected and washed with water. The pellet from 250 ml was then lysed in lysis buffer as described in Example 162. The suspension was left for 1 hour at 5° C. followed by centrifugation. The supernatant was collected, and half the amount thereof was diluted with 40 ml lysis buffer and introduced onto a 5 ml immobilised $Ni^{2+}$-tacn column at a rate of 1 ml/min, followed by 20 ml buffer. The column was then washed with 50 ml lysis buffer with a content of 2% elution buffer (20 mM $Na_2HPO_4$, 500 mM NaCl, 500 ml imidazole, pH 8) and 50 ml lysis buffer with a content of 4% elution buffer. Gradient elution using from 4% to 100% elution buffer over a total volume of 25 ml was then performed, followed by elution with 25 ml 100% elution buffer.

Eluted fractions containing the desired tagged product were identified by electrophoresis, and were pooled and desalted against lysis buffer. The desalted pool was diluted 5× with lysis buffer and introduced onto a 5 ml $Cu^{2+}$-tacn column. Elution buffers and rates were as described above for the $Ni^{2+}$-tacn column. Likewise, respective fractions containing the tagged hGH product were pooled and desalted.

Selected samples were analysed by SDS-Page as shown in FIG. 61 below.

The results demonstrate that a substantial reduction in the content of non-hGH related material was achieved using the two different $M^{2+}$-tacn columns successively.

The invention claimed is:

1. A polymer substrate functionalized with a metal ion coordinating functionality of general formula (I)

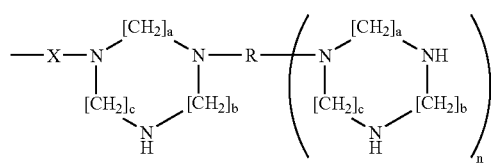

Formula (I)

wherein n is 1, 2 or 3;

each of a, b and c in each triazacycloalkane ring, independently of each other and independently of any other triazacycloalkane ring, is 1, 2 or 3;

one or both hydrogen atoms of each —$CH_2$— group in each triazacycloalkane ring, independently of each other and independently of any other triazacycloalkane ring, may optionally and independently be substituted with a substituent;

the hydrogen atom of each —NH— group in each triazacycloalkane ring, independently of each other and independently of any other triazacycloalkane ring, may optionally be substituted with a substituent;

when n is 1, R is a bifunctional group, said bifunctional group optionally comprising one or more metal ion coordinating donor atoms;
when n is 2 or 3, R is an (n+1)-functional group, said (n+1)-functional group optionally comprising one or more metal ion coordinating donor atoms; and
X is a linker/spacer group.

2. A functionalized polymer substrate according to claim 1, wherein the optional substituent substituting a hydrogen atom in a ring —CH$_2$— group is selected from the group consisting of optionally substituted lower alkyl groups and optionally substituted aryl groups, the optional substituent(s) on said lower alkyl group or aryl group optionally comprising one or more metal ion coordinating donor atoms.

3. A functionalized polymer substrate according to claim 1, wherein the optional substituent substituting the hydrogen atom in a ring —NH— group is selected from the group consisting of optionally substituted lower alkyl groups and optionally substituted aryl groups, the optional substituent(s) on said lower alkyl group or aryl group optionally comprising one or more metal ion coordinating donor atoms.

4. A functionalized polymer substrate according to claim 1, wherein said polymer is substantially water-insoluble.

5. A functionalized polymer substrate according to claim 1, wherein said polymer is selected from the group consisting of polysaccharides and derivatives thereof, polyalkylene glycols and derivatives thereof, polyvinyl alcohols and derivatives thereof, polyacrylamides, surface-modified silicas, and surface-modified metal oxides.

6. A functionalized polymer substrate according to claim 5, wherein said polymer is selected from the group consisting of agarose and derivatives thereof, dextran and derivatives thereof, and cellulose and derivatives thereof.

7. A functionalized polymer substrate according to claim 6, wherein said polymer substrate is an agarose;
n is 1, 2 or 3;
a, b and c in each triazacycloalkane ring is 2;
when n is 1, R is selected from the group consisting of —[CH$_2$]$_m$—, wherein m is 2, 3 or 4,

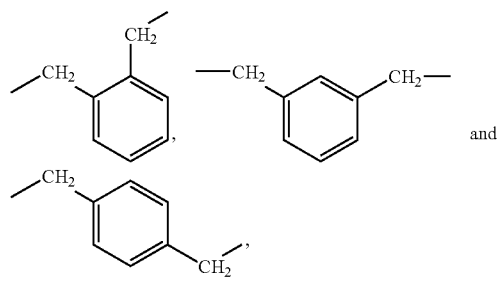

and substituted derivatives thereof,
when n is 2, R is selected from the group consisting of:

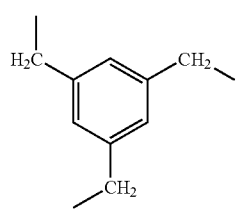

and substituted derivatives thereof;

when n is 3, R is selected from the group consisting of:

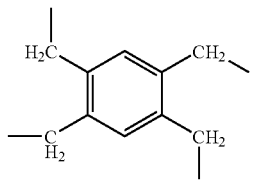

and substituted derivatives thereof;
and X is a group derivable from epichlorohydrin by reaction thereof with agarose, and subsequent reaction of the resulting product with a ring —NH— group of that triazacycloalkane ring which becomes bound to X.

8. A functionalized polymer substrate according to claim 1, further comprising a metal ion coordinated to at least one of the triazacycloalkane ligand groups in said functionality.

9. A functionalized polymer substrate according to claim 8, wherein said coordinated metal ion is a divalent or trivalent metal ion.

10. A functionalized polymer substrate according to claim 9, wherein said metal ion is selected from the group consisting of $Ca^{2+}$, $Mg^{2+}$, $Cu^{2+}$, $Zn^{2+}$, $Ni^{2+}$, $Mn^{2+}$, $Co^{2+}$, $Fe^{3+}$ and $Cr^{3+}$.

11. A process for preparing a functionalized polymer substrate according to claim 1, said process comprising the steps of:
selecting a polymer substrate having a reactive functional group capable of undergoing a first reaction with a first functional group of a bifunctional reagent having a first and a second functional group,
said first reaction resulting in covalent bond formation between said polymer substrate and said bifunctional reagent,
said second functional group of the resulting covalently bound reagent being subsequently capable of undergoing a second reaction with a reactive functional group present in a species of general formula (II):

Formula (II)

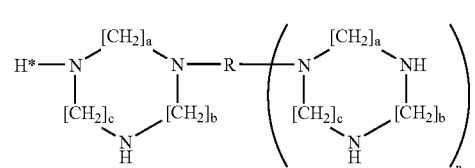

wherein n, a, b, c and R are as defined in claim 1;
one or both hydrogen atoms of each —CH$_2$— group in each triazacycloalkane ring, independently of each other and independently of any other triazacycloalkane ring, may optionally and independently be substituted with a substituent, said optional substituent optionally comprising one or more metal ion coordinating donor atoms;
the hydrogen atom of each —NH— group in each triazacycloalkane ring, with the exception of H*, independently of each other and independently of any other triazacycloalkane ring, may optionally be substituted with a substituent, said optional substituent optionally comprising one or more metal ion coordinating donor atoms;

said second reaction resulting in covalent bond formation between said species of general formula (II) and said covalently bound reagent;

reacting said polymer substrate with said bifunctional reagent to produce said covalently bound reagent; and reacting said resulting covalently bound reagent with said species of general formula (II) to produce said functionalized polymer substrate.

12. A process according to claim 11, wherein the optional substituent substituting a hydrogen atom in a ring —CH$_2$- group is selected from the group consisting of: optionally substituted lower alkyl groups; and optionally substituted aryl groups.

13. A process according to claim 11, wherein the optional substituent substituting the hydrogen atom in a ring —NH- group is selected from the group consisting of optionally substituted lower alkyl groups and optionally substituted aryl groups.

14. A process according to claim 11, wherein said polymer is substantially water-insoluble.

15. A process according to claim 11, wherein said polymer is selected from the group consisting of polysaccharides and derivatives thereof, polyalkylene glycols and derivatives thereof, polyvinyl alcohols and derivatives thereof, polyacrylamides; surface-modified silicas, and surface-modified metal oxides.

16. A process according to claim 15, wherein said polymer is selected from the group consisting of agarose and derivatives thereof, dextran and derivatives thereof, and cellulose and derivatives thereof.

17. A process according to claim 16, wherein said polymer substrate is an agarose;

n is 1, 2 or 3;

a, b and c in each triazacycloalkane ring is 2;

when n is 1, R is selected from the group consisting of —[CH$_2$]$_m$— wherein m is 2, 3 or 4,

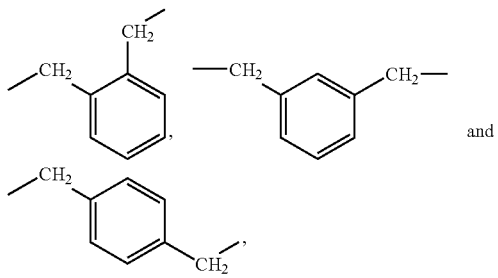

and substituted derivatives thereof, when n is 2, R is selected from the group consisting of:

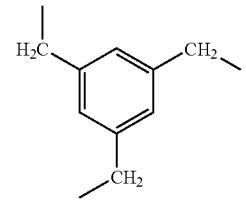

and substituted derivatives thereof, when n is 3, R is selected from the group consisting of:

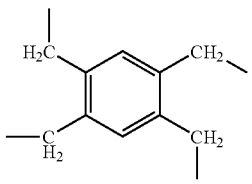

and substituted derivatives thereof and said bifunctional reagent is epichlorohydrin.

18. A process according to claim 17, wherein a reducing agent is incorporated in the reaction mixture when reacting said polymer substrate with said bifunctional reagent.

19. A process according to claim 18, wherein said reducing agent is sodium borohydride.

20. A functionalized polymer substrate obtainable by a process according to claim 11.

21. A process according to claim 11, wherein a metal ion is coordinated to at least one of the triazacycloalkane ligand groups in said species of general formula (II) and an aqueous solution of an inorganic or organic salt of said metal ion coordinated to at least one of the triazacycloalkane ligand groups in said species of general formula (II) is reacted with said covalently bound reagent to produce a metal ion-containing functionalized polymer substrate.

22. A metal ion-containing functionalized polymer substrate obtainable by a process according to claim 21.

* * * * *

SEQUENCE LISTING

<160> NUMBER OF SEQ ID NOS: 7

<210> SEQ ID NO 1
<211> LENGTH: 12
<212> TYPE: PRT
<213> ORGANISM: Artificial
<220> FEATURE:
<223> OTHER INFORMATION: Amino acid sequences of non-natural origin

<400> SEQUENCE: 1

His His His Asn Ser Trp Asp His Asp Ile Asn Arg
1               5                   10

<210> SEQ ID NO 2
<211> LENGTH: 14
<212> TYPE: PRT
<213> ORGANISM: Artificial
<220> FEATURE:
<223> OTHER INFORMATION: Amino acid sequences of non-natural origin

<400> SEQUENCE: 2

His Thr Asn Ile His Gln Asp Gln His Asn His Phe His Arg
1               5                   10

<210> SEQ ID NO 3
<211> LENGTH: 13

```
-continued

<212> TYPE: PRT
<213> ORGANISM: Artificial
<220> FEATURE:
<223> OTHER INFORMATION: Amino acid sequences of non-natural origin

<400> SEQUENCE: 3

His Ala Met Leu Asp Arg Ala His Asp His Gly Thr Arg
1               5                   10

<210> SEQ ID NO 4
<211> LENGTH: 12
<212> TYPE: PRT
<213> ORGANISM: Artificial
<220> FEATURE:
<223> OTHER INFORMATION: Amino acid sequences of non-natural origin

<400> SEQUENCE: 4

Ser Leu His Glu His His Ser Gly Asp Asn Leu Arg
1               5                   10

<210> SEQ ID NO 5
<211> LENGTH: 13
<212> TYPE: PRT
<213> ORGANISM: Artificial
<220> FEATURE:
<223> OTHER INFORMATION: Amino acid sequences of non-natural origin

<400> SEQUENCE: 5

Thr His Tyr Asn Ala Val His Ser His Asn Thr Leu Gln
1               5                   10

<210> SEQ ID NO 6
<211> LENGTH: 14
<212> TYPE: PRT
<213> ORGANISM: Artificial
<220> FEATURE:
<223> OTHER INFORMATION: Amino acid sequences of non-natural origin

<400> SEQUENCE: 6

Asp Ile His His Trp Thr Asp His Leu Gln Ser Ser Thr His
1               5                   10

<210> SEQ ID NO 7
<211> LENGTH: 14
<212> TYPE: PRT
<213> ORGANISM: Artificial
<220> FEATURE:
<223> OTHER INFORMATION: Amino acid sequences of non-natural origin

<400> SEQUENCE: 7

Leu Tyr Asn His Tyr Ser His Thr Ala His Val Asn His Leu
1               5                   10
```